US005652842A

United States Patent [19]
Siegrist, Jr. et al.

[11] Patent Number: 5,652,842
[45] Date of Patent: Jul. 29, 1997

[54] ANALYSIS AND REPORTING OF PERFORMANCE OF SERVICE PROVIDERS

[75] Inventors: Richard B. Siegrist, Jr., Acton; Donald W. Siegrist, Harvard, both of Mass.

[73] Assignee: Healthshare Technology, Inc., Acton, Mass.

[21] Appl. No.: 205,033

[22] Filed: Mar. 1, 1994

[51] Int. Cl.⁶ .................................................. G06F 17/21
[52] U.S. Cl. .......................... 395/202; 395/615; 395/777; 395/942; 395/943; 395/140
[58] Field of Search ...................... 395/145–149, 395/600, 140, 202, 615, 777, 942, 943; 364/401–409

[56] References Cited

U.S. PATENT DOCUMENTS

| | | | |
|---|---|---|---|
| 4,315,309 | 2/1982 | Coli | 364/200 |
| 4,763,274 | 8/1988 | Junker et al. | 364/481 |
| 4,849,879 | 7/1989 | Chinnaswamy et al. | 364/200 |
| 5,018,067 | 5/1991 | Mohlenbrock et al. | 364/413.02 |
| 5,132,899 | 7/1992 | Fox | 364/408 |
| 5,189,608 | 2/1993 | Lyons et al. | 364/408 |
| 5,239,487 | 8/1993 | Horejsi et al. | 364/552 |
| 5,262,943 | 11/1993 | Thibado et al. | 364/413.01 |
| 5,307,262 | 4/1994 | Ertel | 364/413.01 |
| 5,326,270 | 7/1994 | Ostby et al. | 434/362 |
| 5,365,425 | 11/1994 | Torma et al. | 364/401 |
| 5,490,204 | 2/1996 | Gulledge | 379/59 |
| 5,550,734 | 8/1996 | Tarter et al. | 364/401 R |

FOREIGN PATENT DOCUMENTS

92/14206  8/1992  WIPO ............................ G06F 11/00

*Primary Examiner*—Joseph H. Feild
*Attorney, Agent, or Firm*—Fish & Richardson P.C.

[57] ABSTRACT

A computer-based method aids comparison of competitive performance of a first provider of services with other providers of the services, where the services are provided to a mix of customers belonging to different classes and the performance in providing the services is different for customers belonging to different classes. Data representing the first provider's competitive performance in providing various services to its customers is stored. Also stored is mix data representing the mix of its customers to which the services are provided. Similar data is stored representing each of the other providers' competitive performance in providing various services to its customers. The data of the other providers is adjusted in accordance with the mix data of the first provider. The unadjusted data of the first provider is visually provided together with the adjusted data of the other providers. Other aspects include automatically generating a printed report of information comparing performance of a first provider of services with performances of other providers of the services; and more broadly generating a report of an analysis of data.

19 Claims, 21 Drawing Sheets

| Dep | Abbrev | Description | Dept Group |
|---|---|---|---|
| 101 | M/S Rout | Medical/Surgical Routine | 10 |
| 102 | OB Rout | Obstetrics Routine | 10 |
| 103 | Ped Rout | Pediatric Routine | 10 |
| 104 | Psyc Rout | Psychiatric Routine | 10 |
| 105 | Other Rout | Other Routine | 10 |
| 106 | Newborn | Newborn Routine | 10 |
| 201 | Neonat ICU | Neonatal ICU | 20 |
| 202 | M/S ICU | Medical/Surgical ICU | 20 |
| 203 | Ped ICU | Pediatric ICU | 20 |
| 204 | Psyc ICU | Psychiatric ICU | 20 |
| 205 | Burn Unit | Burn Unit | 20 |
| 206 | Other ICU | Other ICU | 20 |
| 207 | CCU | Coronary Care Unit | 20 |
| 301 | Pharmacy | Pharmacy | 60 |
| 302 | IV Therapy | IV Therapy | 80 |
| 303 | M/S Suppl | Medical/Surgical Supplies | 60 |
| 304 | Labs | Laboratory | 30 |
| 305 | Diag Rad | Diagnostic Radiology | 40 |
| 306 | Ther Rad | Therapeutic Radiology | 40 |
| 307 | Nuc Med | Nuclear Medicine | 40 |
| 308 | CAT Scan | CAT Scanner | 40 |
| 309 | OR | Operating Room | 50 |
| 310 | Anesth | Anesthesiology | 50 |
| 311 | Blood | Blood. | 60 |
| 312 | Blood Adm | Blood Storage Proc. & Admin | 60 |
| 313 | RT | Respiratory Therapy | 80 |
| 314 | PT | Physical Therapy | 80 |
| 315 | OT | Occupational Therapy | 80 |
| 316 | Speech | Speech Therapy | 80 |
| 317 | ER | Emergency Room | 80 |
| 318 | Pulm Func | Pulmonary Function | 80 |
| 319 | Audiology | Audiology | 80 |
| 320 | Card Cath | Cardiac Catheterization | 30 |
| 321 | Ambulance | Ambulance | 80 |
| 322 | RR | Recovery Room | 50 |
| 323 | Labor/Del | Labor & Delivery | 50 |
| 324 | EKG | EKG | 70 |
| 325 | EEG | EEG | 70 |
| 326 | Renal Dial | Renal Dialysis | 80 |
| 327 | Kidney Acq | Kidney Acquisition | 80 |
| 328 | Psyc | Psychology/Psychiatry | 80 |
| 329 | Oth Ancill | Other Ancillary | 80 |

FIG. 4

FEDERAL DEPARTMENTS

- Anesthesiology
- Blood
- Blood Storage Proc. & Admin
- Diagnostic Radiology
- EEG
- EKG
- Emergency Room
- IV Therapy
- Kidney Acquisition
- Labor & Delivery
- Laboratory
- Medical/Surgical Supplies
- Nuclear Medicine
- Occupational Therapy
- Operating Room
- Other Ancillary
- Pharmacy
- Physical Therapy
- Recovery Room
- Renal Dialysis
- Respiratory Therapy
- Routine
- Special Care
- Speech Therapy
- Therapeutic Radiology

FIG. 5

MAPPING OF STATE CATEGORIES TO FEDERAL DEPARTMENTS

| Federal Departments | State Departments (Massachussetts) |
|---|---|
| Anesthesiology | 310 Anesthesiology |
| Blood | 311 Blood |
| Blood Storage Proc. & Admin. | 312 Blood Storage Proc & Admin. |
| Diagnostic Radiology | 305 Diagnostic Radiology |
|  | 208 CAT Scanner |
| EEG | 325 EEG |
| EKG | 324 EKG |
| Emergency Room | 317 Emergency Room |
| IV Therapy | 302 IV Therapy |
| Kidney Acquisition | 327 Kidney Acquisition |
| Labor & Delivery | 323 Labor & Delivery |
| Laboratory | 304 Laboratory |
|  | 320 Cardiac Catheter |
| Medical/Surgical Supplies | 303 Medical/Surgical Supp |
| Nuclear Medicine | 307 Nuclear Medicine |
| Occupational Therapy | 315 Occupational Therapy |
| Operating Room | 309 Operating Room |
| Other Ancillary | 329 Other Ancillary |
|  | 321 Ambulance |
|  | 328 Psychology/Psychiatry |
| Pharmacy | 301 Pharmacy |
| Physical Therapy | 314 Physical Therapy |
| Recovery Room | 322 Recovery Room |
| Renal Dialysis | 326 Renal Dialysis |
| Respiratory Therapy | 313 Respiratory Therapy |
|  | 318 Pulmonary Function |
| Routine | 101 Medical/Surgical |
|  | 102 Obstetrics Routine |
|  | 103 Pediatric Routine |
|  | 104 Psyciatric Routine |
|  | 105 Other Routine |
|  | 106 Newborn Routine |
| Special Care | 201 Neonatal ICU |
|  | 202 Medical/Surgical ICU |
|  | 203 Pediatric ICU |
|  | 204 Psychiatric ICU |
|  | 205 Burn Unit |
|  | 206 Other ICU |
|  | 207 Coronary Care Unit |
| Speech Therapy | 316 Speech Therapy |
|  | 319 Audiology |
| Therapeutic Radiology | 306 Therapeutic Radiology |

HEALTHSHARE TECHNOLOGY, INC.
Case Mix Adjustment Example

| | Col. C1 Your Hospital | | Col. C2 Other Hospital | | Col. C3 Other Hospital | |
|---|---|---|---|---|---|---|
| DRG | Cases | Cost per Case | Cases | Cost per Case | Adjusted Cases | Cost per Case |
| A | 700 | 4,500 | 200 | 5,000 | 700 | 5,000 |
| B | 500 | 3,000 | 500 | 3,500 | 500 | 3,500 |
| C | 100 | 2,500 | 300 | 3,000 | 100 | 3,000 |
| D | 1,500 | 1,000 | 2,100 | 1,500 | 1,500 | 1,500 |
| E | 400 | 2,000 | 0 | 0 | 400 | 2,000 |
| F | 800 | 3,500 | 400 | 4,000 | 800 | 4,000 |
| Total | 4,000 | 2,500 | 3,500 | 2,400 | 4,000 | 2,950 |

215

| | Cost per Case | Pct Diff | |
|---|---|---|---|
| Your Hospital | 2,500 | | your hospital's case mix * your hospital's cost per case |
| Other Hospital | 2,400 | -4.0% | other hospital's case mix * other hospital's cost per case (unadjusted cost) |
| Other Hospital (Case Mix Adjusted) | 2,950 | 18.0% | your hospital's case mix * other hospital's cost per case (case mix adjusted cost) |

In this example, your hospital's overall cost per case is $2,500, while the other Hospital's overall cost per case (before adjustment) is $2,400 or 4% lower.

After adjusting for case mix, which is done by taking your hospital's case mix times the other Hospital's cost per case, the other Hospital's overall cost per case is $2,950, or 18% higher than your hospital's overall cost per case.

Note that The other hospital does not have any cases for DRG E. When this happens, the adjustment algorithm uses your hospital's number of cases and cost per case to avoid skewing the overall cost per case.

NOTE: This same adjustment process applies to comparative length of stay and patient age.

FIG. 10

Cost per Case

221 → 's average total cost per 222 ↓ case was 223 ↓. The average of its 224 ↓ major competitors was 225 ↓ - 226 ↓ or 227 ↓ than 228 ↓. 229 ↓ had the 231 ↓
Specifically, the cost per case for each hospital as compared to 233 ↓ was as follows:

CostTable ↩ 234

The graph below shows the composition of the cost per case by department group for 235 ↓ and its competitors CostGraph ↩ 236

Cost2Table ← 239

237 238
↳ 's ↓ were composed of the following:

As shown in the above table, 240 ↘ ↙ 241

FIG. 11a

Cost per Case (DRG Mix Adjusted)

Brockton's average total cost per cardiology case was $4,385. The average of its seven major competitors was $4,119 - $266 or 6% lower than Brockton Hospital. Brockton had the highest total cost per case. Cardinal Cushing General Hospital had the lowest total cost with $3,518. Specifically, the cost per case for each hospital as compared to Brockton Hospital was as follows:

|  | Total Cost Per Case | % Diff than Brockton | Direct Cost Per Case | % Diff than Brockton |
|---|---|---|---|---|
| Brockton | $4,385 |  | $2,490 |  |
| St. Luke/NB | $4,273 | -3% | $2,317 | -7% |
| South Shore | $4,185 | -5% | $2,121 | -15% |
| Charlton | $4,359 | -1% | $2,186 | -12% |
| Cape Cod | $4,305 | -2% | $2,205 | -11% |
| Norwood | $4,096 | -7% | $1,842 | -26% |
| Goddard | $4,098 | -7% | $2,011 | -19% |
| Cardinal | $3,518 | -20% | $1,741 | -30% |
| Average ex. Brockton | $4,119 | -6% | $2,060 | -17% |

The graph below shows the composition of the cost per case by department group for Brockton and its competitors.

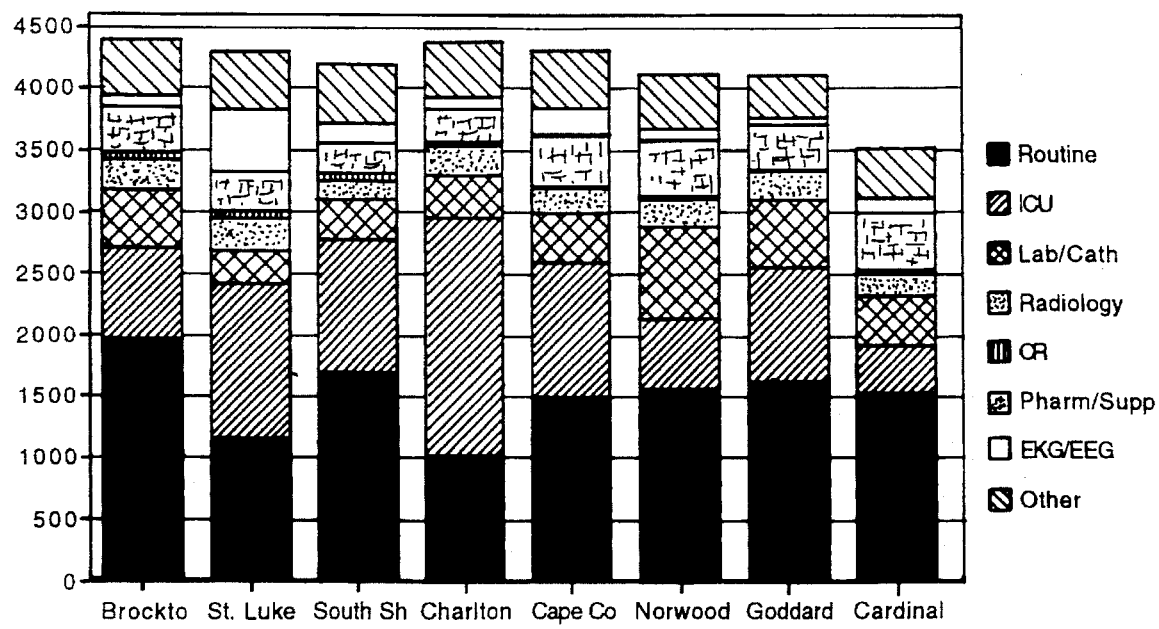

FIG. 11b

Brockton's $867 higher total cost per case than the lowest cost competitor, Cardinal Cushing General Hospital, and $266 higher total cost per case than the competitors' average were composed of the following:

|  | $ < than Cardinal | Pct < than Cardinal | $ < than Comp Avg | Pct < than Comp Avg |
|---|---|---|---|---|
| Routine | -$440 | -22.5% | -$533 | -27.3% |
| ICU | -$359 | -45.9% | $282 | 36.0% |
| Lab/Cath | -$49 | -11.3% | -$9 | -2.0% |
| Radiology | -$70 | -27.2% | -$39 | -15.2% |
| OR | -$23 | -44.9% | -$27 | -52.5% |
| Pharm/Supp | $94 | 25.9% | -$2 | -0.4% |
| EKG/EEG | $29 | 27.4% | $73 | 68.3% |
| Other | -$49 | -11.2% | -$11 | -2.4% |
| Total | -$867 | -19.8% | -$266 | -6.1% |

As shown in the above table, Brockton's total cost for routine care and intensive care were significantly above the lowest cost competitor. Brockton's total costs were not significantly lower than their lowest cost competitor in any key areas.

FIG. 11c

ANALYSIS AND REPORTING OF PERFORMANCE OF SERVICE PROVIDERS

BACKGROUND OF THE INVENTION

This invention relates to analysis and reporting of performance of service providers.

Hospitals, for example, can remain competitive only by frequent analysis of their cost and revenue performance versus competitors. Hospitals typically hire staff analysts or contract with consultants to provide such analyses. The work is usually based on a combination of publicly available and internal patient and financial data, and ends with a formal written report to the hospital's administration. The cost and time for doing the report is often high.

One excellent public source of data is the Healthcare Finance Administration (HCFA) of the federal government. HCFA has created a diagnosis classification system for use in administering Medicare claims. Costs and charges for every hospital in the United States fall into one of twenty-five departments, such as "Operating Room" or "Anesthesiology." A list of the twenty-five departments is attached as FIG. 5. A small portion of the type of data generated by the HCFA, which can be attained by submitting form MCR-2552 to the HCFA, is shown in Table I.

Even more detailed patient information is available from many individual state governments. For example, the state of Massachusetts makes available yearly information on every healthcare patient in the state. Included in this state-provided information are demographic data, such as the age, sex, race, and home zip code of each patient; clinical data, such as length of stay and discharge date for each patient; and charge data, including total amount charged by the healthcare provider for services rendered. All patient information provided by the state of Massachusetts is divided into forty-two healthcare charge categories. Each charge category represents a group of services provided by the healthcare industry and can be linked to one of the twenty-five federally defined departments discussed above. A list of the forty-two charge categories defined by the state of Massachusetts is attached as FIG. 4. Patient level information is available from the Rate Setting Commission of the Commonwealth of Massachussetts.

SUMMARY OF THE INVENTION

In general, in one aspect, the invention features a computer-based method of aiding comparison of competitive performance of a first provider of services with other providers of the services, where the services are provided to a mix of customers belonging to different classes and the performance in providing the services is different for customers belonging to different classes. Data representing the first provider's competitive performance in providing various services to its customers is stored. Also stored is mix data representing the mix of its customers to which the services are provided. Similar data is stored representing each of the other providers' competitive performance in providing various services to its customers. The data of the other providers is adjusted in accordance with the mix data of the first provider. The unadjusted data of the first provider is visually provided together with the adjusted data of the other providers.

Implementations of the invention may include the following features. The providers may be health-care providers. The data may relate to length of stay, charges, or costs. The customers may be patients and the classes may be distinct groups, e.g., demographically distinct. The step of presenting the data may include printing a report. The reporting step may include selecting a report template, creating a graphical representation of the data, and merging the report template and the graphical representation. An action plan describing a competitive strategy for the first service provider may be included in the report. A user may provide selections of sections to be included in the report. The user may also give choices of a level of detail for each of the sections. The data may includes hospital departmental cost information.

In general, in another aspect, the invention features automatically generating a printed report of information comparing performance of a first provider of services with performances of other providers of the services. Raw data is stored in a database. From the raw data in the database, a set of pertinent data is generated appropriate to comparing the performances of the service providers. Rules are stored for selecting which of the pertinent data has greater significance in comparing the performances of the service providers. The rules are automatically applied to the pertinent data to select the information for the printed report.

Implementations of the invention may include the following features. The raw data may include data for services provided. The rules may be based on which of the pertinent data represent the greatest difference in performance of the first provider of services compared to performance of the other providers, or on which of the pertinent data represent the greatest opportunities for improved performance.

In general, in another aspect, the invention features generating a report of an analysis of data. the data is stored. A user provides instructions on how to perform the analysis. Thereafter, the analysis of the data is automatically performed based on the instructions. Corresponding results are automatically generated. Printable narrative text and non-text graphics representations of the results are generated automatically, ready for printing in a single integrated report.

Implementations of the invention may include the following features. The data may include data (e.g., financial data) concerning the competitive performance of a medical service business. The non-text graphics representations may include tables and charts.

Advantages of the invention include the following. High-quality useful reports are generated automatically for service providers, i.e., hospitals, at low cost. In each report, a client service provider is compared to its peers in several areas of competition for a particular consumer group. The consumer group is selected by a user and may be predefined or may be created by the user. The information used to compare a service provider to its competitors is determined according to parameters generated by the user. Prior to comparison, data representing the performance of the competitors is adjusted to reflect the clientele of the service provider. This adjustment does not affect the service provider's data. The invention is also able to provide multiple levels of comparison, depending upon the level of detail required by the user.

The invention uses stored rules for selecting information of particular interest to the service provider. This information is used to generate a report which focuses the attention of the service provider on the most promising opportunities for cost savings, profit improvements, and improved competition. The report also lays out an action plan for achieving these improvements.

Other advantages will become apparent from the following description, and from the claims.

DESCRIPTION

FIG. 4 is a chart of state-defined hospital charge categories;

FIG. 5 is a chart of federally-defined hospital departments;

FIG. 6 is a mapping of state categories to federal departments;

FIGS. 8A–8C are screen shots of report request parameter entry;

FIG. 10 is an example of case mix adjustment;

FIGS. 11A–11C are an example of the generation of a report section.

Figure 1:
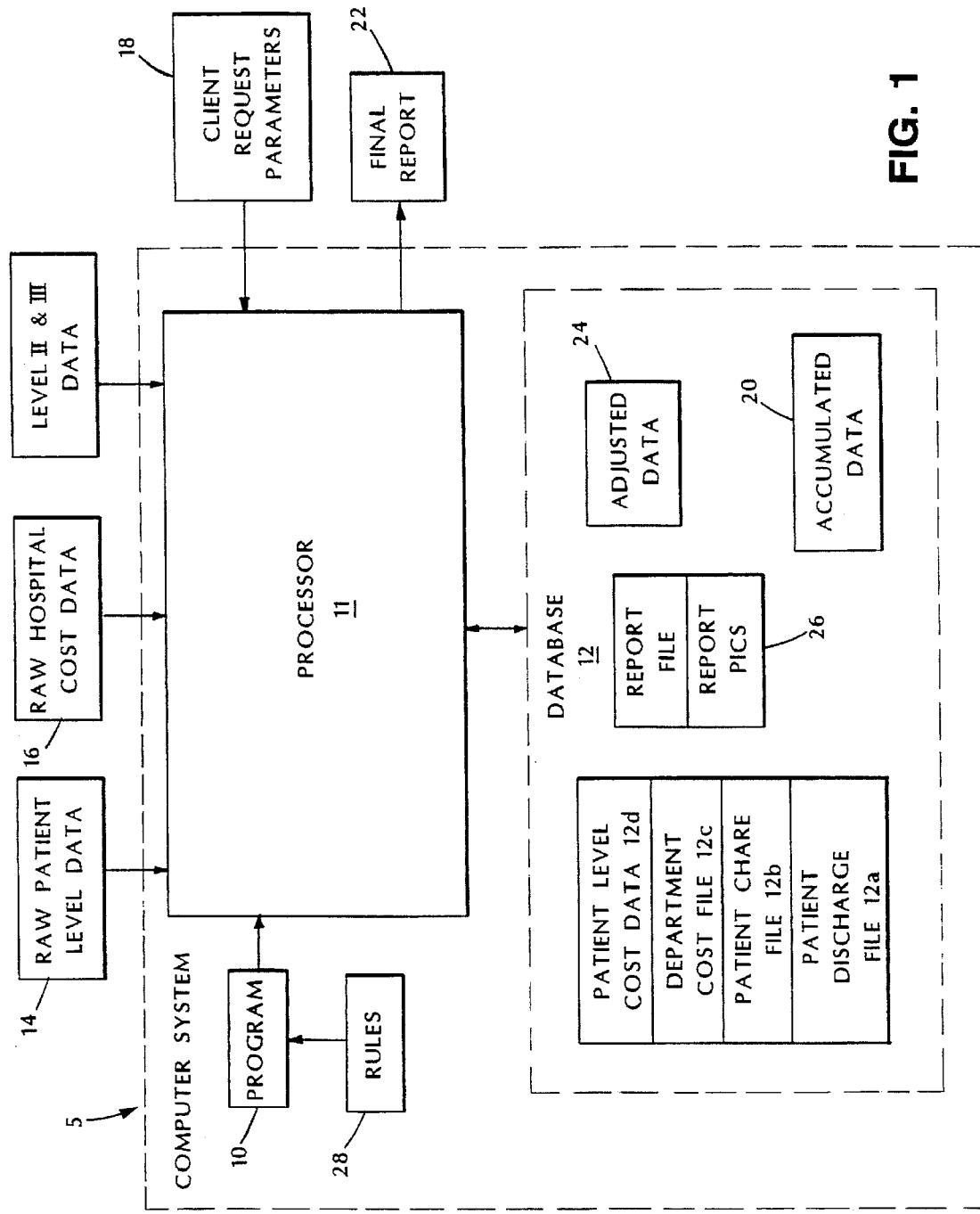
FIG. 1 is a block diagram of a computer-based system for analyzing and reporting healthcare information.

Referring to FIG. 1, healthcare facility (i.e., hospital) financial information is managed by a computer system 5 controlled by a program 10. This financial information is used by the system to analyze the comparative performance of competing hospitals and produce a report on the results. The report helps hospitals plan strategies for cutting costs and improving their competitive position.

Figure 2:
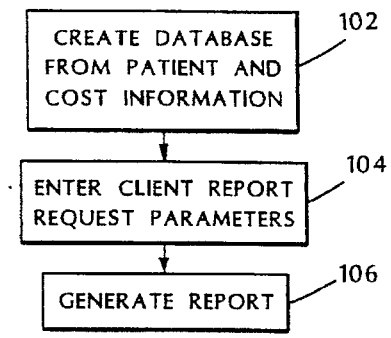
FIG. 2 is a flow chart of a process for using the system.
Figure 3:
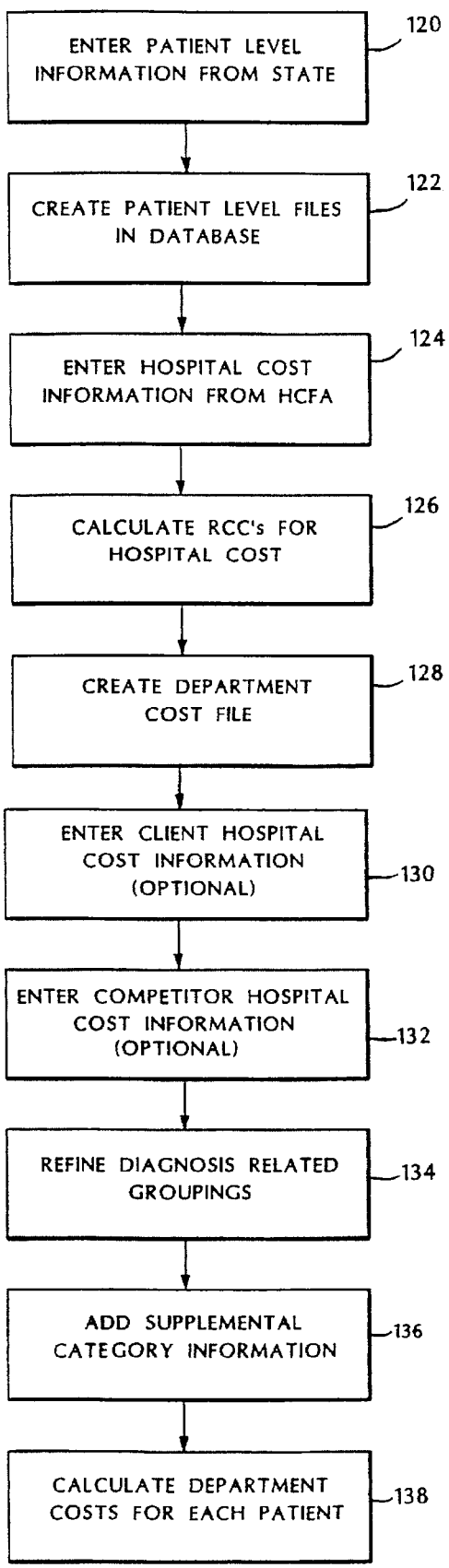
FIG. 3 is a flow chart for creation of a database of healthcare information.
Figure 7:
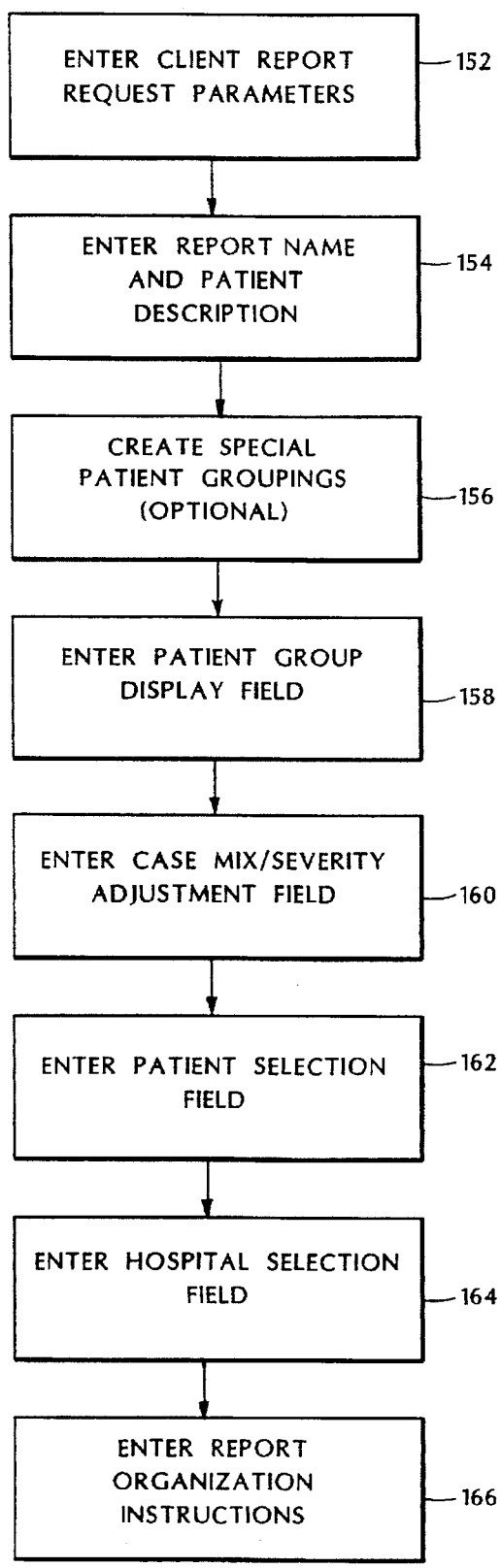
FIG. 7 is a flow diagram of a process for the entry of report request parameters.

Referring also to FIG. 2, in a first main step, a database 12 is created 102 from raw patient level information 14 and raw hospital cost information 16. Patient level information 14 is usually acquired from a state government and generally provides patient-by-patient healthcare data in several state-defined charge categories for each healthcare patient in a given year. Massachusetts, for example, provides patient level information which includes demographic, clinical, and charge data in forty-two charge categories for each patient, as described above. Hospital cost information 16 is usually acquired from the HCFA in the form of a Medicare Cost Report, which includes cost and charge information for the twenty-five departments for every hospital in the United States. The patient level information 14 and hospital cost information 16 are combined in the database 12 to provide patient level cost and charge information 12d for every department of every hospital.

The cost and charge information provided by the state and federal governments is sufficient for generation of many comparison reports, and is called Level I analysis. A client hospital may also need a report which includes a financial analysis at levels beyond the government defined departments. At a so-called Level II, the client hospital's internal cost and charge information is entered into the database and combined with the public information. A hospital's internal information may include, for example, the total charges of its physicians within each department, or total costs incurred for certain procedures, such as x-rays or lab work, performed by a department.

The client hospital may need even more detail in the report. At a Level III, cost and charge information similar to Level II information is entered into the database for each of the competing hospitals. This allows a more detailed comparison between a client hospital and its competitors.

In a second main step, a hospital comparison report is requested. To request a report, a user must enter 104 report request parameters 18 which are used by the computer system 5 to retrieve and manipulate the cost and charge information stored in the database 12. The parameters 18 input by the user determine, for example, which patient groups to compare in which hospitals and, therefore, which of the patient level cost and charge information 12d to retrieve from the database 12. Once the appropriate information has been retrieved, the information is accumulated to create total cost and charge information 20 for the chosen patient groups in the chosen hospitals. Even though the maintenance of cost and charge information for every patient of every hospital in a city (or even the nation) requires an enormous database, retrieval and combination of data according to user-defined parameters eliminates unnecessary manipulation of data irrelevant to the particular report being generated.

In a third main step, a final printed report 22 is generated 106 to provide, among other things, a hospital-by-hospital comparison of adjusted cost and charge information 24 for the patient group specified by the user. The adjusted cost and charge data 24 is created by adjusting the accumulated data 20 for each hospital to conform to a Mix Adjustment Field of a reference hospital (the client hospital). Mix Adjustment Fields are described in more detail below.

The final report 22 not only presents a mathematical and graphical comparison according to the user's parameters 18, but it also constructs an English-language prose explanation of the results of the comparison. A report may contain one or more of several sections. These sections include analyses of the client hospital's market share, payor mix, patient demographics, admit source, case mix, length of stay, and cost per case. The report also searches for comparison results of particular interest to the client hospital. Internal rules 28 cause the system 5 to determine, for example, if the client hospital has significantly (more than 110%) higher costs than its competitors, or which single competitor is most superior in a particular report area. In addition, the report includes an "Opportunity Analysis/Action Plan" section which provides suggestions to help the client hospital improve its competitiveness.

For each section of the report, the system 5 selects a report file 26, which provides guidelines for generating text and creating graphical representations of the results of the hospital comparisons. The graphical representations and text are merged according to the report file 26 to produce an easily readable final report 22 on the requested information. The final report is of a quality and style that is as good as or better than what might be prepared by hand by a consultant on a one-shot custom basis. The report also highlights the information determined by the internal rules 28 to be of particular interest to the client hospital. An example of such a report is shown in Appendix H.

Referring to FIGS. 3 through 6, the database is created by entering and combining the appropriate cost and charge information. For a healthcare cost and charge database for hospitals in the state of Massachusetts, patient level demographic, clinical, and charge information from a given year is entered 120 for each patient according to the forty-two state-defined charge categories, which are detailed in FIG. 4. For example, from the state-provided information, a patient's age, sex, and race are entered as demographic data. Then clinical information such as Length of Stay (LOS) and days spent in intensive care (ICU) is entered. In addition, the total amount (in dollars) charged to the patient in each category is entered into the database.

The patient level information is then divided and stored 122 in two database files. The first file is a "Patient Summary" file 12a (FIG. 1) which includes individual patient discharge information derived from the demographic and clinical data described above. The second file is a "Patient Charge" file 12b (FIG. 1). This file contains patient level charge information for each state-defined charge category. Creation of the "Patient Summary" and "Patient Charge" files allows maintenance of demographic and clinical information separately from charge information.

Along with patient level information, cost and charge information for each of twenty-five federally-defined departments in every hospital in the United States is entered 124 from a Medicare Cost Report provided by the HCFA. As shown in FIG. 5, the Medicare Cost Report covers twenty-five departments in a hospital and divides costs into direct and indirect (overhead) costs. The cost report further divides indirect costs into salary related and non-salary related costs. The cost report also provides total charge information for each of the twenty-five departments. Using this charge information, a ratio of cost to charge (RCC) is calculated 126 for total cost, direct cost, salary cost and non-salary cost in each of the twenty-five departments. The forty-two state-defined charge categories are then mapped to the twenty-five federal departments, and the results are stored 128 along with the corresponding RCCs in a "Department Cost" file 12c (FIG. 1). The mapping of the forty-two Massachusetts state departments to the twenty-five federal departments is shown in FIG. 6.

The patient level information and hospital cost information provided by the state and federal governments are sufficient to create a Level I comparison. However, for a Level II comparison, as described above, hospital specific internal cost information must be supplied 130 to the database. For example, if a hospital requests a department-by-department charge comparison of several of its doctors, detailed charge information for each doctor must be entered into the database. To perform a Level III comparison, the database requires 132 similar internal cost information for the hospitals in which the client hospital is interested. For example, if the client hospital requests a report on its departmental x-ray costs as compared to its chief competitors, detailed internal cost information from each competing hospital must be entered into the database. Level II and III information is optional.

As discussed above, all hospital services are divided among federally-defined Diagnosis Related Groups (DRG). In order to enhance the comparison capabilities of the invention, the DRGs are "refined" 134 according to a methodology developed at Yale University and marketed by Karen Schneider Associates located in New Haven, Conn. Refining a DRG includes the addition of "level of severity" information to each group. In other words, the DRGs are further defined by describing each diagnosis in terms of three or four levels of medical severity (refinement classes). The calculation of a severity level for each patient within a DRG considers whether the DRG is a grouping of medical or surgical diagnoses, the patient's sex, the patient's age, length of stay, whether the patient died within two days of admission, and whether the patient was discharged against medical advice. For example, an infant requiring heart surgery and intensive care for weeks is likely to place a greater drain on resources than a middle-aged victim of a minor heart attack. Even though these patients fall into the same DRG, the cost attributed to the treatment of each can be more accurately analyzed due to the refining of the DRG. In this manner, refined DRGs group patients according to resource intensity, and thus allow more accurate comparisons.

In addition to departmental cost and charge information, supplemental code tables are entered 136 into the database. Supplemental code tables are description or translation tables which allow the report generator to "translate" the data from the database into information understood by the user. For example, payor data may be handled for "Payor 1" and "Payor 2". To provide a useful report, however, the report generator must inform the user who "Payor 1" and "Payor 2" are. Therefore, a supplemental code table will indicate that "Payor 1" and "Payor 2" are, for example, Medicare and Blue Cross, respectively. Supplemental code tables will also indicate, for example, that data under "DRG 103" represents heart transplant patients.

After all mandatory and optional information has been entered into the database, costs are calculated 138 for each patient by combining patient level information with hospital cost information. The RCCs and charge category/department mappings in the "Department Cost" file are applied to the patient level charge information in the "Patient Charge" file. The total costs, direct costs, salary related costs, and non-salary related costs in each charge category are determined for each patient by multiplying the corresponding RCC with the category charge for the patient. In this manner, a database containing departmental costs and charges for every patient is created. From this departmental cost database, hospital comparisons are performed according to patient groups defined by the user, as described below.

A diagram showing the structure for the completed database is shown in FIGS. 12a–12d. The database comprises several structure groups, each of which contains at least one field of information. For example, a "Patient Summary" structure 310 includes a patient's unique ID 312 (in the form of a long integer, L), identification 314 of the hospital at which the patient was treated (in the form of a four-character alphanumeric word, A), the patient's age 316 (in the form of an integer, I), the patient's home zip code 318 (in the form of a five character alphanumeric word), and many other critical information fields.

Some of the fields within a structure may be linked to a substructure which provides further detail for the field. For example, within the "Patient Summary" structure 310, the "Zip Code" field 318 is linked to a "Zip Code" structure 320. The "Zip Code" structure 320 further defines the "Zip Code" field 318 by storing zip code, town and community information for each patient. In addition, a field within a structure may not contain data in and of itself, but instead may comprise a subfile which holds several critical subfields related to that field. For example, within a "Patient Cost" structure 322, a "Cost" field 324 comprises a "Cost" subfile 326 which includes "Department Code", "Charges", "Total Cost", and "Direct Cost" subfields 328, all of which describe the "Cost" field 324 of the "Patient Cost" 322 structure group.

Many fields within the database contain critical information which is to be available quickly without the usual search process. These critical fields, such as a patient's unique ID or a hospital code, are indexed for easy retrieval from the database. The indexed fields are shown in bold type in the database structure diagram of FIGS. 12a–12d. The database structures and field definitions are shown in Table II.

In addition to demographic data, clinical data, and cost and charge data, the database contains report files and report graphics. A "Report File" data structure 330 comprises fields which indicate the report ID, the study group compared in the report, and the client hospital, as well as information on the report organization options chosen by the user. A "Report Pics" data structure 332 holds the ID for each report and graphical representations (such as cost tables and cost graphs) of the results of the comparisons. The report files and report pictures are described in more detail below.

Referring to FIGS. 7 and 8A through 8C, parameters 18 (FIG. 1) for generation of a comparison report are derived from a request form completed by a client hospital. Report request parameters determine which fields of information are retrieved from the database for analysis. Despite the vast amount of healthcare information stored in the database, the report request parameters allow the retrieval of only that information requested by the client hospital. For example, if the client hospital requests an analysis of its performance against its five primary competitors in pediatric services, only pediatric-related DRG data for six hospitals is needed. This limited amount of information is easily accumulated and adjusted for comparison. In this manner, report request parameters allow the creation of a useful, low cost report from a large, comprehensive database of healthcare information.

Figure 8A:
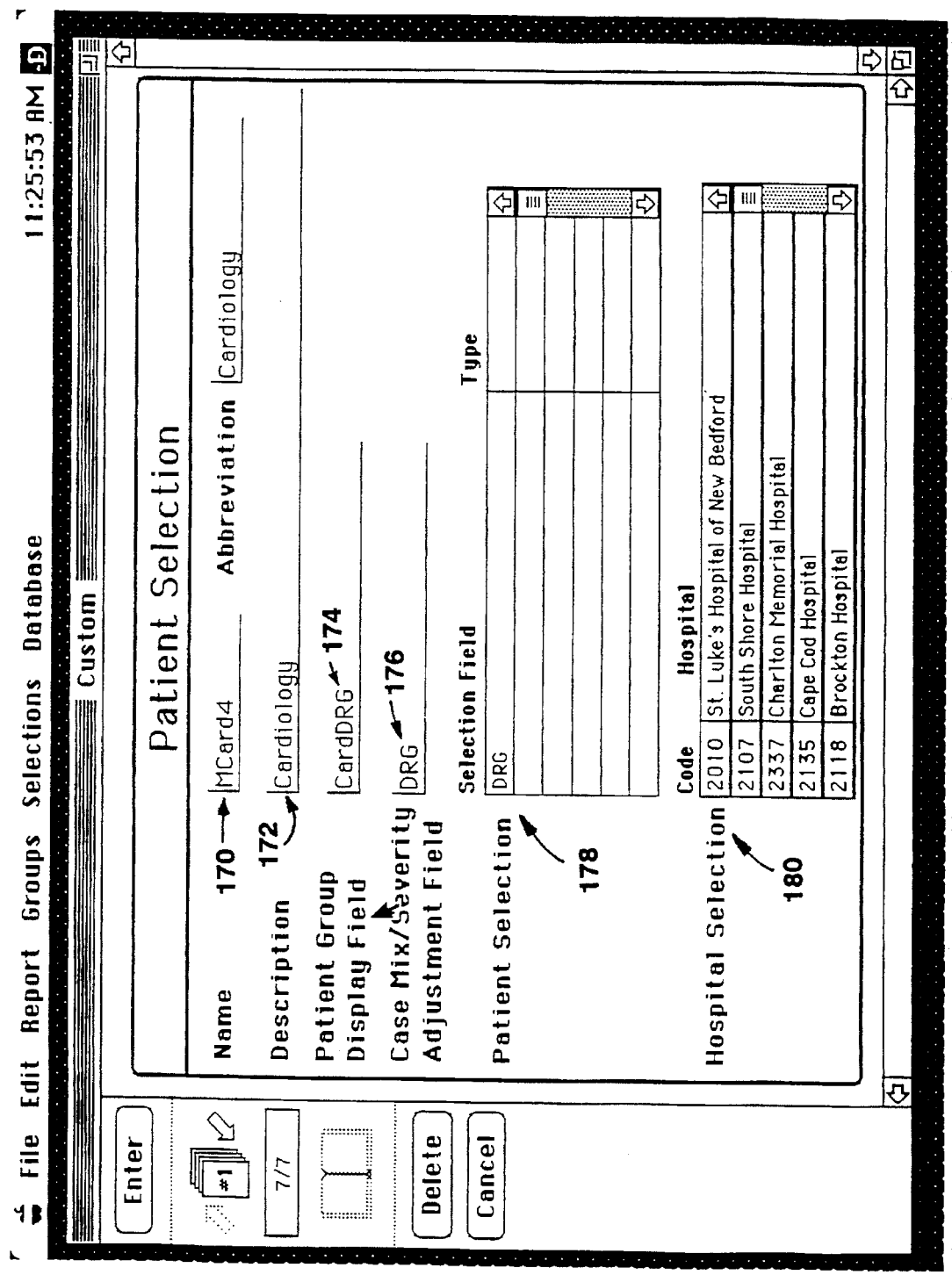
Figure 8B:
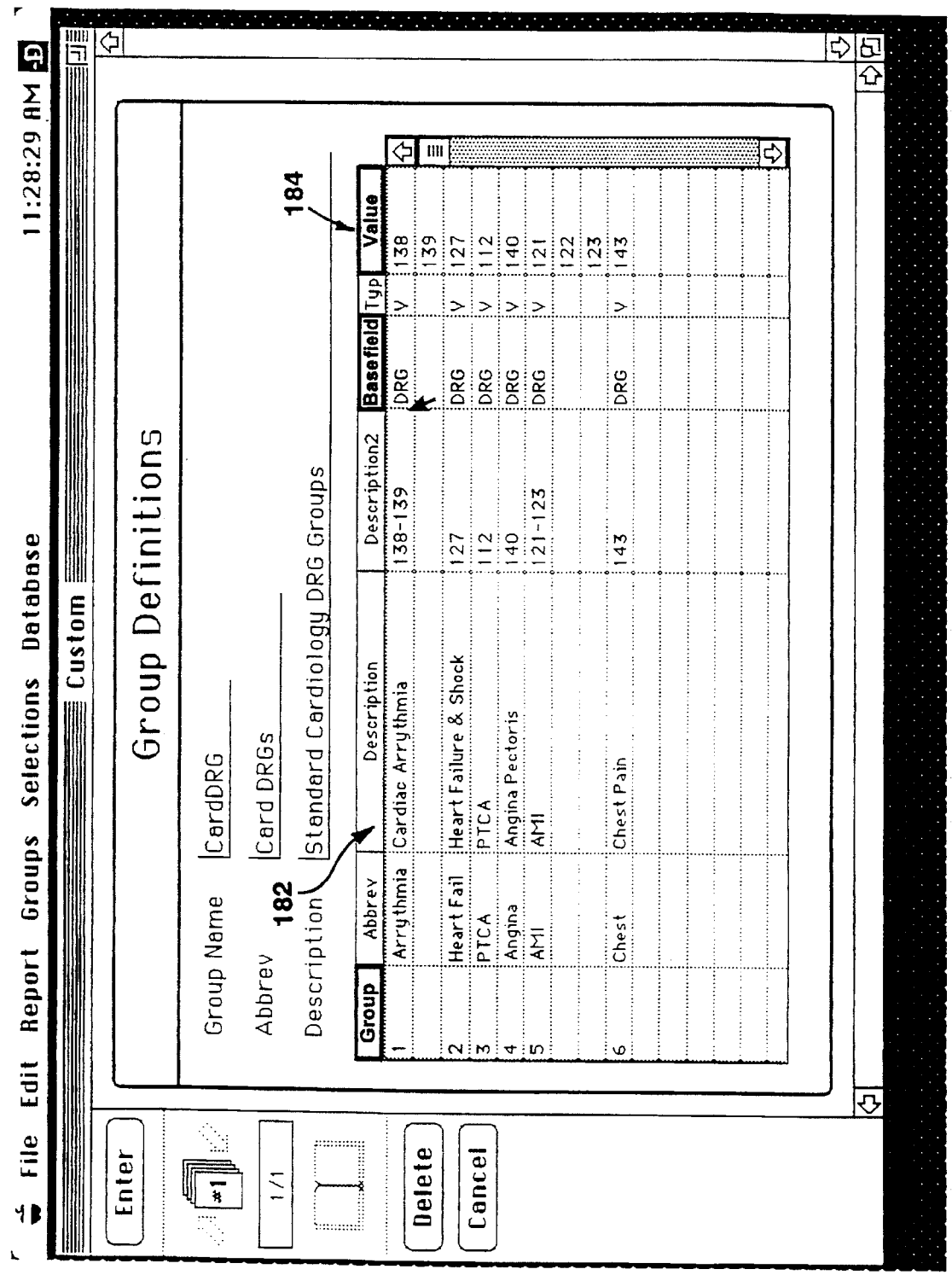
Figure 8C:
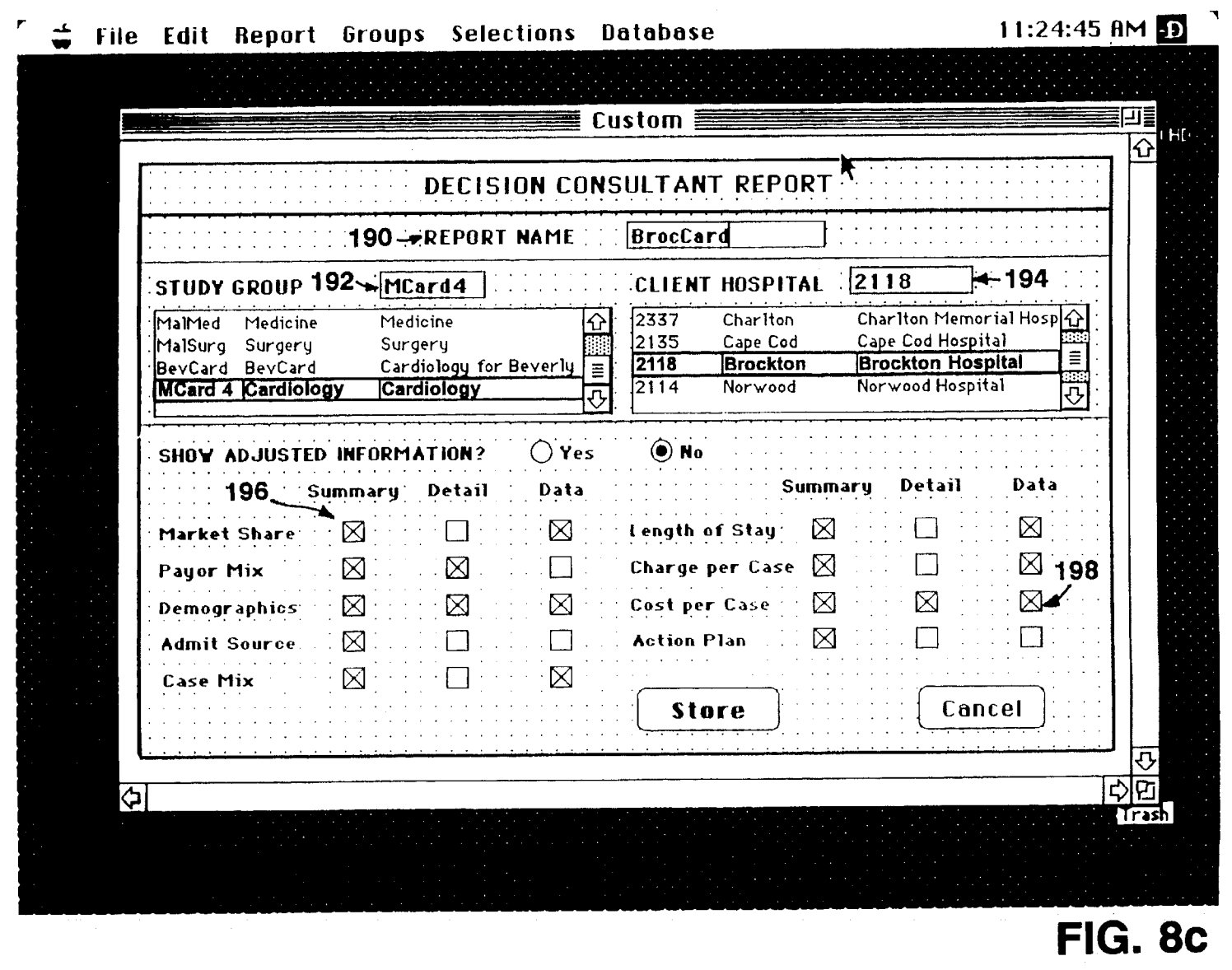
Figure 12:
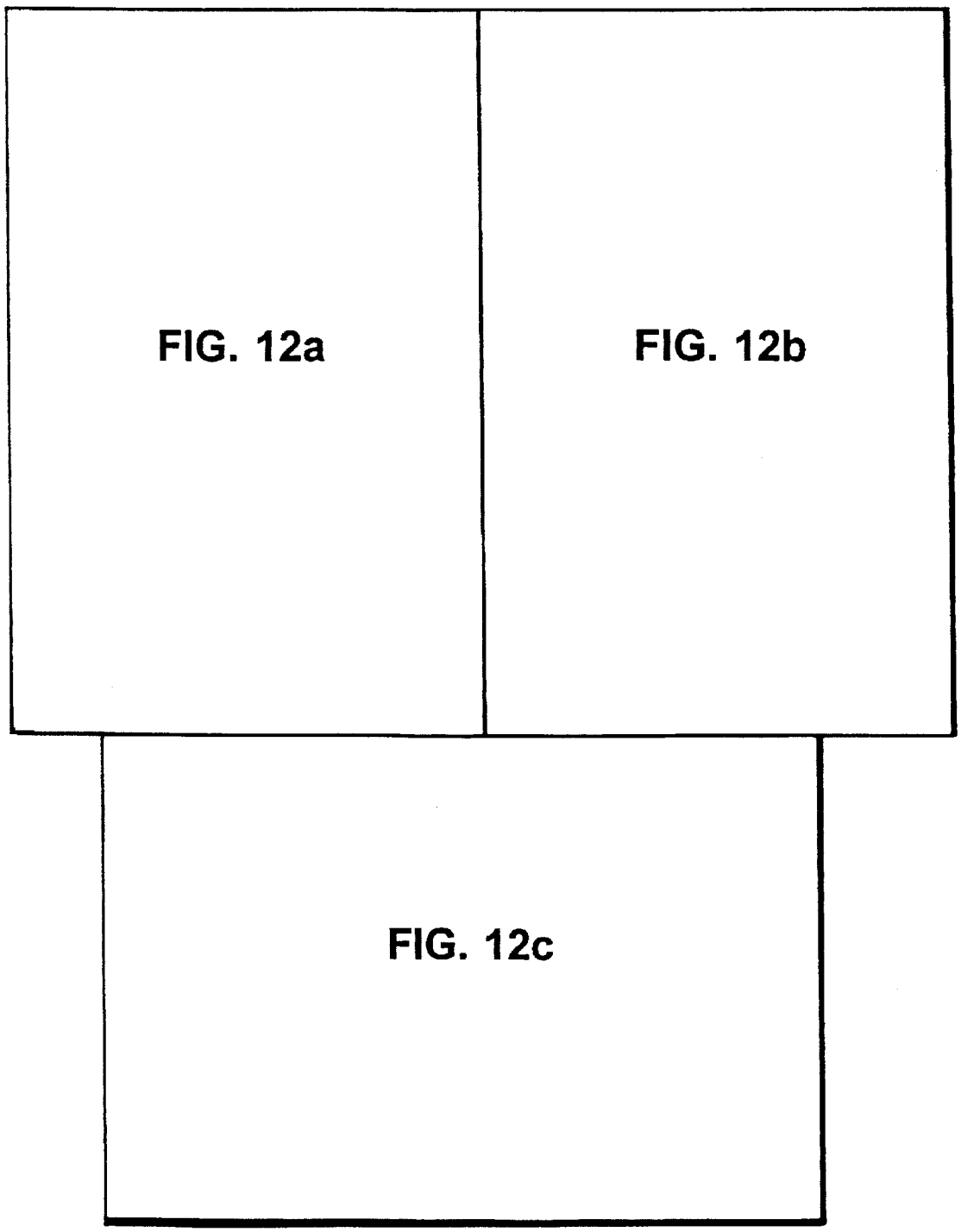
FIG. 12 is a key to FIGS. 12a–12d.
Figure 12A:
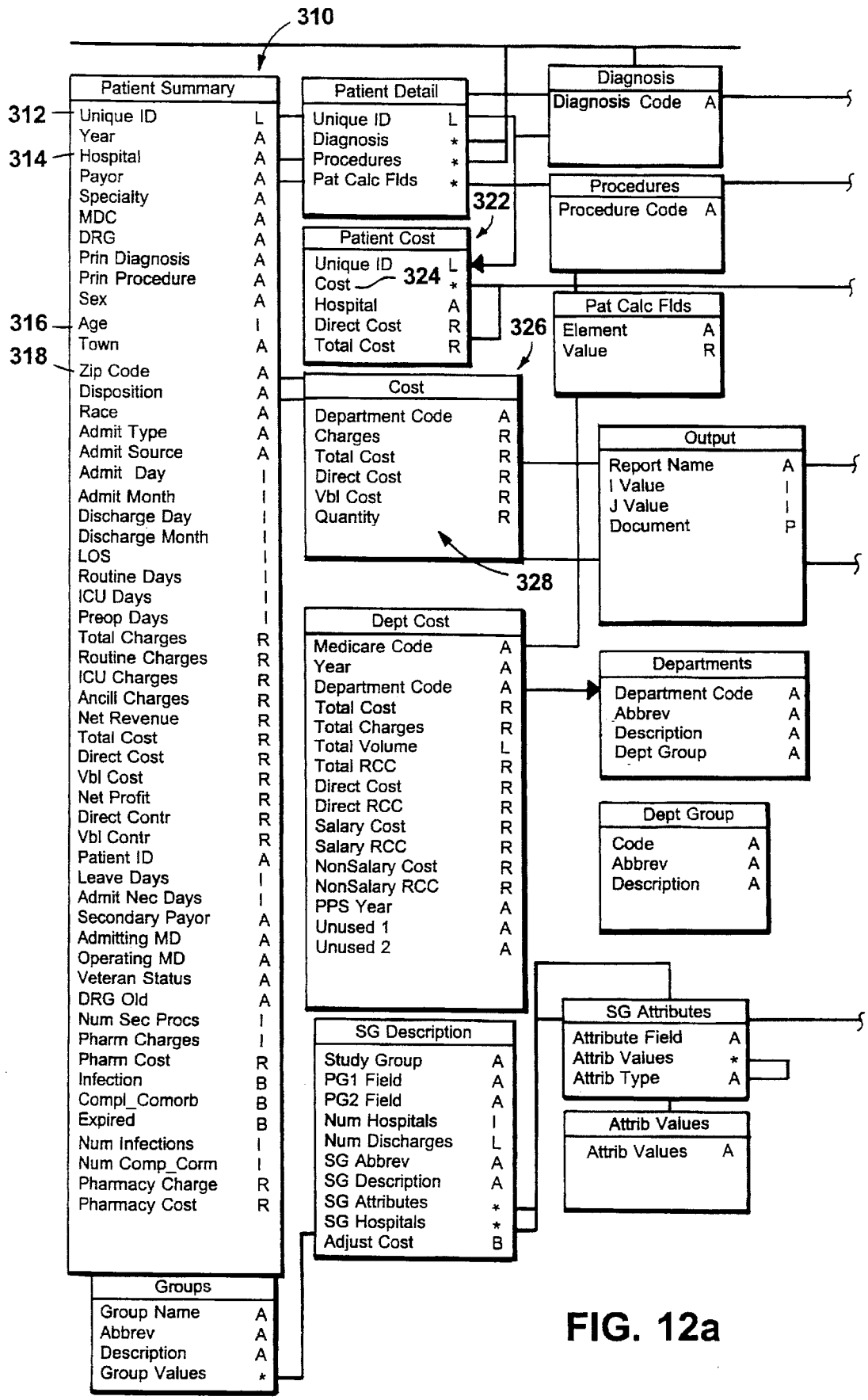
FIGS. 12a–12d are components of a database structure diagram.
Figure 12B:
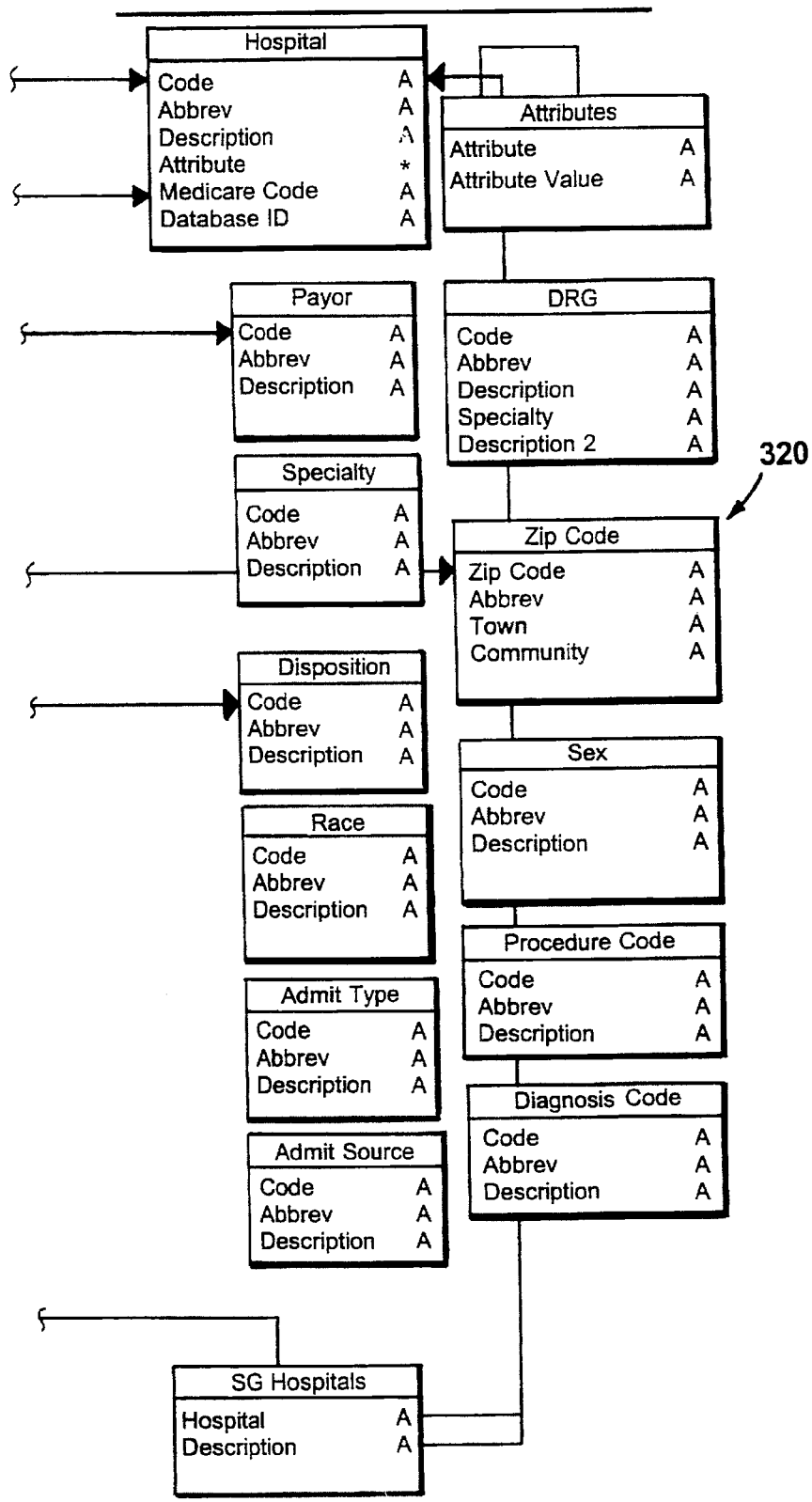
Figure 12C:
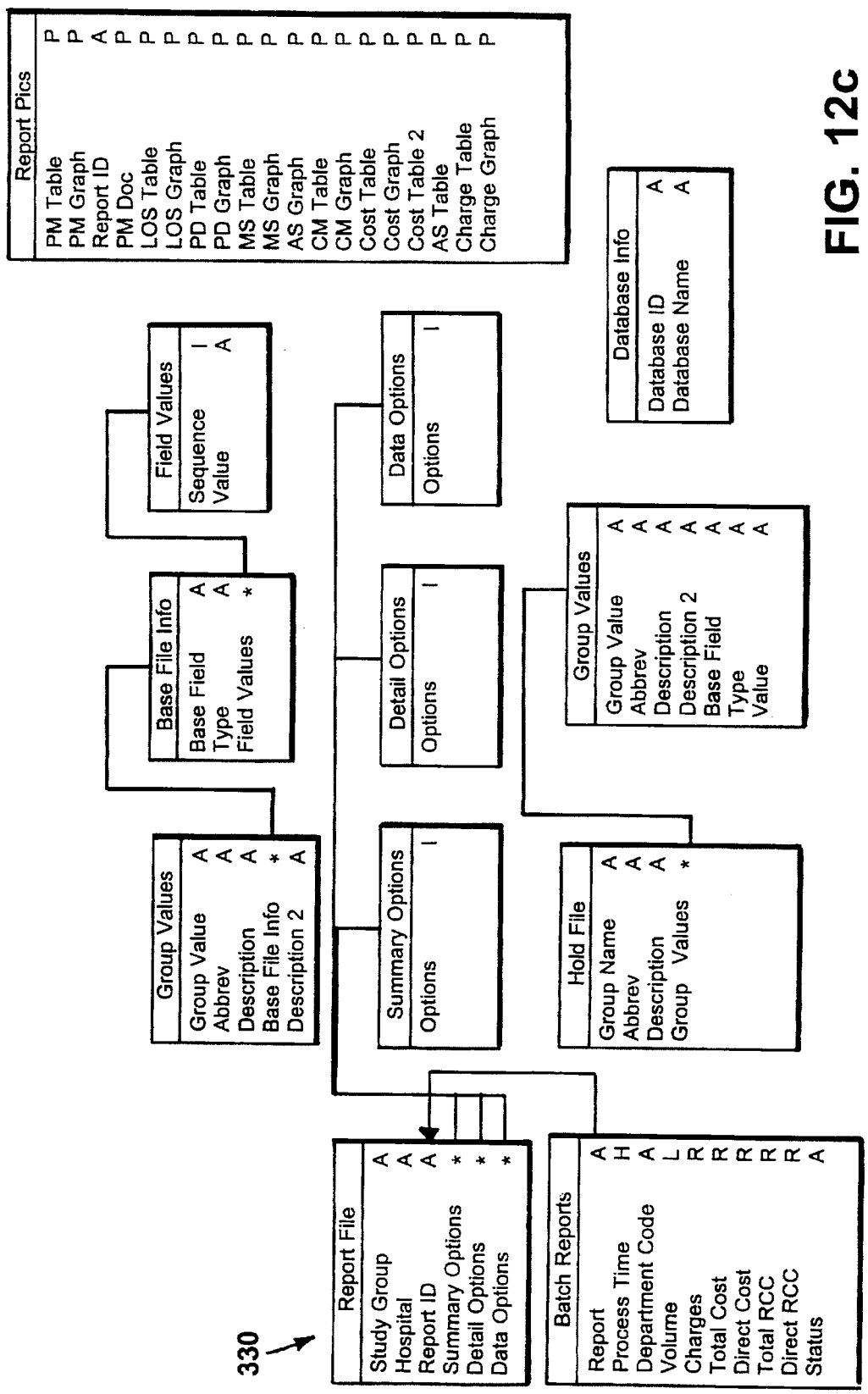
Figure 12D:
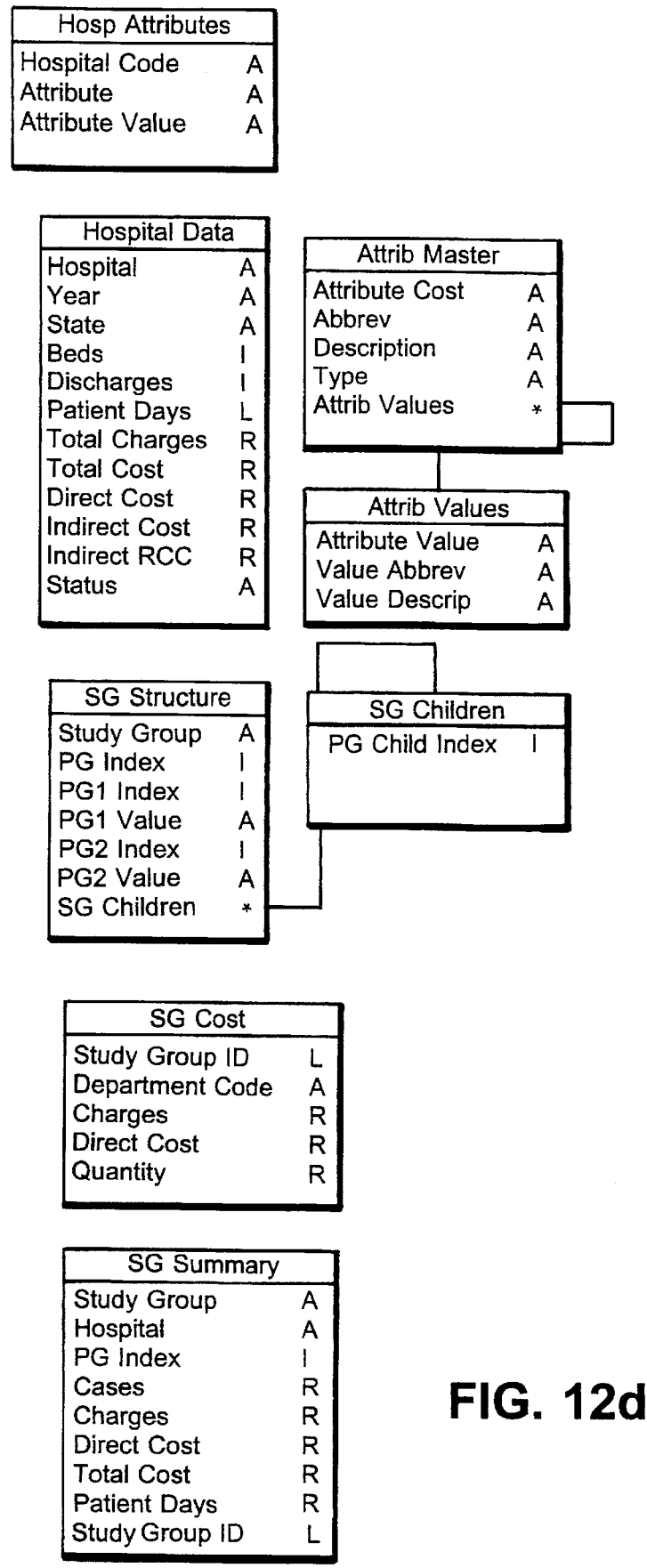

In FIGS. 8A–8C, the report request parameters 18 for a comparison report of a so-called "MCard4" study group are entered 152 into an Apple Macintosh computer. This report compares only the cardiology-related DRGs within the hospitals selected by the user. In this example, the user enters 154 the report name 170 and a description 172 of the patient group to be compared. Any special patient groupings are then defined 156 by the user. In this example, patients are grouped according to a user-defined "CardDRG" grouping, which will be described in more detail below. The user then enters 158 the selected patient group into a patient group display field 174. The patent group display field 174 determines which patients will be displayed in the report.

The case mix or severity field 176 by which comparison data is adjusted (Mix Adjustment Field) is then entered 160. The user then enters 162 a patient selection field 178 which determines the broad group of patients to be included in the comparison data. Finally, the user enters 164 the names and/or identification codes 180 of the hospitals to be included in the comparison report. Included in the hospital selection list is the client hospital requesting the report (Brockton Hospital).

In FIG. 8B, the "CardDRG" patient group display field 174 of FIG. 8A is created by the user. This custom patient group creates a comparison of the standard cardiology DRGs of the selected hospitals. To create the "CardDRG" group, the user selects the specific DRGs to be included in the group and enters the appropriate DRG descriptions 182 and ID values 184. The DRG descriptions and values are listed in Table III below. As will be described in more detail below, the "MCard4" report is generated by combining and comparing cost, charge, and demographic information for every patient of the user-selected cardiology DRGs for each of the selected hospitals.

In FIG. 8C, the user enters 166 the report organization instructions. To do so, the user assigns a name 190 to the report, selects the study group 192 to be included (as discussed with reference to FIG. 8A above), and selects the client hospital 194, from whose perspective the report will be generated. The user then selects the amount and type of comparison data 196 to be included in the generated report. For example, one section of the report compares the cost per cardiology case 198 for each hospital, providing a summary of the results, a detailed analysis of the results, and the data from which the results were determined. The "MCard4" report is described in detail hereinafter, with focus on the "Cost per Case" section.

Figure 9:
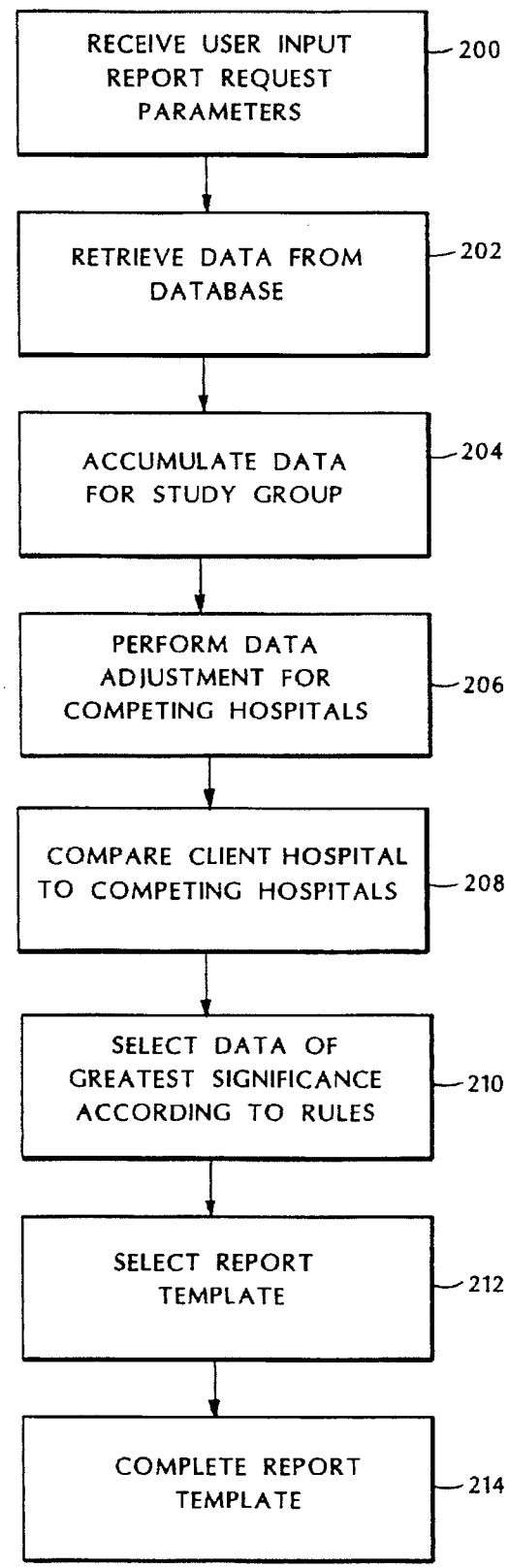
FIG. 9 is a flow diagram of the report generation process.

Referring to FIG. 9, the report request parameters input 200 by the user are used to create the requested report. These report request parameters allow the system to retrieve 202 only the information requested by the user. Once the appropriate information has been retrieved from the database, patient level information is accumulated 204 for each hospital as summary data. In Table IV, summary data, including total cases, total patient age, total days, routine days, ICU days, and total charges, is shown for the "MCard4" study group for each selected hospital, including the client hospital. For example, Table IV shows that St. Luke's Hospital of New Bedford charged a total of $1,074,529 for 64 cases in DRG 116.

In addition to summary data, detailed cost and charge information is accumulated 204 for the patient group. This detailed information may, for example, show total charge by charge category for the patient group in each hospital. Table V shows total cost information for the "MCard4" patient group broken down into the forty-two charge categories defined by the state of Massachusetts. For example, Table V shows that within DRG 127, Cape Cod Hospital charged $104,634 for medical/surgical supplies.

Tables IV and V indicate the vast amount of information that the user may request from the database. Table V, in particular, shows the power of combining patient level charge information acquired from the state with hospital cost information provided by the HCFA. The healthcare reports, however, are not limited to the detail provided in Tables IV and V. Instead, an important feature of the invention is its ability to accumulate and compare data according to almost any combination of factors chosen by the user.

Once the summary and detailed data is accumulated, the data for each of the selected hospitals is adjusted 206 for direct comparison with the data for the client hospital. In performing a mix adjustment of competing hospital data, consideration is given to what the cost, length of stay, and charges would be for the competing hospitals if the competing hospitals treated the exact same mix of patients (or treated the same severity levels) as the client hospital. Therefore, the client hospital's case mix is assigned to the competing hospitals, and the competing hospital data is adjusted accordingly. The client hospital's data, however, is unaffected by mix adjustment.

Referring to FIG. 10, in a simple example of case mix adjustment, the total number of cases and cost per case for six DRGs (A–F) are shown for "Your" hospital (in column C1) and an "Other" hospital (in column C2). Line 215 shows that for Your hospital there are 4,000 total cases at $2,500 per case, while at the Other hospital there are 3,500 cases for $2,400 per case. In view of these values, it appears that the Other hospital controls its costs better than Your hospital. However, in column C3 the Other hospital's cases are adjusted to reflect the case mix of Your hospital, while the cost per case in each DRG is held constant. After the adjustment in column C3, line 215 shows that when the Other hospital treats the same 4,000 cases as Your hospital, its cost per case rises to $2,950, or $550 greater than the cost per case of Your hospital. The adjustment in column C3 provides a more accurate comparison and reveals that Your hospital's cost is actually lower than the Other hospital's cost.

Column C2 shows that the Other hospital had no cases in DRG "E". As a result, DRG "E" has no cost per case. When this situation occurs, the cost per case for Your hospital is assigned to the Other hospital during adjustment. Therefore, in column C3, the adjusted data for the Other hospital includes 400 cases for DRG "E" at $2,000 per case. Adjusting the data in this manner prevents skewing of the overall cost per case for the Other hospital.

Table IV shows the adjusted summary data for the "Cost per Case" section of the "MCard4" report. Brockton Hospital, whose summary data appears in Table IV, is the client hospital, so each competing hospital is assigned Brockton's case mix during adjustment. Therefore, each DRG under one hospital has the same number of cases as the same DRG under every other hospital. The remaining data fields (age, charges, etc.) are adjusted for each competing hospital by multiplying the average per case from the unadjusted summary data (Table V) by the adjusted number of cases. Similarly, the total costs, direct costs, and total charges for each of the forty-two state-defined charge categories within each hospital are calculated from the adjusted data. Table VII shows the adjusted charge and cost data in each of the forty-two categories for each of the selected hospitals.

In the "MCard4" example of Tables IV through VII, a user-selected group of cardiology DRGs serves as the basis for mix adjustment. However, while DRGs or refined DRGs are typically selected as the basis for adjustment, the invention is not limited to the use of these groups. Instead, the user may select any field or user-defined group. For example, mix adjustment may be performed according to fields such as patient age, payor, length of stay, principal diagnosis, or discharge status, as well as many other fields contained in the database. In addition, a combination of fields may be used as the basis for adjustment. As described above, the mix adjustment field is determined by the report request parameters entered by the user.

Referring again to FIG. 9, after the data for the competing hospitals has been adjusted, the data for all of the hospitals is analyzed and compared. For the "Cost per Case" section of the "MCard4" report, the total number of cardiology cases is determined from Table VI, and the total cost (not shown) is determined. The cost per cardiology case is then calculated for each hospital, and the cost per case for the client hospital is compared 208 to the adjusted cost per case of each of the other hospitals. During the comparison, internal rules 28 (FIG. 1) cause the system to look 210 for results which may be of particular interest to the client hospital. For example, in the "MCard4" report, if the client hospital's cost per case is less than 110% of the average adjusted cost per case of the competing hospitals, the comparison focuses on the differences between the client hospital and the hospital with the lowest adjusted cost per case. This special comparison allows the report to display the client hospital's performance with respect to the average competitors, while at the same time focusing on the changes necessary to compete more effectively with the highest performing competitor.

The internal rules determine information of particular interest in each of the report sections described above. Other examples of information gathered according to the internal rules are as follows: comparing the proportion of revenues paid by each of the client hospital's top three payors to the average proportion paid by the same three payors at all of the compared hospitals (see FIG. 13A); comparing the proportion of minority patients at the client hospital to the average proportion of minority patients (see FIG. 13B); comparing the proportion of the client hospital's patients admitted through its primary admission source to the average proportion of patients admitted through the same source (see FIG. 13C). Many areas of particular interest are determined according to the internal rules and reported to the user, most of which are clearly presented in the final report, an example of which is described below with respect to FIGS. 13A through 13F.

Once comparison of the hospital is complete, a report template for the "Cost per Case" section is selected 212. The template is then completed 214 by inserting text, graphs, and charts according to the comparison results.

Referring to FIGS. 11A through 11C, the "Cost per Case" report section is generated by inserting the appropriate information into the report template. First, the abbreviation of the client hospital's name (Brockton) is inserted at 221. The description of the comparison group (cardiology) is inserted at 222, and the average total cost per case for the client hospital ($4,385) is inserted at 223. The system then inserts the number of competing hospitals (seven) at 224 and the average total cost per case of the competing hospitals ($4,119) at 225. The dollar difference ($266) and percentage difference (6% lower) between the average total cost per case for the competing hospitals and the total cost per case for the client hospital are determined and inserted at 225 and 226, respectively. The name of the client hospital (Brockton Hospital) and the abbreviation of the client's name (Brockton) are inserted at 228 and 229.

The relative rank of the client hospital's total cost per case in relation to the average total cost per case of the competing hospitals is then determined. This rank is used to report information of special interest to the client hospital according to the internal rules 28 (FIG. 1), as described above. If the client hospital has the lowest total cost per case (ranked first), the phrase "lowest total cost per case, followed by X with Y" is inserted at 231. The name of the second ranking hospital replaces "X", and the total cost per case of the second ranking hospital replaces "Y". If the client hospital has the highest total cost per case, the phrase "highest total cost per case" is inserted at 231. If the client hospital's total cost per case is greater than the competitor average, but not the highest, the rank of the client hospital's total cost per case is inserted at 231, followed by the phrase "highest total cost per case." If the client hospital's total cost per case is less than or equal to the competitor's average, but is not the lowest, the rank of the client hospital's total cost per case is inserted at 231, followed by the phrase "lowest total cost per case." For all of the above situations, except where the client hospital is ranked first, the phrase "X had the lowest total cost with Y dollars" is inserted after the last phrase at 231. In this case, the abbreviation of the name of the first ranked hospital replaces "X" and the first ranked hospital's total cost per case replaces "Y". At 233, the description of the client hospital (Brockton Hospital) is inserted.

A cost table depicting the comparison between the hospitals is inserted at 234. The cost table is created by inserting the adjusted data into five columns of a preformatted spreadsheet. The abbreviations of the names of the hospitals are inserted in column 1, with the client hospital inserted into the first row. The phrase "average excluding Z", where "Z" is replaced by the abbreviation of the name of the client hospital, is inserted into the last row. The adjusted total cost per case for each hospital is then inserted into column 2. An average of these values, excluding the client hospital, is placed in the final row. In column 3, the percentage difference between each competing hospital's total cost per case and the client hospital's total cost per case is inserted. In the last row, the percentage difference between the average total cost per case and the client hospital's total cost per case is inserted. Columns 4 and 5 are similar to columns 2 and 3, except that direct cost per case and percentage difference of direct cost per case are inserted. When the cost graph is complete, the graph is stored as a picture in the "Report Pics" file 332 (FIG. 12C) in the database.

At 235, the abbreviation of the name of the client hospital is inserted. The system then inserts at 236 a column chart which shows the adjusted total cost per case for several cardiology department groups for each hospital. The cardiology department groups are defined by the user during entry of the report request parameters. The data for the client hospital is placed in the first column of the chart, and the column chart is stored as a picture in the "Report Pics" file.

The abbreviation of the name of the client hospital is inserted at 237. The difference between the total cost per case of the client hospital and the total cost per case of the highest (first) ranking hospital (or second ranking if the client is highest ranking) is inserted at 238. If the client hospital is the highest ranking hospital, the difference inserted at 238 is followed by the word "lower"; otherwise the difference is followed by the word "higher". This word is then followed by the phrase "total cost per case than the lowest cost competitor X and", where the name of the lowest cost competitor replaces "X". The difference between the total cost per case of the client hospital and the average total cost per case for the competing hospitals is inserted along with the word "higher" or "lower", depending on this difference value. The phrase "total cost per case than the competitor's average" is then inserted as the last phrase at 238.

The system then inserts another cost table at 239. The cost table compares the total cost per case for the client hospital to the adjusted total cost per case for the lowest ranking hospital in each of the user defined department groups. The table also compares total cost per case for the client hospital to the average cost per case of all of the competing hospitals in the user-defined department groups. The completed cost graph is stored in the database file "Report Pics".

At 240, a phrase is inserted indicating in which user-defined department groups Brockton's total cost exceeds the total cost of the lowest cost competitor by more than $100. No more than two department groups are listed. At 241 a phrase is inserted which indicates in which department groups Brockton's total cost is lower than the total cost of the lowest cost competitor by more than $100. The phrase "significantly above" is used when Brockton's costs exceed the competitor's by more than $100, and the phrase "significantly lower" is used when Brockton's costs are lower than the competitors by more than $100.

Referring to FIGS. 13A through 13F, the printed report may, in one embodiment, look as follows.

Executive Summary

Central Caribbean Medical Center treated 1,328 Cardiology patients in 1992. This volume compared with 1,601 cases for St. Thomas Hospital, 1,743 cases for Aruba Hospital, 1,553 cases for Martinique Hospital, 2,250 cases for St. John Hospital, 1862 cases for St. Bart's Hospital, and 1,271 cases for St. Croix Hospital.

Medicare dominated the Cardiology payor mix at Central Caribbean medical Center with 66.7% of the patients, followed by Blue Cross with 13.0%, and HMO with 7.2%. Central Caribbean Medical Center had the second highest proportion of Medicare for Cardiology patients, had an average percentage of Blue Cross patients, and had a below average share of HMO patients compared with the hospitals in the group.

Central Caribbean Medical Center's Cardiology patients were about the same age as the average of its competitors (69.5 years compared to 68.6 years). The largest source of admissions for Central Caribbean Medical Center's Cardiology patients was emergency room (75% of patients), followed by physician referral (20%) and unknown (4%). Central Caribbean had an above average proportion of emergency room for Cardiology patients compared to the other hospitals in the group, and had an average percentage of physician referral patients.

The top five Cardiology patient groups for Central Caribbean Medical Center accounted for 1,066 or 80% of the hospital's total Cardiology cases. These groups were Angina Pectoris (23%), Heart Failure & Shock (20%), AMI (18%), Cardiac Arrhythmia (12%), and Chest Pain (7%).

Central Caribbean Medical Center's average length of stay per Cardiology case was 6.8 days, 0.1 days or 1% lower than the case mix adjusted average of its six major competitors of 6.9 days. St. Bart's Hospital had the lowest length of stay of 5.6 days, 1.2 days of 18% lower than Central Caribbean's.

Central Caribbean's average total cost per Cardiology case was $5,240. The case mix adjusted average of its six major competitors was $4,633–$608 or 12% lower than Central Caribbean Medical Center. Central Caribbean had the highest cost per case. St. Thomas Hospital had the lowest cost with $4,099. When examining major cost components, the key area of lower total cost for Central Caribbean was EKG/EEG. Central Caribbean's total cost for routine care, laboratory/cath, radiology, and other services were significantly above St. Thomas Hospital's costs.

For additional cost savings, Central Caribbean should consider ways to reduce Routine Care, Laboratory/Cath, Radiology, and Other Services costs for Cardiology cases to the cost of St. Thomas Hospital and to emulate the length of stay achieved by St. Bart's Hospital. Such actions have the potential to save Central Caribbean Medical Center $609,123 to $1,015,206 a year—$192,018 to $320,029 related to ancillary services and $417,106 to $695,176 related to length of stay reductions.

Payor Mix

Medicare dominated the Cardiology payor mix at Central Caribbean Medical Center with 66.7% of the patients, followed by Blue Cross with 13.0%, and HMO with 7.2%. Central Caribbean's payor mix as compared with the Cardiology payor mix for all hospitals in the comparison group was as shown in Table VIII.

Figure 13A:
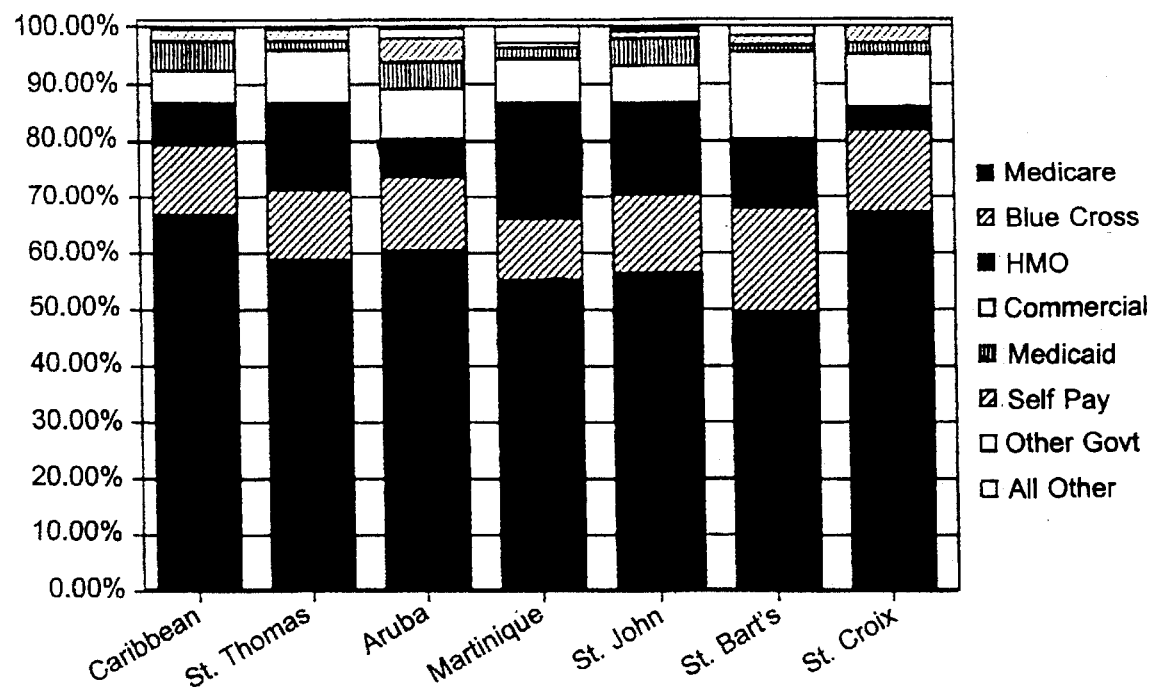
FIGS. 13A through 13F are bar graphs included in a report.

FIG. 13A compares the Cardiology payor mix for Central Caribbean Medical Center with that of its primary Cardiology competitors.

Central Caribbean Medical Center had the second highest proportion of Medicare for Cardiology patients, had an average percentage of Blue Cross patients, and had a below average share of HMO patients compared with the hospitals in the group.

Patent Demographics

As shown in Table IX, Central Caribbean Medical Center's Cardiology patients were about the same age as the average of its competitors (69.5 years compared to 68.6 years). Males represented a lower proportion of Cardiology (47% versus 52%), while minorities mad up an average share of patients compared to the competitor average (3.8% versus 3.5%).

Figure 13B:
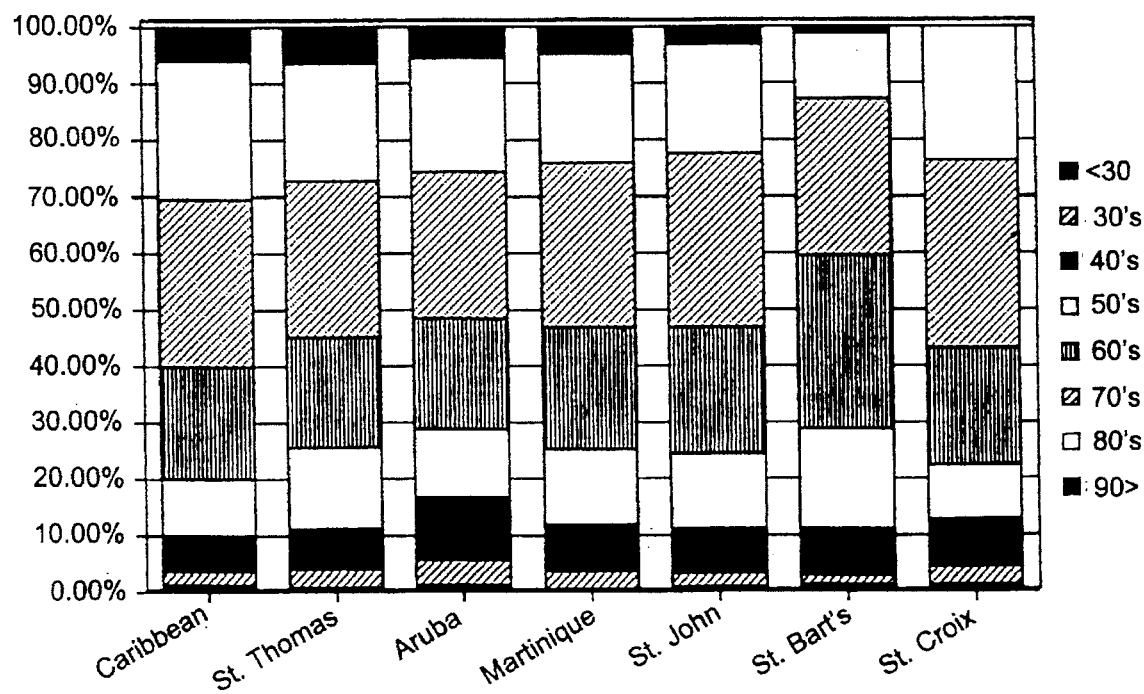

FIG. 13B provides more detail on the age distribution of Central Caribbean's patients compared to its competitors.

Admit Source

Figure 13C:
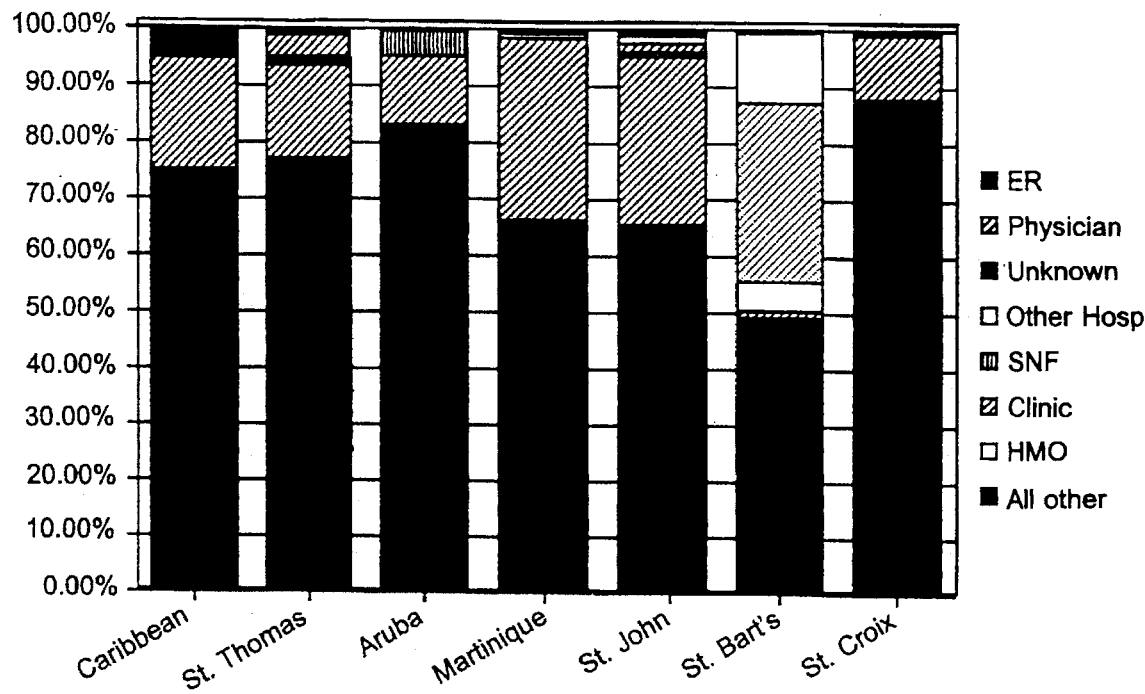

The largest source of admissions for Central Caribbean Medical Center's Cardiology patients was emergency room (75% of patients), followed by physician referral (20%) and unknown (4%). FIG. 13C compares the admit source of Central Caribbean's Cardiology patients with that of its primary competitors.

Emergency Room, the largest source of admissions for Central Caribbean Medical Center, was also the largest source of admissions for all the other hospitals in the group. Central Caribbean had an above average proportion of emergency room for Cardiology patients compared to the other hospitals in the group, and had an average percentage of physician referral patients.

Case Mix

The top five Cardiology patient groups for Central Caribbean Medical Center accounted for 1,066 or 80% of the hospital's total Cardiology cases. These key patient groups were as shown in Table X.

Figure 13D:
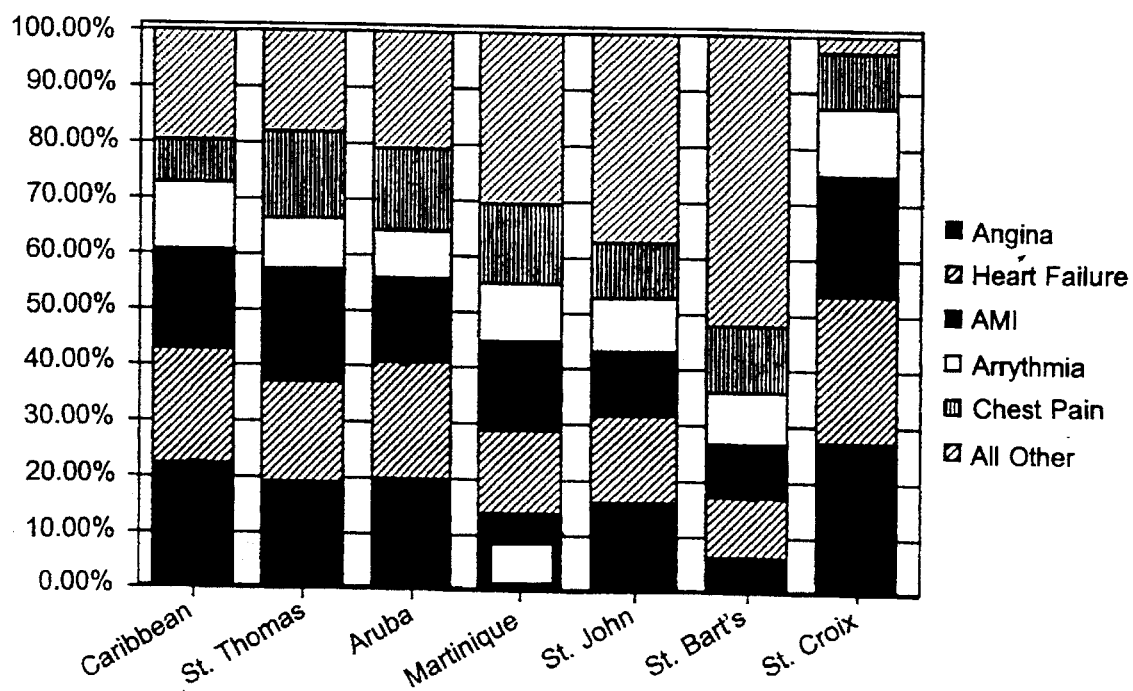

FIG. 13D shows the specialty mix of these Cardiology patient groups for Central Caribbean versus its six main competitors.

Central Caribbean had an above average proportion of angina pectoris cases and an above average proportion of heart failure and shock cases compared with the other six hospitals in the group.

Length of Stay (Case Mix Adjusted)

As shown in Table XI, Central Caribbean Medical Center's average length of stay per Cardiology case was 6.8 days, 0.1 days or 1% lower than the average of its six major competitors of 6.9 days. St. Bart's Hospital had the lowest length of stay of 5.6 days, 1.2 days or 18% lower than Central Caribbean's.

Figure 13E:
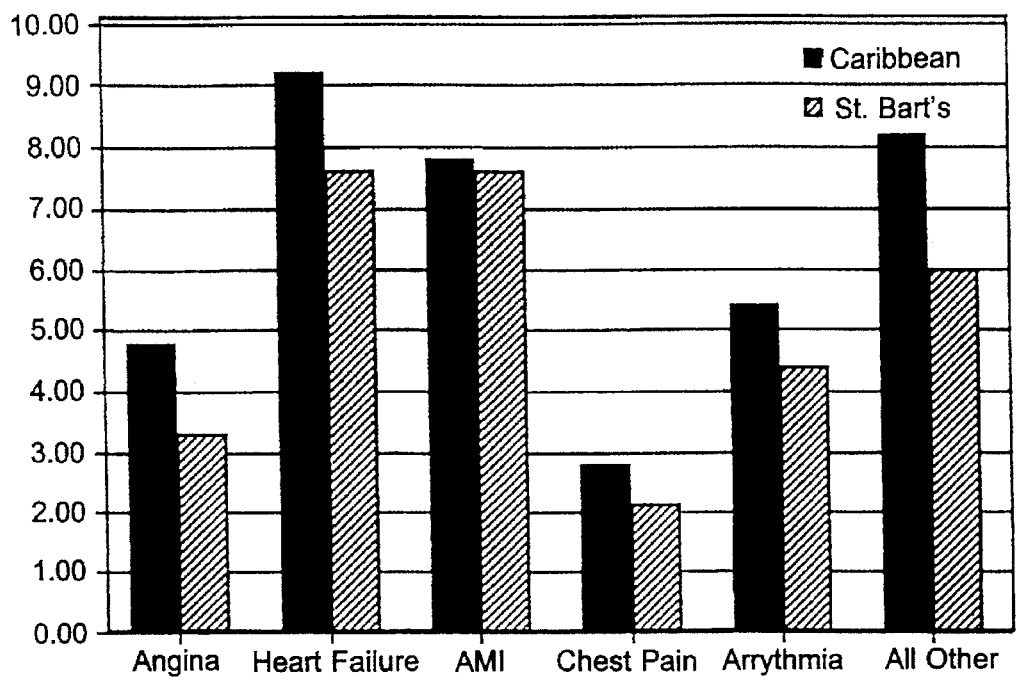

Central Caribbean's length of stay was consistently above St. Bart's LOS across the key patient groups. FIG. 13E shows a comparison of Central Caribbean Medical Center with St. Bart's Hospital.

Cost per Case (Case Mix Adjusted)

Central Caribbean's average total cost per Cardiology case was $5,240. The average of its six major competitors was $4,633–$608 or 12% lower than Central Caribbean Medical Center. Control Caribbean had the highest cost per case. St. Thomas Hospital had the lowest cost with $4,099. Specifically, the cost per case for each hospital as compared to Central Caribbean Medical Center was as shown in Table XII.

Figure 13F:
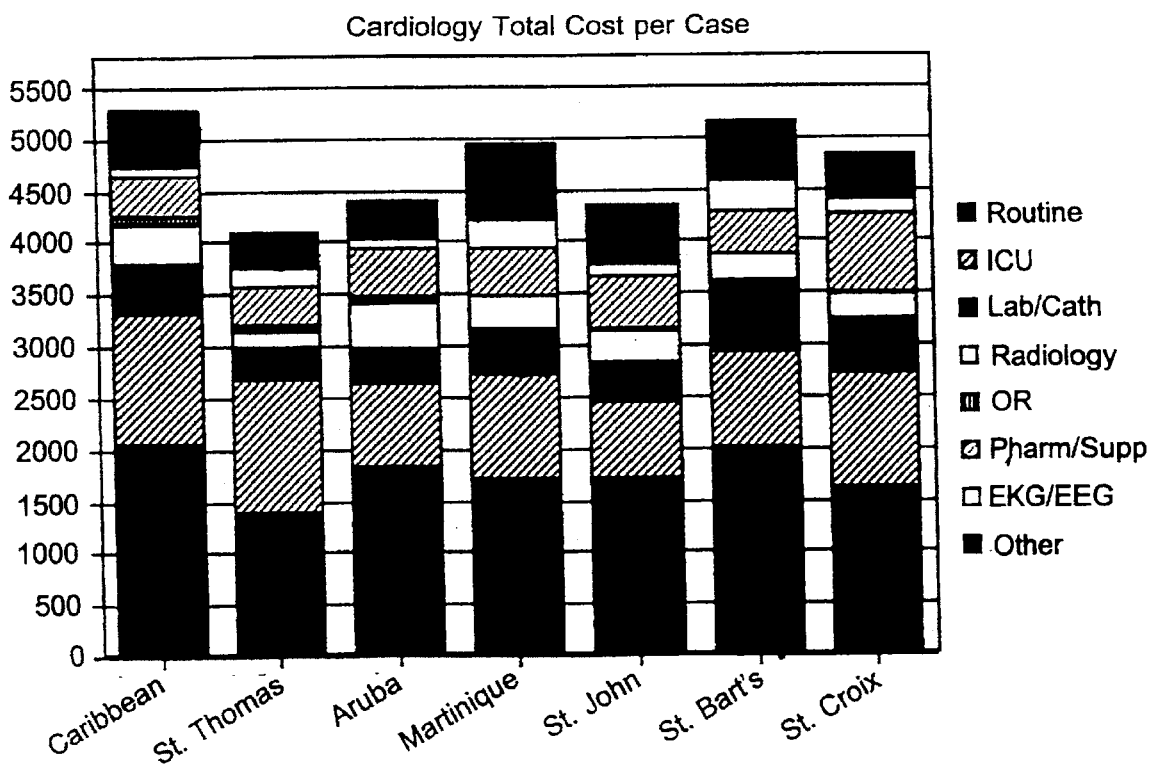

FIG. 13F shows the composition of the cost per case by department group for Central Caribbean and its competitors.

The $1,141 lower cost per case for St. Thomas Hospital compared to Central Caribbean Medical Center was composed of the elements shown in Table XIII.

As shown in Table XIII, the key area of lower total cost for Central Caribbean was EKG/EEG. Central Caribbean's total costs for routine care, laboratory/cath, radiology, and other services were significantly above St. Thomas Hospital's costs.

Opportunity Analysis/Action Plan

Central Caribbean Medical Center spent $806,847 more treating its 1,328 Cardiology cases than if it had performed at the comparative average (1,328 cases * $608 per case). This increased cost was primarily due to its significantly higher Routine Care, Intensive Care, and Radiology costs than its competitors.

For additional cost savings, Central Caribbean should consider ways to reduce Routine Care, Laboratory/Cath, Radiology, and Other Services costs for Cardiology cases to the cost of St. Thomas Hospital and to emulate the length of stay achieved by St. Bart's Hospital. Such actions have the potential to save Central Caribbean Medical Center $609,123 to $1,015,206 a year—$192,108 to $320,029 related to ancillary services and $417,106 to $695,176 related to length of stay reductions.

To achieve the potential savings, Central Caribbean Medical Center should focus on meeting the following goals:

Reduce the average length of stay in the Intensive Care Units from 1.3 days to the 0.8 days of St. Bart's Hospital (savings of $201,662 to $336,104)

Reduce the average length of stay in the Routine Units from 5.5 days to the 4.8 days of St. Bart's Hospital (savings of $81,248 to $135,414)

Reduce Routine Care cost per day by 25% to the cost of St. Thomas Hospital (savings of $134,195 to $223,659)

Reduce Radiology expenditure by 63% to the cost of St. Thomas Hospital (savings of $89,387 to $148,979)

Reduce Laboratory/Cath expenditure by 32% to the cost of St. Thomas Hospital (savings of $50,832 to $84,720)

Reduce Other Services expenditure by 32% to the cost of St. Thomas Hospital (savings of $51,798 to $86,330).

Other embodiments are within the scope of the following claims. For example, the technique could be applied to a comparison of educational institutions, such as colleges or universities, or to any other kind of service organization for which comparable data is available.

TABLE I

FY 1992 (AS FILED) MCR-2552 COST REPORT
KBO & CO. / COSTREP+ MICRO - 2552-92   FILE: YE92   VERSION: 155   1/28/1993   15:25   s3
                                       PROVIDER NO.: 22-0053   PERIOD:
HOSPITAL AND HOSPITAL-HEALTH CARE COMPLEX                      FROM   10/01/91
STATISTICAL DATA                       SYMMES HOSPITAL         TO     9/30/92

| COMPONENT | NO. OF BEDS 1 | BED DAYS AVAILABLE 2 | TITLE V 3 | TITLE XVIII 4 | TITLE XIX 5 | TOTAL ALL PATIENTS 6 |
|---|---|---|---|---|---|---|
| 1.01 HOSPITAL (EXCLUDING SWING BED) | 114 | 41,724 | 0 | 20,368 | 302 | 27,608 |
| 1.02 HOSPITAL - SWING BED SNF | *** | *** | *** | 0 | *** | 0 |
| 1.03 HOSPITAL - SWING BED NF | *** | *** | 0 | *** | 0 | 0 |
| 1.04 HOSPICE | *** | *** | *** | 0 | 0 | 0 |

TABLE I-continued

| | | | | | | | |
|---|---|---|---|---|---|---|---|
| 1.05 | TOTAL ADULTS/PED. (EX. OBS. BEDS) | 114 | 41,724 | 0 | 20,368 | 302 | 27,608 |
| 2 | INTENSIVE CARE UNIT | 8 | 2,928 | 0 | 1,307 | 26 | 1,925 |
| 3 | CORONARY CARE UNIT | 0 | 0 | 0 | 0 | 0 | 0 |
| 4 | BURN INTENSIVE CARE UNIT | 0 | 0 | 0 | 0 | 0 | 0 |
| 5 | SURG INTENSIVE CARE UNIT | 0 | 0 | 0 | 0 | 0 | 0 |
| 6 | | 0 | 0 | 0 | 0 | 0 | 0 |
| 7 | NURSERY | 0 | 0 | 0 | 0 | 0 | 0 |
| 8 | TOTAL HOSPITAL (SUM LINES 1.05–7) | 122 | 44,652 | 0 | 21,675 | 328 | 29,533 |
| 9 | SUBPROVIDER 1 | 0 | 0 | 0 | 0 | 0 | 0 |
| 11 | SKILLED NURSING FACILITY 1 | 0 | 0 | 0 | 0 | 0 | 0 |
| 12 | OTHER NURSING FACILITY 1 | 0 | 0 | 0 | *** | 0 | 0 |
| 13 | OTHER LONG TERM CARE | 0 | 0 | *** | *** | *** | 0 |
| 14.01 | HOME HEALTH AGENCY 2 | *** | *** | *** | *** | *** | *** |
| 15 | CORF | *** | *** | *** | *** | *** | *** |
| 16 | ASC | *** | *** | *** | *** | *** | *** |
| 17 | HOSPICE | 0 | 0 | *** | 0 | 0 | 0 |
| 18 | TOTAL (SUM OF LINES 8–17) | 122 | 44,652 | 0 | 21,675 | 328 | 29,533 |
| 19 | OBSERVATION BED DAYS | *** | *** | *** | *** | *** | 0 |

FY 1992 (AS FILED) MCR-2552 COST REPORT
KBO & CO. / COSTREP+ MICRO - 2552-92  FILE: YE92  VERSION: 155  1/28/1993  15:26  A
RECLASSIFICATION AND ADJUSTMENT  PROVIDER NO.: 22-0053  PERIOD:
OF TRAIL BALANCE OF EXPENSES  FROM  10/01/91
SYMMES HOSPITAL  TO  9/30/92

| COST CENTER DESCRIPTION (OMIT CENTS) | | SALARIES (1) | OTHER (2) | TOTAL (3) | RECLASSI- FICATIONS (4) | RECLASSED TRIAL BALANCE (5) | ADJUST- MENTS (6) | NET EXPENSE FOR ALLOCATION (7) |
|---|---|---|---|---|---|---|---|---|
| | GENERAL SERVICES C.C.'S | *** | *** | *** | *** | *** | *** | *** |
| 0100 | OLD CAPITAL - BLDG + FIX | *** | 1,469,513 | 1,469,513 | 538,577 | 2,008,090 | 0 | 2,008,090 |
| 0200 | OLD CAPITAL - MOV EQUIP | *** | 0 | 0 | 1,047,987 | 1,047,987 | (101,081) | 946,906 |
| 0300 | NEW CAPITAL - BLDG + FIX | *** | 0 | 0 | 11,003 | 11,003 | 0 | 11,003 |
| 0400 | NEW CAPITAL - MOV EQUIP | *** | 0 | 0 | 424,684 | 424,684 | (112,701) | 311,983 |
| 0500 | EMPLOYEE BENEFITS | 159,624 | 2,415,466 | 2,575,090 | 0 | 2,575,090 | 0 | 2,575,090 |
| 0600 | ADMINISTRATIVE + GENERAL | 2,536,338 | 2,536,338 | 5,295,632 | (37,495) | 5,258,137 | (86,045) | 5,172,092 |
| 0700 | MAINTENANCE AND REPAIRS | 205,124 | 234,706 | 439,830 | (57) | 439,773 | 0 | 439,773 |
| 0800 | OPERATION OF PLANT | 153,403 | 524,654 | 678,057 | 0 | 678,057 | (2,809) | 675,248 |
| 0900 | LAUNDRY AND LINEN SERVICE | 15,659 | 179,318 | 194,977 | 0 | 194,977 | 0 | 194,977 |
| 1000 | HOUSEKEEPING | 360,130 | 84,632 | 444,762 | 0 | 444,762 | 0 | 444,762 |
| 1100 | DIETARY | 606,342 | 311,297 | 917,639 | (365,088) | 552,551 | 0 | 552,551 |
| 1200 | CAFETERIA | 0 | 0 | 0 | 361,880 | 361,880 | 0 | 361,880 |
| 1300 | MAINTENANCE OF PERSONNEL | 0 | 0 | 0 | 0 | 0 | 0 | 0 |
| 1400 | NURSING ADMINISTRATION | 294,300 | 25,972 | 320,272 | 0 | 320,272 | 0 | 320,272 |
| 1500 | CENTRAL SERVICES + SUPPLY | 84,419 | 64,872 | 149,291 | 977,577 | 1,126,868 | (4,225) | 1,122,643 |
| 1600 | PHARMACY | 214,147 | 626,143 | 840,290 | 96,311 | 936,601 | (14,580) | 922,021 |
| 1700 | MEDICAL RECORDS + LIBRARY | 328,090 | 125,082 | 453,172 | 0 | 453,172 | (19,509) | 433,663 |
| 1800 | SOCIAL SERVICE | 142,900 | 4,364 | 147,264 | 0 | 147,264 | 0 | 147,264 |
| | | 0 | 0 | 0 | 0 | 0 | 0 | 0 |
| 2000 | NONPHYSICIAN ANESTHETISTS | 0 | 0 | 0 | 0 | 0 | 0 | 0 |
| 2100 | NURSING SCHOOL | 0 | 0 | 0 | 0 | 0 | 0 | 0 |
| 2200 | INTERN-RESIDENT (SALARY) | 0 | 0 | 0 | 0 | 0 | 0 | 0 |
| 2300 | INTERN-RESIDENT (OTHER) | 0 | 0 | 0 | 0 | 0 | 0 | 0 |
| | PARAMEDICAL EDUCATION | 0 | 0 | 0 | 0 | 0 | 0 | 0 |
| | I/P ROUT. SRVC COST CNTRS. | *** | *** | *** | *** | *** | *** | *** |
| 2500 | ADULTS AND PEDIATRICS | 3,612,021 | 867,000 | 4,479,021 | (254,947) | 4,224,074 | (335,633) | 3,888,441 |
| 2600 | INTENSIVE CARE UNIT | 809,374 | 110,007 | 919,381 | (51,483) | 867,898 | 0 | 867,898 |
| 2700 | CORONARY CARE UNIT | 0 | 0 | 0 | 0 | 0 | 0 | 0 |
| 2800 | BURN INTENSIVE CARE UNIT | 0 | 0 | 0 | 0 | 0 | 0 | 0 |
| 2900 | SURG INTENSIVE CARE UNIT | 0 | 0 | 0 | 0 | 0 | 0 | 0 |
| | | 0 | 0 | 0 | 0 | 0 | 0 | 0 |
| | | 0 | 0 | 0 | 0 | 0 | 0 | 0 |
| 3300 | NURSERY | 0 | 0 | 0 | 0 | 0 | 0 | 0 |
| | | 0 | 0 | 0 | 0 | 0 | 0 | 0 |
| | | 0 | 0 | 0 | 0 | 0 | 0 | 0 |
| | | 0 | 0 | 0 | 0 | 0 | 0 | 0 |
| | ANCILLARY SERVICE C.C.'S | *** | *** | *** | *** | *** | *** | *** |
| 3700 | OPERATING ROOM | 731,692 | 1,341,210 | 2,072,902 | (447,636) | 1,625,266 | 0 | 1,625,266 |
| 3800 | RECOVERY ROOM | 297,115 | 39,537 | 336,652 | (13,932) | 322,720 | 0 | 322,720 |
| 3900 | DELIVERY AND LABOR ROOMS | 0 | 0 | 0 | 0 | 0 | 0 | 0 |
| 4000 | ANESTHESIOLOGY | 0 | 88,224 | 88,224 | (74,762) | 13,462 | 0 | 13,462 |
| 4100 | RADIOLOGY - DIAGNOSTIC | 661,900 | 642,348 | 1,304,248 | (65,915) | 1,238,333 | (735) | 1,237,598 |
| 4200 | RADIOLOGY - THERAPEUTIC | 0 | 0 | 0 | 0 | 0 | 0 | 0 |
| 4300 | RADIOISOTOPE | 56,871 | 86,080 | 142,951 | (1,538) | 141,413 | 0 | 141,413 |
| 4400 | LABORATORY | 1,004,169 | 906,714 | 1,910,883 | 75,172 | 1,986,055 | (90,000) | 1,896,055 |
| 4500 | PBP CLINICAL LAB SERVICE | *** | 0 | 0 | 0 | 0 | 0 | 0 |
| 4600 | WHOLE BLOOD AND PRBC'S | 0 | 0 | 0 | 0 | 0 | 0 | 0 |

TABLE I-continued

| | | | | | | | |
|---|---|---|---|---|---|---|---|
| 4700 | BLOOD STORING + PROCESSING | 0 | 0 | 0 | 0 | 0 | 0 | 0 |
| 4800 | INTRAVENOUS THERAPY | 118,163 | 31,404 | 149,567 | (128,650) | 20,917 | 0 | 20,917 |
| 4900 | RESPIRATORY THERAPY | 367,431 | 114,874 | 482,305 | 14,811 | 497,116 | (65,427) | 431,689 |
| 5000 | PHYSICAL THERAPY | 281,361 | 6,277 | 287,638 | (2,043) | 285,595 | (31,842) | 253,753 |
| 5100 | OCCUPATIONAL THERAPY | 20,751 | 3,993 | 24,744 | (2,876) | 21,868 | 0 | 21,868 |
| 5200 | SPEECH PATHOLOGY | 9,746 | 492 | 10,238 | 0 | 10,238 | 0 | 10,238 |
| 5300 | ELECTROCARDIOLOGY | 69,805 | 101,540 | 171,345 | (3,963) | 167,382 | (17,600) | 149,782 |
| 5400 | ELECTROENCEPHALOGRAPHY | 22,816 | 2,776 | 25,592 | (123) | 25,469 | 0 | 25,469 |
| 5500 | MED. SUPPL. CHD. TO PATIENTS | 0 | 0 | 0 | 0 | 0 | 0 | 0 |
| 5600 | DRUGS CHARGED TO PATIENTS | 0 | 0 | 0 | 0 | 0 | 0 | 0 |
| 5700 | RENAL DIALYSIS | 0 | 0 | 0 | 0 | 0 | 0 | 0 |
| 5800 | ASC (NON-DISTINCT PART) | 0 | 0 | 0 | 0 | 0 | 0 | 0 |
| | | 0 | 0 | 0 | 0 | 0 | 0 | 0 |
| | OUTPAT. SERVICE C.C.'S | *** | *** | *** | *** | *** | *** | *** |
| 6000 | CLINIC | 381,083 | 160,268 | 541,351 | (34,262) | 507,089 | (7,713) | 499,376 |
| 6100 | EMERGENCY | 1,168,539 | 340,064 | 1,508,603 | (81,520) | 1,427,083 | (725,920) | 701,163 |
| 6200 | OBSERVATION BEDS (NON-D) | *** | *** | *** | *** | *** | *** | *** |
| 6101 | ADVANCED LIFE SUPPORT | 350,048 | 390,691 | 740,739 | (7,711) | 733,028 | (11,440) | 721,588 |
| | | 0 | 0 | 0 | 0 | 0 | 0 | 0 |
| | OTHER REIMBURSABLE C.C.'S | *** | *** | *** | *** | *** | *** | *** |
| | | 0 | 0 | 0 | 0 | 0 | 0 | 0 |
| 6500 | AMBULANCE SERVICES | 0 | 0 | 0 | 0 | 0 | 0 | 0 |
| 6600 | DURABLE MED. EQUIP.-RENTED | 0 | 0 | 0 | 0 | 0 | 0 | 0 |
| 6700 | DURABLE MED. EQUIP.-SOLD | 0 | 0 | 0 | 0 | 0 | 0 | 0 |
| | | 0 | 0 | 0 | 0 | 0 | 0 | 0 |
| 7000 | INTERN-RESIDENT (NOT APPR) | 0 | 0 | 0 | 0 | 0 | 0 | 0 |

FY 1992 (AS FILED) MCR-2552 COST REPORT
KBO & CO. / COSTREP+ MICRO - 2552-92  FILE: YE92  VERSION: 155  1/28/1993  15:38 C
PROVIDER NO.: 22-0053  PERIOD:
COMPUTATION OF RATIOS OF COSTS TO CHARGES  FROM 10/01/91
SYMMES HOSPITAL  TO 9/30/92

| COST CENTER DESCRIPTION | WKST. 8, PT 1 COL. 27 (1) | RT/PT LIMIT ADJUSTMENT (2) | TOTAL COSTS (3) | RCE DISALLOWANCE (4) | TOTAL COSTS (5) | TOTAL CHARGES (6) |
|---|---|---|---|---|---|---|
| I/P ROUT. SRVC COST. CNTRS. | *** | *** | *** | *** | *** | *** |
| ADULTS AND PEDIATRICS | 10,225,629 | *** | 10,225,629 | 0 | 10,225,629 | 9,431,026 |
| INVENSIVE CARE UNIT | 1,704,674 | *** | 1,704,674 | 0 | 1,704,674 | 1,046,068 |
| CORONARY CARE UNIT | 0 | *** | 0 | 0 | 0 | 0 |
| BURN INTENSIVE CARE UNIT | 0 | *** | 0 | 0 | 0 | 0 |
| SURG INTENSIVE CARE UNIT | 0 | *** | 0 | 0 | 0 | 0 |
| | 0 | *** | 0 | 0 | 0 | 0 |
| | 0 | *** | 0 | 0 | 0 | 0 |
| NURSERY | 0 | *** | 0 | 0 | 0 | 0 |
| | 0 | *** | 0 | 0 | 0 | 0 |
| | 0 | *** | 0 | 0 | 0 | 0 |
| | 0 | *** | 0 | 0 | 0 | 0 |
| ANCILLARY SERVICE C.C.'S | *** | *** | *** | *** | *** | *** |
| OPERATING ROOM | 3,165,571 | *** | 3,165,571 | 0 | 3,165,571 | 6,536,725 |
| RECOVERY ROOM | 622,489 | *** | 622,489 | 0 | 622,489 | 2,145,544 |
| DELIVERY AND LABOR ROOMS | 0 | *** | 0 | 0 | 0 | 0 |
| ANESTHESIOLOGY | 249,139 | *** | 249,139 | 0 | 249,139 | 1,209,934 |
| RADIOLOGY - DIAGNOSTIC | 2,465,401 | *** | 2,465,401 | 0 | 2,465,401 | 6,465,992 |
| RADIOLOGY - THERAPEUTIC | 0 | *** | 0 | 0 | 0 | 0 |
| RADIOISOTOPE | 346,227 | *** | 346,227 | 0 | 346,227 | 849,177 |
| LABORATORY | 3,041,904 | *** | 3,041,904 | 0 | 3,041,904 | 4,582,858 |
| PBP CLINICAL LAB SERVICE | 0 | *** | 0 | 0 | 0 | 0 |
| WHOLE BLOOD AND PRBC'S | 0 | *** | 0 | 0 | 0 | 0 |
| BLOOD STORING + PROCESSING | 0 | *** | 0 | 0 | 0 | 0 |
| INTRAVENOUS THERAPY | 85,909 | *** | 85,909 | 0 | 85,909 | 120,013 |
| RESPIRATORY THERAPY | 784,800 | 0 | 784,800 | 0 | 784,800 | 234,401 |
| PHYSICAL THERAPY | 488,724 | 0 | 488,724 | 0 | 488,724 | 1,128,458 |
| OCCUPATIONAL THERAPY | 51,645 | *** | 51,645 | 0 | 51,645 | 109,970 |
| SPEECH PATHOLOGY | 22,409 | *** | 22,409 | 0 | 22,409 | 46,681 |
| ELECTROCARDIOLOGY | 306,098 | *** | 306,098 | 0 | 306,098 | 1,906,873 |
| ELECTROENCEPHALOGRAPHY | 47,326 | *** | 47,326 | 0 | 47,326 | 48,917 |
| MED. SUPPL. CHD. TO PATIENTS | 717,671 | *** | 717,671 | 0 | 717,671 | 2,185,222 |
| DRUGS CHARGED TO PATIENTS | 999,755 | *** | 999,755 | 0 | 999,755 | 1,105,642 |
| RENAL DIALYSIS | 0 | *** | 0 | 0 | 0 | 0 |
| ASC (NON-DISTINCT PART) | 0 | *** | 0 | 0 | 0 | 0 |
| | 0 | *** | 0 | 0 | 0 | 0 |
| OUTPAT. SERVICE C.C.'S | *** | *** | *** | *** | *** | *** |
| CLINIC | 1,011,380 | *** | 1,011,380 | 0 | 1,011,380 | 237,003 |
| EMERGENCY | 1,597,000 | *** | 1,597,000 | 0 | 1,597,000 | 1,086,739 |
| OBSERVATION BEDS (NON-D) | 0 | *** | 0 | *** | 0 | 0 |
| 01 ADVANCED LIFE SUPPORT | 1,012,834 | *** | 1,012,834 | *** | 1,012,834 | 707,130 |
| | 0 | *** | 0 | 0 | 0 | 0 |
| OTHER REIMBURSABLE C.C.'S | *** | *** | *** | *** | *** | *** |

TABLE I-continued

|  | | | | | | |
|---|---:|---|---:|---:|---:|---:|
| AMBULANCE SERVICES | 0 | *** | 0 | 0 | 0 | 0 |
| DURABLE MED. EQUIP.-RENTED | 0 | *** | 0 | 0 | 0 | 0 |
| DURABLE MED. EQUIP.-SOLD | 0 | *** | 0 | 0 | 0 | 0 |
|  | 0 | *** | 0 | 0 | 0 | 0 |
| SUBTOTAL | 28,946,585 | *** | 28,946,585 | 0 | 28,946,585 | 41,184,373 |
| LESS OBSERVATION BEDS | 0 | *** | 0 | *** | 0 | *** |
| TOTAL | 28,946,585 | *** | 28,946,585 | 0 | 28,946,585 | 41,184,373 |

TABLE II

Structure: Patient Summary

| | | |
|---|---|---|
| Unique ID | Long Integer | Indexed; Unique; Enterable; Modifiable |
| Year | Alpha 2 | Enterable; Modifiable |
| Hospital | Alpha 4 | Indexed; Enterable; Modifiable |
| Payor | Alpha 4 | Indexed; Enterable; Modifiable |
| Specialty | Alpha 2 | Indexed; Enterable; Modifiable |
| MDC | Alpha 2 | Indexed; Enterable; Modifiable |
| DRG | Alpha 3 | Indexed; Enterable; Modifiable |
| Prin Diagnosis | Alpha 5 | Indexed; Enterable; Modifiable |
| Prin Procedure | Alpha 4 | Indexed; Enterable; Modifiable |
| Sex | Alpha 2 | Indexed; Enterable; Modifiable |
| Age | Integer | Indexed; Enterable; Modifiable |
| Town | Alpha 20 | Indexed; Enterable; Modifiable |
| Zip Code | Alpha 5 | Indexed; Enterable; Modifiable |
| Disposition | Alpha 2 | Indexed; Enterable; Modifiable |
| Race | Alpha 2 | Indexed; Enterable; Modifiable |
| Admit Type | Alpha 2 | Enterable; Modifiable |
| Admit Source | Alpha 2 | Indexed; Enterable; Modifiable |
| Admit Day | Integer | Enterable; Modifiable |
| Admit Month | Integer | Enterable; Modifiable |
| Discharge Day | Integer | Enterable; Modifiable |
| Discharge Month | Integer | Enterable; Modifiable |
| LOS | Integer | Indexed; Enterable; Modifiable |
| Routine Days | Integer | Enterable; Modifiable |
| ICU Days | Integer | Enterable; Modifiable |
| Preop Days | Integer | Enterable; Modifiable |
| Total Charges | Real | Enterable; Modifiable |
| Routine Charges | Real | Enterable; Modifiable |
| ICU Charges | Real | Enterable; Modifiable |
| Ancill Charges | Real | Enterable; Modifiable |
| Net Revenue | Real | Enterable; Modifiable |
| Total Cost | Real | Enterable; Modifiable |
| Direct Cost | Real | Enterable; Modifiable |
| Vbl Cost | Real | Enterable; Modifiable |
| Net Profit | Real | Enterable; Modifiable |
| Direct Contr | Real | Enterable; Modifiable |
| Vbl Contr | Real | Enterable; Modifiable |
| Patient ID | Alpha 10 | Enterable; Modifiable |
| Leave Days | Integer | Enterable; Modifiable |
| Admin Nec Days | Integer | Enterable; Modifiable |
| Secondary Payor | Alpha 2 | Enterable; Modifiable |
| Admitting MD | Alpha 2 | Enterable; Modifiable |
| Operating MD | Alpha 2 | Enterable; Modifiable |
| Veteran Status | Alpha 2 | Enterable; Modifiable |
| DRG Old | Alpha 3 | Enterable; Modifiable |
| Num Sec Procs | Integer | Enterable; Modifiable |
| Pharm Charges | Integer | Enterable; Modifiable |
| Pharm Cost | Real | Enterable; Modifiable |
| Infection | Boolean | Enterable; Modifiable |
| Compl_Comorb | Boolean | Enterable; Modifiable |
| Expired | Boolean | Enterable; Modifiable |
| Num Infections | Integer | Enterable; Modifiable |
| Num Comp_Corm | Integer | Enterable; Modifiable |
| Pharmacy Charge | Real | Enterable; Modifiable |
| Pharmacy Cost | Real | Enterable; Modifiable |
| Supplies Charge | Real | Enterable; Modifiable |
| Supplies Cost | Real | Enterable; Modifiable |
| Lab Charge | Real | Enterable; Modifiable |
| Lab Cost | Real | Enterable; Modifiable |
| RGN | Alpha 4 | Enterable; Modifiable |

Structure: Patient Detail

| | | |
|---|---|---|
| Unique ID | Long Integer | Indexed; Unique; Enterable; Modifiable |
| Diagnoses | Subfile | |
| Procedures | Subfile | |
| Pat Calc Flds | Subfile | |

Structure: Diagnoses

| | | |
|---|---|---|
| Diagnosis Code | Alpha 5 | Enterable; Modifiable |

Structure Procedures

| | | |
|---|---|---|
| Procedure Code | Alpha 4 | Enterable; Modifiable |

Structure: Pat Calc Flds

| | | |
|---|---|---|
| Element | Alpha 10 | Mandatory; Enterable; Modifiable |
| Value | Real | Enterable; Modifiable |

Structure: Patient Cost

| | | |
|---|---|---|
| Unique ID | Long Integer | Indexed; Unique; Enterable; Modifiable |
| Cost | Subfile | |
| Hospital | Alpha 4 | Enterable; Modifiable |
| Direct Cost | Real | Enterable; Modifiable |
| Total Cost | Real | Enterable; Modifiable |

Structure: Cost

| | | |
|---|---|---|
| Department Code | Alpha 3 | Enterable; Modifiable |
| Charges | Real | Enterable; Modifiable |
| Total Cost | Real | Enterable; Modifiable |
| Direct Cost | Real | Enterable; Modifiable |
| Vbl Cost | Real | Enterable; Modifiable |
| Quantity | Real | Enterable; Modifiable |

Structure: Dept Cost

| | | |
|---|---|---|
| Medicare Code | Alpha 6 | Indexed; Enterable; Modifiable |
| Year | Alpha 2 | Enterable; Modifiable |
| Department Code | Alpha 3 | Indexed; Enterable; Modifiable |
| Total Cost | Real | Enterable; Modifiable |
| Total Charges | Real | Enterable; Modifiable |
| Total Volume | Long Integer | Enterable; Modifiable |
| Total RCC | Real | Enterable; Modifiable |
| Direct Cost | Real | Enterable; Modifiable |
| Direct RCC | Real | Enterable; Modifiable |
| Salary Cost | Real | Enterable; Modifiable |
| Salary RCC | Real | Enterable; Modifiable |
| NonSalary Cost | Real | Enterable; Modifiable |
| NonSalary RCC | Real | Enterable; Modifiable |
| PPS Year | Alpha 2 | Indexed; Enterable; Modifiable |
| Unused1 | Alpha 2 | Enterable; Modifiable |
| Unused2 | Alpha 2 | Enterable; Modifiable |

Structure: Hospital

| | | |
|---|---|---|
| Code | Alpha 4 | Indexed; Enterable; Modifiable |
| Abbrev | Alpha 12 | Enterable; Modifiable |
| Description | Alpha 40 | Indexed; Enterable; Modifiable |

TABLE II-continued

| | | |
|---|---|---|
| Attributes | Subfile | |
| Medicare Code | Alpha 6 | Indexed; Unique; Enterable; Modifiable |
| Database ID | Alpha 2 | Enterable; Modifiable |

Structure: Attributes

| | | |
|---|---|---|
| Attribute | Alpha 6 | Indexed; Enterable; Modifiable |
| Attribute Value | Alpha 6 | Indexed; Enterable; Modifiable |

Structure: Payor

| | | |
|---|---|---|
| Code | Alpha 2 | Indexed; Unique; Enterable; Modifiable |
| Abbrev | Alpha 10 | Enterable; Modifiable |
| Description | Alpha 30 | Enterable; Modifiable |

Structure: Specialty

| | | |
|---|---|---|
| Code | Alpha 20 | Indexed; Unique; Enterable; Modifiable |
| Abbrev | Alpha 10 | Enterable; Modifiable |
| Description | Alpha 30 | Enterable; Modifiable |

Structure: Disposition

| | | |
|---|---|---|
| Code | Alpha 2 | Indexed; Unique; Enterable; Modifiable |
| Abbrev | Alpha 10 | Enterable; Modifiable |
| Description | Alpha 40 | Enterable; Modifiable |

Structure: Departments

| | | |
|---|---|---|
| Department Code | Alpha 3 | Indexed; Unique; Enterable; Modifiable |
| Abbrev | Alpha 10 | Enterable; Modifiable |
| Description | Alpha 40 | Enterable; Modifiable |
| Dept Group | Alpha 2 | Indexed; Enterable; Modifiable |

Structure: Race

| | | |
|---|---|---|
| Code | Alpha 2 | Indexed; Unique; Enterable; Modifiable |
| Abbrev | Alpha 10 | Enterable; Modifiable |
| Description | Alpha 20 | Enterable; Modifiable |

Structure: Admit Type

| | | |
|---|---|---|
| Code | Alpha 2 | Indexed; Enterable; Modifiable |
| Abbrev | Alpha 10 | Enterable; Modifiable |
| Description | Alpha 30 | Enterable; Modifiable |

Structure: Admit Source

| | | |
|---|---|---|
| Code | Alpha 2 | Indexed; Enterable; Modifiable |
| Abbrev | Alpha 10 | Enterable; Modifiable |
| Description | Alpha 30 | Enterable; Modifiable |

Structure: Procedure Code

| | | |
|---|---|---|
| Code | Alpha 5 | Indexed; Unique; Enterable; Modifiable |
| Abbrev | Alpha 10 | Enterable; Modifiable |
| Description | Alpha 40 | Enterable; Modifiable |
| Infection | Integer | Enterable; Modifiable |
| Compl_Comorb | Integer | Enterable; Modifiable |

Structure: Diagnosis Code

| | | |
|---|---|---|
| Code | Alpha 5 | Indexed; Unique; Enterable; Modifiable |
| Abbrev | Alpha 10 | Enterable; Modifiable |
| Description | Alpha 40 | Enterable; Modifiable |
| Infection | Integer | Enterable; Modifiable |
| Compl_Comorb | Integer | Enterable; Modifiable |

Structure: BatchReports

| | | |
|---|---|---|
| Report | Alpha 20 | Indexed; Enterable; Modifiable |
| Process Time | Time | Enterable; Modifiable |
| Department Code | Alpha 3 | Enterable; Modifiable |
| Volume | Long Integer | Enterable; Modifiable |
| Charges | Real | Enterable; Modifiable |
| Total Cost | Real | Indexed; Enterable; Modifiable |
| Direct Cost | Real | Enterable; Modifiable |
| Total RCC | Real | Enterable; Modifiable |
| Direct RCC | Real | Enterable; Modifiable |
| Status | Alpha 2 | Enterable; Modifiable |

Structure: Hospital Data

| | | |
|---|---|---|
| Hospital | Alpha 4 | Indexed; Mandatory; Enterable; Modifiable |
| Year | Alpha 2 | Indexed; Enterable; Modifiable |
| State | Alpha 2 | Indexed; Enterable; Modifiable |
| Beds | Integer | Enterable; Modifiable |
| Discharges | Integer | Enterable; Modifiable |
| Patient Days | Long Integer | Enterable; Modifiable |
| Total Charges | Real | Enterable; Modifiable |
| Total Cost | Real | Enterable; Modifiable |
| Direct Cost | Real | Enterable; Modifiable |
| Indirect Cost | Real | Enterable; Modifiable |
| Indirect RCC | Real | Enterable; Modifiable |
| Status | Alpha 2 | Indexed; Enterable; Modifiable |

Structure: Hosp Attributes

| | | |
|---|---|---|
| Hospital Code | Alpha 4 | Indexed; Mandatory; Enterable; Modifiable |
| Attribute | Alpha 5 | Indexed; Enterable; Modifiable |
| Attribute Value | Alpha 6 | Indexed; Enterable; Modifiable |

Structure: Attrib Master

| | | |
|---|---|---|
| Attribute Code | Alpha 6 | Indexed; Unique; Enterable; Modifiable |
| Abbrev | Alpha 10 | Enterable; Modifiable |
| Description | Alpha 40 | Enterable; Modifiable |
| Type | Alpha 2 | Indexed; Enterable; Modifiable |
| Attrib Values | Subfile | |

Structure: Attrib Values

| | | |
|---|---|---|
| Attribute Value | Alpha 6 | Indexed; Unique; Enterable; Modifiable |
| Value Abbrev | Alpha 10 | Enterable; Modifiable |
| Value Descrip | Alpha 40 | Enterable; Modifiable |

Structure: SG Summary

| | | |
|---|---|---|
| Study Group | Alpha 6 | Indexed; Mandatory; Enterable; Modifiable |
| Hospital | Alpha 4 | Indexed; Enterable; Modifiable |
| PG Index | Integer | Indexed; Enterable; Modifiable |
| Cases | Real | Enterable; Modifiable |
| Charges | Real | Enterable; Modifiable |
| Direct Cost | Real | Enterable; Modifiable |
| Total Cost | Real | Enterable; Modifiable |
| Patient Days | Real | Enterable; Modifiable |
| Study Group ID | Long Integer | Indexed; Enterable; Modifiable |

Structure: SG Cost

| | | |
|---|---|---|
| Study Group ID | Long Integer | Indexed; Enterable; Modifiable |
| Department Code | Alpha 3 | Indexed; Enterable; Modifiable |
| Charges | Real | Enterable; Modifiable |
| Direct Cost | Real | Enterable; Modifiable |
| Quantity | Real | Enterable; Modifiable |

Structure: SG Structure

| | | |
|---|---|---|
| Study Group | Alpha 6 | Indexed; Enterable; Modifiable |
| PG Index | Integer | Indexed; Enterable; Modifiable |
| PG1 Index | Integer | Indexed; Enterable; Modifiable |
| PG1 Value | Alpha 10 | Indexed; Enterable; Modifiable |
| PG2 Index | Integer | Indexed; Enterable; Modifiable |
| PG2 Value | Alpha 10 | Indexed; Enterable; Modifiable |

TABLE II-continued

| SG Children | Subfile | |
|---|---|---|
| Structure: SG Children | | |
| PG Child Index | Integer | Indexed; Enterable; Modifiable |
| Structure: SG Description | | |
| Study Group | Alpha 10 | Indexed; Mandatory; Enterable; Modifiable |
| PG1 Field | Alpha 20 | Enterable; Modifiable |
| PG2 Field | Alpha 20 | Enterable; Modifiable |
| Num Hospitals | Integer | Enterable; Modifiable |
| Num Discharges | Long Integer | Enterable; Modifiable |
| SG Abbrev | Alpha 15 | Enterable; Modifiable |
| SG Description | Alpha 40 | Enterable; Modifiable |
| SG Attributes | Subfile | |
| SG Hospitals | Subfile | |
| Adjust Cost | Boolean | Enterable; Modifiable |
| Structure: SG Attributes | | |
| Attribute Field | Alpha 20 | Enterable; Modifiable |
| Attrib Values | Subfile | |
| Attrib Type | Alpha 2 | Enterable; Modifiable |
| Structure: Attrib Values | | |
| Attrib Values | Alpha 20 | Enterable; Modifiable |
| Structure: SG Hospitals | | |
| Hospital | Alpha 4 | Indexed; Enterable; Modifiable |
| Description | Alpha 40 | Indexed; Enterable; Modifiable |
| Structure: Report Pics | | |
| PMTable | Picture | Enterable; Modifiable |
| PMGraph | Picture | Enterable; Modifiable |
| Report ID | Alpha 10 | Indexed; Enterable; Modifiable |
| PMDoc | Picture | Enterable; Modifiable |
| LOSTable | Picture | Enterable; Modifiable |
| LOSGraph | Picture | Enterable; Modifiable |
| PDTable | Picture | Enterable; Modifiable |
| PDGraph | Picture | Enterable; Modifiable |
| MSTable | Picture | Enterable; Modifiable |
| MSGraph | Picture | Enterable; Modifiable |
| ASGraph | Picture | Enterable; Modifiable |
| CMTable | Picture | Enterable; Modifiable |
| CMGraph | Picture | Enterable; Modifiable |
| CostTable | Picture | Enterable; Modifiable |
| CostGraph | Picture | Enterable; Modifiable |
| CostTable2 | Picture | Enterable; Modifiable |
| ASTable | Picture | Enterable; Modifiable |
| ChargeTable | Picture | Enterable; Modifiable |
| ChargeGraph | Picture | Enterable; Modifiable |
| Structure: Groups | | |
| Group Name | Alpha 10 | Indexed; Enterable; Modifiable |
| Abbrev | Alpha 15 | Enterable; Modifiable |
| Description | Alpha 40 | Enterable; Modifiable |
| Group Values | Subfile | |
| Description2 | Alpha 30 | Enterable; Modifiable |
| Structure: Group Values | | |
| Group Value | Alpha 6 | Indexed; Enterable; Modifiable |
| Abbrev | Alpha 15 | Enterable; Modifiable |
| Description | Alpha 40 | Indexed; Enterable; Modifiable |
| Base File Info | Subfile | |
| Description2 | Alpha 20 | Enterable; Modifiable |
| Structure: Base File Info | | |
| Base Field | Alpha 20 | Enterable; Modifiable |
| Type | Alpha 2 | Enterable; Modifiable |
| Field Values | Subfile | |
| Structure: Field Values | | |
| Sequence | Integer | Enterable; Modifiable |
| Value | Alpha 10 | Enterable; Modifiable |
| Structure: Report File | | |
| Study Group | Alpha 10 | Choices; Mandatory; Enterable; Modifiable |
| Hospital | Alpha 4 | Choices; Mandatory; Enterable; Modifiable |
| Report ID | Alpha 10 | Indexed; Mandatory; Enterable; Modifiable |
| Summary Options | Subfile | |
| Detail Options | Subfile | |
| Data Options | Subfile | |
| Option11 | Integer | Enterable; Modifiable |
| Option12 | Integer | Enterable; Modifiable |
| Option13 | Integer | Enterable; Modifiable |
| Option21 | Integer | Enterable; Modifiable |
| Option22 | Integer | Enterable; Modifiable |
| Option23 | Integer | Enterable; Modifiable |
| Option31 | Integer | Enterable; Modifiable |
| Option32 | Integer | Enterable; Modifiable |
| Option33 | Integer | Enterable; Modifiable |
| Option41 | Integer | Enterable; Modifiable |
| Option42 | Integer | Enterable; Modifiable |
| Option43 | Integer | Enterable; Modifiable |
| Option51 | Integer | Enterable; Modifiable |
| Option52 | Integer | Enterable; Modifiable |
| Option53 | Integer | Enterable; Modifiable |
| Option61 | Integer | Enterable; Modifiable |
| Option62 | Integer | Enterable; Modifiable |
| Option63 | Integer | Enterable; Modifiable |
| Option71 | Integer | Enterable; Modifiable |
| Option72 | Integer | Enterable; Modifiable |
| Option73 | Integer | Enterable; Modifiable |
| Option81 | Integer | Enterable; Modifiable |
| Option82 | Integer | Enterable; Modifiable |
| Option83 | Integer | Enterable; Modifiable |
| Adjust Info | Boolean | Enterable; Modifiable |
| Option91 | Integer | Enterable; Modifiable |
| Option92 | Integer | Enterable; Modifiable |
| Option93 | Integer | Enterable; Modifiable |
| Structure: Summary Options | | |
| Options | Integer | Enterable; Modifiable |
| Structure: Detail Options | | |
| Options | Integer | Enterable; Modifiable |
| Structure: Data Options | | |
| Options | Integer | Enterable; Modifiable |
| Structure: DRG | | |
| Code | Alpha 3 | Indexed; Enterable; Modifiable |
| Abbrev | Alpha 15 | Enterable; Modifiable |
| Description | Alpha 30 | Enterable; Modifiable |
| Specialty | Alpha 2 | Indexed; Enterable; Modifiable |
| Description2 | Alpha 3 | Enterable; Modifiable |
| Structure: Zip Code | | |
| Zip Code | Alpha 5 | Indexed; Enterable; Modifiable |
| Abbrev | Alpha 20 | Enterable; Modifiable |
| Town | Alpha 20 | Enterable; Modifiable |
| Community | Alpha 20 | Indexed; Enterable; Modifiable |
| Structure: Sex | | |
| Code | Alpha 2 | Indexed; Enterable; Modifiable |
| Abbrev | Alpha 10 | Enterable; Modifiable |
| Description | Alpha 20 | Enterable; Modifiable |

TABLE II-continued

Structure: Dept Group

| Code | Alpha 2 | Indexed; Enterable; Modifiable |
|---|---|---|
| Abbrev | Alpha 10 | Enterable; Modifiable |
| Description | Alpha 40 | Enterable; Modifiable |

Structure: Output

| Report Name | Alpha 20 | Indexed; Enterable; Modifiable |
|---|---|---|
| I Value | Integer | Indexed; Enterable; Modifiable |
| J Value | Integer | Indexed; Enterable; Modifiable |
| Document | Picture | Enterable; Modifiable |

Structure: Hold File

| Group Name | Alpha 10 | Enterable; Modifiable |
|---|---|---|
| Abbrev | Alpha 15 | Enterable; Modifiable |
| Description | Alpha 40 | Enterable; Modifiable |
| Group Values | Subfile | |

Structure: Group Values

| Group Value | Value 6 | Enterable; Modifiable |
|---|---|---|
| Abbrev | Alpha 15 | Enterable; Modifiable |
| Description | Alpha 40 | Enterable; Modifiable |
| Description2 | Alpha 20 | Enterable; Modifiable |
| Base Field | Alpha 20 | Enterable; Modifiable |
| Type | Alpha 2 | Enterable; Modifiable |

| Value | Alpha 10 | Enterable; Modifiable |
|---|---|---|

Structure: Database Info

| Database ID | Alpha 2 | Enterable; Modifiable |
|---|---|---|
| Database Name | Alpha 20 | Enterable; Modifiable |

TABLE III

DRG Descriptions, Average Lengths of Stay, Day Outlier Thresholds and Relative Weights

| DRG No. | Type | Description | | Fiscal 91 Geometric Mean Length of Stay | Fiscal 90 Day Outlier Threshold | Fiscal 91 Day Outlier Threshold | Fiscal 90 Relative Weights | Fiscal 91 Relative Weights | FY 90–91 Charge in Relative Weights |
|---|---|---|---|---|---|---|---|---|---|
| MDC 01-DISEASES & DISORDERS OF THE NERVOUS SYSTEM | | | | | | | | | |
| 1 | Surg | Craniotomy Except Trauma | Age > 17 | 12.9 | 42 | 42 | 3.5670 | 3.3580 | −0.2090 |
| 2 | Surg | Craniotomy for Trauma | Age > 17 | 12.1 | 41 | 41 | 4.1379 | 3.5485 | −0.5894 |
| 3 | Surg | Craniotomy | Age 0–17 | 12.7 | 41 | 42 | 2.8830 | 2.8830 | 0.0000 |
| 4 | Surg | Spinal Procedures | | 10.8 | 40 | 40 | 2.6483 | 2.4532 | −0.1951 |
| 5 | Surg | Extracranial Vascular Procedures | | 5.8 | 34 | 35 | 1.5214 | 1.5246 | 0.0032 |
| 6 | Surg | Carpal Tunnel Release | | 2.0 | 17 | 19 | 0.4709 | 0.4823 | 0.0114 |
| 7 | Surg | Periph & Cran. Nerve & Other Nerv. Sys. Proc. | With C.C. | 11.5 | 41 | 41 | 3.1110 | 2.6823 | −0.4287 |
| 8 | Surg | Periph & Cran. Nerve & Other Nerv. Sys. Proc. | W/O C.C. | 3.0 | 31 | 32 | 0.7355 | 0.7451 | 0.0096 |
| 9 | Med | Spinal Disorders & Injuries | | 6.9 | 35 | 36 | 1.4058 | 1.2229 | −0.1829 |
| 10 | Med | Nervous System Neoplasms | With C.C. | 7.8 | 36 | 37 | 1.2449 | 1.2765 | 0.0316 |
| 11 | Med | Nervous System Neoplasms | W/O C.C. | 4.7 | 33 | 34 | 0.7451 | 0.7771 | 0.0320 |
| 12 | Med | Degenerative Nervous System Disorders | | 6.9 | 35 | 36 | 0.9391 | 0.9256 | −0.0135 |
| 13 | Med | Multiple Sclerosis & Cerebellar Ataxia | | 7.1 | 35 | 36 | 0.8699 | 0.8726 | 0.0027 |
| 14 | Med | Spec Cerebrovascular Disorders Ex TIA | | 7.3 | 35 | 36 | 1.2260 | 1.2212 | −0.0048 |
| 15 | Med | Transient Ischemic Attacks & Precerebral Occ. | | 4.2 | 32 | 33 | 0.6350 | 0.6420 | 0.0070 |
| 16 | Med | Nonspecific Cerebrovascular Disorders | With C.C. | 6.7 | 35 | 36 | 1.0949 | 1.0703 | −0.0246 |
| 17 | Med | Nonspecific Cerebrovascular Disorders | W/O C.C. | 4.4 | 33 | 33 | 0.6452 | 0.6326 | −0.0126 |
| 18 | Med | Cranial & Peripheral Nerve Disorders | With C.C. | 6.0 | 34 | 35 | 0.9640 | 0.8749 | −0.0891 |
| 19 | Med | Cranial & Peripheral Nerve Disorders | W/O C.C. | 3.9 | 32 | 33 | 0.5869 | 0.5629 | −0.0240 |
| 20 | Med | Nerv Sys. Infection Ex. Viral Meningitis | | 8.4 | 36 | 37 | 1.7817 | 1.8683 | 0.0866 |
| 21 | Med | Viral Meningitis | | 7.5 | 36 | 37 | 1.4190 | 1.4439 | 0.0249 |
| 22 | Med | Hypertensive Encephalopathy | | 4.4 | 32 | 33 | 0.6981 | 0.7206 | 0.0225 |
| 23 | Med | Nontraumatic Stupor & Coma | | 4.3 | 32 | 33 | 0.8698 | 0.8322 | −0.0376 |
| 24 | Med | Seizure & Headache | Age > 17 w/C.C. | 5.3 | 33 | 34 | 0.9689 | 0.9602 | −0.0067 |
| 25 | Med | Seizure & Headache | Age > 17 w/o C.C. | 3.5 | 29 | 28 | 0.5270 | 0.5197 | −0.0073 |
| 26 | Med | Seizure & Headache | Age 0–17 | 4.0 | 31 | 33 | 0.7313 | 0.8176 | 0.0863 |
| 27 | Med | Traumatic Stupor & Coma, Coma > 1 Hr. | | 4.3 | 33 | 33 | 1.6124 | 1.3481 | −0.2643 |
| 28 | Med | Traumatic Stupor & Coma, Coma < 1 Hr. | Age > 17 w/C.C. | 5.9 | 34 | 35 | 1.2750 | 1.2060 | −0.0690 |
| 29 | Med | Traumatic Stupor & Coma, Coma < 1 Hr. | Age > 17 w/o C.C. | 3.3 | 31 | 32 | 0.5730 | 0.5674 | −0.0056 |
| 30 | Med | Traumatic Stupor & Coma, Coma < 1 Hr. | Age 0–17 | 2.0 | 17 | 17 | 0.3496 | 0.3496 | 0.0000 |
| 31 | Med | Concussion | Age > 17 w/C.C. | 4.2 | 32 | 33 | 0.7007 | 0.6933 | −0.0074 |
| 32 | Med | Concussion | Age > 17 w/o C.C. | 2.7 | 25 | 25 | 0.4038 | 0.4100 | 0.0062 |

TABLE III-continued

DRG Descriptions, Average Lengths of Stay, Day Outlier Thresholds and Relative Weights

| DRG No. | Type | Description | | Fiscal 91 Geometric Mean Length of Stay | Fiscal 90 Day Outlier Threshold | Fiscal 91 Day Outlier Threshold | Fiscal 90 Relative Weights | Fiscal 91 Relative Weights | FY 90-91 Charge in Relative Weights |
|---|---|---|---|---|---|---|---|---|---|
| 33 | Med | Concussion | Age 0-17 | 1.6 | 9 | 9 | 0.2427 | 0.2427 | 0.0000 |
| 34 | Med | Other Disorders of Nervous System | w/C.C. | 6.0 | 34 | 35 | 1.2069 | 1.1714 | -0.0355 |
| 35 | Med | Other Disorders of Nervous System | w/o C.C. | 3.6 | 32 | 33 | 0.5597 | 0.5464 | -0.0133 |
| MDC 02-DISEASES & DISORDERS OF THE EYE | | | | | | | | | |
| 36 | Surg | Retinal Procedures | | 2.3 | 14 | 13 | 0.6443 | 0.6487 | 0.0044 |
| 37 | Surg | Orbital Procedures | | 2.9 | 31 | 32 | 0.7415 | 0.7431 | 0.0016 |
| 38 | Surg | Primary Iris Procedures | | 2.2 | 16 | 17 | 0.3550 | 0.3614 | 0.0064 |
| 39 | Surg | Lens Procedures w/ or w/o Vitrectomy | | 1.6 | 7 | 8 | 0.4494 | 0.4456 | -0.0038 |
| 40 | Surg | Extraocular Procedures Except Orbit | Age > 17 | 2.0 | 20 | 21 | 0.4762 | 0.4923 | 0.0161 |
| 41 | Surg | Extraocular Procedures Except Orbit | Age 0-17 | 1.6 | 7 | 7 | 0.3613 | 0.3613 | 0.0000 |
| 42 | Surg | Intraccular Proc. Ex. Retina, Iris & Lens | | 2.2 | 16 | 16 | 0.6305 | 0.6202 | -0.0103 |
| 43 | Med | Hyphema | | 4.0 | 24 | 32 | 0.3350 | 0.3867 | 0.0517 |
| 44 | Med | Acute Major Eye Infections | | 5.5 | 33 | 35 | 0.6035 | 0.5879 | -0.0056 |
| 45 | Med | Neurological Eye Disorders | | 3.4 | 30 | 29 | 0.5454 | 0.5650 | 0.0196 |
| 46 | Med | Other Disorders of the Eye | Age > 17 with C.C. | 4.2 | 32 | 33 | 0.6495 | 0.6701 | 0.0206 |
| 47 | Med | Other Disorders of the Eye | Age > 17 w/o C.C. | 2.6 | 28 | 28 | 0.3539 | 0.3608 | 0.0069 |
| 48 | Med | Other Disorders of the Eye | Age 0-17 | 2.9 | 30 | 30 | 0.3969 | 0.3969 | 0.0000 |
| MDC 03-DISEASES & DISORDERS OTHE EAR, NOSE & THROAT | | | | | | | | | |
| 49 | Surg | Major Head & Neck Procedures | | 7.4 | 39 | 36 | 2.8633 | 2.3273 | -0.5360 |
| 50 | Surg | Sialodenectomy | | 2.2 | 15 | 14 | 0.6298 | 0.6413 | 0.0115 |
| 51 | Surg | Salivary Gland Proc. Ex. Sialodenectomy | | 2.1 | 18 | 20 | 0.5647 | 0.5822 | 0.0175 |
| 52 | Surg | Cleft Up & Palate Repair | | 2.6 | 26 | 25 | 0.8129 | 0.7394 | -0.0735 |
| 53 | Surg | Sinus & Mastoid Procedures | Age > 17 | 1.9 | 20 | 19 | 0.6161 | 0.6308 | 0.0147 |
| 54 | Surg | Sinus & Mastoid Procedures | Age 0-17 | 3.2 | 22 | 22 | 0.6805 | 0.6805 | 0.0000 |
| 55 | Surg | Miscellaneous Ear, Nose & Throat Proc. | | 1.6 | 14 | 13 | 0.4879 | 0.4905 | 0.0026 |
| 56 | Surg | Rhinoplasty | | 1.7 | 14 | 13 | 0.4881 | 0.4982 | 0.0101 |
| 57 | Surg | T & A Proc. Except Tonsil and/or Adenoid | Age > 17 | 3.4 | 32 | 32 | 0.9313 | 0.8774 | -0.0539 |
| 58 | Surg | T & A Proc. Except Tonsil and/or Adenoid | Age 0-17 | 1.5 | 4 | 4 | 0.3060 | 0.3060 | 0.0000 |
| 59 | Surg | Tonsillectomy and/or Adenoidectomy | Age > 17 | 1.6 | 11 | 12 | 0.3878 | 0.4192 | 0.0314 |
| 60 | Surg | Tonsillectomy and/or Adenoidectomy | Age 0-17 | 1.5 | 4 | 4 | 0.2584 | 0.2584 | 0.0000 |
| 61 | Surg | Myringotomy w/ Tube Insertion | Age > 17 | 2.3 | 30/31 | 0.6945 | 0.7656 | 0.0711 | |
| 62 | Surg | Myringotomy w/ Tube Insertion | Age 0-17 | 1.3 | 5 | 5 | 0.3052 | 0.3052 | 0.0000 |
| 63 | Surg | Other Ear, Nose, Mouth & Throat O. R. Proc. | | 3.8 | 32 | 33 | 1.1822 | 1.0111 | -0.1771 |
| 64 | Med | Ear, Nose, Mouth & Throat Malignancy | | 5.0 | 33 | 34 | 1.1762 | 1.0651 | -0.1111 |
| 65 | Med | Dysequilibrium | | 3.3 | 23 | 23 | 0.4564 | 0.4636 | 0.0072 |
| 66 | Med | Epistaxis | | 3.3 | 24 | 24 | 0.4496 | 0.4526 | 0.0032 |
| 67 | Med | Epiglotitis | | 4.3 | 32 | 33 | 0.8589 | 0.8478 | -0.0111 |
| 68 | Med | Otitis Media & Uri | Age > 17 w/C.C. | 4.9 | 33 | 33 | 0.7232 | 0.7209 | -0.0023 |
| 69 | Med | Otitis Media & Uri | Age > 17 w/o C.C. | 3.8 | 25 | 24 | 0.5281 | 0.5086 | -0.0195 |
| 70 | Med | Otitis Media & Uri | Age 0-17 | 2.3 | 22 | 13 | 0.4589 | 0.2830 | -0.1759 |
| 71 | Med | Larynogotracheitis | | 4.3 | 32 | 27 | 0.7307 | 0.7030 | -0.0277 |
| 72 | Med | Nasal Trauma & Deformity | | 3.2 | 31 | 32 | 0.5528 | 0.5547 | 0.0019 |
| 73 | Med | Other Ear, Nose, Mouth & Throat Diagnosis | Age > 17 | 4.1 | 32 | 33 | 0.7525 | 0.7291 | -0.0234 |
| 74 | Med | Other Ear, Nose, Mouth & Throat Diagnosis | Age 0-17 | 2.1 | 20 | 20 | 0.3386 | 0.3386 | 0.0000 |
| MDC 04-DISEASES & DISORDERS OF THE RESPIRATORY SYSTEM | | | | | | | | | |
| 75 | Surg | Major Chest Procedures | | 11.7 | 40 | 41 | 2.9603 | 2.9860 | 0.0257 |
| 76 | Surg | Other Resp. System O.R. Procedures | w/C.C. | 10.5 | 38 | 39 | 2.3038 | 2.3074 | 0.0036 |
| 77 | Surg | Other Resp. System O.R. Procedures | w/0 C.C. | 4.6 | 33 | 34 | 1.0895 | 1.0413 | -0.0482 |
| 78 | Med | Pulmonary Embolism | | 8.8 | 37 | 38 | 1.4320 | 1.4372 | 0.0052 |
| 79 | Med | Respiratory Infections & Inflammations | Age > 17 w/C.C. | 9.3 | 37 | 38 | 1.8530 | 1.8144 | -0.0386 |
| 80 | Med | Respiratory Infections & Inflammations | Age > 18 w/o C.C. | 6.8 | 35 | 36 | 1.1382 | 1.0404 | -0.0978 |
| 81 | Med | Respiratory Infections & Inflammations | Age 0-17 | 6.1 | 34 | 35 | 1.0899 | 1.0899 | 0.0000 |
| 82 | Med | Respiratory Neoplasms | | 6.7 | 35 | 36 | 1.2016 | 1.2178 | 0.0162 |
| 83 | Med | Major Chest Trauma | w/C.C. | 6.3 | 35 | 35 | 1.0064 | 0.9628 | -0.0436 |
| 84 | Med | Major Chest Trauma | w/o C.C. | 3.7 | 32 | 28 | 0.5009 | 0.4846 | -0.0163 |
| 85 | Med | Pleural Effusion | w/C.C. | 6.8 | 35 | 36 | 1.1437 | 1.1509 | 0.0072 |
| 86 | Med | Pleural Effusion | w/o C.C. | 4.4 | 33 | 33 | 0.7223 | 0.6961 | -0.0262 |
| 87 | Med | Pulmonary Edema & Respiratory Failure | | 6.0 | 34 | 35 | 1.4597 | 1.3895 | -0.0702 |
| 88 | Med | Chronic Obstructive Pulmonary Disease | | 5.9 | 34 | 35 | 1.0153 | 0.9973 | -0.0180 |
| 89 | Med | Simple Pneumonia & Pleurisy | Age > 17 w/C.C. | 7.2 | 35 | 36 | 1.2059 | 1.1878 | -0.0181 |
| 90 | Med | Simple Pneumonia & Pleurisy | Age > 17 w/o C.C. | 5.6 | 32 | 31 | 0.7790 | 0.7538 | -0.0252 |
| 91 | Med | Simple Pneumonia & Pleurisy | Age 0-17 | 5.2 | 30 | 34 | 0.7465 | 0.8141 | 0.0676 |
| 92 | Med | Interstitial Lung Disease | w/C.C. | 6.9 | 36 | 36 | 1.2182 | 1.2131 | -0.0051 |

TABLE III-continued

DRG Descriptions, Average Lengths of Stay, Day Outlier Thresholds and Relative Weights

| DRG No. | Type | Description | | Fiscal 91 Geometric Mean Length of Stay | Fiscal 90 Day Outlier Threshold | Fiscal 91 Day Outlier Threshold | Fiscal 90 Relative Weights | Fiscal 91 Relative Weights | FY 90-91 Charge in Relative Weights |
|---|---|---|---|---|---|---|---|---|---|
| 93 | Med | Interstitial Lung Disease | w/o C.C. | 4.9 | 33 | 34 | 0.7936 | 0.7598 | −0.0338 |
| 94 | Med | Pneumothorax | w/C.C. | 7.2 | 35 | 36 | 1.3378 | 1.2763 | −0.0615 |
| 95 | Med | Pneumothorax | w/o C.C. | 4.6 | 33 | 34 | 0.6685 | 0.6533 | −0.0132 |
| 96 | Med | Bronchitis & Asthma | Age > 17 w/C.C. | 6.0 | 34 | 35 | 0.9734 | 0.9568 | −0.0166 |
| 97 | Med | Bronchitis & Asthma | Age > 17 w/o C.C. | 4.6 | 27 | 26 | 0.6810 | 0.6561 | −0.0249 |
| 98 | Med | Bronchitis & Asthma | Age 0–17 | 4.6 | 34 | 22 | 0.8942 | 0.6135 | −0.2807 |
| 99 | Med | Respiratory Signs & Symptoms | w/C.C. | 4.4 | 32 | 33 | 0.8493 | 0.8361 | −0.0132 |
| 100 | Med | Respiratory Signs & Symptoms | w/o C.C. | 2.7 | 20 | 19 | 0.5125 | 0.5090 | −0.0035 |
| 101 | Med | Other Respiratory Diagnoses | w/C.C. | 5.1 | 33 | 34 | 0.9966 | 0.9181 | −0.0785 |
| 102 | Med | Other Respiratory Diagnoses | w/o C.C. | 3.4 | 31 | 32 | 0.5593 | 0.5400 | −0.0193 |
| MDC 05-DISEASES & DISORDERS OF THE CIRCULATORY SYSTEM | | | | | | | | | |
| 103 | Surg | Heart Transplant | | 25.0 | 54 | 54 | 13.2352 | 12.9086 | −0.3266 |
| 104 | Surg | Cardiac Valve Procedure | with Cardiac Cath | 18.3 | 45 | 47 | 7.8432 | 8.0641 | 0.2209 |
| 105 | Surg | Cardiac Valve Procedure | w/o Cardiac Cath | 13.0 | 41 | 42 | 5.9965 | 6.0750 | 0.0785 |
| 106 | Surg | Coronary Bypass | with Cardiac Cath | 13.9 | 42 | 43 | 5.6558 | 5.4227 | −0.2331 |
| 107 | Surg | Coronary Bypass | w/o Cardiac Cath | 11.2 | 39 | 40 | 4.2260 | 4.7899 | 0.5639 |
| 108 | Surg | Other Cardiothoracic Procedures | | 12.9 | 39 | 42 | 5.7332 | 5.9649 | 0.2317 |
| 109 | Surg | Other Cardiothoracic Procedures | No Longer Valid | 0.0 | 36 | 0 | 3.7746 | 0.0000 | −3.7746 |
| 110 | Surg | Major Cardiovascular Procedures | w/C.C. | 10.5 | 40 | 39 | 3.5967 | 4.2644 | 0.6677 |
| 111 | Surg | Major Cardiovascular Procedures | w/o C.C. | 8.1 | 36 | 37 | 2.0351 | 2.4493 | 0.4142 |
| 112 | Surg | Percutaneous Cardiovascular Procedures | | 4.9 | 33 | 34 | 1.9106 | 1.9910 | 0.0804 |
| 113 | Surg | Amputation for Circ. System Disorders | Ex. Upper Limb & Toe | 14.5 | 42 | 44 | 2.4616 | 2.6279 | 0.1663 |
| 114 | Surg | Upper Limb & Toe Amputation | for Circ Disorders | 9.3 | 38 | 38 | 1.6119 | 1.5827 | −0.0292 |
| 115 | Surg | Permanent Cardiac Pacemaker Implant | with AMI or CHF or Shock | 12.1 | 41 | 41 | 3.8541 | 3.7705 | −0.0836 |
| 116 | Surg | Permanent Cardiac Pacemaker Implant | w/o AMI or CHF or Shock | 5.8 | 34 | 35 | 2.5793 | 2.5190 | −0.0603 |
| 117 | Surg | Cardiac Pacemaker Revision exc. Device Rapl. | | 3.8 | 33 | 33 | 1.8867 | 1.3520 | −0.5347 |
| 118 | Surg | Cardiac Pacemaker Device Replacement | | 3.0 | 32 | 32 | 2.0267 | 1.7375 | −0.2892 |
| 119 | Surg | Vein Ligation & Stripping | | 3.4 | 32 | 32 | 0.8269 | 0.8169 | −0.0100 |
| 120 | Surg | Other O.R Proc. - Circulatory System | | 10.2 | 39 | 39 | 2.7059 | 2.5143 | −0.1916 |
| 121 | Med | Circulatory Disorders with AMI & C.V. | Comp. Disch. Alive | 8.2 | 37 | 37 | 1.6228 | 1.5772 | −0.0456 |
| 122 | Med | Circulatory Disorders with AMI w/o C.V | Comp. Disch. Alive | 5.9 | 34 | 35 | 1.1233 | 1.1152 | −0.0081 |
| 123 | Med | Circulatory Disorders with AMI | Expired | 3.0 | 31 | 32 | 1.3934 | 1.3704 | −0.0230 |
| 124 | Med | Circulatory Disorders Exc. AMI with | Cath. & Complex Diag. | 4.3 | 32 | 33 | 1.1876 | 1.1816 | −0.0060 |
| 125 | Med | Circulatory Disorders Exc. AMI with | Cath. w/o Compl Diag. | 2.2 | 20 | 21 | 0.6874 | 0.7015 | 0.0141 |
| 126 | Med | Acute and Subacute Endocarditis | | 17.0 | 45 | 46 | 2.9894 | 2.9543 | −0.0351 |
| 127 | Med | Heart Failure & Shock | | 6.1 | 34 | 35 | 1.0169 | 1.0040 | −0.0129 |
| 128 | Med | Deep Vein Thrombophlebitis | | 7.7 | 35 | 34 | 0.8129 | 0.8061 | −0.0068 |
| 129 | Med | Cardiac Arrest, Unexplained | | 2.6 | 31 | 32 | 1.3986 | 1.3242 | −0.0744 |
| 130 | Med | Peripheral Vascular Disorders | w/C.C. | 6.0 | 34 | 35 | 0.8921 | 0.8969 | 0.0048 |
| 131 | Med | Peripheral Vascular Disorders | w/o C.C. | 4.4 | 32 | 33 | 0.5814 | 0.5841 | 0.0027 |
| 132 | Med | Atherosclerosis | w/C.C. | 4.1 | 32 | 33 | 0.7565 | 0.7252 | −0.0313 |
| 133 | Med | Atherosclerosis | w/o C.C. | 3.1 | 27 | 26 | 0.5420 | 0.5205 | −0.0215 |
| 134 | Med | Hypertension | | 4.2 | 32 | 33 | 0.5964 | 0.5992 | 0.0028 |
| 135 | Med | Cardiac Congenital & Valvular Disorders | Age > 17 w/C.C. | 4.9 | 33 | 34 | 0.9018 | 0.8623 | −0.0395 |
| 136 | Med | Cardiac Congenital & Valvular Disorders | Age > 17 w/o C.C. | 3.3 | 29 | 26 | 0.5488 | 0.5507 | 0.0019 |
| 137 | Med | Cardiac Congenital & Valvular Disorders | Age 0–17 | 3.3 | 31 | 32 | 0.6239 | 0.6239 | 0.0000 |
| 138 | Med | Cardiac Arrythmia & Conduction Disorders | w/C.C. | 4.6 | 33 | 34 | 0.8707 | 0.8331 | −0.0376 |
| 139 | Med | Cardiac Arrythmia & Conduction Disorders | w/o C.C. | 3.2 | 26 | 24 | 0.5715 | 0.5325 | −0.0390 |
| 140 | Med | Angina Pectoris | | 3.8 | 25 | 25 | 0.6387 | 0.6296 | −0.0091 |
| 141 | Med | Syncope & Collapse | w/C.C. | 4.4 | 32 | 33 | 0.6920 | 0.6899 | −0.0021 |
| 142 | Med | Syncope & Collapse | w/o C.C. | 3.2 | 23 | 22 | 0.5149 | 0.5012 | −0.0137 |
| 143 | Med | Chest Pain | | 2.8 | 19 | 18 | 0.5226 | 0.5140 | −0.0086 |
| 144 | Med | Other Circulatory Diagnoses | with C.C. | 5.5 | 34 | 34 | 1.1035 | 1.0849 | −0.0186 |
| 145 | Med | Other Circulatory Diagnoses | w/o C.C. | 3.2 | 31 | 29 | 0.6236 | 0.5933 | −0.0303 |
| MDC 06-DISEASES OF THE DIGESTIVE SYSTEM | | | | | | | | | |
| 146 | Surg | Rectal Resection | w/C.C. | 13.0 | 42 | 42 | 2.7386 | 2.5864 | −0.1522 |
| 147 | Surg | Rectal Resection | w/o C.C. | 9.5 | 37 | 36 | 1.7349 | 1.6406 | −0.0943 |
| 148 | Surg | Major Small & Large Bowel Procedures | w/C.C. | 13.9 | 42 | 43 | 3.2705 | 3.1996 | −0.0709 |
| 149 | Surg | Major Small & Large Bowel Procedures | w/o C.C. | 9.4 | 32 | 31 | 1.6636 | 1.6044 | −0.0592 |
| 150 | Surg | Peritoneal Adhesiolysis | w/C.C. | 11.8 | 40 | 41 | 2.6617 | 2.5312 | −0.1306 |
| 151 | Surg | Peritoneal Adhesiolysis | w/o C.C. | 7.4 | 36 | 36 | 1.3478 | 1.2777 | −0.0701 |

TABLE III-continued

DRG Descriptions, Average Lengths of Stay, Day Outlier Thresholds and Relative Weights

| DRG No. | Type | Description | | Fiscal 91 Geometric Mean Length of Stay | Fiscal 90 Day Outlier Threshold | Fiscal 91 Day Outlier Threshold | Fiscal 90 Relative Weights | Fiscal 91 Relative Weights | FY 90–91 Charge in Relative Weights |
|---|---|---|---|---|---|---|---|---|---|
| 152 | Surg | Minor Small & Large Bowel Procedures | w/C.C. | 7.6 | 36 | 37 | 1.4678 | 1.4769 | 0.0091 |
| 153 | Surg | Minor Small & Large Bowel Procedures | w/o C.C. | 6.4 | 33 | 33 | 1.0149 | 1.0170 | 0.0021 |
| 154 | Surg | Stomach, Esophageal & Duodenal Procedures | Age > 17 w/C.C. | 12.4 | 41 | 41 | 3.8172 | 3.6320 | −0.1852 |
| 155 | Surg | Stomach, Esophageal & Duodenal Procedures | Age > 17 w/o C.C. | 7.4 | 36 | 36 | 1.6050 | 1.4768 | −0.1262 |
| 156 | Surg | Stomach, Esophageal & Duodenal Procedures | Age 0–17 | 6.0 | 34 | 35 | 0.8281 | 0.8281 | 0.0000 |
| 157 | Surg | Anal & Stomal Procedures | w/C.C. | 4.8 | 33 | 34 | 0.9571 | 0.9248 | −0.0323 |
| 158 | Surg | Anal & Stomal Procedures | w/o C.C. | 2.6 | 23 | 19 | 0.5136 | 0.4877 | −0.0259 |
| 159 | Surg | Hernia Procedures Ex. Inguinal & Femoral | Age > 17 w/C.C. | 5.1 | 33 | 34 | 1.1057 | 1.0797 | −0.0260 |
| 160 | Surg | Hernia Procedures Ex. Inguinal & Femoral | Age > 17 w/o C.C. | 3.1 | 23 | 22 | 0.6314 | 0.6166 | −0.0148 |
| 161 | Surg | Inguinal & Femoral Hernia Procedures | Age > 17 w/C.C. | 3.3 | 32 | 32 | 0.7337 | 0.7238 | −0.0099 |
| 162 | Surg | Inguinal & Femoral Hernia Procedures | Age > 17 w/o C.C. | 2.0 | 14 | 12 | 0.4485 | 0.4428 | −0.0057 |
| 163 | Surg | Hernia Procedures | Age 0–17 | 3.2 | 26 | 32 | 0.7729 | 0.6397 | −0.1332 |
| 164 | Surg | Appendectomy-Complicated Princ. Diag. | w/C.C. | 10.3 | 39 | 39 | 2.3737 | 2.2699 | −0.1038 |
| 165 | Surg | Appendectomy-Complicated Princ. Diag. | w/o C.C. | 7.2 | 26 | 25 | 1.3377 | 1.2944 | −0.0433 |
| 166 | Surg | Appendectomy w/o Complicated Princ. Diag. | w/C.C. | 6.6 | 35 | 36 | 1.3991 | 1.3818 | −0.0173 |
| 167 | Surg | Appendectomy w/o Complicated Princ. Diag. | w/o C.C. | 4.2 | 17 | 16 | 0.7922 | 0.7745 | −0.0177 |
| 168 | Surg | Mouth Procedures | w/C.C. | 3.7 | 32 | 33 | 1.0050 | 0.9806 | −0.0244 |
| 169 | Surg | Mouth Procedures | w/o C.C. | 2.1 | 19 | 18 | 0.5463 | 0.5558 | 0.0095 |
| 170 | Surg | Other Digestive System O.R. Procedures | w/C.C. | 11.1 | 39 | 40 | 2.8091 | 2.7171 | −0.0920 |
| 171 | Surg | Other Digestive System O.R. Procedures | w/o C.C. | 5.7 | 34 | 35 | 1.2563 | 1.1583 | −0.0980 |
| 172 | Med | Digestive Malignancy | w/C.C. | 7.2 | 35 | 36 | 1.2216 | 1.2445 | 0.0229 |
| 173 | Med | Digestive Malignancy | w/o C.C. | 3.8 | 32 | 33 | 0.6657 | 0.6358 | −0.0299 |
| 174 | Med | G.I. Hemorrhage | w/C.C. | 5.5 | 34 | 34 | 0.9620 | 0.9537 | −0.0083 |
| 175 | Med | G.I. Hemorrhage | w/o C.C. | 3.9 | 25 | 24 | 0.5983 | 0.5756 | −0.0227 |
| 176 | Med | Complicated Peptic Ulcer | | 5.9 | 34 | 35 | 0.9831 | 0.9830 | −0.0001 |
| 177 | Med | Uncomplicated Peptic Ulcer | w/C.C. | 5.2 | 32 | 33 | 0.7637 | 0.7803 | 0.0166 |
| 178 | Med | Uncomplicated Peptic Ulcer | w/o C.C. | 3.9 | 23 | 22 | 0.5650 | 0.5564 | −0.0086 |
| 179 | Med | Inflammatory Bowel Disease | | 7.1 | 35 | 36 | 1.0648 | 1.0895 | 0.0247 |
| 180 | Med | G.I. Obstruction | w/C.C. | 5.8 | 34 | 35 | 0.9134 | 0.9165 | 0.0031 |
| 181 | Med | G.I. Obstruction | w/o C.C. | 4.0 | 28 | 27 | 0.5229 | 0.5130 | −0.0099 |
| 182 | Med | Esophagitix, Gastroent & Misc. Digest. Dis. | Age > 17 w/C.C. | 4.9 | 33 | 34 | 0.7414 | 0.7497 | 0.0083 |
| 183 | Med | Esophagitix, Gastroent & Misc. Digest. Dis. | Age > 17 w/o C.C. | 3.5 | 26 | 25 | 0.5215 | 0.5200 | −0.0015 |
| 184 | Med | Esophagitix, Gastroent & Misc. Digest. Dis. | Age 0–17 | 3.2 | 31 | 32 | 0.5408 | 0.6801 | 0.1393 |
| 185 | Med | Dental & Oral Dis. Ex Extract & Restor. | Age > 17 | 4.3 | 32 | 33 | 0.7627 | 0.7548 | −0.0079 |
| 186 | Med | Dental & Oral Dis. Ex Extract & Restor. | Age 0–17 | 2.9 | 23 | 23 | 0.4062 | 0.4062 | 0.0000 |
| 187 | Med | Dental Extractions & Restorations | | 2.2 | 20 | 22 | 0.3856 | 0.4814 | −0.0042 |
| 188 | Med | Other Digestive System Diagnoses | Age > 17 w/C.C. | 5.1 | 33 | 34 | 0.9730 | 0.9632 | −0.0098 |
| 189 | Med | Other Digestive System Diagnoses | Age > 17 w/o C.C. | 2.9 | 31 | 32 | 0.4767 | 0.4802 | 0.0035 |
| 190 | Med | Other Digestive System Diagnoses | Age 0–17 | 4.0 | 32 | 28 | 0.7671 | 0.6312 | −0.1359 |
| MDC 07-DISEASES & DISORDERS OTHE HEPATOBILIARY SYSTEM & PANCREAS | | | | | | | | | |
| 191 | Surg | Pancreas, Liver & Shunt Procedures | w/C.C. | 15.9 | 45 | 45 | 5.0674 | 4.6941 | −0.3733 |
| 192 | Surg | Pancreas, Liver & Shunt Procedures | w/o C.C. | 9.2 | 38 | 38 | 2.1816 | 1.9662 | −0.2154 |
| 193 | Surg | Biliary Tract Proc. Ex Tot. Cholecystectomy | w/C.C. | 14.3 | 43 | 43 | 3.0026 | 3.0102 | 0.0076 |
| 194 | Surg | Biliary Tract Proc. Ex Tot. Cholecystectomy | w/o C.C. | 9.8 | 38 | 39 | 1.7802 | 1.7387 | −0.0415 |
| 195 | Surg | Total Cholecystectomy with C.D.E. | w/C.C. | 11.0 | 40 | 40 | 2.2810 | 2.2175 | −0.0635 |
| 196 | Surg | Total Cholecystectomy with C.D.E. | w/o C.C. | 8.2 | 30 | 30 | 1.5106 | 1.4183 | −0.0923 |
| 197 | Surg | Total Cholecystectomy w/o C.D.E. | w/C.C. | 8.6 | 37 | 38 | 1.7378 | 1.7336 | −0.0042 |
| 198 | Surg | Total Cholecystectomy w/o C.D.E. | w/o C.C. | 5.5 | 21 | 20 | 0.9865 | 0.9445 | −0.0420 |
| 199 | Surg | Hepatobiliary Diag. Proc. for Malignancy | | 11.9 | 40 | 41 | 2.2585 | 2.3168 | 0.0583 |
| 200 | Surg | Hepatobiliary Diag. Proc. for Non-Malig | | 10.1 | 38 | 39 | 2.7160 | 2.8940 | 0.1780 |
| 201 | Surg | Other Hepatobiliary or Pancreas O.R. Proc. | | 8.9 | 37 | 38 | 2.4093 | 2.4210 | 0.0117 |
| 202 | Med | Cirrhosis & Alcoholic Hepatitis | | 7.2 | 35 | 36 | 1.1953 | 1.2019 | 0.0066 |
| 203 | Med | Malig of Hepatobiliary Syst or Pancreas | | 6.8 | 35 | 36 | 1.1174 | 1.1301 | 0.0127 |
| 204 | Med | Disorders of Pancreas Except Malignancy | | 6.1 | 34 | 35 | 1.0387 | 1.0617 | 0.0230 |
| 205 | Med | Disorders of Liver Ex. Malig. Cirr. Alc. Hepa. | w/C.C. | 6.7 | 35 | 36 | 1.2068 | 1.1985 | −0.0083 |
| 206 | Med | Disorders of Liver Ex. Malig. Cirr. Alc. Hepa. | w/o C.C. | 3.8 | 32 | 33 | 0.6124 | 0.6210 | 0.0086 |
| 207 | Med | Disorders of the Biliary Tract | w/C.C. | 5.5 | 34 | 35 | 0.9566 | 0.9569 | 0.0003 |

TABLE III-continued

DRG Descriptions, Average Lengths of Stay, Day Outlier Thresholds and Relative Weights

| DRG No. | Type | Description | | Fiscal 91 Geometric Mean Length of Stay | Fiscal 90 Day Outlier Threshold | Fiscal 91 Day Outlier Threshold | Fiscal 90 Relative Weights | Fiscal 91 Relative Weights | FY 90-91 Charge in Relative Weights |
|---|---|---|---|---|---|---|---|---|---|
| 208 | Med | Disorders of the Biliary Tract | w/o C.C. | 3.4 | 29 | 27 | 0.5658 | 0.5599 | −0.0059 |
| MDC 06-DISEASES & DISORDERS OF THE MUSCULOSKELETAL SYSTEM & CONNECTIVE TISSUE | | | | | | | | | |
| 209 | Surg | Major Joint & Limb Reattachment Procedures | | 10.6 | 39 | 38 | 2.3437 | 2.3689 | 0.0252 |
| 210 | Surg | Hip & Femur Procedures Exc. Major Joint Age > 17 w/C.C. | | 12.0 | 41 | 41 | 2.0536 | 1.9939 | −0.0597 |
| 211 | Surg | Hip & Femur Procedures Exc. Major Joint Age > 17 w/o C.C. | | 9.6 | 38 | 38 | 1.4716 | 1.4302 | −0.0414 |
| 212 | Surg | Hip & Femur Procedures Exc. Major Joint Age 0–17 | | 4.5 | 31 | 16 | 1.4023 | 0.9981 | −0.4042 |
| 213 | Surg | Amputations for Musculoskeletal System & Conn. Tissue Disorders | | 9.7 | 38 | 39 | 1.7701 | 1.7562 | −0.0139 |
| 214 | Surg | Back & Neck Procedures | w/C.C. | 10.0 | 39 | 39 | 1.9997 | 1.9298 | −0.0699 |
| 215 | Surg | Back & Neck Procedures | w/o C.C. | 6.6 | 35 | 35 | 1.2155 | 1.1550 | −0.0605 |
| 216 | Surg | Biopsies of Musculoskeletal System & Connective Tissue | | 9.5 | 37 | 38 | 1.7852 | 1.8502 | 0.0650 |
| 217 | Surg | Wnd Debrid & Skin Grft Exc. Hand for Muscskelt. & Conn Tissue Dis | | 14.1 | 42 | 43 | 3.0640 | 3.1173 | 0.0533 |
| 218 | Surg | Lwr Extrem & Humer Proc. Exc. Hip, Ft, Femur | Age > 17 w/C.C. | 7.7 | 36 | 37 | 1.5359 | 1.4748 | −0.0611 |
| 219 | Surg | Lwr Extrem & Humer Proc. Exc. Hip, Ft, Femur | Age > 17 w/o C.C. | 4.9 | 33 | 31 | 0.9363 | 0.9194 | −0.0169 |
| 220 | Surg | Lwr Extrem & Humer Proc. Exc. Hip, Ft, Femur | Age 0–17 | 5.3 | 33 | 34 | 0.9130 | 0.9130 | 0.0000 |
| 221 | Surg | Knee Procedures | w/C.C. | 6.9 | 35 | 36 | 1.5408 | 1.5919 | 0.0511 |
| 222 | Surg | Knee Procedures | w/o C.C. | 3.8 | 32 | 33 | 0.8855 | 0.9134 | 0.0279 |
| 223 | Surg | Major shoulder/elbos proc, or oth upper ext. proc | w/C.C. | 3.5 | 32 | 28 | 0.8405 | 0.8260 | −0.0145 |
| 224 | Surg | Shoulder, elbow or forearm proc, exc major joint proc | w/o C.C. | 2.6 | 19 | 17 | 0.6248 | 0.6224 | −0.0024 |
| 225 | Surg | Foot Procedures | | 3.2 | 31 | 32 | 0.7063 | 0.7421 | 0.0358 |
| 226 | Surg | Soft Tissue Procedures | w/C.C. | 6.3 | 35 | 35 | 1.4308 | 1.3371 | −0.0937 |
| 227 | Surg | Soft Tissue Procedures | w/o C.C. | 2.9 | 30 | 26 | 0.6618 | 0.6604 | −0.0014 |
| 228 | Surg | Major thumb or joint proc, or oth hand or wrist | w/C.C. | 2.7 | 28 | 30 | 0.7911 | 0.8148 | 0.0237 |
| 229 | Surg | Hand or wrist proc, except major joint proc | w/o C.C. | 1.9 | 15 | 16 | 0.5117 | 0.5358 | 0.0241 |
| 230 | Surg | Local Excision & Removal of Int. Fix Devices of Hip & Femur | | 4.0 | 32 | 33 | 0.8763 | 0.8508 | −0.0255 |
| 231 | Surg | Local Excision & Removal of Int. Fix Devices Exc Hip & Femur | | 3.6 | 32 | 33 | 0.9107 | 0.9306 | 0.0199 |
| 232 | Surg | Arthroscopy | | 3.6 | 32 | 33 | 1.1229 | 0.9981 | −0.1248 |
| 233 | Surg | Other Muscul Sys. & Conn. Tiss. O.R. Proc. | w/C.C. | 8.9 | 37 | 38 | 1.7280 | 1.8416 | 0.1136 |
| 234 | Surg | Other Muscul Sys. & Conn. Tiss. O.R. Proc. | w/o C.C. | 4.1 | 33 | 33 | 0.8477 | 0.8322 | −0.0155 |
| 235 | Med | Fractures of Femur | | 7.8 | 36 | 37 | 1.1575 | 1.1383 | −0.0192 |
| 236 | Med | Fractures of Hip & Pelvis | | 6.7 | 35 | 36 | 0.8565 | 0.8516 | −0.0049 |
| 237 | Med | Sprains, Strains & Dislocations of Hip, Pelvis & Thigh | | 4.3 | 33 | 33 | 0.5662 | 0.5424 | −0.0238 |
| 238 | Med | Osteomyelitis | | 10.4 | 38 | 39 | 1.5778 | 1.5682 | −0.0096 |
| 239 | Med | Pathological Fractures & Musculoskeletal & Conn. Tiss. Malignan | | 7.5 | 36 | 37 | 0.9843 | 1.0035 | 0.0192 |
| 240 | Med | Connective Tissue Disorders | w/C.C. | 7.1 | 35 | 36 | 1.0769 | 1.1197 | 0.0428 |
| 241 | Med | Connective Tissue Disorders | w/o C.C. | 4.8 | 33 | 34 | 0.6218 | 0.5852 | −0.0366 |
| 242 | Med | Septic Arthritis | | 8.2 | 37 | 37 | 1.3229 | 1.2566 | −0.0663 |
| 243 | Med | Medical Back Problems | | 5.0 | 33 | 34 | 0.6501 | 0.6580 | 0.0079 |
| 244 | Med | Bone Diseases & Specific Arthropathies | w/C.C. | 5.4 | 33 | 34 | 0.7134 | 0.7228 | 0.0094 |
| 245 | Med | Bone Diseases & Specific Arthropathies | w/o C.C. | 4.0 | 32 | 33 | 0.5106 | 0.5008 | −0.0100 |
| 246 | Med | Non-Specific Arthropathies | | 4.5 | 33 | 33 | 0.5910 | 0.5736 | −0.0174 |
| 247 | Med | Signs & Symptoms of Musculeskeletal System & Conn. Tissue | | 3.7 | 32 | 33 | 0.5285 | 0.5332 | 0.0047 |
| 248 | Med | Tendonitis, Myositis & Bursitis | | 4.4 | 32 | 33 | 0.6120 | 0.6342 | 0.0222 |
| 249 | Med | Aftercare, Musculoskeletal System & Connective Tissue | | 3.9 | 32 | 33 | 0.6287 | 0.6320 | 0.0033 |
| 250 | Med | Fx, Sprns, Strns & Disl. of Forearm, Hand, Ft | Age > 17 w/C.C. | 4.4 | 33 | 33 | 0.6806 | 0.6757 | −0.0049 |
| 251 | Med | Fx, Sprns, Strns & Disl. of Forearm, Hand, Ft | Age > 17 w/o C.C. | 2.5 | 24 | 24 | 0.4230 | 0.4315 | 0.0085 |
| 252 | Med | Fx, Sprns, Strns & Disl. of Forearm, Hand, Ft | Age o–17 | 1.8 | 15 | 15 | 0.3454 | 0.3454 | 0.0000 |
| 253 | Med | Fx, Sprns, Strns & Disl. of UpArm, LowLeg, ExFoot | Age > 17 w/C.C. | 5.9 | 34 | 35 | 0.7983 | 0.7871 | −0.0112 |

TABLE III-continued

DRG Descriptions, Average Lengths of Stay, Day Outlier Thresholds and Relative Weights

| DRG No. | Type | Description | | Fiscal 91 Geometric Mean Length of Stay | Fiscal 90 Day Outlier Threshold | Fiscal 91 Day Outlier Threshold | Fiscal 90 Relative Weights | Fiscal 91 Relative Weights | FY 90–91 Charge in Relative Weights |
|---|---|---|---|---|---|---|---|---|---|
| 254 | Med | Fx, Sprns, Strns & Disl. of UpArm, LowLeg, ExFoot | Age > 17 w/o C.C. | 3.6 | 32 | 33 | 0.4346 | 0.4303 | −0.0043 |
| 255 | Med | Fx, Sprns, Strns & Disl. of UpArm, LowLeg, ExFoot | Age 0–17 | 2.9 | 31 | 32 | 0.4582 | 0.4582 | 0.0000 |
| 256 | Med | Other Musculoskeletal System & Connective Tissue DIagnosis | | 3.9 | 32 | 33 | 0.6251 | 0.6267 | 0.0016 |
| MDC 09-DISEASES & DISORDERS OF THE SKIN, SUBCUTANEOUS TISSUE & BREAST | | | | | | | | | |
| 257 | Surg | Total Mastectomy for Malignancy | w/C.C. | 5.0 | 27 | 26 | 0.9402 | 0.9219 | −0.0183 |
| 258 | Surg | Total Mastectomy for Malignancy | w/o C.C. | 4.0 | 18 | 16 | 0.7467 | 0.7178 | −0.0289 |
| 259 | Surg | Subtotal Mastectomy for Malignancy | w/C.C. | 4.4 | 33 | 33 | 0.9987 | 0.9581 | −0.0406 |
| 260 | Surg | Subtotal Mastectomy for Malignancy | w/o C.C. | 2.5 | 18 | 16 | 0.5654 | 0.5764 | 0.0110 |
| 261 | Surg | Breast Proc. for Non-Malig Except Biopsy & Loc. Exc. | | 2.3 | 16 | 15 | 0.6285 | 0.6509 | 0.0224 |
| 262 | Surg | Breast Biopsy & Local Excision for Non-Malignancy | | 1.9 | 13 | 15 | 0.4464 | 0.4537 | 0.0073 |
| 263 | Surg | Skn Graft &/or Debrid for Skn Ulc or Cellulitis | w/C.C. | 16.0 | 44 | 45 | 2.6691 | 2.7750 | 0.1059 |
| 264 | Surg | Skn Graft &/or Debrid for Skn Ulc or Cellulitis | w/o C.C. | 9.2 | 38 | 38 | 1.4197 | 1.3569 | −0.0628 |
| 265 | Surg | Skin Grafts Exc for Skin Ulcer or Cellulitis | with C.C. | 6.1 | 36 | 35 | 1.3903 | 1.3538 | −0.0365 |
| 266 | Surg | Skin Grafts Exc for Skin Ulcer or Cellulitis | w/o C.C. | 3.0 | 31 | 32 | 0.6867 | 0.6682 | −0.0185 |
| 267 | Surg | Perianal & Pilonidal Procedures | | 2.8 | 31 | 32 | 0.5738 | 0.6003 | 0.0265 |
| 268 | Surg | Skin, Subcutaneous Tissue & Breast Plastic Procedures | | 2.7 | 30 | 32 | 0.6431 | 0.7210 | 0.0779 |
| 269 | | Other Skin, Subcut, Tiss. & Breast O.R. Proc | w/C.C. | 8.3 | 36 | 37 | 1.7287 | 1.7063 | −0.0224 |
| 270 | | Other Skin, Subcut, Tiss. & Breast O.R. Proc | w/o C.C. | 3.2 | 31 | 32 | 0.6744 | 0.6709 | −0.0035 |
| 271 | Med | Skin Ulcers | | 9.0 | 37 | 38 | 1.1808 | 1.2568 | 0.0760 |
| 272 | Med | Major Skin Disorders | w/C.C. | 7.2 | 35 | 36 | 1.0183 | 1.0177 | −0.0006 |
| 273 | Med | Major Skin Disorders | w/o C.C. | 5.5 | 34 | 35 | 0.6811 | 0.6664 | −0.0147 |
| 274 | Med | Malignant Breast Disorders | w/C.C. | 6.6 | 34 | 36 | 1.0610 | 1.1101 | 0.0491 |
| 275 | Med | Malignant Breast Disorders | w/o C.C. | 3.2 | 31 | 32 | 0.5793 | 0.5443 | −0.0350 |
| 276 | Med | Non-Malignant Breast Disorders | | 3.6 | 31 | 33 | 0.5602 | 0.5710 | 0.0108 |
| 277 | Med | Cellulitis | Age > 17 w/C.C. | 7.1 | 35 | 36 | 0.9392 | 0.9269 | −0.0123 |
| 278 | Med | Cellulitis | Age > 17 w/o C.C. | 5.4 | 32 | 31 | 0.6492 | 0.6278 | −0.0214 |
| 279 | Med | Cellulitis | Age 0–17 | 4.2 | 24 | 24 | 0.7278 | 0.7278 | 0.0000 |
| 280 | Med | Trauma to the Skin, Subcut, Tiss. & Breast | Age > 17 w/C.C. | 4.6 | 33 | 34 | 0.6597 | 0.6538 | −0.0059 |
| 281 | Med | Trauma to the Skin, Subcut, Tiss. & Breast | Age > 17 w/o C.C. | 3.2 | 31 | 31 | 0.4233 | 0.4169 | −0.0064 |
| 282 | Med | Trauma to the Skin, Subcut, Tiss. & Breast | Age 0–17 | 2.2 | 19 | 19 | 0.3383 | 0.3383 | 0.0000 |
| 283 | Med | Minor Skin Disorders | w/C.C. | 5.4 | 34 | 34 | 0.7624 | 0.7401 | −0.0223 |
| 284 | Med | Minor Skin Disorders | w/o C.C. | 3.6 | 32 | 33 | 0.4659 | 0.4544 | −0.0115 |
| MDC 10-ENDOCRINE, NUTRITIONAL & METABOLIC DISEASES & DISORDERS | | | | | | | | | |
| 285 | Surg | Amput. of lower limb for Endocrine, Nutritional & Metabolic Disorders | | 15.5 | 44 | 45 | 2.8191 | 2.7822 | −0.0369 |
| 286 | Surg | Adrenal & Pituitary Procedures | | 10.1 | 39 | 39 | 2.5261 | 2.4946 | −0.0315 |
| 287 | Surg | Skin Grafts & Wound Debride for Endoc., Nutrit. & Metab Disorders | | 13.6 | 42 | 43 | 2.2372 | 2.2311 | −0.0061 |
| 288 | Surg | O.R. Procedures for Obesity | | 7.4 | 35 | 36 | 1.8656 | 1.9691 | 0.1035 |
| 289 | Surg | Parathyroid Procedures | | 4.3 | 33 | 33 | 1.0587 | 0.9954 | −0.0633 |
| 290 | Surg | Thyroid Procedures | | 3.0 | 21 | 18 | 0.7805 | 0.7394 | −0.0411 |
| 291 | Surg | Thyroglossal Procedures | | 1.8 | 10 | 10 | 0.4589 | 0.4882 | 0.0293 |
| 292 | Surg | Other Endocrine, Nutrit & Metab. O.R. Proc. | w/C.C. | 12.1 | 40 | 41 | 2.7779 | 2.8203 | 0.0424 |
| 293 | Surg | Other Endocrine, Nutrit & Metab. O.R. Proc. | w/o C.C. | 5.6 | 34 | 35 | 1.1289 | 1.0686 | −0.0603 |
| 294 | Med | Diabetes | Age > 35 | 5.9 | 34 | 35 | 0.7509 | 0.7533 | 0.0024 |
| 295 | Med | Diabetes | Age 0–35 | 4.4 | 32 | 33 | 0.7252 | 0.7433 | 0.0181 |
| 296 | Med | Nutritional & Misc. Metabolic Disorders | Age > 17 w/C.C. | 6.1 | 34 | 35 | 0.9404 | 0.9387 | −0.0017 |
| 297 | Med | Nutritional & Misc. Metabolic Disorders | Age > 17 w/o C.C. | 4.1 | 32 | 32 | 0.5480 | 0.5361 | −0.0119 |
| 298 | Med | Nutritional & Misc. Metabolic Disorders | Age 0–17 | 3.2 | 32 | 32 | 0.6768 | 0.5694 | −0.1074 |
| 299 | Med | Inborn Errors of Metabolism | | 4.6 | 33 | 34 | 0.8623 | 0.8009 | −0.0614 |
| 300 | Med | Endocrine Disorders | w/C.C. | 7.1 | 35 | 36 | 1.1086 | 1.1216 | 0.0130 |
| 301 | Med | Endocrine Disorders | w/o C.C. | 4.3 | 32 | 33 | 0.6250 | 0.6187 | −0.0063 |

TABLE III-continued

DRG Descriptions, Average Lengths of Stay, Day Outlier Thresholds and Relative Weights

| DRG No. | Type | Description | | Fiscal 91 Geometric Mean Length of Stay | Fiscal 90 Day Outlier Threshold | Fiscal 91 Day Outlier Threshold | Fiscal 90 Relative Weights | Fiscal 91 Relative Weights | FY 90-91 Charge in Relative Weights |
|---|---|---|---|---|---|---|---|---|---|
| MDC 11-DISEASES & DISORDERS OF THE KIDNEY & URINARY TRACT | | | | | | | | | |
| 302 | Surg | Kidney Transplant | | 14.6 | 43 | 44 | 3.7905 | 3.9581 | 0.1676 |
| 303 | Surg | Kidney, Ureter & Major Bladder Procedure for Neoplasm | | 11.9 | 40 | 41 | 2.6773 | 2.6416 | -0.0357 |
| 304 | Surg | Kidney, Ureter & Maj. Bldr. Proc. Non-Neopl. | w/C.C. | 10.3 | 39 | 39 | 2.4944 | 2.4192 | -0.0752 |
| 305 | Surg | Kidney, Ureter & Maj. Bldr. Proc. Non-Neopl. | w/o C.C. | 5.5 | 34 | 34 | 1.2807 | 1.2168 | -0.0639 |
| 306 | Surg | Prostatectomy | w/C.C. | 7.2 | 36 | 36 | 1.4060 | 1.3240 | -0.0820 |
| 307 | Surg | Prostatectomy | w/o C.C. | 4.2 | 28 | 24 | 0.7931 | 0.7334 | -0.0597 |
| 308 | Surg | Minor Bladder Procedures | w/C.C. | 6.5 | 35 | 36 | 1.5067 | 1.4736 | -0.0331 |
| 309 | Surg | Minor Bladder Procedures | w/o C.C. | 3.3 | 32 | 32 | 0.7882 | 0.7815 | -0.0067 |
| 310 | Surg | Transurethral Procedures | w/C.C. | 4.1 | 32 | 33 | 0.9014 | 0.8741 | -0.0273 |
| 311 | Surg | Transurethral Procedures | w/o C.C. | 2.4 | 18 | 17 | 0.5211 | 0.5178 | -0.0033 |
| 312 | Surg | Urethral Procedures | Age > 17 w/C.C. | 3.8 | 32 | 33 | 0.8071 | 0.7898 | -0.0173 |
| 313 | Surg | Urethral Procedures | Age > 17 w/o C.C. | 2.3 | 21 | 20 | 0.4757 | 0.4769 | 0.0012 |
| 314 | Surg | Urethral Procedures | Age 0-17 | 2.3 | 26 | 26 | 0.4271 | 0.4271 | 0.0000 |
| 315 | Surg | Other Kidney & Urinary Tract O.R. Procedures | | 7.5 | 36 | 36 | 2.3366 | 2.1922 | -0.1444 |
| 316 | Med | Renal Failure | | 6.4 | 34 | 35 | 1.2688 | 1.2684 | -0.0004 |
| 317 | Med | Admit for Renal Dialysis | | 2.2 | 22 | 21 | 0.3814 | 0.3499 | -0.0315 |
| 318 | Med | Kidney & Urinary Tract Neoplasms | w/C.C. | 6.1 | 34 | 35 | 1.0637 | 1.0885 | 0.0248 |
| 319 | Med | Kidney & Urinary Tract Neoplasms | w/o C.C. | 2.7 | 31 | 32 | 0.5453 | 0.5586 | 0.0133 |
| 320 | Med | Kidney & Urinary Tract Infections | Age > 17 w/C.C. | 6.7 | 35 | 36 | 1.0261 | 1.0055 | -0.0206 |
| 321 | Med | Kidney & Urinary Tract Infections | Age > 17 w/o C.C. | 5.0 | 31 | 29 | 0.6830 | 0.6507 | -0.0323 |
| 322 | Med | Kidney & Urinary Tract Infections | Age 0-17 | 4.4 | 33 | 29 | 0.7006 | 0.6387 | -0.0619 |
| 323 | Med | Urinary Stones &/or ESW Lithotripsy | w/C.C. | 2.9 | 31 | 32 | 0.7726 | 0.7510 | -0.0216 |
| 324 | Med | Urinary Stones | w/o C.C. | 2.2 | 16 | 15 | 0.3964 | 0.3932 | -0.0032 |
| 325 | Med | Kidney & Urinary Tract Signs & Symptoms | Age > 17 w/C.C. | 4.4 | 32 | 33 | 0.6673 | 0.6666 | -0.0007 |
| 326 | Med | Kidney & Urinary Tract Signs & Symptoms | Age > 17 w/o C.C. | 3.0 | 25 | 25 | 0.4276 | 0.4286 | 0.0010 |
| 327 | Med | Kidney & Urinary Tract Signs & Symptoms | Age 0-17 | 3.1 | 31 | 32 | 0.5444 | 0.5444 | 0.0000 |
| 328 | Med | Urethral Stricture | Age > 17 w/C.C. | 3.8 | 32 | 33 | 0.6445 | 0.6346 | -0.0099 |
| 329 | Med | Urethral Stricture | Age > 17 w/o C.C. | 2.3 | 19 | 18 | 0.4020 | 0.4168 | 0.0148 |
| 330 | Med | Urethral Stricture | Age 0-17 | 1.6 | 9 | 9 | 0.2754 | 0.2754 | 0.0000 |
| 331 | Med | Other Kidney & Urinary Tract Diagnoses | Age > 17 w/C.C. | 5.3 | 33 | 34 | 0.9501 | 0.9493 | -0.0008 |
| 332 | Med | Other Kidney & Urinary Tract Diagnoses | Age > 17 w/o C.C. | 3.2 | 31 | 32 | 0.5557 | 0.5447 | -0.0110 |
| 333 | Med | Other Kidney & Urinary Tract Diagnoses | Age 0-17 | 5.1 | 33 | 34 | 0.8884 | 1.0415 | 0.1531 |
| MDC 12-DISEASES & DISORDERS OF THE MALE REPRODUCTIVE SYSTEM | | | | | | | | | |
| 334 | Surg | Major Male Pelvic Procedures | with C.C. | 9.4 | 38 | 36 | 1.8224 | 1.7911 | -0.0313 |
| 335 | Surg | Major Male Pelvic Procedures | w/o C.C. | 7.9 | 24 | 23 | 1.3462 | 1.3375 | -0.0087 |
| 336 | Surg | Transurethral Prostatectomy | w/C.C. | 5.3 | 30 | 28 | 0.9827 | 0.9326 | -0.0501 |
| 337 | Surg | Transurethral Prostatectomy | w/o C.C. | 3.9 | 15 | 13 | 0.6603 | 0.6329 | -0.0274 |
| 338 | Surg | Testes Procedures, For Malignancy | | 3.0 | 31 | 32 | 0.7604 | 0.7662 | 0.0058 |
| 339 | Surg | Testes Procedures, Non-Malignant | Age > 17 | 2.4 | 30 | 29 | 0.5847 | 0.5880 | 0.0033 |
| 340 | Surg | Testes Procedures, Non-Malignant | Age 0-17 | 2.4 | 13 | 13 | 0.4283 | 0.4283 | 0.0000 |
| 341 | Surg | Penis Procedures | | 3.5 | 29 | 28 | 0.9851 | 0.9850 | -0.0001 |
| 342 | Surg | Circumcision | Age > 17 | 2.3 | 23 | 24 | 0.4806 | 0.4971 | 0.0165 |
| 343 | Surg | Circumcision | Age 0-17 | 1.7 | 6 | 6 | 0.3742 | 0.3742 | 0.0000 |
| 344 | Surg | Other Male Reprod System O.R. Procedures For Malignancy | | 4.8 | 33 | 34 | 1.0569 | 1.0811 | 0.0242 |
| 345 | Surg | Other Male Reprod System O.R. Procedures Except for Malig. | | 3.8 | 32 | 33 | 0.7877 | 0.7450 | -0.0427 |
| 346 | Med | Malignancy, Male Reproductive System, | w/C.C. | 5.8 | 34 | 35 | 0.9214 | 0.9561 | 0.0347 |
| 347 | Med | Malignancy, Male Reproductive System, | w/o C.C. | 2.5 | 29 | 32 | 0.4664 | 0.4852 | 0.0188 |
| 348 | Med | Benign Prostatic Hypertrophy | w/C.C. | 3.9 | 32 | 33 | 0.6635 | 0.6835 | 0.0200 |
| 349 | Med | Benign Prostatic Hypertrophy | w/o C.C. | 2.2 | 19 | 20 | 0.3828 | 0.3847 | 0.0019 |
| 350 | Med | Inflammation of the Male Reprod. System | | 4.9 | 29 | 29 | 0.6716 | 0.6657 | -0.0059 |
| 351 | Med | Sterilization, Male | | 1.3 | 5 | 5 | 0.3293 | 0.3293 | 0.0000 |
| 352 | Med | Other Male Reproductive System Diagnoses | | 3.0 | 31 | 30 | 0.5500 | 0.5158 | -0.0342 |
| MDC 13-DISEASES & DISORDERS OF THE FEMALE REPRODUCTIVE SYSTEM | | | | | | | | | |
| 353 | Surg | Pelvic Evisceration, Radical Hysterectomy & Vulvectomy | | 10.9 | 39 | 40 | 2.0645 | 2.1148 | 0.0503 |
| 354 | Surg | Uterine, adnexa proc for non-ovar/adoexal maligh | w/C.C. | 7.6 | 36 | 35 | 1.4248 | 1.3937 | -0.0311 |

TABLE III-continued

DRG Descriptions, Average Lengths of Stay, Day Outlier Thresholds and Relative Weights

| DRG No. | Type | Description | | Fiscal 91 Geometric Mean Length of Stay | Fiscal 90 Day Outlier Threshold | Fiscal 91 Day Outlier Threshold | Fiscal 90 Relative Weights | Fiscal 91 Relative Weights | FY 90-91 Charge in Relative Weights |
|---|---|---|---|---|---|---|---|---|---|
| 355 | Surg | Uterine, adnexa proc for non-ovar/adoexal malign | w/o C.C. | 5.4 | 15 | 15 | 0.8943 | 0.8676 | −0.0267 |
| 356 | Surg | Female Reprod. System Reconstructive Proc. | | 4.4 | 19 | 18 | 0.7291 | 0.7139 | −0.0152 |
| 357 | Surg | Uterine & adnexa proc. for ovar or adoexal malign | | 10.6 | 39 | 40 | 2.1705 | 2.2286 | 0.0581 |
| 358 | Surg | Uterine & Adnexa proc for Non-malignancy | w/C.C. | 6.5 | 29 | 26 | 1.2032 | 1.1515 | −0.0517 |
| 359 | Surg | Uterine & Adnexa proc for Non-malignancy | w/o C.C. | 4.9 | 14 | 13 | 0.8132 | 0.7887 | −0.0245 |
| 360 | Surg | Vagina, Cervix & Vulva Procedures | | 4.2 | 32 | 33 | 0.7760 | 0.7643 | −0.0117 |
| 361 | Surg | Laparoscopy & Incisional tubel interruption | | 3.2 | 31 | 32 | 0.6859 | 0.8125 | 0.1266 |
| 362 | Surg | Endoscopic Tubel Interruption | | 2.1 | 6 | 23 | 0.3490 | 0.4921 | 0.1431 |
| 363 | Surg | D&C, Conization & Radio-Implant, for Malignancy | | 3.3 | 32 | 30 | 0.6987 | 0.6421 | −0.0566 |
| 364 | Surg | D&C, Conization Except for Malignancy | | 2.4 | 21 | 24 | 0.4669 | 0.4876 | 0.0207 |
| 365 | Surg | Other Female Reproductive System O.R. Procedures | | 7.9 | 37 | 37 | 1.8928 | 1.7521 | −0.1407 |
| 366 | Med | Malignancy, Female Reproductive System | w/C.C. | 6.6 | 35 | 36 | 1.1726 | 1.1937 | 0.0211 |
| 367 | Med | Malignancy, Female Reproductive System | w/o C.C. | 2.8 | 31 | 32 | 0.4896 | 0.4791 | −0.0105 |
| 368 | Med | Infections, Female Reproductive System | | 6.0 | 34 | 35 | 0.8927 | 0.8639 | −0.0288 |
| 369 | Med | Menstrual & Other Female Reproductive System Disorders | | 3.3 | 31 | 32 | 0.5109 | 0.5198 | 0.0089 |
| MDC 14-PREGNANCY, CHILDBIRTH & THE PUERPERIUM | | | | | | | | | |
| 370 | Surg | Ceserean Section | with C.C. | 6.0 | 34 | 33 | 0.9848 | 0.9284 | −0.0564 |
| 371 | Surg | Ceserean Section | w/o C.C. | 4.3 | 13 | 11 | 0.6544 | 0.6277 | −0.0267 |
| 372 | Med | Vaginal Delivery with Complicating Diagnoses | | 3.0 | 20 | 19 | 0.4540 | 0.4541 | 0.0001 |
| 373 | Med | Vaginal Delivery w/o Complicating Diagnoses | | 2.1 | 8 | 8 | 0.2987 | 0.2963 | −0.0024 |
| 374 | Surg | Vaginal Delivery with Sterilization and/or D&C | | 2.8 | 8 | 12 | 0.4981 | 0.5204 | 0.0223 |
| 375 | Surg | Vaginal Delivery with O.R. Proc. Except and/or D&C | | 4.4 | 29 | 29 | 0.6735 | 0.6735 | 0.0000 |
| 376 | Med | Postpartum & Post Abortion Diagnoses w/o O.R. Procedure | | 2.6 | 25 | 22 | 0.3502 | 0.3646 | 0.0144 |
| 377 | Surg | Postpartum & Post Abortion Diagnoses w/ O.R. Procedure | | 3.0 | 32 | 32 | 1.5119 | 0.6757 | −0.8362 |
| 378 | Med | Ectopic Pregnancy | | 3.6 | 15 | 16 | 0.7232 | 0.6686 | −0.0546 |
| 379 | Med | Threatened Abortion | | 2.1 | 14 | 18 | 0.2493 | 0.2651 | 0.0158 |
| 380 | Med | Abortion w/o D&C | | 1.9 | 14 | 12 | 0.2644 | 0.2943 | 0.0299 |
| 381 | Med | Abortion with D&C Aspiration Curettage or Hysterotomy | | 1.5 | 13 | 10 | 0.3769 | 0.3727 | −0.0042 |
| 382 | Med | False Labor | | 1.1 | 4 | 3 | 0.1186 | 0.1101 | −0.0085 |
| 383 | Med | Other Anterpartum Diagnoses with Medical Complications | | 3.4 | 31 | 32 | 0.3759 | 0.3854 | 0.0095 |
| 384 | Med | Other Anterpartum Diagnoses w/o Medical Complications | | 2.3 | 29 | 27 | 0.3279 | 0.2833 | −0.0446 |
| MDC 15-NEWBORNS & OTHER NEONATES WITH CONDITION ORIG. IN PERINATAL PERIOD | | | | | | | | | |
| 385 | | Neonates, Died or Transferred | | 1.8 | 30 | 31 | 1.2084 | 1.2084 | 0.0000 |
| 386 | | Extreme Immaturity or Respiratory Distress Syndrome, Neonate | | 17.9 | 46 | 47 | 3.6039 | 3.6039 | 0.0000 |
| 387 | | Prematurity with Major Problems | | 13.3 | 41 | 42 | 1.8046 | 1.8046 | 0.0000 |
| 388 | | Prematurity w/o Major Problems | | 8.6 | 37 | 38 | 1.1431 | 1.1431 | 0.0000 |
| 389 | | Full Term Neonate with Major Problems | | 5.3 | 35 | 34 | 2.4098 | 1.4266 | −0.9832 |
| 390 | | Neonate with Other Significant Problems | | 4.5 | 32 | 34 | 0.8111 | 1.0001 | 0.1890 |
| 391 | | Normal Newborns | | 3.1 | 11 | 11 | 0.2191 | 0.2191 | 0.0000 |
| MDC 16-DISEASES & DISORDERS OF THE BLOOD & BLOOD FORMING ORGANS | | | | | | | | | |
| 392 | Surg | Splenectomy | Age > 17 | 12.1 | 40 | 41 | 3.5891 | 3.2611 | −0.3280 |
| 393 | Surg | Splenectomy | Age 0-17 | 9.1 | 37 | 38 | 1.5022 | 1.5022 | 0.0000 |
| 394 | Surg | Other O.R. Procedures of the Blood & Blood Forming Organs | | 5.7 | 34 | 35 | 1.5355 | 1.5388 | 0.0033 |
| 395 | Med | Red Blood Cell Disorders | Age > 17 | 4.6 | 33 | 34 | 0.7466 | 0.7471 | 0.0005 |
| 396 | Med | Red Blood Cell Disorders | Age 0-17 | 2.1 | 15 | 23 | 0.3575 | 0.3615 | 0.0040 |
| 397 | Med | Coagulation Disorders | | 5.5 | 34 | 35 | 1.0955 | 1.1571 | 0.0616 |
| 398 | Med | Reticuloendothelial & Immunity Disorders | w/C.C. | 6.5 | 36 | 35 | 1.2279 | 1.1795 | −0.0484 |

TABLE III-continued

DRG Descriptions, Average Lengths of Stay, Day Outlier Thresholds and Relative Weights

| DRG No. | Type | Description | | Fiscal 91 Geometric Mean Length of Stay | Fiscal 90 Day Outlier Threshold | Fiscal 91 Day Outlier Threshold | Fiscal 90 Relative Weights | Fiscal 91 Relative Weights | FY 90–91 Charge in Relative Weights |
|---|---|---|---|---|---|---|---|---|---|
| 399 | Med | Reticuloendothelial & Immunity Disorders | w/o C.C. | 3.9 | 32 | 33 | 0.6906 | 0.6576 | –0.0330 |
| MDC 17-MYELOPROLIFERATIVE DISORDERS | | | | | | | | | |
| 400 | Surg | Lymphoma or Leukemia with Major O.R. Procedures | | 10.1 | 38 | 39 | 2.6981 | 2.7073 | 0.0092 |
| 401 | Surg | Lymphoma & non-acute Leukemia with oth OR Proc | w/C.C. | 10.2 | 38 | 39 | 2.2572 | 2.2071 | –0.0501 |
| 402 | Surg | Lymphoma & non-acute Leukemia with oth OR Proc | w/o C.C. | 3.9 | 32 | 33 | 0.8945 | 0.8877 | –0.0068 |
| 403 | Med | Lymphoma & non-acute Leukemia | w/C.C. | 8.2 | 36 | 37 | 1.6044 | 1.6019 | –0.0025 |
| 404 | Med | Lymphoma & non-acute Leukemia | w/o C.C. | 4.3 | 33 | 33 | 0.7753 | 0.7474 | –0.0279 |
| 405 | Med | Acute Leukemia w/o major OR Proc | Age 0–17 | 4.9 | 33 | 34 | 1.0281 | 1.0281 | 0.0000 |
| 406 | Surg | Myeloprolif Disord or Poorly Dif Neoplsm & Maj O.R. Proc & C.C. | | 11.4 | 40 | 40 | 2.7445 | 2.6994 | –0.0451 |
| 407 | Surg | Myeloprolif Disord or Poorly Dif Neoplsm w/Maj O.R. & w/o C.C. | | 6.0 | 34 | 35 | 1.3042 | 1.2438 | –0.0604 |
| 408 | Surg | Myeloprolif Disord or Poorly Dif Neoplsm With Other O.R.Proc | | 4.2 | 32 | 33 | 0.9592 | 1.0511 | 0.0919 |
| 409 | Med | Radiotherapy | | 6.7 | 35 | 36 | 1.0357 | 1.0213 | –0.0144 |
| 410 | Med | Chemotherapy | | 2.7 | 20 | 19 | 0.4890 | 0.5123 | 0.0233 |
| 411 | Med | History of Malignancy w/o Endoscopy | | 2.5 | 27 | 28 | 0.4543 | 0.4320 | –0.0223 |
| 412 | Med | History of Malignancy with Endoscopy | | 2.2 | 20 | 21 | 0.4046 | 0.4072 | 0.0026 |
| 413 | Med | Other Myelop Disord or Poorly Dif Neopl Dx | w/C.C. | 7.4 | 35 | 36 | 1.2853 | 1.3073 | 0.0220 |
| 414 | Med | Other Myelop Disord or Poorly Dif Neopl Dx | w/o C.C. | 4.4 | 33 | 33 | 0.7557 | 0.7062 | –0.0495 |
| MDC 18-INFECTIOUS & PARASITIC DISEASES | | | | | | | | | |
| 415 | Surg | O.R. Procedure for Infectious & Parasitic Diseases | | 15.0 | 43 | 44 | 3.6424 | 3.5957 | –0.0467 |
| 416 | Med | Septecemia | Age > 17 | 7.5 | 35 | 37 | 1.5346 | 1.5320 | –0.0026 |
| 417 | Med | Septecemia | Age 0–17 | 5.3 | 33 | 34 | 0.8929 | 1.0768 | 0.1839 |
| 418 | Med | Postoperative & Post-Traumatic Infections | | 6.7 | 35 | 36 | 0.9641 | 0.9816 | 0.0175 |
| 419 | Med | Fever of Unknown Origin | Age > 17 w/C.C. | 5.9 | 34 | 35 | 0.9552 | 0.9515 | –0.0037 |
| 420 | Med | Fever of Unknown Origin | Age > 17 w/o C.C. | 4.5 | 33 | 31 | 0.6805 | 0.6612 | –0.0193 |
| 421 | Med | Viral Illness | Age > 17 | 4.3 | 31 | 32 | 0.6337 | 0.6517 | 0.0180 |
| 422 | Med | Viral Illness & Fever of Unknown Origin | Age 0–17 | 3.7 | 27 | 33 | 0.5874 | 0.7604 | 0.1730 |
| 423 | Med | Other Infections & Parasitic Diseases Diagnoses | | 8.0 | 36 | 37 | 1.5845 | 1.5928 | 0.0083 |
| MDC 19-MENTAL DISEASES & DISORDERS | | | | | | | | | |
| 424 | Surg | O.R. Procedures with Principal Diagnosis of Mental Illness | | 13.3 | 42 | 42 | 2.3418 | 2.3652 | 0.0234 |
| 425 | Med | Acute Adjut. React. & Disturbances of Psychosocial Dysfunction | | 4.6 | 32 | 34 | 0.6470 | 0.6890 | 0.0420 |
| 426 | Med | Depressive Neuroses | | 5.7 | 34 | 35 | 0.6255 | 0.6290 | 0.0035 |
| 427 | Med | Neuroses Except Depressive | | 5.6 | 33 | 35 | 0.6133 | 0.6428 | 0.0295 |
| 428 | Med | Disorders of Personality & Impulse Control | | 6.4 | 34 | 35 | 0.7325 | 0.7065 | –0.0260 |
| 429 | Med | Organic Disturbances & Mental Retardation | | 7.6 | 35 | 37 | 0.9016 | 0.9216 | 0.0200 |
| 430 | Med | Psychoses | | 8.9 | 37 | 38 | 0.8957 | 0.9026 | 0.0069 |
| 431 | Med | Childhood Mental Disorders | | 5.4 | 34 | 34 | 0.6347 | 0.6422 | 0.0075 |
| 432 | Med | Other Mental Disorders Diagnoses | | 4.3 | 32 | 33 | 0.7329 | 0.7405 | 0.0076 |
| MDC 20-ALCOHOL AND SUBSTANCE ABUSE | | | | | | | | | |
| 433 | | Alc/Drug Abuse or Dependence, Left AMA | | 3.1 | 31 | 32 | 0.3829 | 0.3829 | 0.0000 |
| 434 | | Alc/Drug Abuse or Dependence, Detox or Other Sympi Trt w/C.C. | | 7.0 | 34 | 36 | 0.8830 | 0.8830 | 0.0000 |
| 435 | | Alc/Drug Abuse or Dependence, Detox or Other Sympi Trt w/o C.C. | | 7.0 | 33 | 36 | 0.7177 | 0.7177 | 0.0000 |
| 436 | | Alc/Drug Dependence w/ Rehabilitation Therapy | | 8.1 | 40 | 37 | 0.9873 | 0.9873 | 0.0000 |
| 437 | | Alc/Drug Dependence Combined Rehab & Detox Therapy | | 3.5 | 42 | 33 | 1.2005 | 1.2005 | 0.0000 |
| 438 | | NO LONGER VALID | | 0.0 | 0 | 0 | 0.0000 | 0.0000 | 0.0000 |

TABLE III-continued

DRG Descriptions, Average Lengths of Stay, Day Outlier Thresholds and Relative Weights

| DRG No. | Type | Description | | Fiscal 91 Geometric Mean Length of Stay | Fiscal 90 Day Outlier Threshold | Fiscal 91 Day Outlier Threshold | Fiscal 90 Relative Weights | Fiscal 91 Relative Weights | FY 90–91 Charge in Relative Weights |
|---|---|---|---|---|---|---|---|---|---|
| MDC 21 INJURIES, POISONINGS & TOX EFFECTS OF DRUGS | | | | | | | | | |
| 439 | Surg | Skin Grafts for Injuries | | 7.2 | 35 | 36 | 1.6731 | 1.6689 | −0.0042 |
| 440 | Surg | Wound Debridements for Injuries | | 10.6 | 29 | 40 | 2.4992 | 2.5374 | 0.0382 |
| 441 | Surg | Hand Procedures for Injuries | | 2.6 | 31 | 32 | 0.7381 | 0.7189 | −0.0192 |
| 442 | Surg | Other O.R. Procedures for Injuries | w/C.C. | 5.6 | 34 | 35 | 1.8642 | 1.8473 | −0.0169 |
| 443 | Surg | Other O.R. Procedures for Injuries | w/o C.C. | 4.0 | 32 | 33 | 1.1906 | 1.1467 | −0.0439 |
| 444 | Med | Multiple Trauma | Age > 17 w/C.C. | 5.1 | 33 | 34 | 0.7694 | 0.7621 | −0.0073 |
| 445 | Med | Multiple Trauma | Age > 17 w/o C.C. | 3.6 | 32 | 32 | 0.4950 | 0.4906 | −0.0044 |
| 446 | Med | Multiple Trauma | Age 0–17 | 2.4 | 22 | 22 | 0.4738 | 0.4738 | 0.0000 |
| 447 | Med | Allergic Reactions | Age > 17 | 2.6 | 24 | 24 | 0.4702 | 0.4822 | 0.0120 |
| 448 | Med | Allergic Reactions | Age 0–17 | 2.9 | 17 | 17 | 0.3428 | 0.3428 | 0.0000 |
| 449 | Med | Poisoning and Toxic Effects of Drugs | Age > 17 w/C.C. | 4.3 | 32 | 33 | 0.7983 | 0.7904 | −0.0079 |
| 450 | Med | Poisoning and Toxic Effects of Drugs | Age > 17 w/o C.C. | 2.6 | 28 | 25 | 0.4648 | 0.4485 | −0.0163 |
| 451 | Med | Poisoning and Toxic Effects of Drugs | Age 0–17 | 3.8 | 16 | 33 | 0.3947 | 0.5126 | 0.1179 |
| 452 | Med | Complications of Treatment | w/C.C. | 4.7 | 33 | 34 | 0.8932 | 0.9317 | 0.0385 |
| 453 | Med | Complications of Treatment | w/o C.C. | 3.1 | 31 | 32 | 0.4752 | 0.4775 | 0.0023 |
| 454 | Med | Other Injuries, Poisonings & Toxic Eff. Diag. | w/C.C. | 4.5 | 33 | 34 | 0.9104 | 0.9488 | 0.0384 |
| 455 | Med | Other Injuries, Poisonings & Toxic Eff. Diag. | w/o C.C. | 2.5 | 27 | 25 | 0.4226 | 0.4282 | 0.0056 |
| MDC 22-BURNS | | | | | | | | | |
| 456 | | Burns, Transferred to Another Acute Care Facility | | 4.1 | 34 | 33 | 3.1114 | 1.5138 | −1.5976 |
| 457 | Med | Extensive Burns w/o OR Procedure | | 2.9 | 31 | 32 | 1.8725 | 2.1317 | 0.2592 |
| 458 | Surg | Non-Extensive Burns with Skin Grafts | | 15.8 | 44 | 45 | 3.8130 | 3.7539 | −0.0591 |
| 459 | Surg | Non-Extensive Burns with Wound Debridement & Other O.R. Proc. | | 10.9 | 38 | 40 | 1.9164 | 2.0711 | 0.1547 |
| 460 | Med | Non-Extensive Burns w/o O.R. Procedure | | 6.4 | 34 | 35 | 1.0165 | 1.0607 | 0.0442 |
| MDC 23-FACTORS INFLUENCING HEALTH STATUS & OTHER CONTACTS WITH HEALTH SERVICES | | | | | | | | | |
| 461 | Surg | O.R. Proc. with Diagnoses of Other Contact with Health Services | | 2.4 | 31 | 31 | 0.7762 | 0.7771 | 0.0009 |
| 462 | Med | Rehabilitation | | 14.1 | 42 | 43 | 1.9047 | 1.8435 | −0.0612 |
| 463 | Med | Signs & Symptoms | with C.C. | 5.1 | 33 | 34 | 0.7540 | 0.7462 | −0.0078 |
| 464 | Med | Signs & Symptoms | w/o c.C. | 3.2 | 31 | 31 | 0.4719 | 0.4700 | −0.0019 |
| 465 | Med | Aftercare with History of Malignancy as Secondary Dx | | 1.9 | 12 | 21 | 0.3282 | 0.3995 | 0.0713 |
| 466 | Med | Aftercare with History of Malignancy as Secondary Dx | | 2.6 | 31 | 32 | 0.5463 | 0.5749 | 0.0286 |
| 467 | Med | Other Factors Infuencing Health Status | | 2.5 | 30 | 31 | 0.4339 | 0.4226 | −0.0113 |
| OTHER | | | | | | | | | |
| 468 | | Unrelated Operating Procedure to a given MDC | | 13.4 | 41 | 42 | 3.3150 | 3.4146 | 0.0996 |
| 469 | | Primary Diagnosis Invalid as Discharge Diagnosis | | 0.0 | 0 | 0 | 0.0000 | 0.0000 | 0.0000 |
| 470 | | UNGROUPABLE | | 0.0 | 0 | 0 | 0.0000 | 0.0000 | 0.0000 |
| 471 | Surg | Bilateral or Multiple Major Joint Proc. of Lower Extremity | | 14.2 | 43 | 43 | 3.9672 | 3.9492 | −0.0180 |
| 472 | Surg | Extensive Burns w/ O.R. Procedures | | 21.0 | 47 | 50 | 12.7129 | 11.7637 | −0.9492 |
| 473 | | Acute Leukemia w/o Major O.R. Procedure | Age < 17 | 9.9 | 37 | 39 | 3.0963 | 3.2953 | 0.1990 |
| 474 | | Respiratory System Diagnosis with Tracheostomy | No Longer Valid | 0.0 | 66 | 0 | 13.4688 | 0.000 | −13.4688 |
| 475 | Med | Respiratory System Diagnosis with Ventilator | | 9.7 | 38 | 39 | 3.6290 | 3.5492 | −0.0798 |
| 476 | | Prostatic O.R. Procedure Unrelated to Principal Diagnosis | | 14.4 | 43 | 43 | 2.2425 | 2.1816 | −0.0609 |
| 477 | | Non-extensive O.R. Procedure Unrelated to Principal Diagnosis | | 6.2 | 35 | 35 | 1.4318 | 1.4395 | 0.0077 |
| Additions for Fiscal 1991-Effective October 1, 1990 | | | | | | | | | |
| 478 | Surg | Other Vascular Procedures | w/C.C. | 9.10 | N/A | 38 | N/A | 2.4189 | N/A |
| 479 | Surg | Other Vascular Procedures | w/o C.C. | 4.60 | N/A | 34 | N/A | 1.3208 | N/A |
| 480 | Surg | Liver Transplant | | 22.80 | N/A | 52 | N/A | 15.2645 | N/A |
| 481 | Surg | Bone Marrow Transplant | | 36.60 | N/A | 66 | N/A | 12.4485 | N/A |
| 482 | Surg | Tracheostomy W Mouth, Larynx, Pharynx Disorder | | 14.20 | N/A | 43 | N/A | 3.2660 | N/A |
| 483 | Surg | Tracheostomy Ex For Mouth, Larynx, | | 40.00 | N/A | 69 | N/A | 14.0597 | N/A |

TABLE III-continued

DRG Descriptions, Average Lengths of Stay, Day Outlier Thresholds and Relative Weights

| DRG No. | Type | Description | Fiscal 91 Geometric Mean Length of Stay | Fiscal 90 Day Outlier Threshold | Fiscal 91 Day Outlier Threshold | Fiscal 90 Relative Weights | Fiscal 91 Relative Weights | FY 90–91 Charge in Relative Weights |
|---|---|---|---|---|---|---|---|---|
| 484 | Surg | Pharynx Dis. Craniotomy For Multiple Significant Trauma | 13.50 | N/A | 43 | N/A | 6.9972 | N/A |
| 485 | Surg | Hip, Femur & Limb Reattach. Procs For Multi Sign Trauma | 14.60 | N/A | 44 | N/A | 3.2621 | N/A |
| 486 | Surg | Other O.R. Procedures For Multiple Significant Trauma | 12.50 | N/A | 41 | N/A | 4.9603 | N/A |
| 487 | Med | Other Multiple Significant Trauma | 7.60 | N/A | 37 | N/A | 1.8324 | N/A |
| 488 | Surg | HIV W Extensive O.R. Procedure | 18.80 | N/A | 48 | N/A | 4.1296 | N/A |
| 489 | Med | HIV W Major Related Condition | 10.20 | N/A | 39 | N/A | 2.0674 | N/A |
| 490 | Med | HIV W or W/O Other Related Condition | 5.90 | N/A | 35 | N/A | 1.1808 | N/A |

TABLE IV

| | Cases | Age | Tot Days | Rout Days | ICU Days | Charges |
|---|---|---|---|---|---|---|
| St. Luke's Hospital of New Bedford | | | | | | |
| 112 | 0 | 0 | 0 | 0 | 0 | 0 |
| 115 | 11 | 830 | 154 | 50 | 104 | 206,285 |
| 116 | 64 | 4,866 | 498 | 189 | 309 | 1,074,529 |
| 117 | 1 | 77 | 4 | 3 | 1 | 915 |
| 118 | 11 | 858 | 29 | 15 | 14 | 130,380 |
| 121 | 226 | 16,344 | 2,267 | 892 | 1,375 | 910,059 |
| 122 | 187 | 11,964 | 1,329 | 294 | 1,035 | 498,771 |
| 123 | 55 | 4,187 | 339 | 125 | 214 | 230,409 |
| 124 | 42 | 2,735 | 145 | 67 | 78 | 122,408 |
| 125 | 39 | 2,263 | 61 | 38 | 23 | 99,566 |
| 126 | 10 | 486 | 238 | 221 | 17 | 74,215 |
| 127 | 610 | 45,426 | 5,348 | 4,254 | 1,094 | 1,581,368 |
| 128 | 33 | 2,219 | 316 | 316 | 0 | 66,353 |
| 129 | 6 | 339 | 33 | 7 | 26 | 22,574 |
| 130 | 69 | 4,943 | 475 | 463 | 12 | 213,997 |
| 131 | 29 | 1,680 | 148 | 147 | 1 | 46,397 |
| 132 | 6 | 362 | 72 | 62 | 10 | 14,126 |
| 133 | 4 | 201 | 11 | 2 | 9 | 6,551 |
| 134 | 23 | 1,446 | 75 | 52 | 23 | 26,556 |
| 135 | 10 | 666 | 55 | 36 | 19 | 14,827 |
| 136 | 2 | 105 | 3 | 2 | 1 | 1,911 |
| 137 | 0 | 0 | 0 | 0 | 0 | 0 |
| 138 | 174 | 12,568 | 1,122 | 608 | 514 | 492,325 |
| 139 | 80 | 5,236 | 286 | 134 | 152 | 142,327 |
| 140 | 472 | 31,792 | 2,204 | 959 | 1,245 | 753,349 |
| 141 | 85 | 5,775 | 505 | 397 | 108 | 185,644 |
| 142 | 69 | 4,485 | 298 | 206 | 92 | 122,417 |
| 143 | 227 | 12,918 | 893 | 505 | 388 | 375,660 |
| 144 | 55 | 3,416 | 489 | 405 | 84 | 166,902 |
| 145 | 17 | 994 | 81 | 53 | 28 | 33,648 |
| South Shore Hospital | | | | | | |
| 112 | 0 | 0 | 0 | 0 | 0 | 0 |
| 115 | 4 | 325 | 104 | 72 | 32 | 113,587 |
| 116 | 34 | 2,546 | 299 | 193 | 106 | 585,150 |
| 117 | 1 | 71 | 1 | 0 | 1 | 3,654 |
| 118 | 7 | 557 | 19 | 13 | 6 | 79,024 |
| 121 | 167 | 11,501 | 1,498 | 813 | 685 | 1,481,089 |
| 122 | 163 | 10,340 | 1,065 | 583 | 482 | 1,107,913 |
| 123 | 41 | 3,155 | 198 | 86 | 112 | 261,971 |
| 124 | 0 | 0 | 0 | 0 | 0 | 0 |
| 125 | 0 | 0 | 0 | 0 | 0 | 0 |
| 126 | 1 | 62 | 10 | 10 | 0 | 9,753 |
| 127 | 444 | 33,679 | 3,631 | 3,152 | 479 | 2,626,762 |
| 128 | 20 | 1,249 | 143 | 141 | 2 | 87,541 |
| 129 | 3 | 185 | 7 | 1 | 6 | 15,201 |
| 130 | 49 | 3,489 | 318 | 310 | 8 | 224,574 |
| 131 | 34 | 1,955 | 194 | 194 | 0 | 120,697 |
| 132 | 6 | 447 | 26 | 15 | 11 | 33,082 |
| 133 | 1 | 56 | 3 | 0 | 3 | 3,104 |
| 134 | 30 | 1,878 | 121 | 115 | 6 | 86,050 |
| 135 | 10 | 741 | 65 | 61 | 4 | 49,935 |
| 136 | 1 | 29 | 1 | 0 | 1 | 1,991 |
| 137 | 0 | 0 | 0 | 0 | 0 | 0 |
| 138 | 189 | 13,599 | 1,261 | 1,029 | 232 | 1,008,712 |
| 139 | 92 | 5,874 | 268 | 225 | 43 | 229,958 |
| 140 | 518 | 34,826 | 2,171 | 1,562 | 609 | 1,827,545 |
| 141 | 88 | 6,358 | 416 | 395 | 21 | 316,771 |
| 142 | 54 | 3,575 | 154 | 146 | 8 | 132,853 |
| 143 | 465 | 26,820 | 1,350 | 1,007 | 343 | 1,251,787 |
| 144 | 50 | 3,170 | 349 | 245 | 104 | 389,601 |
| 145 | 18 | 995 | 60 | 41 | 19 | 58,608 |
| Charlton Memorial Hospital | | | | | | |
| 112 | 3 | 229 | 39 | 16 | 23 | 71,634 |
| 115 | 50 | 3,756 | 521 | 186 | 335 | 906,332 |
| 116 | 8 | 656 | 76 | 49 | 27 | 94,810 |
| 117 | 1 | 78 | 4 | 0 | 4 | 13,119 |
| 118 | 237 | 17,149 | 2,581 | 1,091 | 1,490 | 2,600,355 |
| 121 | 226 | 14,328 | 1,791 | 636 | 1,155 | 1,862,755 |
| 122 | 51 | 3,933 | 357 | 157 | 200 | 525,887 |
| 123 | 1 | 67 | 13 | 0 | 13 | 15,100 |
| 124 | 3 | 161 | 10 | 5 | 5 | 20,372 |
| 125 | 9 | 644 | 359 | 343 | 16 | 110,276 |
| 126 | 462 | 34,317 | 4,191 | 3,009 | 1,182 | 3,831,544 |
| 127 | 30 | 2,001 | 298 | 296 | 2 | 183,098 |
| 128 | 2 | 134 | 3 | 0 | 3 | 11,131 |
| 129 | 51 | 3,603 | 431 | 415 | 16 | 311,377 |
| 130 | 26 | 1,633 | 159 | 154 | 5 | 124,870 |
| 131 | 15 | 1,012 | 276 | 212 | 64 | 167,024 |
| 132 | 7 | 473 | 42 | 29 | 13 | 36,751 |
| 133 | 36 | 2,395 | 217 | 192 | 25 | 181,351 |
| 134 | 4 | 325 | 39 | 18 | 21 | 29,266 |
| 135 | 1 | 53 | 2 | 0 | 2 | 2,313 |
| 136 | 147 | 10,395 | 859 | 347 | 512 | 868,374 |
| 137 | 130 | 8,340 | 512 | 124 | 388 | 540,868 |
| 138 | 427 | 28,867 | 2,129 | 994 | 1,135 | 2,058,967 |
| 139 | 82 | 5,831 | 502 | 342 | 160 | 461,240 |
| 140 | 57 | 3,901 | 244 | 156 | 88 | 237,176 |
| 141 | 422 | 24,945 | 1,501 | 793 | 708 | 1,618,566 |
| 142 | 46 | 2,810 | 294 | 184 | 110 | 337,094 |
| 143 | 16 | 799 | 42 | 14 | 28 | 56,659 |
| 144 | 0 | 0 | 0 | 0 | 0 | 0 |
| 145 | 0 | 0 | 0 | 0 | 0 | 0 |

TABLE IV-continued

| | Cases | Age | Tot Days | Rout Days | ICU Days | Charges |
|---|---|---|---|---|---|---|
| Cape Cod Hospital | | | | | | |
| 112 | 0 | 0 | 0 | 0 | 0 | 0 |
| 115 | 2 | 168 | 26 | 16 | 10 | 45,873 |
| 116 | 74 | 5,732 | 478 | 367 | 111 | 1,051,377 |
| 117 | 14 | 1,133 | 63 | 40 | 23 | 114,391 |
| 118 | 3 | 219 | 6 | 3 | 3 | 18,589 |
| 121 | 169 | 12,250 | 1,322 | 774 | 548 | 1,577,342 |
| 122 | 188 | 12,787 | 1,089 | 573 | 516 | 1,355,656 |
| 123 | 43 | 3,429 | 189 | 83 | 106 | 276,924 |
| 124 | 0 | 0 | 0 | 0 | 0 | 0 |
| 125 | 0 | 0 | 0 | 0 | 0 | 0 |
| 126 | 9 | 557 | 166 | 159 | 7 | 137,384 |
| 127 | 420 | 32,699 | 2,870 | 2,493 | 377 | 2,704,085 |
| 128 | 24 | 1,726 | 192 | 189 | 3 | 156,397 |
| 129 | 5 | 356 | 12 | 2 | 10 | 27,398 |
| 130 | 59 | 4,279 | 330 | 320 | 10 | 285,914 |
| 131 | 44 | 3,139 | 159 | 154 | 5 | 136,871 |
| 132 | 7 | 508 | 34 | 13 | 21 | 52,789 |
| 133 | 6 | 420 | 27 | 16 | 11 | 29,667 |
| 134 | 11 | 684 | 37 | 31 | 6 | 38,527 |
| 135 | 9 | 643 | 59 | 50 | 9 | 59,649 |
| 136 | 1 | 27 | 1 | 0 | 1 | 1,764 |
| 137 | 1 | 0 | 1 | 1 | 0 | 719 |
| 138 | 154 | 11,390 | 941 | 714 | 227 | 1,115,043 |
| 139 | 130 | 9,396 | 440 | 314 | 126 | 538,211 |
| 140 | 454 | 32,556 | 1,708 | 968 | 740 | 1,969,111 |
| 141 | 57 | 4,487 | 337 | 312 | 25 | 328,169 |
| 142 | 40 | 2,839 | 134 | 112 | 22 | 159,662 |
| 143 | 314 | 19,490 | 907 | 477 | 430 | 1,159,274 |
| 144 | 43 | 2,834 | 282 | 249 | 33 | 311,912 |
| 145 | 16 | 1,068 | 39 | 25 | 14 | 57,596 |
| Brockton Hospital | | | | | | |
| 112 | 0 | 0 | 0 | 0 | 0 | 0 |
| 115 | 3 | 238 | 53 | 30 | 23 | 96,246 |
| 116 | 19 | 1,438 | 157 | 117 | 40 | 386,684 |
| 117 | 0 | 0 | 0 | 0 | 0 | 0 |
| 118 | 3 | 214 | 31 | 23 | 8 | 63,573 |
| 121 | 133 | 9,064 | 1,225 | 916 | 309 | 1,253,767 |
| 122 | 79 | 4,909 | 518 | 378 | 140 | 512,349 |
| 123 | 22 | 1,674 | 138 | 85 | 53 | 214,770 |
| 124 | 0 | 0 | 0 | 0 | 0 | 0 |
| 125 | 0 | 0 | 0 | 0 | 0 | 0 |
| 126 | 9 | 503 | 214 | 214 | 0 | 134,183 |
| 127 | 294 | 22,198 | 2,270 | 2,133 | 137 | 1,890,188 |
| 128 | 14 | 917 | 137 | 137 | 0 | 83,332 |
| 129 | 3 | 201 | 3 | 0 | 3 | 8,099 |
| 130 | 61 | 4,164 | 414 | 396 | 18 | 438,256 |
| 131 | 32 | 2,083 | 164 | 162 | 2 | 127,703 |
| 132 | 5 | 364 | 43 | 36 | 7 | 71,424 |
| 133 | 1 | 61 | 1 | 1 | 0 | 1,276 |
| 134 | 14 | 857 | 89 | 89 | 0 | 65,208 |
| 135 | 1 | 87 | 21 | 21 | 0 | 10,976 |
| 136 | 1 | 23 | 2 | 2 | 0 | 2,053 |
| 137 | 0 | 0 | 0 | 0 | 0 | 0 |
| 138 | 111 | 7,813 | 724 | 640 | 84 | 658,787 |
| 139 | 60 | 3,545 | 199 | 196 | 3 | 175,362 |
| 140 | 308 | 20,437 | 1,229 | 1,021 | 208 | 1,171,258 |
| 141 | 76 | 5,255 | 520 | 517 | 3 | 380,252 |
| 142 | 27 | 1,790 | 110 | 110 | 0 | 103,124 |
| 143 | 186 | 10,305 | 506 | 469 | 37 | 539,606 |
| 144 | 55 | 3,487 | 342 | 316 | 26 | 423,431 |
| 145 | 10 | 627 | 30 | 27 | 3 | 37,514 |
| Norwood Hospital | | | | | | |
| 112 | 1 | 72 | 4 | 4 | 0 | 4,959 |
| 115 | 8 | 613 | 89 | 66 | 23 | 180,463 |
| 116 | 33 | 2,602 | 280 | 263 | 17 | 533,329 |
| 117 | 3 | 241 | 33 | 32 | 1 | 31,699 |
| 118 | 9 | 669 | 47 | 46 | 1 | 133,451 |
| 121 | 120 | 8,718 | 957 | 694 | 263 | 1,382,219 |
| 122 | 102 | 6,412 | 533 | 358 | 175 | 875,377 |
| 123 | 20 | 1,555 | 80 | 35 | 45 | 192,400 |
| 124 | 0 | 0 | 0 | 0 | 0 | 0 |
| 125 | 0 | 0 | 0 | 0 | 0 | 0 |
| 126 | 5 | 375 | 41 | 41 | 0 | 49,052 |
| 127 | 370 | 28,305 | 2,522 | 2,399 | 123 | 2,500,769 |
| 128 | 11 | 690 | 76 | 76 | 0 | 58,318 |
| 129 | 8 | 425 | 23 | 8 | 15 | 68,279 |
| 130 | 28 | 2,069 | 178 | 174 | 4 | 150,373 |
| 131 | 15 | 769 | 79 | 79 | 0 | 74,214 |
| 132 | 4 | 320 | 41 | 36 | 5 | 53,438 |
| 133 | 0 | 0 | 0 | 0 | 0 | 0 |
| 134 | 10 | 593 | 39 | 39 | 0 | 42,423 |
| 135 | 7 | 459 | 32 | 32 | 0 | 35,245 |
| 136 | 3 | 182 | 10 | 9 | 1 | 10,921 |
| 137 | 0 | 0 | 0 | 0 | 0 | 0 |
| 138 | 107 | 7,580 | 480 | 450 | 30 | 555,751 |
| 139 | 67 | 4,032 | 177 | 169 | 8 | 230,005 |
| 140 | 350 | 23,954 | 1,308 | 1,183 | 125 | 1,397,540 |
| 141 | 53 | 3,793 | 343 | 343 | 0 | 241,855 |
| 142 | 51 | 3,046 | 151 | 150 | 1 | 187,181 |
| 143 | 225 | 12,751 | 528 | 496 | 32 | 700,393 |
| 144 | 39 | 2,414 | 242 | 232 | 10 | 276,347 |
| 145 | 12 | 560 | 24 | 22 | 2 | 42,447 |
| Goddard Memorial Hospital | | | | | | |
| 112 | 0 | 0 | 0 | 0 | 0 | 0 |
| 115 | 10 | 804 | 202 | 124 | 78 | 342,709 |
| 116 | 51 | 3,846 | 503 | 410 | 93 | 1,214,734 |
| 117 | 4 | 317 | 23 | 19 | 4 | 43,941 |
| 118 | 5 | 359 | 21 | 19 | 2 | 89,641 |
| 121 | 71 | 4,939 | 492 | 291 | 201 | 549,870 |
| 122 | 77 | 4,980 | 430 | 228 | 202 | 481,084 |
| 123 | 24 | 1,884 | 196 | 72 | 124 | 256,091 |
| 124 | 0 | 0 | 0 | 0 | 0 | 0 |
| 125 | 0 | 0 | 0 | 0 | 0 | 0 |
| 126 | 6 | 303 | 1,003 | 988 | 15 | 448,675 |
| 127 | 209 | 15,544 | 1,684 | 1,393 | 291 | 1,430,383 |
| 128 | 22 | 1,529 | 227 | 226 | 1 | 137,178 |
| 129 | 2 | 105 | 9 | 1 | 8 | 17,279 |
| 130 | 12 | 750 | 35 | 35 | 0 | 29,543 |
| 131 | 21 | 1,273 | 38 | 37 | 1 | 43,678 |
| 132 | 1 | 82 | 13 | 8 | 5 | 13,926 |
| 133 | 0 | 0 | 0 | 0 | 0 | 0 |
| 134 | 18 | 982 | 65 | 44 | 21 | 63,412 |
| 135 | 1 | 51 | 2 | 2 | 0 | 1,613 |
| 136 | 1 | 32 | 1 | 1 | 0 | 1,776 |
| 137 | 0 | 0 | 0 | 0 | 0 | 0 |
| 138 | 107 | 7,537 | 714 | 603 | 111 | 565,967 |
| 139 | 75 | 4,883 | 236 | 198 | 38 | 215,105 |
| 140 | 320 | 21,186 | 1,357 | 998 | 359 | 1,233,676 |
| 141 | 82 | 5,599 | 483 | 451 | 32 | 401,870 |
| 142 | 49 | 2,887 | 190 | 182 | 8 | 164,344 |
| 143 | 238 | 13,515 | 730 | 632 | 98 | 711,766 |
| 144 | 34 | 2,064 | 169 | 155 | 14 | 163,338 |
| 145 | 8 | 419 | 27 | 23 | 4 | 21,265 |
| Cardinal Cushing General Hospital | | | | | | |
| 112 | 6 | 475 | 117 | 84 | 33 | 132,069 |
| 115 | 45 | 3,368 | 616 | 506 | 110 | 768,035 |
| 116 | 3 | 183 | 18 | 12 | 6 | 19,006 |
| 117 | 5 | 344 | 11 | 4 | 7 | 35,625 |
| 118 | 116 | 7,890 | 945 | 615 | 330 | 864,042 |
| 121 | 88 | 5,720 | 561 | 400 | 161 | 494,780 |
| 122 | 28 | 2,241 | 181 | 115 | 66 | 188,010 |
| 123 | 0 | 0 | 0 | 0 | 0 | 0 |
| 124 | 0 | 0 | 0 | 0 | 0 | 0 |
| 125 | 7 | 453 | 126 | 124 | 2 | 80,232 |
| 126 | 374 | 28,321 | 2,762 | 2,459 | 303 | 1,948,897 |
| 127 | 31 | 1,876 | 237 | 237 | 0 | 162,749 |
| 128 | 4 | 276 | 10 | 8 | 2 | 9,888 |
| 129 | 54 | 3,799 | 470 | 461 | 9 | 273,483 |
| 130 | 28 | 1,665 | 201 | 201 | 0 | 111,132 |
| 131 | 1 | 77 | 3 | 3 | 0 | 3,215 |
| 132 | 1 | 78 | 14 | 10 | 4 | 8,501 |
| 133 | 34 | 2,117 | 159 | 130 | 29 | 114,773 |
| 134 | 5 | 306 | 32 | 26 | 6 | 23,325 |
| 135 | 3 | 203 | 9 | 9 | 0 | 4,990 |

TABLE IV-continued

|  | Cases | Age | Tot Days | Rout Days | ICU Days | Charges |
|---|---|---|---|---|---|---|
| 136 | 123 | 8,666 | 753 | 663 | 90 | 528,142 |
| 137 | 54 | 3,324 | 179 | 166 | 13 | 135,474 |
| 138 | 441 | 29,502 | 2,245 | 1,880 | 365 | 1,640,181 |
| 139 | 60 | 4,330 | 412 | 397 | 15 | 255,705 |
| 140 | 32 | 2,091 | 104 | 98 | 6 | 84,350 |
| 141 | 198 | 11,257 | 623 | 559 | 64 | 529,226 |
| 142 | 41 | 2,624 | 251 | 201 | 50 | 243,737 |
| 143 | 5 | 301 | 23 | 19 | 4 | 29,676 |
| 144 | 0 | 0 | 0 | 0 | 0 | 0 |
| 145 | 0 | 0 | 0 | 0 | 0 | 0 |

TABLE V

|  | Medical/Surgical Routine | Obstetrics Routine | Pediatric Routine | Psychiatric Routine | Other Routine | Newborn Routine | Neonatal ICU |
|---|---|---|---|---|---|---|---|
| St. Luke's Hospital of New Bedford | | | | | | | |
| 112 | 0 | 0 | 0 | 0 | 0 | 0 | 0 |
| 115 | 1,268 | 0 | 0 | 0 | 0 | 0 | 0 |
| 116 | 10,501 | 0 | 0 | 0 | 0 | 0 | 0 |
| 117 | 57 | 0 | 0 | 0 | 0 | 0 | 0 |
| 118 | 396 | 0 | 0 | 0 | 0 | 0 | 0 |
| 121 | 29,783 | 0 | 0 | 0 | 0 | 0 | 0 |
| 122 | 7,555 | 0 | 0 | 0 | 0 | 0 | 0 |
| 123 | 3,376 | 0 | 0 | 0 | 0 | 0 | 0 |
| 124 | 4,321 | 0 | 0 | 0 | 0 | 0 | 0 |
| 125 | 2,484 | 0 | 0 | 0 | 0 | 0 | 0 |
| 126 | 6,434 | 0 | 0 | 0 | 0 | 0 | 0 |
| 127 | 120,074 | 0 | 266 | 0 | 0 | 0 | 0 |
| 128 | 7,422 | 0 | 152 | 0 | 0 | 0 | 0 |
| 129 | 137 | 0 | 0 | 0 | 0 | 0 | 0 |
| 130 | 14,321 | 0 | 0 | 0 | 0 | 0 | 0 |
| 131 | 5,220 | 0 | 19 | 0 | 0 | 0 | 0 |
| 132 | 1,508 | 0 | 38 | 0 | 0 | 0 | 0 |
| 133 | 149 | 0 | 0 | 0 | 0 | 0 | 0 |
| 134 | 1,457 | 0 | 0 | 0 | 0 | 0 | 0 |
| 135 | 729 | 0 | 0 | 0 | 0 | 0 | 0 |
| 136 | 42 | 0 | 0 | 0 | 0 | 0 | 0 |
| 137 | 0 | 0 | 0 | 0 | 0 | 0 | 0 |
| 138 | 19,702 | 0 | 38 | 34 | 0 | 0 | 0 |
| 139 | 3,798 | 0 | 0 | 0 | 0 | 0 | 0 |
| 140 | 28,008 | 0 | 19 | 0 | 0 | 0 | 0 |
| 141 | 13,247 | 0 | 57 | 0 | 0 | 0 | 0 |
| 142 | 6,160 | 0 | 23 | 0 | 0 | 0 | 0 |
| 143 | 14,336 | 0 | 42 | 0 | 0 | 0 | 0 |
| 144 | 16,480 | 0 | 133 | 0 | 0 | 0 | 0 |
| 145 | 1,840 | 0 | 0 | 0 | 0 | 0 | 0 |
| South Shore Hospital | | | | | | | |
| 112 | 0 | 0 | 0 | 0 | 0 | 0 | 0 |
| 115 | 31,075 | 0 | 0 | 0 | 0 | 0 | 0 |
| 116 | 81,790 | 0 | 0 | 0 | 0 | 0 | 0 |
| 117 | 0 | 0 | 0 | 0 | 0 | 0 | 0 |
| 118 | 5,485 | 0 | 0 | 0 | 0 | 0 | 0 |
| 121 | 347,900 | 0 | 0 | 0 | 0 | 0 | 0 |
| 122 | 250,020 | 0 | 0 | 0 | 0 | 0 | 0 |
| 123 | 36,905 | 0 | 0 | 0 | 0 | 0 | 0 |
| 124 | 0 | 0 | 0 | 0 | 0 | 0 | 0 |
| 125 | 0 | 0 | 0 | 0 | 0 | 0 | 0 |
| 126 | 4,500 | 0 | 0 | 0 | 0 | 0 | 0 |
| 127 | 1,342,730 | 0 | 0 | 0 | 0 | 0 | 0 |
| 128 | 59,460 | 0 | 0 | 0 | 0 | 0 | 0 |
| 129 | 410 | 0 | 0 | 0 | 0 | 0 | 0 |
| 130 | 132,725 | 0 | 0 | 0 | 0 | 0 | 0 |
| 131 | 81,245 | 0 | 0 | 0 | 0 | 0 | 0 |
| 132 | 6,425 | 0 | 0 | 0 | 0 | 0 | 0 |
| 133 | 0 | 0 | 0 | 0 | 0 | 0 | 0 |
| 134 | 49,015 | 0 | 0 | 0 | 0 | 0 | 0 |

TABLE V-continued

| | | | | | | | |
|---|---:|---:|---:|---:|---:|---:|---:|
| 135 | 25,750 | 0 | 0 | 0 | 0 | 0 | 0 |
| 136 | 0 | 0 | 0 | 0 | 0 | 0 | 0 |
| 137 | 0 | 0 | 0 | 0 | 0 | 0 | 0 |
| 138 | 441,520 | 0 | 0 | 0 | 0 | 0 | 0 |
| 139 | 97,185 | 0 | 0 | 0 | 0 | 0 | 0 |
| 140 | 669,230 | 0 | 0 | 0 | 0 | 0 | 0 |
| 141 | 169,750 | 0 | 0 | 0 | 0 | 0 | 0 |
| 142 | 62,430 | 0 | 0 | 0 | 0 | 0 | 0 |
| 143 | 434,365 | 0 | 0 | 0 | 0 | 0 | 0 |
| 144 | 105,185 | 0 | 0 | 0 | 0 | 0 | 0 |
| 145 | 17,525 | 0 | 0 | 0 | 0 | 0 | 0 |
| Charlton Memorial Hospital | | | | | | | |
| 112 | 6,192 | 0 | 0 | 0 | 0 | 0 | 0 |
| 115 | 55,834 | 0 | 0 | 0 | 0 | 0 | 0 |
| 116 | 19,189 | 0 | 0 | 0 | 0 | 0 | 0 |
| 117 | 0 | 0 | 0 | 0 | 0 | 0 | 0 |
| 118 | 371,237 | 0 | 0 | 0 | 0 | 0 | 0 |
| 121 | 219,182 | 0 | 0 | 0 | 0 | 0 | 0 |
| 122 | 43,672 | 0 | 0 | 0 | 0 | 0 | 0 |
| 123 | 0 | 0 | 0 | 0 | 0 | 0 | 0 |
| 124 | 2,215 | 0 | 0 | 0 | 0 | 0 | 0 |
| 125 | 19,925 | 0 | 0 | 0 | 0 | 0 | 0 |
| 126 | 1,034,659 | 0 | 0 | 0 | 0 | 0 | 0 |
| 127 | 108,856 | 0 | 0 | 0 | 0 | 0 | 0 |
| 128 | 0 | 0 | 0 | 0 | 0 | 0 | 0 |
| 129 | 157,637 | 0 | 0 | 0 | 0 | 0 | 0 |
| 130 | 62,942 | 0 | 0 | 0 | 0 | 0 | 0 |
| 131 | 33,066 | 0 | 0 | 0 | 0 | 0 | 0 |
| 132 | 11,687 | 0 | 0 | 0 | 0 | 0 | 0 |
| 133 | 76,261 | 0 | 0 | 0 | 0 | 0 | 0 |
| 134 | 7,230 | 0 | 0 | 0 | 0 | 0 | 0 |
| 135 | 0 | 0 | 0 | 0 | 0 | 0 | 0 |
| 136 | 144,264 | 0 | 0 | 0 | 0 | 0 | 0 |
| 137 | 48,886 | 0 | 0 | 0 | 0 | 0 | 0 |
| 138 | 377,388 | 0 | 0 | 0 | 0 | 0 | 0 |
| 139 | 108,132 | 0 | 0 | 0 | 0 | 0 | 0 |
| 140 | 53,702 | 0 | 0 | 0 | 0 | 0 | 0 |
| 141 | 324,585 | 0 | 0 | 0 | 0 | 0 | 0 |
| 142 | 73,490 | 0 | 0 | 0 | 0 | 0 | 0 |
| 143 | 5,738 | 0 | 0 | 0 | 0 | 0 | 0 |
| 144 | 0 | 0 | 0 | 0 | 0 | 0 | 0 |
| 145 | 0 | 0 | 0 | 0 | 0 | 0 | 0 |
| Cape Cod Hospital | | | | | | | |
| 112 | 0 | 0 | 0 | 0 | 0 | 0 | 0 |
| 115 | 7,910 | 0 | 0 | 0 | 0 | 0 | 0 |
| 116 | 182,450 | 0 | 0 | 0 | 0 | 0 | 0 |
| 117 | 19,930 | 0 | 0 | 0 | 0 | 0 | 0 |
| 118 | 1,500 | 0 | 0 | 0 | 0 | 0 | 0 |
| 121 | 383,805 | 0 | 0 | 0 | 0 | 0 | 0 |
| 122 | 281,750 | 0 | 0 | 0 | 0 | 0 | 0 |
| 123 | 40,684 | 0 | 0 | 0 | 0 | 0 | 0 |
| 124 | 0 | 0 | 0 | 0 | 0 | 0 | 0 |
| 125 | 0 | 0 | 0 | 0 | 0 | 0 | 0 |
| 126 | 78,410 | 0 | 0 | 0 | 0 | 0 | 0 |
| 127 | 1,225,709 | 0 | 0 | 0 | 0 | 0 | 0 |
| 128 | 90,130 | 0 | 1,650 | 0 | 0 | 0 | 0 |
| 129 | 1,000 | 0 | 0 | 0 | 0 | 0 | 0 |
| 130 | 156,925 | 0 | 0 | 0 | 0 | 0 | 0 |
| 131 | 75,690 | 0 | 0 | 0 | 0 | 0 | 0 |
| 132 | 6,470 | 0 | 0 | 0 | 0 | 0 | 0 |
| 133 | 7,930 | 0 | 0 | 0 | 0 | 0 | 0 |
| 134 | 15,300 | 0 | 0 | 0 | 0 | 0 | 0 |
| 135 | 24,720 | 0 | 0 | 0 | 0 | 0 | 0 |
| 136 | 0 | 0 | 0 | 0 | 0 | 0 | 0 |
| 137 | 0 | 0 | 330 | 0 | 0 | 0 | 0 |
| 138 | 353,235 | 0 | 0 | 0 | 0 | 0 | 0 |
| 139 | 155,798 | 0 | 0 | 0 | 0 | 0 | 0 |
| 140 | 478,106 | 0 | 0 | 0 | 0 | 0 | 0 |
| 141 | 152,175 | 0 | 0 | 0 | 0 | 0 | 0 |
| 142 | 54,430 | 0 | 0 | 0 | 0 | 0 | 0 |
| 143 | 235,018 | 0 | 0 | 0 | 0 | 0 | 0 |
| 144 | 123,255 | 0 | 0 | 0 | 0 | 0 | 0 |
| 145 | 12,382 | 0 | 0 | 0 | 0 | 0 | 0 |
| Brockton Hospital | | | | | | | |
| 112 | 0 | 0 | 0 | 0 | 0 | 0 | 0 |

TABLE V-continued

| | | | | | | | |
|---|---:|---:|---:|---:|---:|---:|---:|
| 115 | 8,398 | 0 | 0 | 0 | 0 | 0 | 0 |
| 116 | 31,102 | 0 | 0 | 0 | 0 | 0 | 0 |
| 117 | 0 | 0 | 0 | 0 | 0 | 0 | 0 |
| 118 | 6,108 | 0 | 0 | 0 | 0 | 0 | 0 |
| 121 | 243,660 | 0 | 0 | 0 | 0 | 0 | 0 |
| 122 | 100,947 | 0 | 0 | 0 | 0 | 0 | 0 |
| 123 | 22,637 | 0 | 0 | 0 | 0 | 0 | 0 |
| 124 | 0 | 0 | 0 | 0 | 0 | 0 | 0 |
| 125 | 0 | 0 | 0 | 0 | 0 | 0 | 0 |
| 126 | 57,434 | 0 | 0 | 0 | 0 | 0 | 0 |
| 127 | 569,749 | 0 | 0 | 0 | 0 | 0 | 0 |
| 128 | 36,305 | 0 | 0 | 0 | 0 | 0 | 0 |
| 129 | 0 | 0 | 0 | 0 | 0 | 0 | 0 |
| 130 | 103,655 | 2,344 | 0 | 0 | 0 | 0 | 0 |
| 131 | 43,092 | 0 | 0 | 0 | 0 | 0 | 0 |
| 132 | 9,540 | 0 | 0 | 0 | 0 | 0 | 0 |
| 133 | 265 | 0 | 0 | 0 | 0 | 0 | 0 |
| 134 | 23,697 | 0 | 0 | 0 | 0 | 0 | 0 |
| 135 | 5,565 | 0 | 0 | 0 | 0 | 0 | 0 |
| 136 | 530 | 0 | 0 | 0 | 0 | 0 | 0 |
| 137 | 0 | 0 | 0 | 0 | 0 | 0 | 0 |
| 138 | 171,172 | 0 | 0 | 0 | 0 | 0 | 0 |
| 139 | 51,529 | 0 | 528 | 0 | 0 | 0 | 0 |
| 140 | 272,258 | 0 | 0 | 0 | 0 | 0 | 0 |
| 141 | 138,051 | 265 | 0 | 0 | 0 | 0 | 0 |
| 142 | 29,241 | 0 | 0 | 0 | 0 | 0 | 0 |
| 143 | 124,163 | 0 | 792 | 0 | 0 | 0 | 0 |
| 144 | 84,192 | 0 | 0 | 0 | 0 | 0 | 0 |
| 145 | 7,194 | 0 | 0 | 0 | 0 | 0 | 0 |
| Norwood Hospital | | | | | | | |
| 112 | 1,336 | 0 | 0 | 0 | 0 | 0 | 0 |
| 115 | 23,794 | 0 | 0 | 0 | 0 | 0 | 0 |
| 116 | 80,898 | 0 | 0 | 0 | 0 | 0 | 0 |
| 117 | 10,688 | 0 | 0 | 0 | 0 | 0 | 0 |
| 118 | 17,100 | 0 | 0 | 0 | 0 | 0 | 0 |
| 121 | 254,498 | 0 | 0 | 0 | 0 | 0 | 0 |
| 122 | 128,222 | 0 | 0 | 0 | 0 | 0 | 0 |
| 123 | 13,648 | 0 | 0 | 0 | 0 | 0 | 0 |
| 124 | 0 | 0 | 0 | 0 | 0 | 0 | 0 |
| 125 | 0 | 0 | 0 | 0 | 0 | 0 | 0 |
| 126 | 15,044 | 0 | 0 | 0 | 0 | 0 | 0 |
| 127 | 857,266 | 0 | 0 | 0 | 0 | 0 | 0 |
| 128 | 27,376 | 0 | 0 | 0 | 0 | 0 | 0 |
| 129 | 2,672 | 0 | 0 | 0 | 0 | 0 | 0 |
| 130 | 62,075 | 0 | 0 | 0 | 0 | 0 | 0 |
| 131 | 29,994 | 0 | 0 | 0 | 0 | 0 | 0 |
| 132 | 13,638 | 0 | 0 | 0 | 0 | 0 | 0 |
| 133 | 0 | 0 | 0 | 0 | 0 | 0 | 0 |
| 134 | 13,926 | 0 | 0 | 0 | 0 | 0 | 0 |
| 135 | 10,838 | 0 | 0 | 0 | 0 | 0 | 0 |
| 136 | 3,356 | 0 | 0 | 0 | 0 | 0 | 0 |
| 137 | 0 | 0 | 0 | 0 | 0 | 0 | 0 |
| 138 | 160,184 | 0 | 0 | 0 | 0 | 0 | 0 |
| 139 | 61,765 | 0 | 0 | 0 | 0 | 0 | 0 |
| 140 | 408,657 | 0 | 0 | 0 | 0 | 0 | 0 |
| 141 | 97,535 | 0 | 0 | 0 | 0 | 0 | 0 |
| 142 | 56,071 | 0 | 0 | 0 | 0 | 0 | 0 |
| 143 | 175,902 | 0 | 0 | 0 | 0 | 0 | 0 |
| 144 | 82,496 | 0 | 0 | 0 | 0 | 0 | 0 |
| 145 | 8,098 | 0 | 0 | 0 | 0 | 0 | 0 |
| Goddard Memorial Hospital | | | | | | | |
| 112 | 0 | 0 | 0 | 0 | 0 | 0 | 0 |
| 115 | 47,086 | 0 | 0 | 0 | 0 | 0 | 0 |
| 116 | 161,633 | 0 | 0 | 0 | 0 | 0 | 0 |
| 117 | 8,241 | 0 | 0 | 0 | 0 | 0 | 0 |
| 118 | 9,880 | 0 | 0 | 0 | 0 | 0 | 0 |
| 121 | 104,701 | 0 | 0 | 0 | 0 | 0 | 0 |
| 122 | 77,788 | 0 | 0 | 0 | 0 | 0 | 0 |
| 123 | 25,830 | 0 | 0 | 0 | 0 | 0 | 0 |
| 124 | 0 | 0 | 0 | 0 | 0 | 0 | 0 |
| 125 | 0 | 0 | 0 | 0 | 0 | 0 | 0 |
| 126 | 325,013 | 0 | 0 | 0 | 0 | 0 | 0 |
| 127 | 501,084 | 0 | 0 | 0 | 0 | 0 | 0 |
| 128 | 78,693 | 0 | 0 | 0 | 0 | 0 | 0 |
| 129 | 372 | 0 | 0 | 0 | 0 | 0 | 0 |
| 130 | 13,146 | 0 | 0 | 0 | 0 | 0 | 0 |

TABLE V-continued

| | | | | | | | |
|---|---:|---:|---:|---:|---:|---:|---:|
| 131 | 14,919 | 0 | 0 | 0 | 0 | 0 | 0 |
| 132 | 2,976 | 0 | 0 | 0 | 0 | 0 | 0 |
| 133 | 0 | 0 | 0 | 0 | 0 | 0 | 0 |
| 134 | 15,626 | 0 | 0 | 0 | 0 | 0 | 0 |
| 135 | 744 | 0 | 0 | 0 | 0 | 0 | 0 |
| 136 | 372 | 0 | 0 | 0 | 0 | 0 | 0 |
| 137 | 0 | 0 | 0 | 0 | 0 | 0 | 0 |
| 138 | 216,631 | 0 | 0 | 0 | 0 | 0 | 0 |
| 139 | 70,744 | 0 | 0 | 0 | 0 | 0 | 0 |
| 140 | 355,365 | 0 | 0 | 0 | 0 | 0 | 0 |
| 141 | 158,755 | 0 | 838 | 0 | 0 | 0 | 0 |
| 142 | 62,829 | 0 | 838 | 0 | 0 | 0 | 0 |
| 143 | 222,617 | 0 | 0 | 0 | 0 | 0 | 0 |
| 144 | 51,155 | 0 | 0 | 0 | 0 | 0 | 0 |
| 145 | 8,291 | 0 | 0 | 0 | 0 | 0 | 0 |
| Cardinal Cushing General Hospital | | | | | | | |
| 112 | 27,930 | 0 | 0 | 0 | 0 | 0 | 0 |
| 115 | 167,102 | 0 | 0 | 0 | 0 | 0 | 0 |
| 116 | 3,866 | 0 | 0 | 0 | 0 | 0 | 0 |
| 117 | 1,412 | 0 | 0 | 0 | 0 | 0 | 0 |
| 118 | 243,095 | 0 | 0 | 0 | 0 | 0 | 0 |
| 121 | 163,868 | 0 | 0 | 0 | 0 | 0 | 0 |
| 122 | 40,415 | 0 | 0 | 0 | 0 | 0 | 0 |
| 123 | 0 | 0 | 0 | 0 | 0 | 0 | 0 |
| 124 | 0 | 0 | 0 | 0 | 0 | 0 | 0 |
| 125 | 40,494 | 0 | 100 | 0 | 0 | 0 | 0 |
| 126 | 923,809 | 0 | 4,484 | 0 | 0 | 0 | 0 |
| 127 | 95,914 | 0 | 4,900 | 0 | 0 | 0 | 0 |
| 128 | 2,700 | 0 | 0 | 0 | 0 | 0 | 0 |
| 129 | 160,204 | 0 | 4,948 | 0 | 0 | 0 | 0 |
| 130 | 72,205 | 0 | 0 | 0 | 0 | 0 | 0 |
| 131 | 1,092 | 0 | 0 | 0 | 0 | 0 | 0 |
| 132 | 2,980 | 0 | 0 | 0 | 0 | 0 | 0 |
| 133 | 45,722 | 0 | 0 | 0 | 0 | 0 | 0 |
| 134 | 8,894 | 0 | 0 | 0 | 0 | 0 | 0 |
| 135 | 2,734 | 0 | 0 | 0 | 0 | 0 | 0 |
| 136 | 254,312 | 0 | 0 | 0 | 0 | 0 | 0 |
| 137 | 59,796 | 0 | 0 | 0 | 0 | 0 | 0 |
| 138 | 696,940 | 0 | 1,400 | 0 | 0 | 0 | 0 |
| 139 | 138,393 | 0 | 100 | 0 | 0 | 0 | 0 |
| 140 | 36,917 | 0 | 0 | 0 | 0 | 0 | 0 |
| 141 | 221,572 | 0 | 2,636 | 0 | 0 | 0 | 0 |
| 142 | 82,791 | 0 | 0 | 0 | 0 | 0 | 0 |
| 143 | 9,696 | 0 | 0 | 0 | 0 | 0 | 0 |
| 144 | 0 | 0 | 0 | 0 | 0 | 0 | 0 |
| 145 | 0 | 0 | 0 | 0 | 0 | 0 | 0 |

| | Medical/Surgical ICU | Pediatric ICU | Psychiatric ICU | Burn Unit | Other ICU | Coronary Care Unit | Pharmacy |
|---|---:|---:|---:|---:|---:|---:|---:|
| St. Luke's Hospital of New Bedford | | | | | | | |
| 112 | 0 | 0 | 0 | 0 | 0 | 0 | 0 |
| 115 | 1,844 | 0 | 0 | 0 | 3,239 | 0 | 3,644 |
| 116 | 3,888 | 0 | 0 | 0 | 16,414 | 0 | 8,672 |
| 117 | 0 | 0 | 0 | 0 | 25 | 0 | 12 |
| 118 | 132 | 0 | 0 | 0 | 254 | 0 | 688 |
| 121 | 41,139 | 0 | 0 | 0 | 34,999 | 0 | 96,427 |
| 122 | 20,085 | 0 | 0 | 0 | 30,194 | 0 | 75,213 |
| 123 | 7,851 | 0 | 0 | 0 | 1,327 | 0 | 30,413 |
| 124 | 2,352 | 0 | 0 | 0 | 4,160 | 0 | 4,660 |
| 125 | 148 | 0 | 0 | 0 | 1,877 | 0 | 702 |
| 126 | 581 | 0 | 0 | 0 | 0 | 0 | 9,756 |
| 127 | 17,692 | 0 | 0 | 0 | 31,712 | 0 | 114,259 |
| 128 | 0 | 0 | 0 | 0 | 0 | 0 | 3,813 |
| 129 | 870 | 0 | 0 | 0 | 0 | 0 | 1,827 |
| 130 | 165 | 0 | 0 | 0 | 183 | 0 | 11,545 |
| 131 | 33 | 0 | 0 | 0 | 0 | 0 | 1,005 |
| 132 | 99 | 0 | 0 | 0 | 739 | 0 | 2,490 |
| 133 | 132 | 0 | 0 | 0 | 575 | 0 | 306 |
| 134 | 313 | 0 | 0 | 0 | 804 | 0 | 770 |
| 135 | 99 | 0 | 0 | 0 | 404 | 0 | 551 |
| 136 | 37 | 0 | 0 | 0 | 0 | 0 | 36 |
| 137 | 0 | 0 | 0 | 0 | 0 | 0 | 0 |
| 138 | 5,276 | 0 | 0 | 0 | 19,214 | 0 | 16,907 |
| 139 | 1,119 | 0 | 0 | 0 | 3,761 | 0 | 3,229 |

TABLE V-continued

| | | | | | | | |
|---|---|---|---|---|---|---|---|
| 140 | 11,837 | 0 | 0 | 0 | 43,055 | 0 | 44,011 |
| 141 | 715 | 0 | 0 | 0 | 4,560 | 0 | 4,476 |
| 142 | 132 | 0 | 0 | 0 | 4,273 | 0 | 1,724 |
| 143 | 3,755 | 0 | 0 | 0 | 9,784 | 0 | 12,003 |
| 144 | 675 | 0 | 0 | 0 | 3,249 | 0 | 16,603 |
| 145 | 484 | 0 | 0 | 0 | 1,241 | 0 | 1,219 |
| South Shore Hospital | | | | | | | |
| 112 | 0 | 0 | 0 | 0 | 0 | 0 | 0 |
| 115 | 23,450 | 0 | 0 | 0 | 0 | 0 | 3,160 |
| 116 | 76,740 | 0 | 0 | 0 | 0 | 0 | 7,783 |
| 117 | 725 | 0 | 0 | 0 | 0 | 0 | 29 |
| 118 | 3,930 | 0 | 0 | 0 | 0 | 0 | 2,582 |
| 121 | 497,575 | 0 | 0 | 0 | 0 | 0 | 163,664 |
| 122 | 353,335 | 0 | 0 | 0 | 0 | 0 | 155,711 |
| 123 | 82,100 | 0 | 0 | 0 | 0 | 0 | 33,001 |
| 124 | 0 | 0 | 0 | 0 | 0 | 0 | 0 |
| 125 | 0 | 0 | 0 | 0 | 0 | 0 | 0 |
| 126 | 0 | 0 | 0 | 0 | 0 | 0 | 748 |
| 127 | 347,260 | 0 | 0 | 0 | 0 | 0 | 122,244 |
| 128 | 1,450 | 0 | 0 | 0 | 0 | 0 | 4,039 |
| 129 | 4,425 | 0 | 0 | 0 | 0 | 0 | 606 |
| 130 | 5,875 | 0 | 0 | 0 | 0 | 0 | 10,618 |
| 131 | 0 | 0 | 0 | 0 | 0 | 0 | 3,429 |
| 132 | 8,125 | 0 | 0 | 0 | 0 | 0 | 5,721 |
| 133 | 2,175 | 0 | 0 | 0 | 0 | 0 | 83 |
| 134 | 4,350 | 0 | 0 | 0 | 0 | 0 | 1,967 |
| 135 | 2,900 | 0 | 0 | 0 | 0 | 0 | 1,553 |
| 136 | 725 | 0 | 0 | 0 | 0 | 0 | 208 |
| 137 | 0 | 0 | 0 | 0 | 0 | 0 | 0 |
| 138 | 169,750 | 0 | 0 | 0 | 0 | 0 | 32,305 |
| 139 | 30,800 | 0 | 0 | 0 | 0 | 0 | 3,268 |
| 140 | 446,000 | 0 | 0 | 0 | 0 | 0 | 45,290 |
| 141 | 15,400 | 0 | 0 | 0 | 0 | 0 | 8,397 |
| 142 | 5,800 | 0 | 0 | 0 | 0 | 0 | 1,064 |
| 143 | 251,160 | 0 | 0 | 0 | 0 | 0 | 22,614 |
| 144 | 76,200 | 0 | 0 | 0 | 0 | 0 | 62,623 |
| 145 | 14,000 | 0 | 0 | 0 | 0 | 0 | 1,809 |
| Charlton Memorial Hospital | | | | | | | |
| 112 | 12,608 | 0 | 0 | 0 | 0 | 0 | 1,823 |
| 115 | 179,896 | 0 | 0 | 0 | 0 | 0 | 13,053 |
| 116 | 13,770 | 0 | 0 | 0 | 0 | 0 | 2,089 |
| 117 | 2,256 | 0 | 0 | 0 | 0 | 0 | 477 |
| 118 | 809,095 | 0 | 0 | 0 | 0 | 0 | 124,409 |
| 121 | 625,635 | 0 | 0 | 0 | 0 | 0 | 114,525 |
| 122 | 111,560 | 0 | 0 | 0 | 0 | 0 | 50,371 |
| 123 | 8,151 | 0 | 0 | 0 | 0 | 0 | 128 |
| 124 | 3,009 | 0 | 0 | 0 | 0 | 0 | 176 |
| 125 | 8,888 | 0 | 0 | 0 | 0 | 0 | 15,012 |
| 126 | 604,630 | 0 | 0 | 0 | 0 | 0 | 132,149 |
| 127 | 1,090 | 0 | 0 | 0 | 0 | 0 | 6,312 |
| 128 | 1,799 | 0 | 0 | 0 | 0 | 0 | 220 |
| 129 | 8,616 | 0 | 0 | 0 | 0 | 0 | 9,657 |
| 130 | 2,820 | 0 | 0 | 0 | 0 | 0 | 1,745 |
| 131 | 33,741 | 0 | 0 | 0 | 0 | 0 | 8,137 |
| 132 | 6,581 | 0 | 0 | 0 | 0 | 0 | 1,085 |
| 133 | 13,660 | 0 | 0 | 0 | 0 | 0 | 3,315 |
| 134 | 10,468 | 0 | 0 | 0 | 0 | 0 | 196 |
| 135 | 1,090 | 0 | 0 | 0 | 0 | 0 | 23 |
| 136 | 271,772 | 0 | 0 | 0 | 0 | 0 | 16,286 |
| 137 | 202,667 | 0 | 0 | 0 | 0 | 0 | 5,311 |
| 138 | 606,989 | 0 | 0 | 0 | 0 | 0 | 33,678 |
| 139 | 84,220 | 0 | 0 | 0 | 0 | 0 | 10,549 |
| 140 | 46,411 | 0 | 0 | 0 | 0 | 0 | 2,648 |
| 141 | 375,553 | 0 | 0 | 0 | 0 | 0 | 21,443 |
| 142 | 60,134 | 0 | 0 | 0 | 0 | 0 | 16,785 |
| 143 | 14,859 | 0 | 0 | 0 | 0 | 0 | 734 |
| 144 | 0 | 0 | 0 | 0 | 0 | 0 | 0 |
| 145 | 0 | 0 | 0 | 0 | 0 | 0 | 0 |
| Cape Cod Hospital | | | | | | | |
| 112 | 0 | 0 | 0 | 0 | 0 | 0 | 0 |
| 115 | 0 | 0 | 0 | 0 | 0 | 8,050 | 1,279 |
| 116 | 0 | 0 | 0 | 0 | 0 | 89,355 | 22,727 |
| 117 | 0 | 0 | 0 | 0 | 0 | 18,515 | 3,624 |
| 118 | 0 | 0 | 0 | 0 | 0 | 2,415 | 171 |

TABLE V-continued

| | | | | | | | |
|---|---|---|---|---|---|---|---|
| 121 | 23,345 | 0 | 0 | 0 | 0 | 418,218 | 130,182 |
| 122 | 21,735 | 0 | 0 | 0 | 0 | 395,196 | 137,612 |
| 123 | 9,660 | 0 | 0 | 0 | 0 | 75,811 | 26,691 |
| 124 | 0 | 0 | 0 | 0 | 0 | 0 | 0 |
| 125 | 0 | 0 | 0 | 0 | 0 | 0 | 0 |
| 126 | 0 | 0 | 0 | 0 | 0 | 5,635 | 9,033 |
| 127 | 38,640 | 0 | 0 | 0 | 0 | 265,973 | 100,997 |
| 128 | 0 | 0 | 0 | 0 | 0 | 2,415 | 4,851 |
| 129 | 2,415 | 0 | 0 | 0 | 0 | 5,635 | 791 |
| 130 | 8,050 | 0 | 0 | 0 | 0 | 0 | 12,584 |
| 131 | 4,025 | 0 | 0 | 0 | 0 | 0 | 10,431 |
| 132 | 4,830 | 0 | 0 | 0 | 0 | 12,075 | 11,004 |
| 133 | 0 | 0 | 0 | 0 | 0 | 8,855 | 327 |
| 134 | 1,610 | 0 | 0 | 0 | 0 | 3,220 | 827 |
| 135 | 2,415 | 0 | 0 | 0 | 0 | 4,830 | 4,230 |
| 136 | 0 | 0 | 0 | 0 | 0 | 805 | 0 |
| 137 | 0 | 0 | 0 | 0 | 0 | 0 | 5 |
| 138 | 8,050 | 0 | 0 | 0 | 0 | 174,685 | 35,970 |
| 139 | 6,440 | 0 | 0 | 0 | 0 | 95,554 | 7,907 |
| 140 | 34,756 | 0 | 0 | 0 | 0 | 562,777 | 54,180 |
| 141 | 4,025 | 0 | 0 | 0 | 0 | 16,100 | 8,625 |
| 142 | 1,610 | 0 | 0 | 0 | 0 | 16,100 | 1,999 |
| 143 | 20,930 | 0 | 0 | 0 | 0 | 325,502 | 17,948 |
| 144 | 4,830 | 0 | 0 | 0 | 0 | 21,735 | 9,813 |
| 145 | 1,610 | 0 | 0 | 0 | 0 | 9,660 | 4,757 |
| Brockton Hospital | | | | | | | |
| 112 | 0 | 0 | 0 | 0 | 0 | 0 | 0 |
| 115 | 0 | 0 | 0 | 0 | 0 | 12,972 | 2,489 |
| 116 | 1,692 | 0 | 0 | 0 | 0 | 20,868 | 5,557 |
| 117 | 0 | 0 | 0 | 0 | 0 | 0 | 0 |
| 118 | 0 | 0 | 0 | 0 | 0 | 4,512 | 2,733 |
| 121 | 12,408 | 0 | 0 | 0 | 0 | 162,736 | 163,454 |
| 122 | 2,256 | 0 | 0 | 0 | 0 | 76,816 | 73,344 |
| 123 | 5,640 | 0 | 0 | 0 | 0 | 24,364 | 24,345 |
| 124 | 0 | 0 | 0 | 0 | 0 | 0 | 0 |
| 125 | 0 | 0 | 0 | 0 | 0 | 0 | 0 |
| 126 | 0 | 0 | 0 | 0 | 0 | 0 | 14,186 |
| 127 | 8,656 | 0 | 0 | 0 | 0 | 69,312 | 106,703 |
| 128 | 0 | 0 | 0 | 0 | 0 | 0 | 5,889 |
| 129 | 0 | 0 | 0 | 0 | 0 | 1,692 | 376 |
| 130 | 7,332 | 0 | 0 | 0 | 0 | 2,820 | 103,576 |
| 131 | 1,128 | 0 | 0 | 0 | 0 | 0 | 7,255 |
| 132 | 2,256 | 0 | 0 | 0 | 0 | 1,692 | 41,128 |
| 133 | 0 | 0 | 0 | 0 | 0 | 0 | 42 |
| 134 | 0 | 0 | 0 | 0 | 0 | 0 | 3,348 |
| 135 | 0 | 0 | 0 | 0 | 0 | 0 | 219 |
| 136 | 0 | 0 | 0 | 0 | 0 | 0 | 0 |
| 137 | 0 | 0 | 0 | 0 | 0 | 0 | 0 |
| 138 | 564 | 0 | 0 | 0 | 0 | 47,008 | 29,495 |
| 139 | 0 | 0 | 0 | 0 | 0 | 1,720 | 3,075 |
| 140 | 4,512 | 0 | 0 | 0 | 0 | 113,528 | 49,922 |
| 141 | 0 | 0 | 0 | 0 | 0 | 1,692 | 9,657 |
| 142 | 0 | 0 | 0 | 0 | 0 | 0 | 2,087 |
| 143 | 1,128 | 0 | 0 | 0 | 0 | 19,852 | 13,862 |
| 144 | 3,948 | 0 | 0 | 0 | 0 | 10,744 | 146,025 |
| 145 | 1,128 | 0 | 0 | 0 | 0 | 564 | 1,545 |
| Norwood Hospital | | | | | | | |
| 112 | 0 | 0 | 0 | 0 | 0 | 0 | 43 |
| 115 | 25,348 | 0 | 0 | 0 | 0 | 0 | 7,806 |
| 116 | 18,604 | 0 | 0 | 0 | 0 | 0 | 12,217 |
| 117 | 1,052 | 0 | 0 | 0 | 0 | 0 | 1,343 |
| 118 | 1,196 | 0 | 0 | 0 | 0 | 0 | 2,697 |
| 121 | 295,828 | 0 | 0 | 0 | 0 | 0 | 146,384 |
| 122 | 196,196 | 0 | 0 | 0 | 0 | 0 | 176,545 |
| 123 | 51,660 | 0 | 0 | 0 | 0 | 0 | 27,539 |
| 124 | 0 | 0 | 0 | 0 | 0 | 0 | 0 |
| 125 | 0 | 0 | 0 | 0 | 0 | 0 | 0 |
| 126 | 0 | 0 | 0 | 0 | 0 | 0 | 5,909 |
| 127 | 136,452 | 0 | 0 | 0 | 0 | 0 | 140,509 |
| 128 | 0 | 0 | 0 | 0 | 0 | 0 | 3,952 |
| 129 | 16,356 | 0 | 0 | 0 | 0 | 0 | 8,130 |
| 130 | 4,208 | 0 | 0 | 0 | 0 | 0 | 13,742 |
| 131 | 0 | 0 | 0 | 0 | 0 | 0 | 5,753 |
| 132 | 5,692 | 0 | 0 | 0 | 0 | 0 | 10,961 |
| 133 | 0 | 0 | 0 | 0 | 0 | 0 | 0 |
| 134 | 0 | 0 | 0 | 0 | 0 | 0 | 1,145 |
| 135 | 0 | 0 | 0 | 0 | 0 | 0 | 1,127 |

TABLE V-continued

| | | | | | | | | |
|---|---|---|---|---|---|---|---|---|
| 136 | 1,052 | 0 | 0 | 0 | 0 | 0 | 0 | 166 |
| 137 | 0 | 0 | 0 | 0 | 0 | 0 | 0 | 0 |
| 138 | 33,288 | 0 | 0 | 0 | 0 | 0 | 0 | 22,124 |
| 139 | 8,848 | 0 | 0 | 0 | 0 | 0 | 0 | 6,534 |
| 140 | 140,140 | 0 | 0 | 0 | 0 | 0 | 0 | 70,486 |
| 141 | 0 | 0 | 0 | 0 | 0 | 0 | 0 | 7,639 |
| 142 | 1,052 | 0 | 0 | 0 | 0 | 0 | 0 | 3,329 |
| 143 | 36,688 | 0 | 0 | 0 | 0 | 0 | 0 | 28,837 |
| 144 | 11,528 | 0 | 0 | 0 | 0 | 0 | 0 | 19,603 |
| 145 | 2,248 | 0 | 0 | 0 | 0 | 0 | 0 | 1,218 |
| Goddard Memorial Hospital | | | | | | | | |
| 112 | 0 | 0 | 0 | 0 | 0 | 0 | 0 | 0 |
| 115 | 6,867 | 0 | 0 | 0 | 0 | 0 | 42,277 | 8,757 |
| 116 | 6,867 | 0 | 0 | 0 | 0 | 0 | 60,432 | 18,833 |
| 117 | 3,052 | 0 | 0 | 0 | 0 | 0 | 0 | 1,082 |
| 118 | 0 | 0 | 0 | 0 | 0 | 0 | 1,526 | 1,323 |
| 121 | 6,258 | 0 | 0 | 0 | 0 | 0 | 133,990 | 64,915 |
| 122 | 5,341 | 0 | 0 | 0 | 0 | 0 | 130,485 | 71,764 |
| 123 | 4,121 | 0 | 0 | 0 | 0 | 0 | 75,698 | 26,950 |
| 124 | 0 | 0 | 0 | 0 | 0 | 0 | 0 | 0 |
| 125 | 0 | 0 | 0 | 0 | 0 | 0 | 0 | 0 |
| 126 | 9,156 | 0 | 0 | 0 | 0 | 0 | 1,374 | 25,982 |
| 127 | 32,355 | 0 | 0 | 0 | 0 | 0 | 162,228 | 52,033 |
| 128 | 0 | 0 | 0 | 0 | 0 | 0 | 458 | 6,352 |
| 129 | 6,104 | 0 | 0 | 0 | 0 | 0 | 0 | 1,312 |
| 130 | 0 | 0 | 0 | 0 | 0 | 0 | 0 | 532 |
| 131 | 458 | 0 | 0 | 0 | 0 | 0 | 0 | 2,842 |
| 132 | 0 | 0 | 0 | 0 | 0 | 0 | 3,815 | 287 |
| 133 | 0 | 0 | 0 | 0 | 0 | 0 | 0 | 0 |
| 134 | 2,442 | 0 | 0 | 0 | 0 | 0 | 11,751 | 1,933 |
| 135 | 0 | 0 | 0 | 0 | 0 | 0 | 0 | 37 |
| 136 | 0 | 0 | 0 | 0 | 0 | 0 | 0 | 25 |
| 137 | 0 | 0 | 0 | 0 | 0 | 0 | 0 | 0 |
| 138 | 8,851 | 0 | 0 | 0 | 0 | 0 | 66,997 | 19,425 |
| 139 | 1,374 | 0 | 0 | 0 | 0 | 0 | 24,875 | 3,033 |
| 140 | 20,756 | 0 | 0 | 0 | 0 | 0 | 218,086 | 40,964 |
| 141 | 8,393 | 0 | 0 | 0 | 0 | 0 | 13,583 | 7,132 |
| 142 | 2,289 | 0 | 0 | 0 | 0 | 0 | 2,290 | 2,716 |
| 143 | 8,394 | 0 | 0 | 0 | 0 | 0 | 55,400 | 14,204 |
| 144 | 2,595 | 0 | 0 | 0 | 0 | 0 | 6,867 | 8,916 |
| 145 | 0 | 0 | 0 | 0 | 0 | 0 | 3,052 | 467 |
| Cardinal Cushing General Hospital | | | | | | | | |
| 112 | 8,640 | 0 | 0 | 0 | 0 | 0 | 18,220 | 3,112 |
| 115 | 23,686 | 0 | 0 | 0 | 0 | 0 | 61,506 | 25,321 |
| 116 | 4,320 | 0 | 0 | 0 | 0 | 0 | 0 | 799 |
| 117 | 0 | 0 | 0 | 0 | 0 | 0 | 5,040 | 287 |
| 118 | 41,666 | 0 | 0 | 0 | 0 | 0 | 225,856 | 99,738 |
| 121 | 14,616 | 0 | 0 | 0 | 0 | 0 | 112,336 | 62,275 |
| 122 | 736 | 0 | 0 | 0 | 0 | 0 | 48,992 | 15,610 |
| 123 | 0 | 0 | 0 | 0 | 0 | 0 | 0 | 0 |
| 124 | 0 | 0 | 0 | 0 | 0 | 0 | 0 | 0 |
| 125 | 0 | 0 | 0 | 0 | 0 | 0 | 1,440 | 7,001 |
| 126 | 73,548 | 0 | 0 | 0 | 0 | 0 | 170,894 | 89,276 |
| 127 | 0 | 0 | 0 | 0 | 0 | 0 | 0 | 6,733 |
| 128 | 640 | 0 | 0 | 0 | 0 | 0 | 720 | 364 |
| 129 | 5,840 | 0 | 0 | 0 | 0 | 0 | 0 | 11,543 |
| 130 | 0 | 0 | 0 | 0 | 0 | 0 | 0 | 8,087 |
| 131 | 0 | 0 | 0 | 0 | 0 | 0 | 0 | 29 |
| 132 | 2,944 | 0 | 0 | 0 | 0 | 0 | 0 | 177 |
| 133 | 0 | 0 | 0 | 0 | 0 | 0 | 23,584 | 2,598 |
| 134 | 0 | 0 | 0 | 0 | 0 | 0 | 4,518 | 1,211 |
| 135 | 0 | 0 | 0 | 0 | 0 | 0 | 0 | 55 |
| 136 | 26,402 | 0 | 0 | 0 | 0 | 0 | 44,296 | 20,283 |
| 137 | 2,800 | 0 | 0 | 0 | 0 | 0 | 7,842 | 1,596 |
| 138 | 60,016 | 0 | 0 | 0 | 0 | 0 | 240,222 | 49,958 |
| 139 | 1,800 | 0 | 0 | 0 | 0 | 0 | 9,840 | 5,675 |
| 140 | 0 | 0 | 0 | 0 | 0 | 0 | 4,616 | 874 |
| 141 | 16,468 | 0 | 0 | 0 | 0 | 0 | 35,858 | 9,587 |
| 142 | 9,070 | 0 | 0 | 0 | 0 | 0 | 32,770 | 20,641 |
| 143 | 0 | 0 | 0 | 0 | 0 | 0 | 4,000 | 9,236 |
| 144 | 0 | 0 | 0 | 0 | 0 | 0 | 0 | 0 |
| 145 | 0 | 0 | 0 | 0 | 0 | 0 | 0 | 0 |

TABLE V-continued

| | IV Therapy | Medical/Surgical Supplies | Laboratory | Diagnostic Radiology | Therapeutic Radiology | Nuclear Medicine | CAT Scanner |
|---|---|---|---|---|---|---|---|
| St. Luke's Hospital of New Bedford | | | | | | | |
| 112 | 0 | 0 | 0 | 0 | 0 | 0 | 0 |
| 115 | 7,595 | 87,725 | 10,889 | 25,106 | 0 | 1,690 | 0 |
| 116 | 16,866 | 534,397 | 28,464 | 97,160 | 0 | 4,040 | 1,636 |
| 117 | 4 | 14 | 253 | 159 | 0 | 0 | 0 |
| 118 | 1,663 | 66,477 | 1,160 | 8,792 | 0 | 0 | 0 |
| 121 | 67,181 | 51,066 | 177,709 | 126,852 | 0 | 47,528 | 5,686 |
| 122 | 33,797 | 4,771 | 87,153 | 53,704 | 0 | 38,455 | 2,892 |
| 123 | 29,665 | 12,683 | 38,618 | 40,663 | 0 | 5,511 | 572 |
| 124 | 2,872 | 412 | 13,159 | 6,158 | 0 | 1,147 | 0 |
| 125 | 1,525 | 587 | 7,711 | 4,230 | 0 | 481 | 0 |
| 126 | 9,771 | 2,185 | 15,956 | 12,533 | 0 | 3,584 | 2,704 |
| 127 | 106,507 | 43,135 | 353,289 | 285,376 | 0 | 97,338 | 14,480 |
| 128 | 11,803 | 1,480 | 9,635 | 24,477 | 0 | 430 | 1,635 |
| 129 | 4,872 | 960 | 3,534 | 2,557 | 0 | 1,030 | 331 |
| 130 | 20,339 | 6,882 | 28,094 | 93,336 | 0 | 4,519 | 6,641 |
| 131 | 6,246 | 1,100 | 6,749 | 17,685 | 0 | 415 | 2,932 |
| 132 | 808 | 92 | 3,251 | 1,734 | 0 | 1,124 | 0 |
| 133 | 290 | 18 | 1,102 | 756 | 0 | 482 | 0 |
| 134 | 689 | 203 | 5,809 | 5,030 | 0 | 3,305 | 858 |
| 135 | 292 | 128 | 2,521 | 4,049 | 0 | 2,373 | 0 |
| 136 | 274 | 7 | 273 | 318 | 0 | 0 | 0 |
| 137 | 0 | 0 | 0 | 0 | 0 | 0 | 0 |
| 138 | 23,612 | 77,455 | 78,929 | 68,488 | 0 | 30,045 | 6,199 |
| 139 | 6,599 | 17,320 | 23,195 | 19,055 | 0 | 8,544 | 1,235 |
| 140 | 31,017 | 9,551 | 143,383 | 124,026 | 0 | 52,968 | 3,189 |
| 141 | 7,849 | 2,991 | 34,970 | 36,632 | 0 | 7,581 | 5,500 |
| 142 | 3,248 | 1,686 | 19,099 | 21,438 | 0 | 6,093 | 6,837 |
| 143 | 13,867 | 5,091 | 61,611 | 87,243 | 0 | 32,808 | 4,421 |
| 144 | 15,001 | 5,233 | 31,814 | 28,902 | 0 | 8,107 | 3,221 |
| 145 | 1,328 | 567 | 6,597 | 6,903 | 0 | 3,569 | 173 |
| South Shore Hospital | | | | | | | |
| 112 | 0 | 0 | 0 | 0 | 0 | 0 | 0 |
| 115 | 951 | 28,019 | 4,308 | 2,171 | 0 | 350 | 257 |
| 116 | 1,999 | 256,117 | 13,523 | 15,190 | 0 | 816 | 1,646 |
| 117 | 36 | 83 | 39 | 334 | 0 | 0 | 0 |
| 118 | 508 | 42,577 | 1,200 | 1,165 | 0 | 0 | 0 |
| 121 | 14,447 | 5,041 | 103,844 | 25,203 | 0 | 18,348 | 4,948 |
| 122 | 8,356 | 904 | 73,732 | 9,175 | 0 | 25,166 | 3,801 |
| 123 | 5,237 | 3,928 | 20,501 | 5,703 | 0 | 0 | 514 |
| 124 | 0 | 0 | 0 | 0 | 0 | 0 | 0 |
| 125 | 0 | 0 | 0 | 0 | 0 | 0 | 0 |
| 126 | 0 | 13 | 820 | 205 | 0 | 0 | 632 |
| 127 | 19,686 | 10,179 | 196,561 | 69,787 | 0 | 17,963 | 19,408 |
| 128 | 738 | 179 | 5,307 | 6,978 | 0 | 700 | 3,248 |
| 129 | 232 | 208 | 2,018 | 655 | 0 | 0 | 514 |
| 130 | 1,454 | 1,258 | 14,484 | 26,359 | 0 | 2,857 | 4,753 |
| 131 | 948 | 787 | 5,842 | 20,288 | 0 | 2,100 | 1,151 |
| 132 | 572 | 749 | 2,666 | 525 | 0 | 298 | 0 |
| 133 | 29 | 22 | 418 | 32 | 0 | 0 | 0 |
| 134 | 330 | 117 | 7,816 | 2,631 | 0 | 1,826 | 2,498 |
| 135 | 245 | 356 | 3,939 | 2,531 | 0 | 716 | 1,815 |
| 136 | 14 | 0 | 86 | 74 | 0 | 0 | 0 |
| 137 | 0 | 0 | 0 | 0 | 0 | 0 | 0 |
| 138 | 7,594 | 3,336 | 86,869 | 19,109 | 0 | 8,778 | 11,352 |
| 139 | 1,267 | 427 | 23,054 | 3,830 | 0 | 1,078 | 1,348 |
| 140 | 11,577 | 2,633 | 148,313 | 34,511 | 0 | 49,735 | 8,311 |
| 141 | 1,924 | 457 | 26,712 | 9,299 | 0 | 984 | 14,403 |
| 142 | 654 | 128 | 12,510 | 4,544 | 0 | 298 | 6,211 |
| 143 | 7,052 | 1,373 | 112,658 | 34,453 | 0 | 39,456 | 8,766 |
| 144 | 4,636 | 4,713 | 26,032 | 16,061 | 0 | 1,622 | 6,638 |
| 145 | 330 | 55 | 4,476 | 1,725 | 0 | 2,492 | 1,863 |
| Charlton Memorial Hospital | | | | | | | |
| 112 | 389 | 28,280 | 3,465 | 8,574 | 52 | 921 | 0 |
| 115 | 5,507 | 353,916 | 43,656 | 87,613 | 40 | 4,231 | 5,776 |
| 116 | 665 | 26,980 | 2,951 | 6,338 | 0 | 0 | 0 |
| 117 | 0 | 8,142 | 563 | 104 | 0 | 0 | 0 |
| 118 | 30,678 | 16,428 | 289,980 | 263,120 | 3,695 | 55,705 | 10,727 |
| 121 | 20,828 | 2,439 | 185,859 | 187,532 | 4,630 | 75,874 | 13,094 |
| 122 | 5,724 | 10,131 | 62,918 | 60,894 | 76 | 2,256 | 4,552 |

TABLE V-continued

| | | | | | | | |
|---|---|---|---|---|---|---|---|
| 123 | 330 | 0 | 1,397 | 286 | 0 | 0 | 0 |
| 124 | 0 | 0 | 1,076 | 1,285 | 0 | 468 | 774 |
| 125 | 3,083 | 1,906 | 20,365 | 16,996 | 0 | 1,398 | 8,258 |
| 126 | 36,319 | 25,194 | 464,435 | 354,601 | 109 | 57,359 | 47,839 |
| 127 | 2,589 | 1,901 | 22,084 | 15,035 | 0 | 2,216 | 6,490 |
| 128 | 0 | 264 | 943 | 572 | 0 | 0 | 736 |
| 129 | 3,691 | 1,553 | 33,049 | 42,588 | 0 | 5,228 | 4,764 |
| 130 | 1,157 | 354 | 11,946 | 29,194 | 0 | 2,813 | 3,558 |
| 131 | 1,708 | 4,272 | 21,224 | 13,973 | 100 | 0 | 2,776 |
| 132 | 440 | 4 | 2,856 | 4,365 | 0 | 1,736 | 1,634 |
| 133 | 990 | 853 | 19,997 | 19,716 | 0 | 2,113 | 13,627 |
| 134 | 221 | 0 | 2,045 | 2,987 | 0 | 909 | 0 |
| 135 | 55 | 0 | 351 | 220 | 0 | 0 | 0 |
| 136 | 8,991 | 12,228 | 110,323 | 86,246 | 0 | 15,296 | 15,840 |
| 137 | 6,399 | 30,401 | 68,315 | 60,935 | 22 | 8,492 | 4,427 |
| 138 | 22,760 | 12,492 | 235,550 | 165,646 | 302 | 75,484 | 22,074 |
| 139 | 4,466 | 1,471 | 54,559 | 43,055 | 0 | 8,573 | 32,637 |
| 140 | 1,711 | 102 | 27,356 | 20,435 | 0 | 2,043 | 24,956 |
| 141 | 15,149 | 3,004 | 211,146 | 179,561 | 112 | 66,952 | 22,549 |
| 142 | 2,809 | 4,827 | 38,523 | 34,358 | 18 | 6,746 | 8,065 |
| 143 | 440 | 107 | 7,962 | 8,284 | 0 | 1,484 | 2,811 |
| 144 | 0 | 0 | 0 | 0 | 0 | 0 | 0 |
| 145 | 0 | 0 | 0 | 0 | 0 | 0 | 0 |
| Cape Cod Hospital | | | | | | | |
| 112 | 0 | 0 | 0 | 0 | 0 | 0 | 0 |
| 115 | 2,062 | 18,637 | 1,285 | 1,130 | 0 | 0 | 0 |
| 116 | 39,888 | 595,139 | 19,063 | 17,208 | 0 | 971 | 2,296 |
| 117 | 5,462 | 52,776 | 1,957 | 1,867 | 0 | 0 | 523 |
| 118 | 412 | 12,949 | 120 | 77 | 0 | 0 | 0 |
| 121 | 99,790 | 79,534 | 94,067 | 33,054 | 0 | 31,116 | 5,686 |
| 122 | 79,206 | 61,113 | 77,432 | 20,405 | 0 | 37,157 | 4,184 |
| 123 | 12,197 | 4,685 | 18,255 | 8,800 | 0 | 298 | 2,615 |
| 124 | 0 | 0 | 0 | 0 | 0 | 0 | 0 |
| 125 | 0 | 0 | 0 | 0 | 0 | 0 | 0 |
| 126 | 13,711 | 3,620 | 5,367 | 2,511 | 0 | 1,729 | 1,665 |
| 127 | 196,059 | 104,634 | 157,218 | 84,321 | 0 | 29,230 | 20,531 |
| 128 | 13,851 | 2,153 | 8,856 | 9,641 | 0 | 2,899 | 3,223 |
| 129 | 721 | 4,326 | 1,901 | 767 | 0 | 0 | 0 |
| 130 | 22,575 | 7,914 | 14,025 | 23,515 | 965 | 4,247 | 3,486 |
| 131 | 11,850 | 0 | 6,831 | 17,480 | 0 | 0 | 634 |
| 132 | 2,267 | 317 | 2,867 | 1,104 | 0 | 909 | 523 |
| 133 | 2,061 | 1,584 | 1,893 | 420 | 0 | 1,066 | 523 |
| 134 | 1,545 | 632 | 3,352 | 1,762 | 0 | 226 | 2,668 |
| 135 | 4,741 | 1,761 | 2,905 | 1,919 | 0 | 752 | 523 |
| 136 | 0 | 0 | 239 | 77 | 0 | 0 | 0 |
| 137 | 0 | 64 | 0 | 77 | 0 | 0 | 0 |
| 138 | 72,766 | 170,415 | 59,370 | 24,534 | 1,447 | 8,207 | 13,752 |
| 139 | 37,220 | 47,546 | 35,101 | 11,798 | 0 | 11,403 | 3,024 |
| 140 | 122,070 | 100,980 | 115,272 | 47,076 | 0 | 58,339 | 8,821 |
| 141 | 21,232 | 14,901 | 16,380 | 10,215 | 508 | 2,859 | 13,008 |
| 142 | 10,529 | 9,488 | 8,210 | 4,937 | 0 | 5,363 | 6,910 |
| 143 | 66,191 | 34,941 | 77,584 | 36,477 | 0 | 52,187 | 6,897 |
| 144 | 23,914 | 34,445 | 13,501 | 10,341 | 0 | 4,696 | 7,069 |
| 145 | 2,697 | 2,098 | 3,825 | 2,049 | 0 | 1,530 | 1,402 |
| Brockton Hospital | | | | | | | |
| 112 | 0 | 0 | 0 | 0 | 0 | 0 | 0 |
| 115 | 203 | 34,268 | 11,195 | 8,920 | 0 | 0 | 0 |
| 116 | 680 | 205,539 | 24,580 | 33,091 | 0 | 0 | 830 |
| 117 | 0 | 0 | 0 | 0 | 0 | 0 | 0 |
| 118 | 249 | 26,752 | 7,857 | 4,298 | 0 | 545 | 0 |
| 121 | 2,892 | 25,452 | 261,760 | 101,121 | 0 | 24,863 | 9,769 |
| 122 | 1,053 | 5,374 | 104,066 | 26,710 | 658 | 12,482 | 1,382 |
| 123 | 1,219 | 13,704 | 46,059 | 25,113 | 0 | 1,090 | 830 |
| 124 | 0 | 0 | 0 | 0 | 0 | 0 | 0 |
| 125 | 0 | 0 | 0 | 0 | 0 | 0 | 0 |
| 126 | 1,434 | 1,605 | 31,780 | 7,409 | 441 | 3,538 | 1,143 |
| 127 | 5,717 | 31,006 | 472,024 | 188,700 | 406 | 24,887 | 24,605 |
| 128 | 177 | 2,235 | 15,821 | 9,144 | 605 | 7,005 | 0 |
| 129 | 34 | 720 | 1,124 | 990 | 0 | 0 | 0 |
| 130 | 1,480 | 8,258 | 63,710 | 78,077 | 0 | 15,402 | 9,873 |
| 131 | 339 | 2,733 | 17,372 | 40,885 | 0 | 3,270 | 728 |
| 132 | 99 | 974 | 8,209 | 2,214 | 0 | 0 | 0 |
| 133 | 3 | 35 | 645 | 0 | 0 | 0 | 0 |
| 134 | 266 | 468 | 13,357 | 7,931 | 0 | 1,090 | 4,464 |
| 135 | 20 | 153 | 2,037 | 888 | 0 | 0 | 0 |
| 136 | 5 | 24 | 517 | 122 | 0 | 0 | 0 |
| 137 | 0 | 0 | 0 | 0 | 0 | 0 | 0 |

TABLE V-continued

| | | | | | | | |
|---|---|---|---|---|---|---|---|
| 138 | 2,085 | 24,560 | 178,317 | 55,322 | 1,491 | 4,682 | 10,609 |
| 139 | 298 | 1,048 | 52,759 | 13,480 | 0 | 2,927 | 2,906 |
| 140 | 2,648 | 13,688 | 304,102 | 97,145 | 0 | 52,495 | 4,570 |
| 141 | 1,167 | 2,304 | 85,059 | 32,931 | 0 | 2,308 | 21,022 |
| 142 | 254 | 604 | 21,847 | 11,143 | 0 | 1,090 | 8,010 |
| 143 | 1,038 | 3,974 | 151,630 | 73,079 | 0 | 28,338 | 5,319 |
| 144 | 2,311 | 8,024 | 61,223 | 37,727 | 0 | 4,192 | 1,558 |
| 145 | 141 | 306 | 5,849 | 13,954 | 0 | 0 | 2,286 |
| Norwood Hospital | | | | | | | |
| 112 | 0 | 33 | 252 | 117 | 0 | 0 | 0 |
| 115 | 0 | 64,308 | 20,316 | 5,260 | 0 | 0 | 872 |
| 116 | 0 | 264,689 | 37,106 | 14,318 | 0 | 0 | 3,243 |
| 117 | 0 | 7,086 | 3,566 | 908 | 0 | 0 | 0 |
| 118 | 0 | 71,122 | 10,376 | 3,819 | 0 | 0 | 872 |
| 121 | 0 | 27,843 | 312,900 | 46,409 | 0 | 5,778 | 8,523 |
| 122 | 0 | 11,834 | 160,792 | 18,668 | 0 | 4,827 | 5,084 |
| 123 | 0 | 6,765 | 47,607 | 10,027 | 0 | 0 | 1,512 |
| 124 | 0 | 0 | 0 | 0 | 0 | 0 | 0 |
| 125 | 0 | 0 | 0 | 0 | 0 | 0 | 0 |
| 126 | 0 | 1,181 | 9,680 | 6,048 | 0 | 1,046 | 2,421 |
| 127 | 0 | 38,540 | 595,985 | 116,570 | 13 | 33,041 | 21,787 |
| 128 | 0 | 1,297 | 17,570 | 3,369 | 0 | 1,094 | 0 |
| 129 | 0 | 2,680 | 18,667 | 3,250 | 0 | 706 | 768 |
| 130 | 0 | 2,916 | 38,120 | 10,203 | 0 | 2,234 | 1,549 |
| 131 | 0 | 1,446 | 19,361 | 5,846 | 0 | 706 | 2,233 |
| 132 | 0 | 552 | 9,021 | 1,421 | 0 | 764 | 1,549 |
| 133 | 0 | 0 | 0 | 0 | 0 | 0 | 0 |
| 134 | 0 | 1,641 | 9,716 | 5,345 | 0 | 1,579 | 1,218 |
| 135 | 0 | 322 | 7,369 | 1,483 | 0 | 2,049 | 346 |
| 136 | 0 | 146 | 1,064 | 598 | 0 | 0 | 436 |
| 137 | 0 | 0 | 0 | 0 | 0 | 0 | 0 |
| 138 | 0 | 6,431 | 120,972 | 19,958 | 0 | 8,566 | 7,044 |
| 139 | 0 | 3,293 | 43,040 | 10,535 | 0 | 3,253 | 679 |
| 140 | 0 | 18,676 | 279,350 | 67,444 | 0 | 35,673 | 8,492 |
| 141 | 0 | 2,557 | 35,305 | 12,188 | 0 | 4,949 | 10,264 |
| 142 | 0 | 1,328 | 26,350 | 13,766 | 0 | 1,532 | 12,747 |
| 143 | 0 | 7,596 | 132,151 | 45,185 | 0 | 33,298 | 9,440 |
| 144 | 0 | 9,279 | 61,521 | 13,967 | 0 | 5,510 | 10,615 |
| 145 | 0 | 654 | 8,351 | 3,937 | 0 | 0 | 3,010 |
| Goddard Memorial Hospital | | | | | | | |
| 112 | 0 | 0 | 0 | 0 | 0 | 0 | 0 |
| 115 | 1,970 | 149,337 | 29,650 | 14,344 | 0 | 836 | 641 |
| 116 | 3,614 | 735,895 | 45,724 | 38,271 | 0 | 170 | 3,687 |
| 117 | 246 | 20,534 | 1,746 | 1,140 | 0 | 0 | 0 |
| 118 | 98 | 62,663 | 2,181 | 2,031 | 0 | 0 | 641 |
| 121 | 4,057 | 11,300 | 78,190 | 34,721 | 0 | 5,457 | 2,784 |
| 122 | 4,321 | 2,720 | 61,871 | 22,539 | 0 | 6,942 | 1,211 |
| 123 | 3,340 | 8,637 | 38,822 | 19,461 | 0 | 963 | 695 |
| 124 | 0 | 0 | 0 | 0 | 0 | 0 | 0 |
| 125 | 0 | 0 | 0 | 0 | 0 | 0 | 0 |
| 126 | 8,462 | 4,600 | 26,079 | 10,083 | 0 | 1,036 | 3,638 |
| 127 | 7,638 | 8,795 | 255,835 | 82,615 | 318 | 30,983 | 13,867 |
| 128 | 2,315 | 1,982 | 20,233 | 8,674 | 0 | 3,034 | 2,086 |
| 129 | 218 | 574 | 3,599 | 1,191 | 0 | 0 | 0 |
| 130 | 202 | 614 | 2,791 | 7,747 | 0 | 451 | 573 |
| 131 | 693 | 631 | 2,587 | 15,362 | 0 | 1,483 | 0 |
| 132 | 109 | 0 | 2,506 | 1,116 | 0 | 0 | 0 |
| 133 | 0 | 0 | 0 | 0 | 0 | 0 | 0 |
| 134 | 323 | 152 | 11,538 | 4,378 | 0 | 2,418 | 393 |
| 135 | 0 | 0 | 308 | 182 | 0 | 0 | 0 |
| 136 | 0 | 5 | 372 | 182 | 0 | 0 | 0 |
| 137 | 0 | 0 | 0 | 0 | 0 | 0 | 0 |
| 138 | 3,176 | 3,396 | 91,320 | 27,559 | 0 | 9,989 | 4,513 |
| 139 | 752 | 482 | 40,071 | 12,709 | 0 | 6,768 | 493 |
| 140 | 9,266 | 7,132 | 177,415 | 76,290 | 0 | 38,517 | 6,625 |
| 141 | 2,857 | 2,065 | 60,125 | 20,751 | 0 | 2,080 | 21,749 |
| 142 | 537 | 593 | 20,411 | 13,676 | 0 | 410 | 9,602 |
| 143 | 2,867 | 2,083 | 112,252 | 52,866 | 0 | 39,611 | 6,329 |
| 144 | 1,641 | 2,743 | 28,700 | 12,823 | 0 | 7,745 | 302 |
| 145 | 71 | 42 | 3,297 | 1,787 | 0 | 0 | 0 |
| Cardinal Cushing General Hospital | | | | | | | |
| 112 | 572 | 50,749 | 6,532 | 3,903 | 0 | 1,000 | 0 |
| 115 | 2,012 | 333,574 | 40,687 | 31,066 | 0 | 9,395 | 4,035 |
| 116 | 93 | 4,562 | 619 | 1,177 | 0 | 0 | 0 |

TABLE V-continued

| | | | | | | | |
|---|---|---|---|---|---|---|---|
| 117 | 81 | 23,116 | 500 | 940 | 0 | 0 | 0 |
| 118 | 4,723 | 6,954 | 82,169 | 41,774 | 0 | 18,380 | 6,610 |
| 121 | 2,221 | 1,777 | 47,428 | 18,170 | 0 | 10,845 | 4,225 |
| 122 | 1,621 | 5,200 | 36,129 | 12,912 | 0 | 2,010 | 715 |
| 123 | 0 | 0 | 0 | 0 | 0 | 0 | 0 |
| 124 | 0 | 0 | 0 | 0 | 0 | 0 | 0 |
| 125 | 360 | 208 | 9,248 | 5,080 | 0 | 5,710 | 2,755 |
| 126 | 6,470 | 11,893 | 248,521 | 111,738 | 0 | 70,050 | 14,810 |
| 127 | 390 | 651 | 10,109 | 5,560 | 0 | 31,445 | 0 |
| 128 | 66 | 175 | 1,560 | 516 | 0 | 0 | 175 |
| 129 | 946 | 3,541 | 21,691 | 16,559 | 0 | 22,425 | 6,405 |
| 130 | 424 | 1,052 | 7,006 | 7,149 | 0 | 9,170 | 0 |
| 131 | 0 | 0 | 256 | 100 | 0 | 1,305 | 0 |
| 132 | 11 | 18 | 698 | 320 | 0 | 465 | 0 |
| 133 | 295 | 369 | 14,307 | 6,194 | 0 | 2,820 | 5,575 |
| 134 | 101 | 29 | 2,599 | 777 | 0 | 0 | 360 |
| 135 | 18 | 13 | 1,096 | 100 | 0 | 0 | 0 |
| 136 | 1,618 | 3,637 | 68,066 | 21,668 | 0 | 15,230 | 6,865 |
| 137 | 239 | 273 | 19,171 | 5,777 | 0 | 13,005 | 4,660 |
| 138 | 4,901 | 4,953 | 187,812 | 74,419 | 0 | 78,497 | 10,940 |
| 139 | 653 | 1,003 | 26,173 | 10,381 | 0 | 4,825 | 14,615 |
| 140 | 167 | 147 | 9,783 | 4,139 | 0 | 2,215 | 6,725 |
| 141 | 1,170 | 1,099 | 73,910 | 34,579 | 0 | 32,840 | 5,620 |
| 142 | 844 | 3,143 | 33,250 | 16,839 | 0 | 16,515 | 4,030 |
| 143 | 81 | 68 | 2,080 | 620 | 0 | 500 | 360 |
| 144 | 0 | 0 | 0 | 0 | 0 | 0 | 0 |
| 145 | 0 | 0 | 0 | 0 | 0 | 0 | 0 |

| | Operating Room | Anesthesiology | Blood | Blood Storage Proc. & Admin | Respiratory Therapy | Physical Therapy | Occupational Therapy |
|---|---|---|---|---|---|---|---|
| St. Luke's Hospital of New Bedford | | | | | | | |
| 112 | 0 | 0 | 0 | 0 | 0 | 0 | 0 |
| 115 | 35,560 | 18,652 | 0 | 154 | 2,091 | 480 | 0 |
| 116 | 216,101 | 101,405 | 153 | 707 | 2,747 | 55 | 0 |
| 117 | 0 | 0 | 0 | 0 | 18 | 0 | 0 |
| 118 | 32,685 | 15,358 | 0 | 32 | 40 | 0 | 0 |
| 121 | 16,485 | 14,112 | 480 | 1,883 | 23,092 | 7,598 | 2,418 |
| 122 | 1,960 | 0 | 321 | 1,438 | 8,141 | 1,544 | 2,418 |
| 123 | 2,755 | 16,524 | 312 | 697 | 6,769 | 966 | 182 |
| 124 | 0 | 612 | 0 | 5 | 825 | 0 | 234 |
| 125 | 0 | 612 | 0 | 0 | 414 | 0 | 234 |
| 126 | 0 | 612 | 178 | 659 | 1,336 | 1,076 | 208 |
| 127 | 40,108 | 18,512 | 2,040 | 5,396 | 58,114 | 10,405 | 1,404 |
| 128 | 0 | 0 | 51 | 71 | 553 | 694 | 0 |
| 129 | 0 | 0 | 25 | 69 | 1,323 | 0 | 0 |
| 130 | 8,845 | 918 | 51 | 668 | 1,082 | 1,944 | 208 |
| 131 | 0 | 0 | 0 | 0 | 34 | 94 | 0 |
| 132 | 0 | 0 | 0 | 0 | 464 | 0 | 0 |
| 133 | 0 | 0 | 0 | 0 | 147 | 0 | 0 |
| 134 | 0 | 306 | 0 | 0 | 288 | 282 | 0 |
| 135 | 0 | 0 | 0 | 0 | 309 | 0 | 0 |
| 136 | 0 | 0 | 0 | 0 | 28 | 0 | 0 |
| 137 | 0 | 0 | 0 | 0 | 0 | 0 | 0 |
| 138 | 24,915 | 16,422 | 152 | 433 | 8,283 | 1,950 | 208 |
| 139 | 7,540 | 12,367 | 0 | 0 | 1,562 | 0 | 78 |
| 140 | 4,680 | 1,224 | 625 | 1,271 | 15,068 | 3,443 | 1,170 |
| 141 | 3,610 | 0 | 0 | 100 | 2,179 | 2,636 | 78 |
| 142 | 3,655 | 0 | 25 | 53 | 760 | 674 | 234 |
| 143 | 13,775 | 0 | 0 | 184 | 5,955 | 550 | 416 |
| 144 | 10,440 | 1,300 | 229 | 738 | 4,369 | 1,066 | 52 |
| 145 | 0 | 0 | 0 | 0 | 618 | 0 | 0 |
| South Shore Hospital | | | | | | | |
| 112 | 0 | 0 | 0 | 0 | 0 | 0 | 0 |
| 115 | 8,774 | 796 | 0 | 92 | 1,441 | 837 | 376 |
| 116 | 80,548 | 7,393 | 0 | 278 | 2,359 | 1,393 | 806 |
| 117 | 2,054 | 199 | 0 | 0 | 5 | 0 | 0 |
| 118 | 14,061 | 1,367 | 0 | 226 | 1,782 | 0 | 0 |
| 121 | 0 | 366 | 0 | 2,893 | 34,882 | 23,943 | 1,051 |
| 122 | 380 | 0 | 0 | 459 | 6,299 | 21,162 | 0 |
| 123 | 0 | 555 | 0 | 936 | 24,600 | 945 | 0 |
| 124 | 0 | 0 | 0 | 0 | 0 | 0 | 0 |
| 125 | 0 | 0 | 0 | 0 | 0 | 0 | 0 |
| 126 | 0 | 0 | 0 | 173 | 211 | 351 | 54 |
| 127 | 13,647 | 1,139 | 0 | 13,489 | 76,205 | 19,882 | 3,574 |

TABLE V-continued

| | | | | | | | |
|---|---|---|---|---|---|---|---|
| 128 | 459 | 0 | 0 | 235 | 197 | 0 | 0 |
| 129 | 0 | 0 | 0 | 0 | 2,685 | 189 | 0 |
| 130 | 1,840 | 199 | 0 | 1,918 | 2,822 | 2,136 | 454 |
| 131 | 0 | 0 | 0 | 76 | 345 | 548 | 0 |
| 132 | 0 | 0 | 0 | 92 | 1,710 | 324 | 0 |
| 133 | 0 | 0 | 0 | 0 | 25 | 0 | 0 |
| 134 | 0 | 0 | 0 | 240 | 1,357 | 243 | 0 |
| 135 | 429 | 0 | 0 | 0 | 943 | 216 | 0 |
| 136 | 0 | 0 | 0 | 0 | 5 | 0 | 0 |
| 137 | 0 | 0 | 0 | 0 | 0 | 0 | 0 |
| 138 | 3,761 | 754 | 0 | 2,913 | 27,922 | 8,660 | 2,728 |
| 139 | 357 | 0 | 0 | 0 | 1,603 | 0 | 0 |
| 140 | 2,698 | 577 | 0 | 2,829 | 13,084 | 4,716 | 616 |
| 141 | 2,808 | 186 | 0 | 586 | 1,664 | 1,935 | 320 |
| 142 | 888 | 0 | 0 | 0 | 395 | 738 | 0 |
| 143 | 5,392 | 186 | 0 | 691 | 8,905 | 2,434 | 860 |
| 144 | 13,218 | 1,354 | 0 | 4,749 | 19,025 | 1,377 | 54 |
| 145 | 0 | 0 | 0 | 0 | 692 | 297 | 0 |
| Charlton Memorial Hospital | | | | | | | |
| 112 | 2,302 | 2,041 | 0 | 0 | 2,770 | 0 | 0 |
| 115 | 43,723 | 36,261 | 0 | 336 | 27,575 | 0 | 0 |
| 116 | 7,680 | 6,506 | 0 | 0 | 1,778 | 0 | 0 |
| 117 | 686 | 612 | 0 | 0 | 0 | 0 | 0 |
| 118 | 2,880 | 49 | 0 | 921 | 348,255 | 0 | 0 |
| 121 | 1,834 | 0 | 0 | 1,465 | 152,552 | 0 | 0 |
| 122 | 1,955 | 808 | 0 | 975 | 113,818 | 0 | 0 |
| 123 | 0 | 0 | 0 | 0 | 702 | 0 | 0 |
| 124 | 0 | 0 | 0 | 105 | 933 | 0 | 0 |
| 125 | 860 | 0 | 0 | 0 | 2,518 | 0 | 0 |
| 126 | 15,539 | 1,272 | 0 | 4,078 | 744,577 | 0 | 0 |
| 127 | 421 | 0 | 0 | 114 | 6,409 | 0 | 0 |
| 128 | 0 | 0 | 0 | 0 | 3,871 | 0 | 0 |
| 129 | 1,124 | 0 | 0 | 570 | 21,771 | 0 | 0 |
| 130 | 271 | 0 | 0 | 0 | 1,039 | 0 | 0 |
| 131 | 3,003 | 0 | 0 | 305 | 22,867 | 0 | 0 |
| 132 | 271 | 0 | 0 | 0 | 1,259 | 0 | 0 |
| 133 | 879 | 420 | 0 | 0 | 1,481 | 0 | 0 |
| 134 | 0 | 0 | 0 | 0 | 1,892 | 0 | 0 |
| 135 | 0 | 0 | 0 | 0 | 0 | 0 | 0 |
| 136 | 6,458 | 4,645 | 0 | 400 | 71,785 | 0 | 0 |
| 137 | 2,627 | 4,065 | 0 | 190 | 21,436 | 0 | 0 |
| 138 | 3,296 | 756 | 0 | 2,475 | 195,293 | 0 | 0 |
| 139 | 2,441 | 0 | 0 | 476 | 26,824 | 0 | 0 |
| 140 | 589 | 0 | 0 | 0 | 4,656 | 0 | 0 |
| 141 | 7,336 | 661 | 0 | 279 | 103,490 | 0 | 0 |
| 142 | 5,193 | 2,064 | 0 | 2,954 | 49,112 | 0 | 0 |
| 143 | 675 | 420 | 0 | 0 | 3,918 | 0 | 0 |
| 144 | 0 | 0 | 0 | 0 | 0 | 0 | 0 |
| 145 | 0 | 0 | 0 | 0 | 0 | 0 | 0 |
| Cape Cod Hospital | | | | | | | |
| 112 | 0 | 0 | 0 | 0 | 0 | 0 | 0 |
| 115 | 0 | 0 | 0 | 0 | 118 | 0 | 0 |
| 116 | 1,307 | 278 | 0 | 792 | 4,760 | 347 | 46 |
| 117 | 0 | 0 | 0 | 0 | 240 | 0 | 0 |
| 118 | 0 | 0 | 0 | 0 | 0 | 0 | 0 |
| 121 | 1,685 | 268 | 0 | 4,488 | 61,503 | 996 | 46 |
| 122 | 0 | 0 | 0 | 2,645 | 17,943 | 765 | 168 |
| 123 | 0 | 0 | 0 | 902 | 30,079 | 301 | 0 |
| 124 | 0 | 0 | 0 | 0 | 0 | 0 | 0 |
| 125 | 0 | 0 | 0 | 0 | 0 | 0 | 0 |
| 126 | 1,062 | 190 | 0 | 0 | 567 | 23 | 23 |
| 127 | 1,705 | 212 | 0 | 13,751 | 106,086 | 4,443 | 1,289 |
| 128 | 0 | 0 | 0 | 902 | 1,922 | 93 | 0 |
| 129 | 0 | 0 | 0 | 343 | 4,687 | 0 | 0 |
| 130 | 781 | 163 | 0 | 1,310 | 3,797 | 905 | 92 |
| 131 | 0 | 0 | 0 | 627 | 654 | 46 | 0 |
| 132 | 0 | 0 | 0 | 0 | 2,627 | 23 | 0 |
| 133 | 0 | 0 | 0 | 0 | 310 | 0 | 0 |
| 134 | 575 | 106 | 0 | 0 | 342 | 0 | 0 |
| 135 | 0 | 0 | 0 | 127 | 484 | 0 | 0 |
| 136 | 0 | 0 | 0 | 0 | 46 | 0 | 0 |
| 137 | 0 | 0 | 0 | 0 | 192 | 0 | 0 |
| 138 | 582 | 97 | 0 | 1,733 | 22,657 | 1,530 | 591 |
| 139 | 1,764 | 0 | 0 | 343 | 4,991 | 208 | 186 |
| 140 | 532 | 0 | 0 | 5,670 | 26,897 | 928 | 678 |
| 141 | 2,639 | 350 | 0 | 691 | 2,130 | 779 | 40 |

TABLE V-continued

| | | | | | | | |
|---|---|---|---|---|---|---|---|
| 142 | 0 | 0 | 0 | 28 | 1,251 | 69 | 0 |
| 143 | 1,063 | 0 | 0 | 277 | 14,422 | 46 | 0 |
| 144 | 6,819 | 1,036 | 0 | 3,166 | 7,346 | 348 | 0 |
| 145 | 0 | 0 | 0 | 515 | 875 | 0 | 0 |
| Brockton Hospital | | | | | | | |
| 112 | 0 | 0 | 0 | 0 | 0 | 0 | 0 |
| 115 | 4,385 | 3,600 | 0 | 0 | 4,286 | 0 | 0 |
| 116 | 25,479 | 13,725 | 0 | 138 | 4,767 | 103 | 0 |
| 117 | 0 | 0 | 0 | 0 | 0 | 0 | 0 |
| 118 | 3,049 | 2,287 | 0 | 0 | 1,759 | 0 | 0 |
| 121 | 475 | 7,709 | 0 | 7,383 | 66,457 | 11,475 | 180 |
| 122 | 0 | 0 | 0 | 2,761 | 20,622 | 6,799 | 0 |
| 123 | 0 | 5,505 | 0 | 1,405 | 17,657 | 848 | 164 |
| 124 | 0 | 0 | 0 | 0 | 0 | 0 | 0 |
| 125 | 0 | 0 | 0 | 0 | 0 | 0 | 0 |
| 126 | 475 | 0 | 0 | 3,920 | 926 | 0 | 0 |
| 127 | 5,911 | 12,757 | 0 | 12,836 | 132,052 | 7,631 | 595 |
| 128 | 475 | 0 | 0 | 294 | 0 | 729 | 112 |
| 129 | 0 | 1,200 | 0 | 0 | 594 | 0 | 0 |
| 130 | 2,454 | 1,800 | 0 | 5,703 | 4,434 | 1,037 | 0 |
| 131 | 0 | 0 | 0 | 832 | 270 | 277 | 0 |
| 132 | 0 | 248 | 0 | 0 | 1,500 | 22 | 0 |
| 133 | 0 | 0 | 0 | 0 | 0 | 0 | 0 |
| 134 | 0 | 0 | 0 | 1,249 | 1,169 | 282 | 346 |
| 135 | 0 | 0 | 0 | 221 | 1,190 | 0 | 0 |
| 136 | 0 | 0 | 0 | 0 | 138 | 0 | 0 |
| 137 | 0 | 0 | 0 | 0 | 0 | 0 | 0 |
| 138 | 2,593 | 8,619 | 0 | 3,840 | 26,060 | 1,710 | 164 |
| 139 | 0 | 2,287 | 0 | 47 | 2,925 | 114 | 0 |
| 140 | 715 | 600 | 0 | 5,193 | 53,679 | 1,846 | 0 |
| 141 | 0 | 0 | 0 | 1,768 | 5,288 | 2,787 | 0 |
| 142 | 0 | 0 | 0 | 205 | 774 | 376 | 0 |
| 143 | 0 | 0 | 0 | 232 | 14,550 | 119 | 0 |
| 144 | 3,821 | 1,800 | 0 | 3,645 | 12,260 | 427 | 212 |
| 145 | 0 | 0 | 0 | 341 | 230 | 0 | 0 |
| Norwood Hospital | | | | | | | |
| 112 | 0 | 0 | 0 | 0 | 37 | 0 | 0 |
| 115 | 7,037 | 474 | 0 | 140 | 3,943 | 1,116 | 0 |
| 116 | 25,520 | 1,883 | 0 | 596 | 7,854 | 799 | 43 |
| 117 | 1,200 | 118 | 0 | 140 | 1,135 | 963 | 108 |
| 118 | 6,546 | 560 | 0 | 318 | 1,579 | 0 | 0 |
| 121 | 20 | 0 | 0 | 5,093 | 65,486 | 9,580 | 539 |
| 122 | 0 | 0 | 0 | 0 | 21,840 | 7,551 | 0 |
| 123 | 40 | 0 | 0 | 1,113 | 12,419 | 246 | 0 |
| 124 | 0 | 0 | 0 | 0 | 0 | 0 | 0 |
| 125 | 0 | 0 | 0 | 0 | 0 | 0 | 0 |
| 126 | 0 | 0 | 0 | 0 | 927 | 75 | 108 |
| 127 | 597 | 0 | 0 | 13,062 | 155,632 | 4,039 | 336 |
| 128 | 0 | 0 | 0 | 0 | 41 | 226 | 0 |
| 129 | 0 | 0 | 0 | 526 | 7,133 | 74 | 0 |
| 130 | 0 | 0 | 0 | 860 | 4,130 | 616 | 0 |
| 131 | 560 | 245 | 0 | 0 | 316 | 0 | 0 |
| 132 | 0 | 0 | 0 | 0 | 1,928 | 291 | 0 |
| 133 | 0 | 0 | 0 | 0 | 0 | 0 | 0 |
| 134 | 0 | 0 | 0 | 0 | 274 | 0 | 0 |
| 135 | 0 | 0 | 0 | 0 | 631 | 0 | 0 |
| 136 | 0 | 0 | 0 | 0 | 360 | 0 | 0 |
| 137 | 0 | 0 | 0 | 0 | 0 | 0 | 0 |
| 138 | 0 | 0 | 0 | 318 | 18,056 | 673 | 49 |
| 139 | 0 | 0 | 0 | 0 | 5,852 | 0 | 0 |
| 140 | 538 | 216 | 0 | 3,805 | 53,825 | 612 | 43 |
| 141 | 0 | 0 | 0 | 0 | 3,976 | 329 | 0 |
| 142 | 20 | 0 | 0 | 0 | 2,144 | 263 | 0 |
| 143 | 20 | 0 | 0 | 280 | 24,353 | 86 | 0 |
| 144 | 5,747 | 498 | 0 | 2,661 | 13,079 | 0 | 0 |
| 145 | 0 | 0 | 0 | 0 | 596 | 0 | 0 |
| Goddard Memorial Hospital | | | | | | | |
| 112 | 0 | 0 | 0 | 0 | 0 | 0 | 0 |
| 115 | 11,836 | 0 | 0 | 1,005 | 10,392 | 2,713 | 63 |
| 116 | 74,523 | 296 | 0 | 1,056 | 7,433 | 3,707 | 0 |
| 117 | 4,660 | 0 | 0 | 477 | 354 | 0 | 0 |
| 118 | 4,698 | 0 | 0 | 1,370 | 178 | 0 | 0 |
| 121 | 0 | 0 | 0 | 4,562 | 20,854 | 5,435 | 1,053 |
| 122 | 151 | 0 | 0 | 778 | 12,366 | 4,808 | 963 |
| 123 | 196 | 0 | 0 | 2,298 | 24,193 | 869 | 40 |

TABLE V-continued

| | | | | | | | |
|---|---|---|---|---|---|---|---|
| 124 | 0 | 0 | 0 | 0 | 0 | 0 | 0 |
| 125 | 0 | 0 | 0 | 0 | 0 | 0 | 0 |
| 126 | 196 | 0 | 0 | 2,365 | 12,708 | 1,330 | 33 |
| 127 | 1,179 | 0 | 0 | 10,228 | 75,070 | 7,462 | 231 |
| 128 | 351 | 0 | 0 | 704 | 3,361 | 1,330 | 180 |
| 129 | 0 | 0 | 0 | 0 | 1,472 | 0 | 0 |
| 130 | 0 | 0 | 0 | 0 | 131 | 286 | 0 |
| 131 | 0 | 0 | 0 | 0 | 73 | 94 | 0 |
| 132 | 0 | 0 | 0 | 176 | 844 | 275 | 0 |
| 133 | 0 | 0 | 0 | 0 | 0 | 0 | 0 |
| 134 | 0 | 0 | 0 | 0 | 1,587 | 347 | 0 |
| 135 | 0 | 0 | 0 | 0 | 16 | 0 | 0 |
| 136 | 0 | 0 | 0 | 0 | 0 | 0 | 0 |
| 137 | 0 | 0 | 0 | 0 | 0 | 0 | 0 |
| 138 | 903 | 0 | 0 | 1,814 | 17,967 | 5,256 | 0 |
| 139 | 0 | 0 | 0 | 176 | 3,386 | 286 | 0 |
| 140 | 1,363 | 0 | 0 | 3,870 | 35,553 | 4,048 | 35 |
| 141 | 0 | 0 | 0 | 923 | 8,638 | 4,719 | 125 |
| 142 | 351 | 0 | 0 | 311 | 1,289 | 1,478 | 0 |
| 143 | 752 | 0 | 0 | 477 | 17,550 | 1,187 | 15 |
| 144 | 4,545 | 0 | 0 | 2,385 | 4,548 | 278 | 0 |
| 145 | 0 | 0 | 0 | 0 | 98 | 0 | 0 |
| Cardinal Cushing General Hospital | | | | | | | |
| 112 | 4,365 | 584 | 347 | 0 | 1,419 | 977 | 0 |
| 115 | 29,440 | 5,948 | 1,841 | 0 | 2,101 | 6,331 | 0 |
| 116 | 2,155 | 264 | 0 | 0 | 54 | 0 | 0 |
| 117 | 2,060 | 720 | 0 | 0 | 21 | 0 | 0 |
| 118 | 505 | 0 | 908 | 0 | 8,004 | 8,717 | 708 |
| 121 | 0 | 0 | 97 | 0 | 2,490 | 5,993 | 0 |
| 122 | 0 | 0 | 876 | 0 | 3,972 | 1,818 | 270 |
| 123 | 0 | 0 | 0 | 0 | 0 | 0 | 0 |
| 124 | 0 | 0 | 0 | 0 | 0 | 0 | 0 |
| 125 | 1,515 | 0 | 720 | 0 | 297 | 405 | 180 |
| 126 | 1,520 | 0 | 4,406 | 0 | 25,813 | 10,110 | 1,346 |
| 127 | 0 | 0 | 0 | 0 | 367 | 45 | 0 |
| 128 | 0 | 0 | 65 | 0 | 450 | 0 | 0 |
| 129 | 825 | 0 | 1,208 | 0 | 766 | 5,175 | 0 |
| 130 | 660 | 0 | 27 | 0 | 233 | 2,058 | 135 |
| 131 | 0 | 0 | 0 | 0 | 11 | 0 | 0 |
| 132 | 0 | 0 | 0 | 0 | 45 | 248 | 0 |
| 133 | 840 | 0 | 46 | 0 | 207 | 500 | 32 |
| 134 | 1,355 | 0 | 574 | 0 | 146 | 0 | 0 |
| 135 | 0 | 0 | 0 | 0 | 0 | 0 | 0 |
| 136 | 765 | 0 | 535 | 0 | 5,755 | 4,199 | 0 |
| 137 | 0 | 0 | 0 | 0 | 353 | 180 | 0 |
| 138 | 345 | 0 | 2,633 | 0 | 11,036 | 6,929 | 0 |
| 139 | 0 | 0 | 241 | 0 | 840 | 4,340 | 0 |
| 140 | 0 | 0 | 0 | 0 | 183 | 76 | 0 |
| 141 | 1,500 | 160 | 54 | 0 | 2,449 | 1,313 | 0 |
| 142 | 720 | 360 | 997 | 0 | 1,406 | 272 | 675 |
| 143 | 360 | 120 | 0 | 0 | 25 | 59 | 0 |
| 144 | 0 | 0 | 0 | 0 | 0 | 0 | 0 |
| 145 | 0 | 0 | 0 | 0 | 0 | 0 | 0 |

| | Speech Therapy | Emergency Room | Pulmonary Function | Audiology | Cardiac Catheterization | Ambulance | Recovery Room |
|---|---|---|---|---|---|---|---|
| St. Luke's Hospital of New Bedford | | | | | | | |
| 112 | 0 | 0 | 0 | 0 | 0 | 0 | 0 |
| 115 | 0 | 3,851 | 0 | 0 | 0 | 0 | 625 |
| 116 | 225 | 16,161 | 0 | 0 | 0 | 0 | 5,125 |
| 117 | 0 | 313 | 0 | 0 | 0 | 0 | 0 |
| 118 | 0 | 847 | 0 | 0 | 0 | 0 | 1,125 |
| 121 | 1,710 | 103,754 | 0 | 0 | 21,708 | 1,588 | 450 |
| 122 | 510 | 79,368 | 0 | 0 | 19,770 | 619 | 0 |
| 123 | 578 | 25,101 | 0 | 0 | 0 | 0 | 0 |
| 124 | 0 | 4,787 | 0 | 0 | 70,732 | 0 | 0 |
| 125 | 0 | 1,404 | 0 | 0 | 72,664 | 0 | 0 |
| 126 | 0 | 3,288 | 0 | 0 | 0 | 840 | 0 |
| 127 | 1,970 | 216,042 | 0 | 0 | 0 | 1,456 | 1,200 |
| 128 | 0 | 3,807 | 0 | 0 | 0 | 0 | 0 |
| 129 | 0 | 3,407 | 0 | 0 | 0 | 0 | 0 |
| 130 | 0 | 12,263 | 0 | 0 | 0 | 683 | 0 |
| 131 | 0 | 4,496 | 0 | 0 | 0 | 82 | 0 |
| 132 | 0 | 1,398 | 0 | 0 | 0 | 0 | 0 |

TABLE V-continued

|     |       |         |       |    |        |       |       |
|-----|-------|---------|-------|----|--------|-------|-------|
| 133 | 0     | 1,649   | 0     | 0  | 0      | 0     | 0     |
| 134 | 52    | 4,469   | 0     | 0  | 0      | 0     | 0     |
| 135 | 0     | 2,755   | 0     | 0  | 0      | 41    | 0     |
| 136 | 0     | 836     | 0     | 0  | 0      | 0     | 0     |
| 137 | 0     | 0       | 0     | 0  | 0      | 0     | 0     |
| 138 | 354   | 64,081  | 0     | 0  | 0      | 2,130 | 2,675 |
| 139 | 0     | 24,942  | 0     | 0  | 0      | 0     | 150   |
| 140 | 156   | 181,940 | 0     | 0  | 0      | 420   | 0     |
| 141 | 440   | 32,170  | 0     | 0  | 0      | 440   | 0     |
| 142 | 0     | 28,346  | 0     | 0  | 0      | 0     | 0     |
| 143 | 0     | 85,906  | 0     | 0  | 0      | 0     | 0     |
| 144 | 0     | 15,268  | 0     | 0  | 0      | 0     | 475   |
| 145 | 0     | 6,391   | 0     | 0  | 0      | 199   | 0     |
| South Shore Hospital | | | | | | | |
| 112 | 0     | 0       | 0     | 0  | 0      | 0     | 0     |
| 115 | 0     | 1,361   | 0     | 0  | 0      | 0     | 220   |
| 116 | 0     | 6,740   | 0     | 0  | 828    | 366   | 2,860 |
| 117 | 0     | 0       | 0     | 0  | 0      | 0     | 0     |
| 118 | 0     | 285     | 0     | 0  | 0      | 0     | 1,020 |
| 121 | 0     | 41,327  | 0     | 0  | 15,898 | 159   | 400   |
| 122 | 0     | 41,326  | 0     | 0  | 20,136 | 0     | 0     |
| 123 | 0     | 8,228   | 0     | 0  | 651    | 0     | 0     |
| 124 | 0     | 0       | 0     | 0  | 0      | 0     | 0     |
| 125 | 0     | 0       | 0     | 0  | 0      | 0     | 0     |
| 126 | 0     | 0       | 0     | 0  | 0      | 0     | 0     |
| 127 | 63    | 95,803  | 0     | 0  | 4,140  | 384   | 6,480 |
| 128 | 0     | 1,860   | 0     | 0  | 0      | 0     | 220   |
| 129 | 0     | 686     | 0     | 0  | 0      | 0     | 0     |
| 130 | 0     | 6,077   | 0     | 0  | 201    | 0     | 220   |
| 131 | 0     | 1,818   | 0     | 0  | 0      | 0     | 0     |
| 132 | 0     | 813     | 0     | 0  | 201    | 0     | 0     |
| 133 | 0     | 120     | 0     | 0  | 0      | 0     | 0     |
| 134 | 0     | 5,258   | 0     | 0  | 1,431  | 0     | 200   |
| 135 | 0     | 2,118   | 0     | 0  | 225    | 0     | 200   |
| 136 | 0     | 120     | 0     | 0  | 0      | 0     | 0     |
| 137 | 0     | 0       | 0     | 0  | 0      | 0     | 0     |
| 138 | 172   | 43,372  | 0     | 0  | 3,454  | 0     | 4,400 |
| 139 | 0     | 21,136  | 0     | 0  | 2,342  | 0     | 1,040 |
| 140 | 0     | 132,055 | 0     | 0  | 40,165 | 170   | 820   |
| 141 | 0     | 19,222  | 0     | 0  | 876    | 183   | 600   |
| 142 | 0     | 12,191  | 0     | 0  | 1,230  | 0     | 640   |
| 143 | 0     | 116,941 | 0     | 0  | 42,392 | 342   | 1,860 |
| 144 | 0     | 8,523   | 0     | 0  | 0      | 530   | 1,460 |
| 145 | 0     | 4,556   | 0     | 0  | 402    | 0     | 0     |
| Charlton Memorial Hospital | | | | | | | |
| 112 | 0     | 687     | 0     | 0  | 0      | 0     | 166   |
| 115 | 0     | 13,560  | 493   | 0  | 482    | 0     | 3,031 |
| 116 | 0     | 590     | 0     | 0  | 0      | 0     | 505   |
| 117 | 0     | 0       | 0     | 0  | 0      | 0     | 0     |
| 118 | 128   | 85,946  | 1,715 | 0  | 10,404 | 0     | 0     |
| 121 | 820   | 74,235  | 488   | 0  | 22,485 | 0     | 0     |
| 122 | 358   | 29,752  | 0     | 0  | 0      | 0     | 151   |
| 123 | 0     | 392     | 0     | 0  | 0      | 0     | 0     |
| 124 | 0     | 392     | 0     | 0  | 0      | 0     | 0     |
| 125 | 0     | 2,271   | 0     | 0  | 0      | 0     | 0     |
| 126 | 1,084 | 139,137 | 3,785 | 64 | 870    | 0     | 0     |
| 127 | 0     | 5,448   | 0     | 0  | 0      | 0     | 0     |
| 128 | 0     | 2,369   | 0     | 0  | 0      | 0     | 0     |
| 129 | 896   | 8,323   | 0     | 0  | 263    | 0     | 0     |
| 130 | 194   | 2,879   | 0     | 0  | 0      | 0     | 0     |
| 131 | 2,874 | 2,855   | 0     | 0  | 219    | 0     | 0     |
| 132 | 0     | 1,860   | 244   | 0  | 438    | 0     | 0     |
| 133 | 0     | 8,506   | 0     | 0  | 0      | 0     | 223   |
| 134 | 0     | 1,029   | 0     | 0  | 0      | 0     | 0     |
| 135 | 0     | 342     | 0     | 0  | 0      | 0     | 0     |
| 136 | 0     | 39,295  | 639   | 42 | 2,717  | 0     | 166   |
| 137 | 0     | 28,822  | 151   | 0  | 2,091  | 0     | 313   |
| 138 | 0     | 124,689 | 1,569 | 0  | 17,860 | 0     | 151   |
| 139 | 124   | 25,759  | 0     | 32 | 263    | 0     | 0     |
| 140 | 0     | 18,551  | 0     | 0  | 0      | 0     | 0     |
| 141 | 0     | 132,453 | 1,859 | 0  | 17,396 | 0     | 203   |
| 142 | 0     | 11,975  | 244   | 0  | 482    | 0     | 446   |
| 143 | 0     | 4,506   | 0     | 0  | 0      | 0     | 0     |
| 144 | 0     | 0       | 0     | 0  | 0      | 0     | 0     |
| 145 | 0     | 0       | 0     | 0  | 0      | 0     | 0     |

TABLE V-continued

| Cape Cod Hospital | | | | | | | |
|---|---|---|---|---|---|---|---|
| 112 | 0 | 0 | 0 | 0 | 0 | 0 | 0 |
| 115 | 0 | 2,167 | 0 | 0 | 0 | 0 | 0 |
| 116 | 0 | 42,481 | 155 | 0 | 0 | 0 | 1,055 |
| 117 | 0 | 6,539 | 0 | 0 | 0 | 0 | 0 |
| 118 | 0 | 842 | 0 | 0 | 0 | 0 | 0 |
| 121 | 23 | 64,070 | 933 | 0 | 0 | 0 | 1,613 |
| 122 | 0 | 66,611 | 242 | 0 | 0 | 0 | 0 |
| 123 | 23 | 18,108 | 0 | 0 | 0 | 0 | 0 |
| 124 | 0 | 0 | 0 | 0 | 0 | 0 | 0 |
| 125 | 0 | 0 | 0 | 0 | 0 | 0 | 0 |
| 126 | 0 | 2,782 | 0 | 0 | 0 | 0 | 0 |
| 127 | 250 | 149,144 | 5,614 | 0 | 0 | 0 | 3,562 |
| 128 | 46 | 7,096 | 0 | 0 | 0 | 0 | 504 |
| 129 | 0 | 1,745 | 0 | 0 | 0 | 0 | 0 |
| 130 | 0 | 11,977 | 576 | 0 | 0 | 0 | 625 |
| 131 | 0 | 5,853 | 0 | 0 | 0 | 0 | 0 |
| 132 | 0 | 2,478 | 0 | 0 | 0 | 0 | 0 |
| 133 | 0 | 2,076 | 0 | 0 | 0 | 0 | 0 |
| 134 | 0 | 3,639 | 0 | 0 | 0 | 0 | 269 |
| 135 | 0 | 2,950 | 0 | 0 | 0 | 0 | 0 |
| 136 | 0 | 340 | 0 | 0 | 0 | 0 | 0 |
| 137 | 0 | 0 | 0 | 0 | 0 | 0 | 0 |
| 138 | 115 | 62,445 | 1,268 | 0 | 0 | 0 | 7,364 |
| 139 | 0 | 44,601 | 74 | 0 | 0 | 0 | 7,930 |
| 140 | 46 | 160,525 | 794 | 0 | 0 | 0 | 0 |
| 141 | 0 | 21,454 | 0 | 0 | 0 | 0 | 0 |
| 142 | 0 | 13,975 | 0 | 0 | 0 | 0 | 0 |
| 143 | 0 | 112,486 | 639 | 0 | 0 | 0 | 0 |
| 144 | 23 | 14,047 | 376 | 0 | 0 | 0 | 1,223 |
| 145 | 0 | 5,207 | 0 | 0 | 0 | 0 | 0 |
| Brockton Hospital | | | | | | | |
| 112 | 0 | 0 | 0 | 0 | 0 | 0 | 0 |
| 115 | 0 | 763 | 452 | 0 | 0 | 0 | 808 |
| 116 | 0 | 2,859 | 1,635 | 0 | 0 | 0 | 4,644 |
| 117 | 0 | 0 | 0 | 0 | 0 | 0 | 0 |
| 118 | 0 | 0 | 818 | 0 | 0 | 0 | 753 |
| 121 | 490 | 32,552 | 10,681 | 0 | 0 | 485 | 226 |
| 122 | 0 | 16,678 | 1,107 | 0 | 0 | 0 | 0 |
| 123 | 1,499 | 6,239 | 5,606 | 0 | 0 | 0 | 0 |
| 124 | 0 | 0 | 0 | 0 | 0 | 0 | 0 |
| 125 | 0 | 0 | 0 | 0 | 0 | 0 | 0 |
| 126 | 0 | 1,761 | 242 | 0 | 0 | 0 | 0 |
| 127 | 466 | 60,699 | 27,725 | 0 | 0 | 970 | 226 |
| 128 | 0 | 1,170 | 206 | 0 | 0 | 0 | 0 |
| 129 | 0 | 834 | 385 | 0 | 0 | 0 | 0 |
| 130 | 0 | 6,900 | 1,813 | 0 | 0 | 0 | 0 |
| 131 | 102 | 1,928 | 313 | 0 | 0 | 0 | 0 |
| 132 | 0 | 709 | 149 | 0 | 0 | 0 | 0 |
| 133 | 0 | 86 | 0 | 0 | 0 | 0 | 0 |
| 134 | 645 | 1,887 | 114 | 0 | 0 | 0 | 0 |
| 135 | 0 | 156 | 127 | 0 | 0 | 0 | 0 |
| 136 | 0 | 234 | 22 | 0 | 0 | 0 | 0 |
| 137 | 0 | 0 | 0 | 0 | 0 | 0 | 0 |
| 138 | 378 | 24,649 | 6,918 | 0 | 0 | 0 | 474 |
| 139 | 0 | 9,086 | 891 | 0 | 0 | 0 | 0 |
| 140 | 0 | 63,420 | 7,940 | 0 | 0 | 0 | 280 |
| 141 | 0 | 15,289 | 1,525 | 0 | 0 | 485 | 0 |
| 142 | 417 | 5,571 | 491 | 0 | 0 | 0 | 0 |
| 143 | 0 | 40,892 | 2,914 | 0 | 0 | 0 | 0 |
| 144 | 0 | 7,820 | 2,364 | 0 | 0 | 0 | 506 |
| 145 | 0 | 1,398 | 102 | 0 | 0 | 0 | 0 |
| Norwood Hospital | | | | | | | |
| 112 | 0 | 153 | 0 | 0 | 2,963 | 0 | 0 |
| 115 | 0 | 2,252 | 48 | 0 | 7,822 | 0 | 847 |
| 116 | 0 | 6,870 | 0 | 0 | 22,747 | 0 | 3,540 |
| 117 | 0 | 863 | 0 | 0 | 1,646 | 0 | 130 |
| 118 | 0 | 2,203 | 0 | 0 | 7,103 | 0 | 994 |
| 121 | 797 | 44,585 | 2,468 | 0 | 47,982 | 0 | 241 |
| 122 | 34 | 27,706 | 774 | 0 | 44,642 | 0 | 0 |
| 123 | 0 | 9,591 | 0 | 0 | 1,269 | 0 | 0 |
| 124 | 0 | 0 | 0 | 0 | 0 | 0 | 0 |
| 125 | 0 | 0 | 0 | 0 | 0 | 0 | 0 |
| 126 | 0 | 192 | 0 | 0 | 0 | 0 | 128 |
| 127 | 345 | 96,483 | 4,284 | 0 | 107,992 | 0 | 2,290 |
| 128 | 0 | 1,044 | 0 | 0 | 699 | 0 | 0 |

TABLE V-continued

| | | | | | | | |
|---|---|---|---|---|---|---|---|
| 129 | 0 | 3,566 | 0 | 0 | 615 | 0 | 0 |
| 130 | 0 | 2,210 | 0 | 0 | 0 | 0 | 128 |
| 131 | 0 | 1,083 | 0 | 0 | 0 | 0 | 728 |
| 132 | 0 | 1,556 | 0 | 0 | 1,398 | 0 | 128 |
| 133 | 0 | 0 | 0 | 0 | 0 | 0 | 0 |
| 134 | 0 | 1,259 | 0 | 0 | 2,210 | 0 | 0 |
| 135 | 0 | 2,355 | 0 | 0 | 2,996 | 0 | 0 |
| 136 | 0 | 1,290 | 0 | 0 | 438 | 0 | 0 |
| 137 | 0 | 0 | 0 | 0 | 0 | 0 | 0 |
| 138 | 0 | 25,371 | 1,102 | 0 | 58,044 | 0 | 378 |
| 139 | 0 | 16,704 | 0 | 0 | 31,817 | 0 | 0 |
| 140 | 0 | 86,069 | 1,875 | 0 | 114,273 | 0 | 1,407 |
| 141 | 0 | 13,338 | 0 | 0 | 14,821 | 0 | 410 |
| 142 | 0 | 11,775 | 0 | 0 | 18,066 | 0 | 113 |
| 143 | 0 | 47,201 | 1,264 | 0 | 100,970 | 0 | 836 |
| 144 | 0 | 8,258 | 2,143 | 0 | 6,678 | 0 | 1,568 |
| 145 | 0 | 3,760 | 0 | 0 | 4,093 | 0 | 0 |
| Goddard Memorial Hospital | | | | | | | |
| 112 | 0 | 0 | 0 | 0 | 0 | 0 | 0 |
| 115 | 0 | 1,583 | 1,479 | 0 | 3,956 | 0 | 0 |
| 116 | 0 | 5,378 | 410 | 0 | 16,238 | 0 | 3,986 |
| 117 | 0 | 207 | 0 | 0 | 0 | 0 | 570 |
| 118 | 0 | 457 | 0 | 0 | 706 | 0 | 710 |
| 121 | 124 | 13,748 | 1,707 | 0 | 21,886 | 0 | 0 |
| 122 | 0 | 12,650 | 234 | 0 | 24,357 | 0 | 0 |
| 123 | 0 | 6,239 | 3,180 | 0 | 4,942 | 0 | 0 |
| 124 | 0 | 0 | 0 | 0 | 0 | 0 | 0 |
| 125 | 0 | 0 | 0 | 0 | 0 | 0 | 0 |
| 126 | 602 | 913 | 1,229 | 0 | 3,514 | 0 | 0 |
| 127 | 0 | 30,831 | 9,840 | 0 | 51,207 | 0 | 215 |
| 128 | 0 | 1,331 | 36 | 0 | 1,412 | 0 | 452 |
| 129 | 0 | 170 | 886 | 0 | 353 | 0 | 355 |
| 130 | 0 | 1,204 | 0 | 0 | 0 | 0 | 994 |
| 131 | 0 | 2,278 | 0 | 0 | 353 | 0 | 402 |
| 132 | 0 | 170 | 0 | 0 | 353 | 0 | 0 |
| 133 | 0 | 0 | 0 | 0 | 0 | 0 | 0 |
| 134 | 0 | 2,584 | 575 | 0 | 2,471 | 0 | 0 |
| 135 | 0 | 170 | 0 | 0 | 0 | 0 | 0 |
| 136 | 0 | 170 | 0 | 0 | 353 | 0 | 0 |
| 137 | 0 | 0 | 0 | 0 | 0 | 0 | 0 |
| 138 | 0 | 13,717 | 1,204 | 0 | 24,710 | 0 | 0 |
| 139 | 0 | 9,114 | 138 | 0 | 15,532 | 0 | 0 |
| 140 | 0 | 45,633 | 2,908 | 0 | 74,836 | 0 | 0 |
| 141 | 0 | 12,732 | 408 | 0 | 17,650 | 0 | 0 |
| 142 | 0 | 7,281 | 0 | 0 | 8,825 | 0 | 0 |
| 143 | 0 | 34,861 | 1,331 | 0 | 52,950 | 0 | 0 |
| 144 | 0 | 4,740 | 518 | 0 | 7,060 | 0 | 785 |
| 145 | 0 | 1,244 | 0 | 0 | 1,059 | 0 | 0 |
| Cardinal Cushing General Hospital | | | | | | | |
| 112 | 0 | 1,956 | 0 | 0 | 0 | 0 | 0 |
| 115 | 0 | 10,707 | 1,010 | 0 | 0 | 0 | 2,607 |
| 116 | 0 | 423 | 0 | 0 | 0 | 0 | 416 |
| 117 | 0 | 695 | 0 | 0 | 0 | 0 | 520 |
| 118 | 0 | 45,928 | 210 | 0 | 0 | 0 | 0 |
| 121 | 0 | 28,701 | 0 | 0 | 0 | 0 | 0 |
| 122 | 0 | 12,169 | 0 | 0 | 0 | 0 | 0 |
| 123 | 0 | 0 | 0 | 0 | 0 | 0 | 0 |
| 124 | 0 | 0 | 0 | 0 | 0 | 0 | 0 |
| 125 | 0 | 1,765 | 800 | 0 | 0 | 0 | 0 |
| 126 | 440 | 110,639 | 15,675 | 0 | 0 | 0 | 0 |
| 127 | 0 | 5,905 | 0 | 0 | 0 | 0 | 0 |
| 128 | 0 | 1,980 | 150 | 0 | 0 | 0 | 0 |
| 129 | 0 | 6,849 | 1,110 | 0 | 0 | 0 | 0 |
| 130 | 0 | 2,607 | 0 | 0 | 0 | 0 | 0 |
| 131 | 0 | 0 | 260 | 0 | 0 | 0 | 0 |
| 132 | 0 | 403 | 0 | 0 | 0 | 0 | 0 |
| 133 | 168 | 7,939 | 310 | 0 | 0 | 0 | 0 |
| 134 | 0 | 1,496 | 0 | 0 | 0 | 0 | 0 |
| 135 | 0 | 595 | 0 | 0 | 0 | 0 | 0 |
| 136 | 0 | 33,698 | 1,010 | 0 | 0 | 0 | 1,325 |
| 137 | 0 | 11,999 | 0 | 0 | 0 | 0 | 0 |
| 138 | 0 | 131,968 | 8,570 | 0 | 0 | 0 | 0 |
| 139 | 0 | 18,778 | 0 | 0 | 0 | 0 | 0 |
| 140 | 0 | 10,180 | 0 | 0 | 0 | 0 | 0 |
| 141 | 0 | 62,164 | 710 | 0 | 0 | 0 | 600 |

TABLE V-continued

| | | | | | | | |
|---|---|---|---|---|---|---|---|
| 142 | 0 | 9,125 | 2,970 | 0 | 0 | 0 | 1,065 |
| 143 | 0 | 1,295 | 0 | 0 | 0 | 0 | 325 |
| 144 | 0 | 0 | 0 | 0 | 0 | 0 | 0 |
| 145 | 0 | 0 | 0 | 0 | 0 | 0 | 0 |

| | Labor & Delivery | EKG | EEG | Renal Dialysis | Kidney Acquisition | Psychology/ Psychiatry | Other Ancillary |
|---|---|---|---|---|---|---|---|
| St. Luke's Hospital of New Bedford | | | | | | | |
| 112 | 0 | 0 | 0 | 0 | 0 | 0 | 0 |
| 115 | 0 | 1,846 | 0 | 0 | 0 | 0 | 26 |
| 116 | 0 | 6,762 | 2,675 | 0 | 0 | 0 | 375 |
| 117 | 0 | 60 | 0 | 0 | 0 | 0 | 0 |
| 118 | 0 | 259 | 472 | 0 | 0 | 0 | 0 |
| 121 | 0 | 30,404 | 2,360 | 0 | 0 | 0 | 3,647 |
| 122 | 0 | 25,354 | 944 | 0 | 0 | 0 | 2,565 |
| 123 | 0 | 4,430 | 1,416 | 0 | 0 | 0 | 0 |
| 124 | 0 | 3,723 | 0 | 0 | 0 | 0 | 2,249 |
| 125 | 0 | 2,516 | 0 | 0 | 0 | 85 | 1,892 |
| 126 | 0 | 282 | 1,416 | 0 | 0 | 0 | 816 |
| 127 | 0 | 33,805 | 3,304 | 0 | 0 | 574 | 2,902 |
| 128 | 0 | 252 | 0 | 0 | 0 | 0 | 78 |
| 129 | 0 | 216 | 1,416 | 0 | 0 | 0 | 0 |
| 130 | 0 | 1,064 | 0 | 0 | 0 | 0 | 246 |
| 131 | 0 | 246 | 0 | 0 | 0 | 0 | 41 |
| 132 | 0 | 355 | 0 | 0 | 0 | 0 | 26 |
| 133 | 0 | 945 | 0 | 0 | 0 | 0 | 0 |
| 134 | 0 | 1,348 | 0 | 0 | 0 | 0 | 573 |
| 135 | 0 | 576 | 0 | 0 | 0 | 0 | 0 |
| 136 | 0 | 60 | 0 | 0 | 0 | 0 | 0 |
| 137 | 0 | 0 | 0 | 0 | 0 | 0 | 0 |
| 138 | 0 | 16,167 | 6,451 | 0 | 0 | 582 | 1,623 |
| 139 | 0 | 6,266 | 1,416 | 0 | 0 | 0 | 151 |
| 140 | 0 | 46,636 | 1,888 | 0 | 0 | 638 | 3,126 |
| 141 | 0 | 7,989 | 16,049 | 0 | 0 | 0 | 1,375 |
| 142 | 0 | 6,603 | 11,328 | 0 | 0 | 0 | 26 |
| 143 | 0 | 22,452 | 944 | 0 | 0 | 85 | 432 |
| 144 | 0 | 2,374 | 944 | 0 | 0 | 0 | 229 |
| 145 | 0 | 1,580 | 0 | 0 | 0 | 0 | 939 |
| South Shore Hospital | | | | | | | |
| 112 | 0 | 0 | 0 | 0 | 0 | 0 | 0 |
| 115 | 0 | 4,449 | 0 | 440 | 0 | 0 | 1,060 |
| 116 | 0 | 23,907 | 428 | 0 | 0 | 0 | 1,640 |
| 117 | 0 | 150 | 0 | 0 | 0 | 0 | 0 |
| 118 | 0 | 1,306 | 0 | 0 | 0 | 0 | 1,530 |
| 121 | 0 | 158,811 | 722 | 1,500 | 0 | 0 | 18,167 |
| 122 | 0 | 136,120 | 209 | 0 | 0 | 0 | 1,622 |
| 123 | 0 | 19,293 | 294 | 300 | 0 | 0 | 18,280 |
| 124 | 0 | 0 | 0 | 0 | 0 | 0 | 0 |
| 125 | 0 | 0 | 0 | 0 | 0 | 0 | 0 |
| 126 | 0 | 627 | 219 | 1,200 | 0 | 0 | 0 |
| 127 | 0 | 202,986 | 1,354 | 18,100 | 0 | 0 | 23,698 |
| 128 | 0 | 2,471 | 0 | 0 | 0 | 0 | 0 |
| 129 | 0 | 1,039 | 603 | 0 | 0 | 0 | 931 |
| 130 | 0 | 6,155 | 0 | 1,760 | 0 | 0 | 409 |
| 131 | 0 | 1,791 | 0 | 0 | 0 | 0 | 329 |
| 132 | 0 | 2,761 | 0 | 0 | 0 | 0 | 2,100 |
| 133 | 0 | 200 | 0 | 0 | 0 | 0 | 0 |
| 134 | 0 | 6,029 | 0 | 0 | 0 | 0 | 742 |
| 135 | 0 | 5,593 | 0 | 0 | 0 | 0 | 406 |
| 136 | 0 | 759 | 0 | 0 | 0 | 0 | 0 |
| 137 | 0 | 0 | 0 | 0 | 0 | 0 | 0 |
| 138 | 0 | 112,789 | 2,776 | 2,540 | 0 | 0 | 11,858 |
| 139 | 0 | 40,220 | 209 | 0 | 0 | 0 | 794 |
| 140 | 0 | 206,889 | 219 | 660 | 0 | 0 | 6,447 |
| 141 | 0 | 31,729 | 8,124 | 660 | 0 | 0 | 552 |
| 142 | 0 | 18,065 | 4,469 | 0 | 0 | 0 | 598 |
| 143 | 0 | 154,268 | 1,797 | 0 | 0 | 0 | 3,822 |
| 144 | 0 | 18,647 | 428 | 4,550 | 0 | 0 | 11,976 |
| 145 | 0 | 7,969 | 209 | 0 | 0 | 0 | 208 |
| Charlton Memorial Hospital | | | | | | | |
| 112 | 0 | 1,308 | 0 | 0 | 0 | 0 | 56 |
| 115 | 0 | 24,389 | 262 | 0 | 0 | 0 | 6,698 |

TABLE V-continued

| | | | | | | | |
|---|---|---|---|---|---|---|---|
| 116 | 0 | 4,752 | 0 | 0 | 0 | 0 | 1,017 |
| 117 | 0 | 279 | 0 | 0 | 0 | 0 | 0 |
| 118 | 0 | 133,666 | 0 | 0 | 0 | 0 | 41,317 |
| 121 | 0 | 121,567 | 1,414 | 0 | 0 | 0 | 36,297 |
| 122 | 0 | 21,969 | 3,215 | 0 | 0 | 0 | 732 |
| 123 | 0 | 1,116 | 0 | 0 | 0 | 0 | 2,598 |
| 124 | 0 | 1,116 | 0 | 0 | 0 | 0 | 8,823 |
| 125 | 0 | 1,602 | 628 | 0 | 0 | 0 | 6,566 |
| 126 | 0 | 126,797 | 1,585 | 0 | 0 | 0 | 35,462 |
| 127 | 0 | 2,088 | 0 | 0 | 0 | 0 | 2,045 |
| 128 | 0 | 357 | 0 | 0 | 0 | 0 | 0 |
| 129 | 0 | 5,208 | 0 | 0 | 0 | 0 | 6,439 |
| 130 | 0 | 2,119 | 0 | 0 | 0 | 0 | 1,839 |
| 131 | 0 | 5,423 | 299 | 0 | 0 | 0 | 10,182 |
| 132 | 0 | 1,747 | 299 | 0 | 0 | 0 | 245 |
| 133 | 0 | 6,183 | 2,049 | 0 | 0 | 0 | 11,078 |
| 134 | 0 | 1,042 | 329 | 0 | 0 | 0 | 918 |
| 135 | 0 | 232 | 0 | 0 | 0 | 0 | 0 |
| 136 | 0 | 53,493 | 1,226 | 0 | 0 | 0 | 6,262 |
| 137 | 0 | 40,388 | 598 | 0 | 0 | 0 | 4,332 |
| 138 | 0 | 145,991 | 0 | 0 | 0 | 0 | 14,524 |
| 139 | 0 | 33,305 | 9,861 | 0 | 0 | 0 | 14,493 |
| 140 | 0 | 22,356 | 4,681 | 0 | 0 | 0 | 6,979 |
| 141 | 0 | 126,794 | 2,183 | 0 | 0 | 0 | 5,858 |
| 142 | 0 | 12,050 | 299 | 0 | 0 | 0 | 6,520 |
| 143 | 0 | 4,163 | 0 | 0 | 0 | 0 | 558 |
| 144 | 0 | 0 | 0 | 0 | 0 | 0 | 0 |
| 145 | 0 | 0 | 0 | 0 | 0 | 0 | 0 |
| Cape Cod Hospital | | | | | | | |
| 112 | 0 | 0 | 0 | 0 | 0 | 0 | 0 |
| 115 | 0 | 2,965 | 0 | 0 | 0 | 0 | 270 |
| 116 | 0 | 30,791 | 0 | 0 | 0 | 155 | 113 |
| 117 | 0 | 2,740 | 218 | 0 | 0 | 0 | 0 |
| 118 | 0 | 103 | 0 | 0 | 0 | 0 | 0 |
| 121 | 0 | 138,590 | 218 | 0 | 0 | 1,783 | 2,329 |
| 122 | 0 | 149,085 | 910 | 0 | 0 | 701 | 796 |
| 123 | 0 | 27,815 | 0 | 0 | 0 | 0 | 0 |
| 124 | 0 | 0 | 0 | 0 | 0 | 0 | 0 |
| 125 | 0 | 0 | 0 | 0 | 0 | 0 | 0 |
| 126 | 0 | 10,222 | 0 | 0 | 0 | 0 | 834 |
| 127 | 0 | 183,408 | 910 | 0 | 0 | 968 | 9,431 |
| 128 | 0 | 4,708 | 0 | 0 | 0 | 0 | 1,457 |
| 129 | 0 | 3,067 | 0 | 0 | 0 | 0 | 0 |
| 130 | 0 | 7,917 | 0 | 0 | 0 | 980 | 2,505 |
| 131 | 0 | 2,750 | 0 | 0 | 0 | 0 | 0 |
| 132 | 0 | 5,295 | 0 | 0 | 0 | 0 | 0 |
| 133 | 0 | 2,622 | 0 | 0 | 0 | 0 | 0 |
| 134 | 0 | 2,319 | 0 | 0 | 0 | 135 | 0 |
| 135 | 0 | 7,292 | 0 | 0 | 0 | 0 | 0 |
| 136 | 0 | 257 | 0 | 0 | 0 | 0 | 0 |
| 137 | 0 | 51 | 0 | 0 | 0 | 0 | 0 |
| 138 | 0 | 91,175 | 673 | 0 | 0 | 933 | 1,449 |
| 139 | 0 | 64,526 | 420 | 0 | 0 | 1,104 | 273 |
| 140 | 0 | 182,490 | 237 | 0 | 0 | 983 | 6,954 |
| 141 | 0 | 35,212 | 2,929 | 0 | 0 | 431 | 1,486 |
| 142 | 0 | 23,717 | 891 | 0 | 0 | 155 | 0 |
| 143 | 0 | 153,132 | 0 | 0 | 0 | 566 | 2,968 |
| 144 | 0 | 23,711 | 218 | 0 | 0 | 0 | 0 |
| 145 | 0 | 8,679 | 0 | 0 | 0 | 310 | 0 |
| Brockton Hospital | | | | | | | |
| 112 | 0 | 0 | 0 | 0 | 0 | 0 | 0 |
| 115 | 0 | 2,961 | 0 | 0 | 0 | 246 | 300 |
| 116 | 0 | 7,496 | 502 | 0 | 0 | 0 | 1,397 |
| 117 | 0 | 0 | 0 | 0 | 0 | 0 | 0 |
| 118 | 0 | 1,627 | 0 | 0 | 0 | 0 | 226 |
| 121 | 0 | 99,174 | 0 | 0 | 0 | 222 | 8,143 |
| 122 | 0 | 52,946 | 0 | 904 | 0 | 412 | 5,032 |
| 123 | 0 | 9,142 | 574 | 0 | 0 | 312 | 818 |
| 124 | 0 | 0 | 0 | 0 | 0 | 0 | 0 |
| 125 | 0 | 0 | 0 | 0 | 0 | 0 | 0 |
| 126 | 0 | 4,367 | 0 | 2,444 | 0 | 111 | 967 |
| 127 | 0 | 109,594 | 215 | 3,750 | 0 | 1,456 | 11,540 |
| 128 | 0 | 1,130 | 0 | 0 | 0 | 0 | 2,035 |
| 129 | 0 | 150 | 0 | 0 | 0 | 0 | 0 |
| 130 | 0 | 6,022 | 574 | 2,059 | 0 | 333 | 8,600 |
| 131 | 0 | 2,263 | 0 | 0 | 0 | 0 | 4,916 |
| 132 | 0 | 1,802 | 0 | 0 | 0 | 0 | 882 |

TABLE V-continued

| | | | | | | | |
|---|---|---|---|---|---|---|---|
| 133 | 0 | 50 | 0 | 0 | 0 | 0 | 150 |
| 134 | 0 | 3,514 | 287 | 0 | 0 | 0 | 1,094 |
| 135 | 0 | 400 | 0 | 0 | 0 | 0 | 0 |
| 136 | 0 | 461 | 0 | 0 | 0 | 0 | 0 |
| 137 | 0 | 0 | 0 | 0 | 0 | 0 | 0 |
| 138 | 0 | 49,925 | 502 | 0 | 0 | 930 | 6,720 |
| 139 | 0 | 25,947 | 287 | 0 | 0 | 111 | 3,397 |
| 140 | 0 | 107,392 | 430 | 3,434 | 0 | 333 | 11,128 |
| 141 | 0 | 42,726 | 4,912 | 0 | 0 | 1,025 | 9,991 |
| 142 | 0 | 14,591 | 1,649 | 0 | 0 | 111 | 4,663 |
| 143 | 0 | 49,949 | 215 | 237 | 0 | 1,566 | 5,757 |
| 144 | 0 | 15,470 | 0 | 12,509 | 0 | 111 | 2,542 |
| 145 | 0 | 2,476 | 0 | 0 | 0 | 0 | 0 |
| Norwood Hospital | | | | | | | |
| 112 | 0 | 25 | 0 | 0 | 0 | 0 | 0 |
| 115 | 0 | 7,805 | 567 | 0 | 0 | 147 | 561 |
| 116 | 0 | 13,015 | 952 | 0 | 0 | 0 | 18,435 |
| 117 | 0 | 647 | 0 | 0 | 0 | 0 | 106 |
| 118 | 0 | 4,794 | 532 | 0 | 0 | 0 | 1,640 |
| 121 | 0 | 98,014 | 1,254 | 0 | 0 | 147 | 7,850 |
| 122 | 0 | 68,517 | 602 | 0 | 0 | 139 | 1,404 |
| 123 | 0 | 8,716 | 226 | 0 | 0 | 0 | 22 |
| 124 | 0 | 0 | 0 | 0 | 0 | 0 | 0 |
| 125 | 0 | 0 | 0 | 0 | 0 | 0 | 0 |
| 126 | 0 | 3,136 | 266 | 632 | 0 | 0 | 2,259 |
| 127 | 0 | 143,395 | 2,342 | 10,688 | 0 | 1,093 | 18,028 |
| 128 | 0 | 609 | 0 | 0 | 0 | 0 | 1,041 |
| 129 | 0 | 2,004 | 0 | 594 | 0 | 0 | 538 |
| 130 | 0 | 3,170 | 0 | 0 | 0 | 0 | 4,212 |
| 131 | 0 | 1,998 | 0 | 0 | 0 | 872 | 3,073 |
| 132 | 0 | 4,085 | 0 | 0 | 0 | 0 | 454 |
| 133 | 0 | 0 | 0 | 0 | 0 | 0 | 0 |
| 134 | 0 | 3,257 | 482 | 0 | 0 | 0 | 371 |
| 135 | 0 | 5,129 | 266 | 0 | 0 | 0 | 334 |
| 136 | 0 | 1,369 | 266 | 0 | 0 | 0 | 380 |
| 137 | 0 | 0 | 0 | 0 | 0 | 0 | 0 |
| 138 | 0 | 63,062 | 1,807 | 2,528 | 0 | 285 | 5,511 |
| 139 | 0 | 36,324 | 300 | 0 | 0 | 0 | 1,061 |
| 140 | 0 | 92,622 | 894 | 632 | 0 | 2,914 | 8,897 |
| 141 | 0 | 23,687 | 4,141 | 1,504 | 0 | 251 | 8,961 |
| 142 | 0 | 26,042 | 5,622 | 0 | 0 | 253 | 6,708 |
| 143 | 0 | 47,312 | 504 | 300 | 0 | 519 | 7,651 |
| 144 | 0 | 14,238 | 0 | 4,846 | 0 | 51 | 2,061 |
| 145 | 0 | 5,713 | 266 | 0 | 0 | 81 | 422 |
| Goddard Memorial Hospital | | | | | | | |
| 112 | 0 | 0 | 0 | 0 | 0 | 0 | 0 |
| 115 | 0 | 6,150 | 0 | 0 | 0 | 0 | 1,767 |
| 116 | 0 | 21,921 | 792 | 630 | 0 | 0 | 3,238 |
| 117 | 0 | 507 | 0 | 1,125 | 0 | 0 | 0 |
| 118 | 0 | 1,179 | 0 | 0 | 0 | 0 | 0 |
| 121 | 0 | 30,887 | 439 | 2,250 | 0 | 0 | 552 |
| 122 | 0 | 36,620 | 338 | 0 | 0 | 0 | 2,837 |
| 123 | 0 | 7,974 | 687 | 225 | 0 | 0 | 731 |
| 124 | 0 | 0 | 0 | 0 | 0 | 0 | 0 |
| 125 | 0 | 0 | 0 | 0 | 0 | 0 | 0 |
| 126 | 0 | 3,728 | 549 | 5,204 | 0 | 0 | 881 |
| 127 | 0 | 64,956 | 878 | 19,648 | 0 | 0 | 10,887 |
| 128 | 0 | 2,352 | 0 | 0 | 0 | 0 | 1,842 |
| 129 | 0 | 414 | 142 | 0 | 0 | 0 | 117 |
| 130 | 0 | 117 | 0 | 0 | 0 | 0 | 755 |
| 131 | 0 | 414 | 0 | 0 | 0 | 0 | 1,089 |
| 132 | 0 | 1,299 | 0 | 0 | 0 | 0 | 0 |
| 133 | 0 | 0 | 0 | 0 | 0 | 0 | 0 |
| 134 | 0 | 3,743 | 0 | 0 | 0 | 0 | 1,151 |
| 135 | 0 | 156 | 0 | 0 | 0 | 0 | 0 |
| 136 | 0 | 297 | 0 | 0 | 0 | 0 | 0 |
| 137 | 0 | 0 | 0 | 0 | 0 | 0 | 0 |
| 138 | 0 | 39,954 | 538 | 5,653 | 0 | 0 | 2,394 |
| 139 | 0 | 23,986 | 0 | 0 | 0 | 0 | 1,186 |
| 140 | 0 | 99,836 | 1,399 | 1,076 | 0 | 0 | 12,703 |
| 141 | 454 | 30,773 | 7,766 | 4,130 | 0 | 0 | 15,224 |
| 142 | 0 | 16,559 | 6,137 | 0 | 0 | 0 | 5,922 |
| 143 | 0 | 72,183 | 607 | 359 | 0 | 0 | 12,811 |
| 144 | 0 | 8,495 | 338 | 5,210 | 0 | 0 | 949 |
| 145 | 0 | 1,632 | 0 | 225 | 0 | 0 | 0 |

TABLE V-continued

Cardinal Cushing General Hospital

| | | | | | | | |
|---|---|---|---|---|---|---|---|
| 112 | 0 | 1,763 | 0 | 0 | 0 | 0 | 0 |
| 115 | 0 | 8,996 | 670 | 0 | 0 | 0 | 0 |
| 116 | 0 | 258 | 0 | 0 | 0 | 0 | 0 |
| 117 | 0 | 233 | 0 | 0 | 0 | 0 | 0 |
| 118 | 0 | 26,537 | 1,560 | 0 | 0 | 0 | 0 |
| 121 | 0 | 17,668 | 2,070 | 0 | 0 | 0 | 0 |
| 122 | 0 | 4,345 | 220 | 0 | 0 | 0 | 0 |
| 123 | 0 | 0 | 0 | 0 | 0 | 0 | 0 |
| 124 | 0 | 0 | 0 | 0 | 0 | 0 | 0 |
| 125 | 0 | 1,819 | 335 | 0 | 0 | 0 | 0 |
| 126 | 0 | 46,390 | 7,065 | 0 | 0 | 0 | 0 |
| 127 | 0 | 363 | 367 | 0 | 0 | 0 | 0 |
| 128 | 0 | 175 | 152 | 0 | 0 | 0 | 0 |
| 129 | 0 | 3,113 | 335 | 0 | 0 | 0 | 0 |
| 130 | 0 | 319 | 0 | 0 | 0 | 0 | 0 |
| 131 | 0 | 162 | 0 | 0 | 0 | 0 | 0 |
| 132 | 0 | 192 | 0 | 0 | 0 | 0 | 0 |
| 133 | 0 | 2,932 | 335 | 0 | 0 | 0 | 0 |
| 134 | 0 | 930 | 335 | 0 | 0 | 0 | 0 |
| 135 | 0 | 379 | 0 | 0 | 0 | 0 | 0 |
| 136 | 0 | 15,998 | 2,480 | 0 | 0 | 0 | 0 |
| 137 | 0 | 6,344 | 1,439 | 0 | 0 | 0 | 0 |
| 138 | 0 | 62,089 | 6,553 | 0 | 0 | 0 | 0 |
| 139 | 0 | 7,989 | 10,059 | 0 | 0 | 0 | 0 |
| 140 | 0 | 3,368 | 4,960 | 0 | 0 | 0 | 0 |
| 141 | 0 | 21,568 | 3,369 | 0 | 0 | 0 | 0 |
| 142 | 0 | 5,584 | 670 | 0 | 0 | 0 | 0 |
| 143 | 0 | 516 | 335 | 0 | 0 | 0 | 0 |
| 144 | 0 | 0 | 0 | 0 | 0 | 0 | 0 |
| 145 | 0 | 0 | 0 | 0 | 0 | 0 | 0 |

TABLE VI

| | Cases | Age | Tot Days | Rout Days | ICU Days | Charges |
|---|---|---|---|---|---|---|
| St. Luke's Hospital of New Bedford | | | | | | |
| 112 | 0 | 0 | 0 | 0 | 0 | 0 |
| 115 | 3 | 226 | 42 | 14 | 28 | 56,260 |
| 116 | 19 | 1,445 | 148 | 56 | 92 | 319,001 |
| 117 | 0 | 0 | 0 | 0 | 0 | 0 |
| 118 | 3 | 234 | 8 | 4 | 4 | 35,558 |
| 121 | 133 | 9,618 | 1,334 | 525 | 809 | 535,566 |
| 122 | 79 | 5,054 | 561 | 124 | 437 | 210,711 |
| 123 | 22 | 1,675 | 136 | 50 | 86 | 92,164 |
| 124 | 0 | 0 | 0 | 0 | 0 | 0 |
| 125 | 0 | 0 | 0 | 0 | 0 | 0 |
| 126 | 9 | 437 | 214 | 199 | 15 | 66,794 |
| 127 | 294 | 21,894 | 2,578 | 2,050 | 527 | 762,168 |
| 128 | 14 | 941 | 134 | 134 | 0 | 28,150 |
| 129 | 3 | 170 | 17 | 4 | 13 | 11,287 |
| 130 | 61 | 4,370 | 420 | 409 | 11 | 189,186 |
| 131 | 32 | 1,854 | 163 | 162 | 1 | 51,197 |
| 132 | 5 | 302 | 60 | 52 | 8 | 11,772 |
| 133 | 1 | 50 | 3 | 1 | 2 | 1,638 |
| 134 | 14 | 880 | 46 | 32 | 14 | 16,165 |
| 135 | 1 | 67 | 6 | 4 | 2 | 1,483 |
| 136 | 1 | 53 | 2 | 1 | 1 | 956 |
| 137 | 0 | 0 | 0 | 0 | 0 | 0 |
| 138 | 111 | 8,018 | 716 | 388 | 328 | 314,069 |
| 139 | 60 | 3,927 | 215 | 101 | 114 | 106,745 |
| 140 | 308 | 20,746 | 1,438 | 626 | 812 | 491,592 |
| 141 | 76 | 5,164 | 452 | 355 | 97 | 165,988 |
| 142 | 27 | 1,755 | 117 | 81 | 36 | 47,902 |
| 143 | 186 | 10,585 | 732 | 414 | 318 | 307,810 |
| 144 | 55 | 3,416 | 489 | 405 | 84 | 166,902 |
| 145 | 10 | 585 | 48 | 31 | 16 | 19,793 |
| South Shore Hospital | | | | | | |
| 112 | 0 | 0 | 0 | 0 | 0 | 0 |
| 115 | 3 | 244 | 78 | 54 | 24 | 85,190 |
| 116 | 19 | 1,423 | 167 | 108 | 59 | 326,996 |
| 117 | 0 | 0 | 0 | 0 | 0 | 0 |
| 118 | 3 | 239 | 8 | 6 | 3 | 33,867 |
| 121 | 133 | 9,159 | 1,193 | 647 | 546 | 1,179,550 |
| 122 | 79 | 5,011 | 516 | 283 | 234 | 536,964 |
| 123 | 22 | 1,693 | 106 | 46 | 60 | 140,570 |
| 124 | 0 | 0 | 0 | 0 | 0 | 0 |
| 125 | 0 | 0 | 0 | 0 | 0 | 0 |
| 126 | 9 | 558 | 90 | 90 | 0 | 87,777 |
| 127 | 294 | 22,301 | 2,404 | 2,087 | 317 | 1,739,342 |
| 128 | 14 | 874 | 100 | 99 | 1 | 61,279 |
| 129 | 3 | 185 | 7 | 1 | 6 | 15,201 |
| 130 | 61 | 4,343 | 396 | 386 | 10 | 279,572 |
| 131 | 32 | 1,840 | 183 | 183 | 0 | 113,597 |
| 132 | 5 | 373 | 22 | 13 | 9 | 27,568 |
| 133 | 1 | 56 | 3 | 0 | 3 | 3,104 |
| 134 | 14 | 876 | 56 | 54 | 3 | 40,157 |
| 135 | 1 | 74 | 7 | 6 | 0 | 4,994 |
| 136 | 1 | 29 | 1 | 0 | 1 | 1,991 |
| 137 | 0 | 0 | 0 | 0 | 0 | 0 |
| 138 | 111 | 7,987 | 741 | 604 | 136 | 592,418 |
| 139 | 60 | 3,831 | 175 | 147 | 28 | 149,973 |
| 140 | 308 | 20,707 | 1,291 | 929 | 362 | 1,086,648 |
| 141 | 76 | 5,491 | 359 | 341 | 18 | 273,575 |
| 142 | 27 | 1,788 | 77 | 73 | 4 | 66,427 |
| 143 | 186 | 10,728 | 540 | 403 | 137 | 500,175 |
| 144 | 55 | 3,487 | 384 | 270 | 114 | 428,561 |
| 145 | 10 | 553 | 33 | 23 | 11 | 32,560 |
| Charlton Memoria Hospital | | | | | | |
| 112 | 0 | 0 | 0 | 0 | 0 | 0 |
| 115 | 3 | 225 | 31 | 11 | 20 | 54,380 |
| 116 | 19 | 1,558 | 181 | 116 | 64 | 225,174 |
| 117 | 0 | 0 | 0 | 0 | 0 | 0 |

TABLE VI-continued

| | Cases | Age | Tot Days | Rout Days | ICU Days | Charges |
|---|---|---|---|---|---|---|
| 118 | 3 | 217 | 33 | 14 | 19 | 32,916 |
| 121 | 133 | 8,432 | 1,054 | 374 | 680 | 1,096,223 |
| 122 | 79 | 6,092 | 553 | 243 | 310 | 814,609 |
| 123 | 22 | 1,474 | 286 | 0 | 286 | 332,200 |
| 124 | 0 | 0 | 0 | 0 | 0 | 0 |
| 125 | 0 | 0 | 0 | 0 | 0 | 0 |
| 126 | 9 | 669 | 82 | 59 | 23 | 74,640 |
| 127 | 294 | 19,610 | 2,920 | 2,901 | 20 | 1,794,360 |
| 128 | 14 | 938 | 21 | 0 | 21 | 77,917 |
| 129 | 3 | 212 | 25 | 24 | 1 | 18,316 |
| 130 | 61 | 3,831 | 373 | 361 | 12 | 292,964 |
| 131 | 32 | 2,159 | 589 | 452 | 137 | 356,318 |
| 132 | 5 | 338 | 30 | 21 | 9 | 26,251 |
| 133 | 1 | 67 | 6 | 5 | 1 | 5,038 |
| 134 | 14 | 1,138 | 137 | 63 | 74 | 102,431 |
| 135 | 1 | 53 | 2 | 0 | 2 | 2,313 |
| 136 | 1 | 71 | 6 | 2 | 3 | 5,907 |
| 137 | 0 | 0 | 0 | 0 | 0 | 0 |
| 138 | 111 | 7,504 | 553 | 258 | 295 | 535,235 |
| 139 | 60 | 4,267 | 367 | 250 | 117 | 337,493 |
| 140 | 308 | 21,079 | 1,318 | 843 | 476 | 1,281,583 |
| 141 | 76 | 4,492 | 270 | 143 | 128 | 291,495 |
| 142 | 27 | 1,649 | 173 | 108 | 65 | 197,860 |
| 143 | 186 | 9,288 | 488 | 163 | 326 | 658,661 |
| 144 | 55 | 3,487 | 342 | 316 | 26 | 423,431 |
| 145 | 10 | 627 | 30 | 27 | 3 | 37,514 |

Cape Cod Hospital

| | Cases | Age | Tot Days | Rout Days | ICU Days | Charges |
|---|---|---|---|---|---|---|
| 112 | 0 | 0 | 0 | 0 | 0 | 0 |
| 115 | 3 | 252 | 39 | 24 | 15 | 68,810 |
| 116 | 19 | 1,472 | 123 | 94 | 29 | 269,948 |
| 117 | 0 | 0 | 0 | 0 | 0 | 0 |
| 118 | 3 | 219 | 6 | 3 | 3 | 18,589 |
| 121 | 133 | 9,641 | 1,040 | 609 | 431 | 1,241,340 |
| 122 | 79 | 5,373 | 458 | 241 | 217 | 569,664 |
| 123 | 22 | 1,754 | 97 | 42 | 54 | 141,682 |
| 124 | 0 | 0 | 0 | 0 | 0 | 0 |
| 125 | 0 | 0 | 0 | 0 | 0 | 0 |
| 126 | 9 | 557 | 166 | 159 | 7 | 137,384 |
| 127 | 294 | 22,889 | 2,009 | 1,745 | 264 | 1,892,860 |
| 128 | 14 | 1,007 | 112 | 110 | 2 | 91,232 |
| 129 | 3 | 214 | 7 | 1 | 6 | 16,439 |
| 130 | 61 | 4,424 | 341 | 331 | 10 | 295,606 |
| 131 | 32 | 2,283 | 116 | 112 | 4 | 99,543 |
| 132 | 5 | 363 | 24 | 9 | 15 | 37,706 |
| 133 | 1 | 70 | 5 | 3 | 2 | 4,945 |
| 134 | 14 | 871 | 47 | 39 | 8 | 49,034 |
| 135 | 1 | 71 | 7 | 6 | 1 | 6,628 |
| 136 | 1 | 27 | 1 | 0 | 1 | 1,764 |
| 137 | 0 | 0 | 0 | 0 | 0 | 0 |
| 138 | 111 | 8,210 | 678 | 515 | 164 | 803,700 |
| 139 | 60 | 4,337 | 203 | 145 | 58 | 248,405 |
| 140 | 308 | 22,086 | 1,159 | 657 | 502 | 1,335,873 |
| 141 | 76 | 5,983 | 449 | 416 | 33 | 437,559 |
| 142 | 27 | 1,916 | 90 | 76 | 15 | 107,772 |
| 143 | 186 | 11,545 | 537 | 283 | 255 | 686,704 |
| 144 | 55 | 3,625 | 361 | 318 | 42 | 398,957 |
| 145 | 10 | 668 | 24 | 16 | 9 | 35,998 |

Brockton Hospital

| | Cases | Age | Tot Days | Rout Days | ICU Days | Charges |
|---|---|---|---|---|---|---|
| 112 | 0 | 0 | 0 | 0 | 0 | 0 |
| 115 | 3 | 238 | 53 | 30 | 23 | 96,246 |
| 116 | 19 | 1,438 | 157 | 117 | 40 | 386,684 |
| 117 | 0 | 0 | 0 | 0 | 0 | 0 |
| 118 | 3 | 214 | 31 | 23 | 8 | 63,573 |
| 121 | 133 | 9,064 | 1,225 | 916 | 309 | 1,253,767 |
| 122 | 79 | 4,909 | 518 | 378 | 140 | 512,349 |
| 123 | 22 | 1,674 | 138 | 85 | 53 | 214,770 |
| 124 | 0 | 0 | 0 | 0 | 0 | 0 |
| 125 | 0 | 0 | 0 | 0 | 0 | 0 |
| 126 | 9 | 503 | 214 | 214 | 0 | 134,183 |
| 127 | 294 | 22,198 | 2,270 | 2,133 | 137 | 1,890,188 |
| 128 | 14 | 917 | 137 | 137 | 0 | 83,332 |
| 129 | 3 | 201 | 3 | 0 | 3 | 8,099 |
| 130 | 61 | 4,164 | 414 | 396 | 18 | 438,256 |
| 131 | 32 | 2,083 | 164 | 162 | 2 | 127,703 |
| 132 | 5 | 364 | 43 | 36 | 7 | 71,424 |
| 133 | 1 | 61 | 1 | 1 | 0 | 1,276 |
| 134 | 14 | 857 | 89 | 89 | 0 | 65,802 |
| 135 | 1 | 87 | 21 | 21 | 0 | 10,976 |
| 136 | 1 | 23 | 2 | 2 | 0 | 2,053 |
| 137 | 0 | 0 | 0 | 0 | 0 | 0 |
| 138 | 111 | 7,813 | 724 | 640 | 84 | 658,787 |
| 139 | 60 | 3,545 | 199 | 196 | 3 | 175,362 |
| 140 | 308 | 20,437 | 1,229 | 1,021 | 208 | 1,171,258 |
| 141 | 76 | 5,255 | 520 | 517 | 3 | 380,252 |
| 142 | 27 | 1,790 | 110 | 110 | 0 | 103,124 |
| 143 | 186 | 10,305 | 506 | 469 | 37 | 539,606 |
| 144 | 55 | 3,487 | 342 | 316 | 26 | 423,431 |
| 145 | 10 | 627 | 30 | 27 | 3 | 37,514 |

Norwood Hospital

| | Cases | Age | Tot Days | Rout Days | ICU Days | Charges |
|---|---|---|---|---|---|---|
| 112 | 0 | 0 | 0 | 0 | 0 | 0 |
| 115 | 3 | 230 | 33 | 25 | 9 | 67,674 |
| 116 | 19 | 1,498 | 161 | 151 | 10 | 307,068 |
| 117 | 0 | 0 | 0 | 0 | 0 | 0 |
| 118 | 3 | 223 | 16 | 15 | 0 | 44,484 |
| 121 | 133 | 9,662 | 1,061 | 769 | 291 | 1,531,959 |
| 122 | 79 | 4,966 | 413 | 277 | 136 | 677,988 |
| 123 | 22 | 1,711 | 88 | 39 | 50 | 211,640 |
| 124 | 0 | 0 | 0 | 0 | 0 | 0 |
| 125 | 0 | 0 | 0 | 0 | 0 | 0 |
| 126 | 9 | 675 | 74 | 74 | 0 | 88,294 |
| 127 | 294 | 22,491 | 2,004 | 1,906 | 98 | 1,987,098 |
| 128 | 14 | 878 | 97 | 97 | 0 | 74,223 |
| 129 | 3 | 159 | 9 | 3 | 6 | 25,605 |
| 130 | 61 | 4,507 | 388 | 379 | 9 | 327,598 |
| 131 | 32 | 1,641 | 169 | 169 | 0 | 158,323 |
| 132 | 5 | 400 | 51 | 45 | 6 | 66,798 |
| 133 | 1 | 61 | 1 | 1 | 0 | 1,276 |
| 134 | 14 | 830 | 55 | 55 | 0 | 59,392 |
| 135 | 1 | 66 | 5 | 5 | 0 | 5,035 |
| 136 | 1 | 61 | 3 | 3 | 0 | 3,640 |
| 137 | 0 | 0 | 0 | 0 | 0 | 0 |
| 138 | 111 | 7,863 | 498 | 467 | 31 | 576,527 |
| 139 | 60 | 3,611 | 159 | 151 | 7 | 205,975 |
| 140 | 308 | 21,080 | 1,151 | 1,041 | 110 | 1,229,835 |
| 141 | 76 | 5,439 | 492 | 492 | 0 | 346,811 |
| 142 | 27 | 1,613 | 80 | 79 | 1 | 99,096 |
| 143 | 186 | 10,541 | 436 | 410 | 26 | 578,992 |
| 144 | 55 | 3,404 | 341 | 327 | 14 | 389,720 |
| 145 | 10 | 467 | 20 | 18 | 2 | 35,373 |

Goddard Memoria Hospital

| | Cases | Age | Tot Days | Rout Days | ICU Days | Charges |
|---|---|---|---|---|---|---|
| 112 | 0 | 0 | 0 | 0 | 0 | 0 |
| 115 | 3 | 241 | 61 | 37 | 23 | 102,813 |
| 116 | 19 | 1,433 | 187 | 153 | 35 | 452,548 |
| 117 | 0 | 0 | 0 | 0 | 0 | 0 |
| 118 | 3 | 215 | 13 | 11 | 1 | 53,785 |
| 121 | 133 | 9,252 | 922 | 545 | 377 | 1,030,038 |
| 122 | 79 | 5,109 | 441 | 234 | 207 | 493,580 |
| 123 | 22 | 1,727 | 180 | 66 | 114 | 234,750 |
| 124 | 0 | 0 | 0 | 0 | 0 | 0 |
| 125 | 0 | 0 | 0 | 0 | 0 | 0 |
| 126 | 9 | 455 | 1,505 | 1,482 | 23 | 673,013 |
| 127 | 294 | 21,866 | 2,369 | 1,960 | 409 | 2,012,118 |
| 128 | 14 | 973 | 144 | 144 | 1 | 87,295 |
| 129 | 3 | 158 | 14 | 2 | 12 | 25,919 |
| 130 | 61 | 3,813 | 178 | 178 | 0 | 150,177 |
| 131 | 32 | 1,940 | 58 | 56 | 2 | 66,557 |
| 132 | 5 | 410 | 65 | 40 | 25 | 69,630 |
| 133 | 1 | 61 | 1 | 1 | 0 | 1,276 |
| 134 | 14 | 764 | 51 | 34 | 16 | 49,320 |
| 135 | 1 | 51 | 2 | 2 | 0 | 1,613 |
| 136 | 1 | 32 | 1 | 1 | 0 | 1,776 |
| 137 | 0 | 0 | 0 | 0 | 0 | 0 |
| 138 | 111 | 7,819 | 741 | 626 | 115 | 587,125 |
| 139 | 60 | 3,906 | 189 | 158 | 30 | 172,084 |

TABLE VI-continued

| | Cases | Age | Tot Days | Rout Days | ICU Days | Charges |
|---|---|---|---|---|---|---|
| 140 | 308 | 20,392 | 1,306 | 961 | 346 | 1,187,413 |
| 141 | 76 | 5,189 | 448 | 418 | 30 | 372,465 |
| 142 | 27 | 1,591 | 105 | 100 | 4 | 90,557 |
| 143 | 186 | 10,562 | 571 | 494 | 77 | 556,254 |
| 144 | 55 | 3,339 | 273 | 251 | 23 | 264,223 |
| 145 | 10 | 524 | 34 | 29 | 5 | 26,581 |

Cardinal Cushing General Hospital

| | Cases | Age | Tot Days | Rout Days | ICU Days | Charges |
|---|---|---|---|---|---|---|
| 112 | 0 | 0 | 0 | 0 | 0 | 0 |
| 115 | 3 | 225 | 41 | 34 | 7 | 51,202 |
| 116 | 19 | 1,159 | 114 | 76 | 38 | 120,371 |
| 117 | 0 | 0 | 0 | 0 | 0 | 0 |
| 118 | 3 | 204 | 24 | 16 | 9 | 22,346 |
| 121 | 133 | 8,645 | 848 | 605 | 243 | 747,793 |
| 122 | 79 | 6,323 | 511 | 324 | 186 | 530,457 |
| 123 | 22 | 1,674 | 138 | 85 | 53 | 214,770 |
| 124 | 0 | 0 | 0 | 0 | 0 | 0 |
| 125 | 0 | 0 | 0 | 0 | 0 | 0 |
| 126 | 9 | 682 | 66 | 59 | 7 | 46,899 |
| 127 | 294 | 17,792 | 2,248 | 2,248 | 0 | 1,543,491 |
| 128 | 14 | 966 | 35 | 28 | 7 | 34,608 |
| 129 | 3 | 211 | 26 | 26 | 1 | 15,194 |
| 130 | 61 | 3,627 | 438 | 438 | 0 | 242,109 |
| 131 | 32 | 2,464 | 96 | 96 | 0 | 102,880 |
| 132 | 5 | 390 | 70 | 50 | 20 | 42,505 |
| 133 | 1 | 62 | 5 | 4 | 1 | 3,376 |
| 134 | 14 | 857 | 90 | 73 | 17 | 65,310 |
| 135 | 1 | 68 | 3 | 3 | 0 | 1,663 |
| 136 | 1 | 70 | 6 | 5 | 1 | 4,294 |
| 137 | 0 | 0 | 0 | 0 | 0 | 0 |
| 138 | 111 | 7,426 | 565 | 473 | 92 | 412,835 |
| 139 | 60 | 4,330 | 412 | 397 | 15 | 255,705 |
| 140 | 308 | 20,126 | 1,001 | 943 | 58 | 811,869 |
| 141 | 76 | 4,321 | 239 | 215 | 25 | 203,137 |
| 142 | 27 | 1,728 | 165 | 132 | 33 | 160,510 |
| 143 | 186 | 11,197 | 856 | 707 | 149 | 1,103,947 |
| 144 | 55 | 3,487 | 342 | 316 | 26 | 423,431 |
| 145 | 10 | 627 | 30 | 27 | 3 | 37,514 |

TABLE VII

Adjusted Charge and Cost Data
(Department by Hospital)

| | St. Luke/NB | South Shore | Charlton | Cape Cod | Brockton | Norwood | Goddard | Cardinal |
|---|---|---|---|---|---|---|---|---|
| TOTAL COST (Department by Hospital) | | | | | | | | |
| Medical/Surgical Routine | 1,724,003 | 2,556,484 | 1,513,960 | 2,266,813 | 2,977,331 | 2,358,867 | 2,444,327 | 2,272,834 |
| Obstetrics Routine | 0 | 0 | 0 | 0 | 3,629 | 0 | 0 | 0 |
| Pediatric Routine | 4,610 | 0 | 0 | 744 | 1,836 | 0 | 1,076 | 38,216 |
| Psychiatric Routine | 196 | 0 | 0 | 0 | 0 | 0 | 0 | 0 |
| Other Routine | 0 | 0 | 0 | 0 | 0 | 0 | 0 | 0 |
| Newborn Routine | 0 | 0 | 0 | 0 | 0 | 0 | 0 | 0 |
| Neonatal ICU | 0 | 0 | 0 | 0 | 0 | 0 | 0 | 0 |
| Medical/Surgical ICU | 696,996 | 1,689,214 | 2,979,096 | 135,231 | 100,594 | 895,774 | 168,592 | 93,281 |
| Pediatric ICU | 0 | 0 | 0 | 0 | 0 | 0 | 0 | 0 |
| Psychiatric ICU | 0 | 0 | 0 | 0 | 0 | 0 | 0 | 0 |
| Burn Unit | 0 | 0 | 0 | 0 | 0 | 0 | 0 | 0 |
| Other ICU | 1,274,420 | 0 | 0 | 0 | 0 | 0 | 0 | 0 |
| Coronary Care Unit | 0 | 0 | 20,007 | 1,581,252 | 1,094,614 | 0 | 1,288,127 | 553,616 |
| Pharmacy | 222,704 | 282,159 | 303,215 | 179,823 | 363,162 | 426,955 | 277,583 | 533,773 |
| IV Therapy | 18,190 | 29,056 | 85,448 | 100,690 | 47,383 | 1 | 15,357 | 28,057 |
| Medical/Surgical Supplies | 272,665 | 86,903 | 65,407 | 434,480 | 144,988 | 250,026 | 248,911 | 147,553 |
| Laboratory | 378,766 | 422,699 | 493,895 | 581,627 | 656,316 | 898,846 | 642,510 | 581,905 |
| Diagnostic Radiology | 166,553 | 139,054 | 258,210 | 116,822 | 196,285 | 195,642 | 242,979 | 120,543 |
| Therapeutic Radiology | 0 | 0 | 2,895 | 4,566 | 2,187 | 9 | 750 | 0 |
| Nuclear Medicine | 263,286 | 59,225 | 36,696 | 149,434 | 171,184 | 75,750 | 65,605 | 126,408 |
| CAT Scanner | 11,045 | 47,910 | 89,792 | 39,035 | 24,785 | 53,376 | 36,410 | 40,222 |
| Operating Room | 21,540 | 48,112 | 36,125 | 9,598 | 29,585 | 21,496 | 22,026 | 26,879 |
| Anesthesiology | 10,193 | 6,108 | 4,248 | 1,167 | 43,286 | 124 | 86 | 9,574 |
| Blood | 5,853 | 0 | 0 | 0 | 0 | 0 | 0 | 5,776 |
| Blood Storage Proc. & Admin | 9,997 | 12,019 | 9,945 | 29,192 | 46,812 | 24,735 | 26,806 | 11,699 |
| Respiratory Therapy | 209,025 | 107,906 | 101,322 | 138,442 | 157,075 | 212,206 | 156,553 | 75,418 |
| Physical Therapy | 17,576 | 47,857 | 159 | 9,132 | 21,953 | 19,472 | 37,460 | 11,855 |
| Occupational Therapy | 2,928 | 5,143 | 159 | 2,727 | 1,596 | 1,283 | 3,199 | 511 |
| Speech Therapy | 1,897 | 128 | 4,947 | 606 | 3,597 | 684 | 899 | 1,328 |

TABLE VII-continued

Adjusted Charge and Cost Data (Department by Hospital)

|  | St. Luke/NB | South Shore | Charlton | Cape Cod | Brockton | Norwood | Goddard | Cardinal |
|---|---|---|---|---|---|---|---|---|
| Emergency Room | 440,682 | 428,001 | 277,581 | 417,442 | 223,310 | 337,577 | 169,491 | 436,137 |
| Pulmonary Function | 0 | 0 | 607 | 4,933 | 31,340 | 7,859 | 16,063 | 26,883 |
| Audiology | 2 | 0 | 16 | 0 | 0 | 0 | 0 | 0 |
| Cardiac Catheterization | 11,691 | 53,805 | 10,691 | 0 | 0 | 243,574 | 180,662 | 0 |
| Ambulance | 4,053 | 1,408 | 0 | 0 | 2,941 | 0 | 0 | 0 |
| Recovery Room | 4,622 | 7,803 | 976 | 4,947 | 7,125 | 15,587 | 3,975 | 7,098 |
| Labor & Delivery | 0 | 0 | 0 | 0 | 0 | 0 | 378 | 0 |
| EKG | 731,857 | 243,688 | 132,365 | 333,119 | 147,860 | 109,855 | 85,163 | 198,374 |
| EEG | 10,278 | 13,080 | 36,904 | 5,002 | 15,627 | 6,746 | 9,994 | 9,845 |
| Renal Dialysis | 0 | 36,423 | 11,258 | 0 | 32,562 | 20,043 | 53,836 | 11,258 |
| Kidney Acquisition | 0 | 0 | 0 | 0 | 0 | 0 | 0 | 0 |
| Psychology/Psychiatry | 836 | 0 | 100 | 5,992 | 11,034 | 5,163 | 0 | 381 |
| Other Ancillary | 8,636 | 68,526 | 179,890 | 20,794 | 136,879 | 73,061 | 59,401 | 3,024 |

TOTAL CHARGES (Department by Hospital)

|  | St. Luke/NB | South Shore | Charlton | Cape Cod | Brockton | Norwood | Goddard | Cardinal |
|---|---|---|---|---|---|---|---|---|
| Medical/Surgical Routine | 190,473 | 2,931,156 | 2,328,527 | 2,931,615 | 2,140,484 | 2,459,541 | 2,813,103 | 2,873,618 |
| Obstetrics Routine | 0 | 0 | 0 | 0 | 2,609 | 0 | 0 | 0 |
| Pediatric Routine | 509 | 0 | 0 | 963 | 1,320 | 0 | 1,238 | 48,318 |
| Psychiatric Routine | 22 | 0 | 0 | 0 | 0 | 0 | 0 | 0 |
| Other Routine | 0 | 0 | 0 | 0 | 0 | 0 | 0 | 0 |
| Newborn Routine | 0 | 0 | 0 | 0 | 0 | 0 | 0 | 0 |
| Neonatal ICU | 0 | 0 | 0 | 0 | 0 | 0 | 0 | 0 |
| Medical/Surgical ICU | 64,187 | 1,521,650 | 1,683,806 | 136,351 | 52,648 | 903,260 | 146,656 | 113,368 |
| Pediatric ICU | 0 | 0 | 0 | 0 | 0 | 0 | 0 | 0 |
| Psychiatric ICU | 0 | 0 | 0 | 0 | 0 | 0 | 0 | 0 |
| Burn Unit | 0 | 0 | 0 | 0 | 0 | 0 | 0 | 0 |
| Other ICU | 117,362 | 0 | 0 | 0 | 0 | 0 | 0 | 0 |
| Coronary Care Unit | 0 | 0 | 11,308 | 1,594,355 | 572,892 | 0 | 1,120,524 | 672,835 |
| Pharmacy | 258,590 | 479,785 | 445,837 | 400,265 | 810,312 | 684,313 | 454,845 | 797,919 |
| IV Therapy | 242,672 | 59,860 | 94,942 | 587,021 | 25,812 | 3 | 65,953 | 25,386 |
| Medical/Surgical Supplies | 350,933 | 209,206 | 151,586 | 680,389 | 413,808 | 345,981 | 433,198 | 109,165 |
| Laboratory | 684,494 | 574,054 | 1,038,286 | 501,429 | 1,942,899 | 1,905,181 | 1,233,805 | 734,834 |
| Diagnostic Radiology | 703,971 | 222,673 | 894,081 | 261,449 | 870,394 | 416,388 | 539,814 | 348,755 |
| Therapeutic Radiology | 0 | 0 | 3,216 | 2,718 | 3,601 | 10 | 447 | 0 |
| Nuclear Medicine | 213,066 | 101,998 | 157,826 | 166,038 | 190,204 | 136,164 | 170,531 | 481,850 |
| CAT Scanner | 46,683 | 76,721 | 310,914 | 87,361 | 109,904 | 113,601 | 80,891 | 116,369 |
| Operating Room | 172,537 | 93,106 | 58,669 | 19,921 | 49,832 | 29,855 | 47,025 | 39,319 |
| Anesthesiology | 86,615 | 9,416 | 27,157 | 2,786 | 62,137 | 2864 | 110 | 14,136 |
| Blood | 2,555 | 0 | 0 | 0 | 0 | 0 | 0 | 6,418 |
| Blood Storage Proc. & Admin | 8,209 | 26,051 | 11,050 | 28,220 | 52,013 | 27,483 | 43,236 | 5,391 |
| Respiratory Therapy | 81,024 | 160,131 | 657,828 | 217,407 | 373,587 | 367,666 | 300,658 | 61,247 |
| Physical Therapy | 21,557 | 63,915 | 427 | 8,907 | 36,582 | 24,900 | 50,829 | 32,533 |
| Occupational Therapy | 5,074 | 7,635 | 212 | 2,164 | 1,773 | 1,172 | 3,666 | 1,928 |
| Speech Therapy | 3,222 | 143 | 7,790 | 375 | 3,997 | 1,184 | 1,135 | 1,515 |
| Emergency Room | 549,487 | 339,706 | 437,480 | 539,489 | 303,580 | 374,497 | 223,644 | 404,335 |
| Pulmonary Function | 0 | 0 | 3,943 | 7,747 | 74,540 | 13,617 | 30,848 | 21,831 |
| Audiology | 4 | 0 | 25 | 0 | 0 | 0 | 0 | 0 |
| Cardiac Catheterization | 21,127 | 73,071 | 22,475 | 0 | 0 | 516,276 | 346,923 | 0 |
| Ambulance | 5,496 | 1,564 | 0 | 0 | 1,940 | 0 | 0 | 0 |
| Recovery Room | 5,136 | 14,289 | 2,466 | 15,848 | 7,917 | 12,177 | 9,969 | 16,347 |
| Labor & Delivery | 0 | 0 | 0 | 0 | 0 | 0 | 421 | 0 |
| EKG | 129,243 | 717,429 | 471,876 | 768,741 | 611,575 | 617,651 | 490,245 | 171,285 |
| EEG | 33,761 | 16,997 | 41,005 | 6,816 | 10,147 | 18,667 | 17,871 | 83,222 |
| Renal Dialysis | 0 | 34,121 | 12,509 | 0 | 25,337 | 22,270 | 59,818 | 12,509 |
| Kidney Acquisition | 0 | 0 | 0 | 0 | 0 | 0 | 0 | 0 |
| Psychology/Psychiatry | 1,134 | 0 | 111 | 6,657 | 7,279 | 6,977 | 0 | 423 |
| Ohter Ancillary | 11,711 | 73,918 | 199,878 | 23,104 | 90,298 | 98,725 | 75,457 | 3,360 |

DIRECT COST (Department by Hospital)

|  | St. Luke/NB | South Shore | Charlton | Cape Cod | Brockton | Norwood | Goddard | Cardinal |
|---|---|---|---|---|---|---|---|---|
| Medical/Surgical Routine | 739,381 | 1,028,675 | 569,387 | 1,028,754 | 1,244,000 | 798,267 | 949,520 | 887,354 |
| Obstetrics Routine | 0 | 0 | 0 | 0 | 1,516 | 0 | 0 | 0 |
| Pediatric Routine | 1,977 | 0 | 0 | 338 | 767 | 0 | 418 | 14,920 |
| Psychiatric Routine | 84 | 0 | 0 | 0 | 0 | 0 | 0 | 0 |
| Other Routine | 0 | 0 | 0 | 0 | 0 | 0 | 0 | 0 |
| Newborn Routine | 0 | 0 | 0 | 0 | 0 | 0 | 0 | 0 |
| Neonatal ICU | 0 | 0 | 0 | 0 | 0 | 0 | 0 | 0 |
| Medical/Surgical ICU | 374,299 | 871,135 | 1,465,645 | 70,240 | 53,278 | 372,014 | 79,468 | 50,770 |
| Pediatric ICU | 0 | 0 | 0 | 0 | 0 | 0 | 0 | 0 |
| Psychiatric ICU | 0 | 0 | 0 | 0 | 0 | 0 | 0 | 0 |
| Burn Unit | 0 | 0 | 0 | 0 | 0 | 0 | 0 | 0 |
| Other ICU | 684,386 | 0 | 0 | 0 | 0 | 0 | 0 | 0 |

TABLE VII-continued

Adjusted Charge and Cost Data
(Department by Hospital)

|  | St. Luke/NB | South Shore | Charlton | Cape Cod | Brockton | Norwood | Goddard | Cardinal |
|---|---|---|---|---|---|---|---|---|
| Coronary Care Unit | 0 | 0 | 9,843 | 821,309 | 579,743 | 0 | 607,172 | 301,316 |
| Pharmacy | 139,639 | 259,084 | 160,594 | 216,143 | 437,568 | 369,529 | 245,617 | 257,753 |
| IV Therapy | 15,005 | 21,584 | 51,269 | 66,828 | 30,262 | 1 | 9,883 | 22,677 |
| Medical/Surgical Supplies | 189,504 | 112,971 | 81,856 | 138,246 | 223,456 | 186,830 | 115,822 | 95,459 |
| Laboratory | 251,403 | 263,642 | 329,697 | 376,510 | 470,077 | 422,598 | 432,381 | 384,563 |
| Diagnostic Radiology | 103,018 | 68,551 | 176,165 | 72,176 | 114,554 | 100,679 | 129,697 | 77,941 |
| Therapeutic Radiology | 0 | 0 | 1,737 | 2,202 | 997 | 6 | 647 | 0 |
| Nuclear Medicine | 156,532 | 33,937 | 18,278 | 89,661 | 102,710 | 18,163 | 42,340 | 74,400 |
| CAT Scanner | 6,831 | 23,619 | 61,261 | 24,117 | 14,465 | 27,468 | 19,435 | 26,007 |
| Operating Room | 11,206 | 26,551 | 19,397 | 2,602 | 14,754 | 7,908 | 8,672 | 15,578 |
| Anesthesiology | 4,749 | 1,817 | 2,400 | 354 | 29,965 | 1,546 | 29 | 6,801 |
| Blood | 3,623 | 0 | 0 | 0 | 0 | 0 | 0 | 3,466 |
| Blood Storage Proc. & Admin | 7,431 | 8,526 | 5,967 | 20,849 | 28,087 | 14,841 | 19,021 | 8,210 |
| Respiratory Therapy | 135,619 | 59,866 | 61,136 | 84,689 | 99,243 | 103,782 | 86,882 | 48,061 |
| Physical Therapy | 10,198 | 26,161 | 99 | 4,633 | 10,403 | 11,286 | 13,591 | 6,004 |
| Occupational Therapy | 1,845 | 3,395 | 99 | 1,501 | 957 | 497 | 1,314 | 302 |
| Speech Therapy | 1,220 | 77 | 3,003 | 312 | 2,158 | 410 | 775 | 1,098 |
| Emergency Room | 229,509 | 180,088 | 125,376 | 121,758 | 100,079 | 168,187 | 81,252 | 215,789 |
| Pulmonary Function | 0 | 0 | 366 | 3,018 | 19,802 | 3,844 | 8,912 | 17,131 |
| Audiology | 1 | 0 | 10 | 0 | 0 | 0 | 0 | 0 |
| Cardiac Catheterization | 7,760 | 33,559 | 7,137 | 0 | 0 | 114,518 | 121,577 | 0 |
| Ambulance | 1,033 | 845 | 0 | 0 | 1,962 | 0 | 0 | 0 |
| Recovery Room | 2,773 | 4,841 | 638 | 2,972 | 4,275 | 7,921 | 1,946 | 3,943 |
| Labor & Delivery | 0 | 0 | 0 | 0 | 0 | 0 | 181 | 0 |
| EKG | 452,267 | 142,598 | 49,283 | 199,613 | 96,217 | 59,150 | 46,056 | 125,015 |
| EEG | 5,294 | 4,173 | 22,143 | 2,776 | 1,795 | 3,752 | 4,988 | 5,050 |
| Renal Dialysis | 0 | 23,688 | 6,755 | 0 | 20,760 | 12,026 | 32,302 | 6,755 |
| Kidney Acquisition | 0 | 0 | 0 | 0 | 0 | 0 | 0 | 0 |
| Psychology/Psychiatry | 213 | 0 | 60 | 3,595 | 7,362 | 458 | 0 | 228 |
| Other Ancillary | 2,201 | 39,916 | 107,934 | 12,476 | 91,325 | 6,479 | 10,872 | 1,814 |

TABLE VIII

|  | Caribbean | Total |
|---|---|---|
| Medicare | 66.7% | 57.4% |
| Blue Cross | 13.0% | 14.0% |
| HMO | 7.2% | 13.0% |
| Commercial | 5.4% | 9.3% |
| Medicaid | 5.2% | 3.0% |
| Self Pay | 2.1% | 2.0% |
| Other Govt | 0.3% | 0.4% |
| All Other | 0.2% | 1.0% |

TABLE IX

|  | Average Patient Age | Percent Male | Percent Minority |
|---|---|---|---|
| Caribbean | 69.5 | 47% | 3.8% |
| St. Thomas | 70.0 | 47% | 1.2% |
| Aruba | 67.6 | 49% | 10.8% |
| Martinique | 69.6 | 52% | 1.2% |
| St. John | 69.1 | 54% | 2.5% |
| St. Bart's | 66.9 | 60% | 1.9% |
| St. Croix | 68.6 | 50% | 3.5% |
| Average ex. Caribbean | 68.6 | 52% | 3.5% |

TABLE X

| DRG Groups | No. of Cases | Pct. of Cases |
|---|---|---|
| Angina Pectoris | 299 | 23% |
| Heart Failure & Shock | 271 | 20% |
| AMI | 236 | 18 |
| Cardiac Arrythmia | 163 | 12% |
| Chest Pain | 97 | 7% |
| All Other | 262 | 20% |
| Total Cardiology | 1,328 | 100% |

TABLE XI

|  | Total LOS | Routine LOS | ICU LOS |
|---|---|---|---|
| Caribbean | 6.8 | 5.5 | 1.3 |
| St. Thomas | 6.0 | 5.0 | 0.9 |
| Aruba | 7.2 | 6.1 | 1.2 |
| Martinique | 7.8 | 6.6 | 1.6 |
| St. John | 6.4 | 5.5 | 0.9 |
| St. Bart's | 5.6 | 4.8 | 0.8 |
| St. Croix | 8.3 | 6.3 | 2.0 |
| Average ex. Caribbean | 6.9 | 5.7 | 1.2 |

TABLE XII

|  | Total Cost Per Case | % Diff than Caribbean's | Direct Cost Per Case | % Diff than Caribbean's |
|---|---|---|---|---|
| Caribbean | 5,240 |  | 2,566 |  |
| St. Thomas | 4,099 | −22% | 2,155 | −16% |
| Aruba | 4,401 | −16% | 2,458 | −4% |

TABLE XII-continued

|  | Total Cost Per Case | % Diff than Caribbean's | Direct Cost Per Case | % Diff than Caribbean's |
|---|---|---|---|---|
| Martinique | 4,954 | −5% | 2,766 | 8% |
| St. John | 4,359 | −17% | 2,381 | −7% |
| St. Bart's | 5,159 | −2% | 2,791 | 9% |
| St. Croix | 4,824 | −8% | 2,670 | 4% |
| Average ex. Caribbean | 4,633 | −12% | 2,537 | −1% |

TABLE XIII

|  | $ > than Caribbean | Pct > than Caribbean | Percent of Total Diff |
|---|---|---|---|
| Routine Care | −$644 | −31.4% | 56.4% |
| ICU Care | −$3 | −0.2% | 0.2% |
| Laboratory/Cath | −$154 | −32.2% | 13.5% |
| Radiology | −$239 | −63.2% | 21.0% |
| Operating Room | −$17 | −27.7% | 1.5% |
| Pharmacy/Supplies | −$18 | −4.5% | 1.6% |
| EKG/EEG | $92 | 108.1% | −8.1% |
| Other | −$158 | −31.6% | 13.8% |
| Total | −$1,141 | −21.8% | 100.0% |

We claim:

1. A computer-based method of aiding comparison of competitive performance of a first provider of services with at least one other provider of the services, where the services are provided to a mix of customers of different types and the performance in providing the services is different for different types of customers, the method comprising:

storing (a) performance data representing the first provider's competitive performance in providing various services to the first provider's customers and (b) customer data indicating the types of customers and the number of customers within each type to which the first provider's services are provided, storing competitor performance data representing the other provider's competitive performance in providing various services to the other provider's customers, adjusting the competitor performance data in accordance with the customer data of the first provider to reflect how the other provider would have performed if it had serviced the types of customers serviced by the first provider, and visually presenting the performance data of the first provider together with the adjusted competitor performance data.

2. The method of claim 1 wherein the providers comprise health-care providers.

3. The method of claim 2 wherein the data relates to length of stay, charges, or costs.

4. The method of claim 1 wherein the customers comprise patients and the types comprise distinct groups.

5. The method of claim 4 wherein the groups are distinguished demographically.

6. The method of claim 1 wherein the services comprise health care services.

7. The method of claim 1 wherein the step of presenting the data comprises generating a report.

8. The method of claim 7 wherein the step of generating a report comprises:

selecting a report template, creating a graphical representation of the performance data and the competitor performance data, and merging the report template and the graphical representation.

9. The method of claim 7 further comprising including in the report a description of a competitive strategy for the first service provider.

10. The method of claim 7 further comprising including in the report a section selected by a user from a group of user-selectable sections.

11. The method of claim 10 further comprising allowing the user to define a level of detail for each of the sections in the report, and producing the sections in accordance with the level of detail.

12. The method of claim 1, wherein the data includes hospital departmental cost information.

13. A computer-based method for automatically generating a report of information comparing performance of a first provider of services with performance of at least one other provider of the services, the method comprising:

storing raw data representing information about the services provided by the first provider and the other provider in a database, extracting from the database a set of comparison data containing similar types of raw data for the first provider and the other provider, storing rules for selecting which of the comparison data to use in comparing the performances of the service providers, and automatically applying the rules to the comparison data to select the information to be presented in the generated report.

14. The method of claim 13 wherein the rules are based on which data represent the greatest difference in performance of the first provider of services compared to performance of the other provider.

15. The method of claim 13 wherein the rules are based on which data represent opportunities for improved performance.

16. A computer-based method of generating a report of an analysis of stored data comprising allowing a user to select which of a group of sections to include in the report, each section corresponding to a particular portion of the data, automatically retrieving the portions of the stored data corresponding to the selected sections, and thereafter automatically performing the analysis on the retrieved data, automatically generating results of the analysis for each selected section, automatically generating printable narrative text and non-text graphics representations of the results for each selected section, and automatically combining the printable narrative text and non-text graphics representations of the selected sections to form an integrated report ready for printing.

17. The method of claim 16 wherein the data comprises data concerning the competitive performance of a medical service business.

18. The method of claim 16 wherein the data comprises financial data.

19. The method of claim 16 wherein the non-text graphics representations comprise tables and charts.

* * * * *